(12) United States Patent
Freestone et al.

(10) Patent No.: US 11,850,365 B2
(45) Date of Patent: Dec. 26, 2023

(54) STRAP ASSEMBLY, STRAP CONNECTOR, HEADGEAR, HEADGEAR ASSEMBLY, METHOD OF FORMING HEADGEAR, TUBULAR CONNECTOR, PATIENT INTERFACE AND METHOD OF JOINING STRAPS

(71) Applicant: Fisher & Paykel Healthcare Limited, Auckland (NZ)

(72) Inventors: Paul Mathew Freestone, Auckland (NZ); Janine Elizabeth Collins, Auckland (NZ); Ryan Anthony Graham, Auckland (NZ); Vitaly Kapelevich, Auckland (NZ); Melissa Catherine Bornholdt, Auckland (NZ); Sophie Kathryn Randles, Auckland (NZ); Silas Sao Jin Siew, Auckland (NZ); Steve Thomas, Auckland (NZ); Ronan Leahy, Auckland (NZ); Max Leon Betteridge, Auckland (NZ); Callum Ross Gordon, Auckland (NZ); Vicky Dan Gao, Auckland (NZ); Cameron Robert Willis, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 179 days.

(21) Appl. No.: 17/646,983

(22) Filed: Jan. 4, 2022

(65) Prior Publication Data
US 2022/0126050 A1 Apr. 28, 2022

Related U.S. Application Data

(63) Continuation of application No. 16/085,304, filed as application No. PCT/IB2017/051373 on Mar. 9, 2017, now Pat. No. 11,253,668.

(Continued)

(51) Int. Cl.
*A61M 16/06* (2006.01)

(52) U.S. Cl.
CPC . *A61M 16/0694* (2014.02); *A61M 2205/0216* (2013.01); *A61M 2210/0618* (2013.01)

(58) Field of Classification Search
CPC ......... A61M 16/06–0694; A61M 16/08–0891; A61M 2016/0661; A61M 2205/0216;
(Continued)

(56) References Cited

U.S. PATENT DOCUMENTS

| 301,111 A | 7/1884 | Genese |
| 472,238 A | 4/1892 | Van Orden |

(Continued)

FOREIGN PATENT DOCUMENTS

| CA | 996301 | 9/1976 |
| CA | 1311662 | 12/1992 |

(Continued)

OTHER PUBLICATIONS cpap.com, InnoMed/Resp Care Bravo Nasal Pillow CPAP Mask with Headgear, (http://web.archive.org/web/*/https://www.cpap.com/productpage/bravo-nasal-interface/), downloaded Feb. 24, 2020, 5 pp.

(Continued)

*Primary Examiner* — Valerie L Woodward
(74) *Attorney, Agent, or Firm* — Knobbe, Martens, Olson & Bear, LLP

(57) ABSTRACT

FIGS. 1-16D & 66A-92D disclose a large variety of methods of forming the headgear for use in combination with a breathing apparatus comprising a unitary plastic core within textile casings. In some configurations, the plastic core material penetrates or bursts-through the textile casing of the straps. Some configurations include over moulding, alignment posts, T-joints and joint housings with injection aper- (Continued)

ture. FIGS. 17-65 & 93A-94C disclose a large variety of different headgear arrangements including top strap, front strap, rear strap and pairs of straps extending from the mask above and below the ear to meet behind the ear. FIGS. 95-121B disclose a large variety of connectors connecting the headgear assembly to the mask assembly where the headgear, mask and connector form a closed loop the connector is disengaged with the mask assembly.

19 Claims, 120 Drawing Sheets

Related U.S. Application Data

(60) Provisional application No. 62/468,915, filed on Mar. 8, 2017, provisional application No. 62/401,462, filed on Sep. 29, 2016, provisional application No. 62/364,767, filed on Jul. 20, 2016, provisional application No. 62/327,942, filed on Apr. 26, 2016, provisional application No. 62/323,459, filed on Apr. 15, 2016, provisional application No. 62/323,489, filed on Apr. 15, 2016, provisional application No. 62/309,400, filed on Mar. 16, 2016.

(58) Field of Classification Search
CPC ...... A61M 2210/0618; A61M 2207/00; A61M 2207/10; A62B 18/02; A62B 18/025; A62B 18/084; A62B 23/02; A62B 23/025
See application file for complete search history.

(56) References Cited

U.S. PATENT DOCUMENTS

| | | |
|---|---|---|
| 577,926 A | 3/1897 | Miller |
| 718,470 A | 1/1903 | Jones |
| 751,091 A | 2/1904 | Moran |
| 770,013 A | 9/1904 | Linn |
| 1,364,104 A | 1/1921 | Geer |
| 1,635,545 A | 7/1927 | Drager |
| 1,942,442 A | 1/1934 | Motsinger |
| 2,199,690 A | 5/1940 | Bullard |
| 2,296,150 A | 9/1942 | Dockson et al. |
| 2,353,643 A | 7/1944 | Bulbulian |
| 2,359,506 A | 10/1944 | Battley et al. |
| 2,388,604 A | 11/1945 | Eisenbud |
| 2,390,233 A | 12/1945 | Akerman et al. |
| 2,508,050 A | 5/1950 | Valente |
| 2,586,851 A | 2/1952 | Monro et al. |
| 2,611,897 A | 9/1952 | Adams |
| 2,661,514 A | 12/1953 | Ada |
| 2,693,800 A | 11/1954 | Caldwell |
| 2,738,788 A | 3/1956 | Matheson et al. |
| 2,843,121 A | 7/1958 | Hudson |
| 2,859,748 A | 11/1958 | Hudson |
| 3,045,672 A | 7/1962 | Croasdaile |
| 3,156,922 A | 11/1964 | Anderson |
| 3,295,529 A | 1/1967 | Corrigall et al. |
| 3,416,521 A | 12/1968 | Humphrey |
| 3,457,564 A | 7/1969 | Holloway |
| 3,490,452 A | 1/1970 | Greenfield |
| 3,500,474 A | 3/1970 | Austin |
| 3,530,031 A | 9/1970 | Loew |
| 3,792,702 A | 2/1974 | Delest |
| 3,834,682 A | 9/1974 | McPhee |
| 3,850,171 A | 11/1974 | Ball et al. |
| 3,887,968 A | 6/1975 | Lynam |
| 3,972,321 A | 8/1976 | Proctor |
| 3,990,757 A | 11/1976 | Gill |
| 3,992,720 A | 11/1976 | Nicolinas |
| 3,994,022 A | 11/1976 | Villari et al. |
| 4,051,556 A | 10/1977 | Davenport et al. |
| 4,062,068 A | 12/1977 | Davenport et al. |
| 4,090,510 A | 5/1978 | Segersten |
| D250,047 S | 10/1978 | Lewis et al. |
| D250,131 S | 10/1978 | Lewis et al. |
| 4,127,130 A | 11/1978 | Naysmith |
| D252,322 S | 7/1979 | Johnson |
| 4,167,185 A | 9/1979 | Lewis |
| 4,201,205 A | 5/1980 | Bartholomew |
| 4,266,540 A | 5/1981 | Panzik et al. |
| 4,278,082 A | 7/1981 | Blackmer |
| 4,288,891 A | 9/1981 | Boden |
| 4,313,437 A | 2/1982 | Martin |
| 4,328,605 A | 5/1982 | Hutchison et al. |
| 4,354,488 A | 10/1982 | Bartos |
| 4,367,735 A | 1/1983 | Dali |
| 4,402,316 A | 9/1983 | Gadberry |
| 4,413,382 A | 11/1983 | Siegmann |
| 4,437,462 A | 3/1984 | Piljay |
| 4,453,292 A | 6/1984 | Bakker |
| 4,458,373 A | 7/1984 | Maslow |
| 4,477,928 A | 10/1984 | Graff |
| 4,606,077 A | 8/1986 | Phillips |
| D293,613 S | 1/1988 | Wingler |
| 4,734,940 A | 4/1988 | Galet et al. |
| 4,753,233 A | 6/1988 | Grimes |
| 4,782,832 A | 11/1988 | Trimble et al. |
| 4,817,596 A | 4/1989 | Gallet |
| 4,848,334 A | 7/1989 | Bellm |
| 4,853,275 A | 8/1989 | Tracy et al. |
| 4,856,508 A | 8/1989 | Tayebi |
| 4,915,105 A | 4/1990 | Lee |
| 4,941,467 A | 7/1990 | Takata |
| 4,944,310 A | 7/1990 | Sullivan |
| 4,947,488 A | 8/1990 | Ashinoff |
| D310,431 S | 9/1990 | Bellm |
| 4,971,051 A | 11/1990 | Toffolon |
| 4,986,269 A | 1/1991 | Hakkinen |
| 5,010,925 A | 4/1991 | Atkinson et al. |
| 5,016,625 A | 5/1991 | Hsu et al. |
| 5,042,478 A | 8/1991 | Kopala et al. |
| D320,677 S | 10/1991 | Kumagai et al. |
| 5,052,084 A | 10/1991 | Braun |
| D321,419 S | 11/1991 | Wallace |
| 5,065,756 A | 11/1991 | Rapoport |
| 5,074,297 A | 12/1991 | Venegas |
| 5,094,236 A | 3/1992 | Tayebi |
| 5,113,857 A | 5/1992 | Dickerman et al. |
| 5,148,578 A | 9/1992 | Clarke et al. |
| 5,148,802 A | 9/1992 | Sanders et al. |
| 5,191,882 A | 3/1993 | Vogliano |
| 5,231,979 A | 8/1993 | Rose |
| 5,245,995 A | 9/1993 | Sullivan et al. |
| D340,317 S | 10/1993 | Cole |
| 5,269,296 A | 12/1993 | Landis et al. |
| D354,128 S | 1/1995 | Rinehart |
| D355,484 S | 2/1995 | Rinehart |
| 5,388,743 A | 2/1995 | Silagy |
| 5,438,979 A | 8/1995 | Johnson et al. |
| 5,477,852 A | 12/1995 | Landis et al. |
| 5,488,948 A | 2/1996 | Dubruille |
| 5,513,634 A | 5/1996 | Jackson |
| 5,529,062 A | 6/1996 | Byrd |
| 5,533,506 A | 7/1996 | Wood |
| 5,546,605 A | 8/1996 | Mallardi |
| 5,551,419 A | 9/1996 | Froehlich et al. |
| 5,566,395 A | 10/1996 | Nebeker |
| 5,595,174 A | 1/1997 | Gwaltney |
| 5,601,078 A | 2/1997 | Schaller et al. |
| D378,610 S | 3/1997 | Reischel et al. |
| 5,657,752 A | 8/1997 | Landis et al. |
| 5,724,965 A | 3/1998 | Handke et al. |
| 5,752,510 A | 5/1998 | Goldstein |
| 5,755,578 A | 5/1998 | Contant et al. |
| 5,774,901 A | 7/1998 | Minami |
| 5,884,624 A | 3/1999 | Barnett et al. |
| 5,921,239 A | 7/1999 | McCall et al. |
| 5,941,245 A | 8/1999 | Hannah et al. |
| 5,941,856 A | 8/1999 | Kovacs et al. |
| 6,017,315 A | 1/2000 | Starr et al. |
| 6,019,101 A | 2/2000 | Cotner et al. |

(56) References Cited

U.S. PATENT DOCUMENTS

| | | |
|---|---|---|
| 6,044,844 A | 4/2000 | Kwok et al. |
| 6,050,260 A | 4/2000 | Daniell et al. |
| 6,119,694 A | 9/2000 | Correa et al. |
| 6,192,886 B1 | 2/2001 | Rudolph |
| D440,302 S | 4/2001 | Wolfe |
| 6,256,798 B1 | 7/2001 | Egolf et al. |
| 6,272,690 B1 | 8/2001 | Carey et al. |
| 6,282,725 B1 | 9/2001 | Vanidestine, Jr. |
| 6,298,850 B1 | 10/2001 | Argraves |
| 6,338,342 B1 | 1/2002 | Fecteau et al. |
| 6,347,631 B1 | 2/2002 | Hansen et al. |
| D455,891 S | 4/2002 | Biedrzycki |
| 6,418,928 B1 | 7/2002 | Bordewick et al. |
| 6,422,238 B1 | 7/2002 | Lithgow |
| 6,431,172 B1 | 8/2002 | Bordewick |
| 6,435,181 B1 | 8/2002 | Jones, Jr. et al. |
| 6,439,234 B1 | 8/2002 | Curti et al. |
| 6,470,886 B1 | 10/2002 | Jestrabek-Hart |
| 6,478,026 B1 | 11/2002 | Wood |
| 6,491,034 B1 | 12/2002 | Gunaratnam et al. |
| 6,536,435 B1 | 3/2003 | Fecteau et al. |
| 6,561,188 B1 | 5/2003 | Ellis |
| 6,561,191 B1 | 5/2003 | Kwok |
| 6,581,594 B1 | 6/2003 | Drew et al. |
| 6,581,601 B2 | 6/2003 | Ziaee |
| 6,588,424 B2 | 7/2003 | Bardel |
| 6,631,718 B1 | 10/2003 | Lovell |
| 6,637,434 B2 | 10/2003 | Noble |
| 6,644,315 B2 | 11/2003 | Ziaee |
| 6,651,658 B1 | 11/2003 | Hill et al. |
| 6,659,102 B1 | 12/2003 | Sico |
| 6,662,803 B2 | 12/2003 | Gradon et al. |
| 6,679,257 B1 | 1/2004 | Robertson et al. |
| 6,679,265 B2 | 1/2004 | Strickland et al. |
| 6,772,761 B1 | 8/2004 | Rucker, Jr. |
| 6,851,425 B2 | 2/2005 | Jaffre et al. |
| 6,883,519 B2 | 4/2005 | Schmidtke et al. |
| 6,886,564 B2 | 5/2005 | Sullivan et al. |
| 6,892,729 B2 | 5/2005 | Smith et al. |
| 6,907,882 B2 | 6/2005 | Ging et al. |
| 6,951,218 B2 | 10/2005 | Gradon et al. |
| 7,004,165 B1 | 2/2006 | Salcido |
| D520,140 S | 5/2006 | Chaggares |
| 7,036,508 B2 | 5/2006 | Kwok |
| 7,062,795 B2 | 6/2006 | Skiba et al. |
| 7,066,179 B2 | 6/2006 | Eaton et al. |
| D526,094 S | 8/2006 | Chen |
| 7,096,864 B1 | 8/2006 | Mayer et al. |
| 7,096,867 B2 | 8/2006 | Smith et al. |
| 7,201,169 B2 | 4/2007 | Wilkie et al. |
| 7,207,333 B2 | 4/2007 | Tohara |
| 7,210,481 B1 | 5/2007 | Lovell et al. |
| 7,219,669 B1 | 5/2007 | Lovell et al. |
| 7,225,811 B2 | 6/2007 | Ruiz et al. |
| 7,318,437 B2 | 1/2008 | Gunaratnam et al. |
| 7,353,826 B2 | 4/2008 | Sleeper et al. |
| 7,353,827 B2 | 4/2008 | Geist |
| 7,814,911 B2 | 10/2010 | Bordewick et al. |
| 7,845,352 B2 | 12/2010 | Sleeper et al. |
| 7,861,715 B2 | 1/2011 | Jones et al. |
| 7,870,860 B2 | 1/2011 | McCormick et al. |
| 7,896,003 B2 | 3/2011 | Matula et al. |
| 7,913,692 B2 | 3/2011 | Kwok |
| 7,967,014 B2 | 6/2011 | Heidmann |
| 8,042,539 B2 | 10/2011 | Chandran et al. |
| 8,047,893 B2 | 11/2011 | Fenske |
| 8,074,651 B2 | 12/2011 | Bierman et al. |
| 8,104,473 B2 | 1/2012 | Woodard et al. |
| 8,132,270 B2 | 3/2012 | Lang et al. |
| 8,136,524 B2 | 3/2012 | Ging et al. |
| 8,297,285 B2 * | 10/2012 | Henry ............... A61M 16/0616 128/207.18 |
| 8,371,302 B2 | 2/2013 | Ging et al. |
| 8,443,807 B2 | 5/2013 | McAuley et al. |
| D686,313 S | 7/2013 | Matula et al. |
| 8,479,741 B2 | 7/2013 | McAuley et al. |
| 8,505,538 B2 | 8/2013 | Amarasinghe |
| 8,517,025 B2 | 8/2013 | Ho et al. |
| 8,522,785 B2 | 9/2013 | Berthon-Jones et al. |
| 8,573,201 B2 | 11/2013 | Rummery et al. |
| 8,596,271 B2 | 12/2013 | Matula, Jr. et al. |
| 8,596,274 B2 | 12/2013 | Hieber et al. |
| 8,631,793 B2 | 1/2014 | Omura et al. |
| 8,636,005 B2 | 1/2014 | Gradon et al. |
| 8,636,007 B2 | 1/2014 | Rummery et al. |
| 8,636,008 B2 | 1/2014 | Flory et al. |
| 8,757,157 B2 | 6/2014 | Price et al. |
| 8,783,257 B2 | 7/2014 | McAuley et al. |
| 8,794,239 B2 | 8/2014 | Gunaratnam |
| 8,839,789 B2 | 9/2014 | Guney et al. |
| 8,856,975 B2 | 10/2014 | Lang et al. |
| 8,857,435 B2 | 10/2014 | Matula, Jr. et al. |
| 8,915,251 B2 | 12/2014 | Lubke et al. |
| 8,950,404 B2 | 2/2015 | Formica et al. |
| 8,997,742 B2 | 4/2015 | Moore et al. |
| 9,032,955 B2 | 5/2015 | Lubke et al. |
| 9,044,564 B2 | 6/2015 | Dravitzki et al. |
| 9,138,555 B2 | 9/2015 | McAuley et al. |
| 9,149,596 B2 | 10/2015 | Valcic et al. |
| 9,265,909 B2 | 2/2016 | Ho et al. |
| 9,302,065 B2 | 4/2016 | Smith et al. |
| 9,320,866 B2 | 4/2016 | McAuley et al. |
| 9,333,315 B2 | 5/2016 | McAuley et al. |
| 9,339,622 B2 | 5/2016 | McAuley et al. |
| 9,480,809 B2 | 11/2016 | Guney et al. |
| 9,517,320 B2 | 12/2016 | Barlow et al. |
| 9,550,038 B2 | 1/2017 | McAuley et al. |
| 9,592,336 B2 | 3/2017 | Nielsen et al. |
| 9,629,974 B2 | 4/2017 | Gibson |
| 9,656,038 B2 | 5/2017 | Rummery et al. |
| 9,744,385 B2 | 8/2017 | Henry |
| 9,782,554 B2 | 10/2017 | Mazzone et al. |
| 9,878,118 B2 | 1/2018 | Formica |
| D810,277 S | 2/2018 | Amarasinghe |
| 9,884,160 B2 | 2/2018 | McAuley |
| 9,901,700 B2 | 2/2018 | McAuley et al. |
| 9,925,349 B2 | 3/2018 | Jablonski |
| 9,974,914 B2 | 5/2018 | McAuley |
| 9,993,606 B2 | 6/2018 | Gibson et al. |
| 10,039,665 B2 | 8/2018 | Blaszczykiewicz et al. |
| 10,065,010 B2 | 9/2018 | Smith et al. |
| 10,071,217 B2 | 9/2018 | Grashow |
| 10,080,856 B2 | 9/2018 | McLaren |
| 10,207,072 B2 | 2/2019 | Dunn et al. |
| 10,279,138 B2 | 5/2019 | Ovzinsky |
| 10,456,546 B2 | 10/2019 | McLaren et al. |
| 10,646,680 B2 | 5/2020 | Huddart et al. |
| 10,668,242 B2 | 6/2020 | Bearne |
| 10,675,428 B2 | 6/2020 | Guney et al. |
| 10,792,451 B2 | 10/2020 | Allan et al. |
| 10,828,449 B2 | 11/2020 | Higgins et al. |
| 10,828,452 B2 | 11/2020 | Huddart et al. |
| 10,874,814 B2 | 12/2020 | Huddart et al. |
| 11,000,663 B2 | 5/2021 | Felix et al. |
| 11,253,668 B2 | 2/2022 | Freestone |
| 2002/0005198 A1 | 1/2002 | Kwok et al. |
| 2002/0020416 A1 | 2/2002 | Namey |
| 2002/0046755 A1 | 4/2002 | Voss |
| 2002/0052568 A1 | 5/2002 | Houser et al. |
| 2002/0053347 A1 | 5/2002 | Ziaee |
| 2002/0059935 A1 | 5/2002 | Wood |
| 2002/0096178 A1 | 7/2002 | Ziaee |
| 2002/0157668 A1 | 10/2002 | Bardel |
| 2003/0005933 A1 | 1/2003 | Izuchukwu |
| 2003/0051732 A1 | 3/2003 | Smith et al. |
| 2003/0079749 A1 | 5/2003 | Strickland et al. |
| 2003/0084903 A1 | 5/2003 | Fecteau et al. |
| 2003/0111080 A1 | 6/2003 | Olsen et al. |
| 2003/0121519 A1 | 7/2003 | Estes et al. |
| 2003/0164170 A1 | 9/2003 | Drew et al. |
| 2003/0172936 A1 | 9/2003 | Wilkie et al. |
| 2003/0196656 A1 | 10/2003 | Moore |
| 2003/0196659 A1 | 10/2003 | Gradon et al. |
| 2003/0196664 A1 | 10/2003 | Jacobson |

(56) References Cited

U.S. PATENT DOCUMENTS

| | | |
|---|---|---|
| 2003/0200970 A1 | 10/2003 | Stenzler et al. |
| 2004/0067333 A1 | 4/2004 | Amarasinghe |
| 2004/0211427 A1 | 10/2004 | Jones et al. |
| 2004/0226566 A1 | 11/2004 | Gunaratnam et al. |
| 2005/0011524 A1 | 1/2005 | Thomlinson et al. |
| 2005/0016067 A1 | 1/2005 | Pettit |
| 2005/0028822 A1 | 2/2005 | Sleeper et al. |
| 2005/0033247 A1 | 2/2005 | Thompson |
| 2005/0066976 A1 | 3/2005 | Wondka |
| 2005/0076913 A1 | 4/2005 | Ho et al. |
| 2005/0098183 A1 | 5/2005 | Nash et al. |
| 2005/0150497 A1 | 7/2005 | Eifler et al. |
| 2005/0161049 A1 | 7/2005 | Wright |
| 2005/0199239 A1 | 9/2005 | Lang et al. |
| 2005/0199242 A1 | 9/2005 | Matula et al. |
| 2005/0205096 A1 | 9/2005 | Matula |
| 2005/0235999 A1 | 10/2005 | Wood et al. |
| 2005/0262619 A1 | 12/2005 | Musal et al. |
| 2006/0060200 A1 | 3/2006 | Ho et al. |
| 2006/0081250 A1 | 4/2006 | Bordewick et al. |
| 2006/0096596 A1 | 5/2006 | Occhialini et al. |
| 2006/0107958 A1 | 5/2006 | Sleeper |
| 2006/0113147 A1 | 6/2006 | Harris |
| 2006/0118117 A1 | 6/2006 | Berthon-Jones et al. |
| 2006/0124131 A1 | 6/2006 | Chandran |
| 2006/0137690 A1 | 6/2006 | Gunaratnam et al. |
| 2006/0174887 A1 | 8/2006 | Chandran et al. |
| 2006/0174892 A1 | 8/2006 | Leksutin et al. |
| 2006/0196510 A1 | 9/2006 | McDonald et al. |
| 2006/0196511 A1 | 9/2006 | Lau et al. |
| 2006/0237018 A1 | 10/2006 | McAuley et al. |
| 2007/0000492 A1 | 1/2007 | Hansel et al. |
| 2007/0010786 A1 | 1/2007 | Casey et al. |
| 2007/0089749 A1 | 4/2007 | Ho et al. |
| 2007/0125385 A1 | 6/2007 | Ho et al. |
| 2007/0125387 A1 | 6/2007 | Zollinger et al. |
| 2007/0130663 A1 | 6/2007 | Lang et al. |
| 2007/0137653 A1 | 6/2007 | Wood |
| 2007/0163600 A1 | 7/2007 | Hoffman |
| 2007/0169777 A1 | 7/2007 | Amarasinghe et al. |
| 2007/0175480 A1 | 8/2007 | Gradon et al. |
| 2007/0209663 A1 | 9/2007 | Marque et al. |
| 2007/0215161 A1 | 9/2007 | Frater et al. |
| 2007/0235033 A1 | 10/2007 | Reier et al. |
| 2007/0295335 A1 | 12/2007 | Nashed |
| 2008/0041388 A1 | 2/2008 | McAuley et al. |
| 2008/0041393 A1 | 2/2008 | Bracken |
| 2008/0047560 A1 | 2/2008 | Veliss et al. |
| 2008/0052806 A1 | 3/2008 | McDaniel |
| 2008/0053450 A1 | 3/2008 | Van Kerkwyk et al. |
| 2008/0060648 A1 | 3/2008 | Thornton et al. |
| 2008/0060653 A1 | 3/2008 | Hallet et al. |
| 2008/0060657 A1 | 3/2008 | McAuley et al. |
| 2008/0065015 A1 | 3/2008 | Fiser |
| 2008/0083412 A1 | 4/2008 | Henry et al. |
| 2008/0092906 A1 | 4/2008 | Gunaratnam et al. |
| 2008/0099024 A1 | 5/2008 | Gunaratnam et al. |
| 2008/0110464 A1 | 5/2008 | Davidson et al. |
| 2008/0134480 A1 | 6/2008 | Shiue |
| 2008/0196728 A1 | 8/2008 | Ho |
| 2008/0230068 A1 | 9/2008 | Rudolph |
| 2008/0230069 A1 | 9/2008 | Valcic et al. |
| 2008/0264422 A1 | 10/2008 | Fishman |
| 2008/0302366 A1 | 12/2008 | McGinnis et al. |
| 2008/0314388 A1 | 12/2008 | Brambilla et al. |
| 2009/0000624 A1 | 1/2009 | Lee et al. |
| 2009/0014007 A1 | 1/2009 | Brambilla et al. |
| 2009/0032026 A1 | 2/2009 | Price et al. |
| 2009/0044808 A1 | 2/2009 | Guney et al. |
| 2009/0044809 A1 | 2/2009 | Welchel et al. |
| 2009/0120442 A1 | 5/2009 | Ho |
| 2009/0133697 A1 | 5/2009 | Kwok et al. |
| 2009/0145429 A1 | 6/2009 | Ging et al. |
| 2009/0173349 A1 | 7/2009 | Hernandez et al. |
| 2009/0178680 A1 | 7/2009 | Chang |
| 2009/0183739 A1 | 7/2009 | Wondka |
| 2009/0211583 A1 | 8/2009 | Carroll |
| 2009/0250060 A1 | 10/2009 | Hacke et al. |
| 2009/0320187 A1 | 12/2009 | Petzl et al. |
| 2010/0000538 A1 | 1/2010 | Edwards et al. |
| 2010/0000544 A1 | 1/2010 | Blaszczykiewicz et al. |
| 2010/0018534 A1 | 1/2010 | Veliss et al. |
| 2010/0037897 A1 | 2/2010 | Wood |
| 2010/0154798 A1 | 6/2010 | Henry et al. |
| 2010/0224199 A1 | 9/2010 | Smith et al. |
| 2010/0258132 A1 | 10/2010 | Moore |
| 2010/0258136 A1 | 10/2010 | Doherty et al. |
| 2010/0282265 A1 | 11/2010 | Melidis et al. |
| 2010/0307502 A1 | 12/2010 | Rummery et al. |
| 2010/0313532 A1 | 12/2010 | Stjernfelt et al. |
| 2010/0313891 A1 | 12/2010 | Veliss et al. |
| 2010/0319700 A1 | 12/2010 | Ng et al. |
| 2011/0048425 A1 | 3/2011 | Chang |
| 2011/0191938 A1 | 8/2011 | Elliott |
| 2011/0197341 A1* | 8/2011 | Formica .................... B32B 5/32 |
| | | 2/209.3 |
| 2011/0220113 A1 | 9/2011 | Newman |
| 2011/0247628 A1 | 10/2011 | Ho |
| 2011/0259335 A1 | 10/2011 | Sullivan |
| 2011/0265791 A1 | 11/2011 | Ging et al. |
| 2011/0265796 A1 | 11/2011 | Amarasinghe et al. |
| 2012/0067349 A1 | 3/2012 | Barlow et al. |
| 2012/0125339 A1 | 5/2012 | Ho et al. |
| 2012/0132209 A1 | 5/2012 | Rummery |
| 2012/0138063 A1 | 6/2012 | Eves et al. |
| 2012/0174355 A1 | 7/2012 | Fraze |
| 2012/0222680 A1 | 9/2012 | Eves et al. |
| 2012/0247490 A1 | 10/2012 | Matthews |
| 2012/0304999 A1 | 12/2012 | Swift et al. |
| 2013/0000648 A1 | 1/2013 | Madaus et al. |
| 2013/0008449 A1 | 1/2013 | Busch et al. |
| 2013/0139822 A1 | 6/2013 | Gibson |
| 2013/0152918 A1 | 6/2013 | Rummery et al. |
| 2013/0152937 A1 | 6/2013 | Jablonski |
| 2013/0160769 A1 | 6/2013 | Ng et al. |
| 2013/0220327 A1* | 8/2013 | Barlow ............. A61M 16/0057 |
| | | 128/205.25 |
| 2013/0228173 A1 | 9/2013 | Busch |
| 2013/0247916 A1 | 9/2013 | Symons |
| 2013/0319421 A1 | 12/2013 | Hitchcock et al. |
| 2014/0026888 A1 | 1/2014 | Matula |
| 2014/0026890 A1 | 1/2014 | Haskard et al. |
| 2014/0083428 A1 | 3/2014 | Rothermel et al. |
| 2014/0102456 A1 | 4/2014 | Ovizinsky |
| 2014/0137870 A1 | 5/2014 | Barlow |
| 2014/0158726 A1 | 6/2014 | Malara |
| 2014/0166019 A1 | 6/2014 | Ho et al. |
| 2014/0190486 A1 | 7/2014 | Dunn et al. |
| 2014/0209098 A1 | 7/2014 | Dunn |
| 2014/0216452 A1 | 8/2014 | Miller et al. |
| 2014/0305439 A1 | 10/2014 | Chodkowski |
| 2014/0358054 A1 | 12/2014 | Capra |
| 2015/0000615 A1 | 1/2015 | Imran et al. |
| 2015/0005685 A1 | 1/2015 | Chetlapalli et al. |
| 2015/0028519 A1 | 1/2015 | Lang et al. |
| 2015/0033457 A1 | 2/2015 | Tryner et al. |
| 2015/0051000 A1 | 2/2015 | Henn |
| 2015/0090268 A1 | 4/2015 | Madaus et al. |
| 2015/0128953 A1 | 5/2015 | Formica et al. |
| 2015/0151070 A1 | 6/2015 | Capra et al. |
| 2015/0190262 A1 | 7/2015 | Capra et al. |
| 2015/0202397 A1 | 7/2015 | Pastoor |
| 2015/0217150 A1 | 8/2015 | Harris |
| 2015/0285337 A1 | 10/2015 | Dingley et al. |
| 2015/0290415 A1 | 10/2015 | Dunn |
| 2016/0022944 A1 | 1/2016 | Chodkowski et al. |
| 2016/0038707 A1 | 2/2016 | Allan et al. |
| 2016/0045700 A1 | 2/2016 | Amarasinghe |
| 2016/0082214 A1 | 3/2016 | Barlow et al. |
| 2016/0166793 A1 | 6/2016 | McLaren et al. |
| 2016/0178027 A1 | 6/2016 | Wetzel |
| 2016/0256655 A1 | 9/2016 | Mah |
| 2016/0278463 A1 | 9/2016 | Stevenson |
| 2016/0375214 A1 | 12/2016 | Chodkowski et al. |

(56) References Cited

U.S. PATENT DOCUMENTS

| | | |
|---|---|---|
| 2017/0136269 A1 | 5/2017 | Jacotey et al. |
| 2017/0182276 A1 | 6/2017 | Hammer |
| 2017/0189636 A1 | 7/2017 | Gibson et al. |
| 2017/0216548 A1 | 8/2017 | Gerhardt |
| 2018/0209618 A1 | 7/2018 | Pontano |
| 2018/0214655 A1 | 8/2018 | Kooij et al. |
| 2018/0264218 A1 | 9/2018 | Chodkowski |
| 2018/0339123 A1 | 11/2018 | Smith et al. |
| 2019/0083734 A1 | 3/2019 | Hammer et al. |
| 2019/0111227 A1 | 4/2019 | Veliss et al. |
| 2019/0118009 A1 | 4/2019 | Vogus |
| 2019/0151592 A1 | 5/2019 | Bornholdt |
| 2020/0129720 A1 | 4/2020 | McLaren et al. |
| 2020/0171260 A1 | 6/2020 | McLaren et al. |
| 2020/0230343 A1 | 7/2020 | Sims et al. |
| 2020/0230344 A1 | 7/2020 | Huddart et al. |
| 2020/0338294 A1 | 10/2020 | McLaren et al. |
| 2021/0008316 A1 | 1/2021 | McLaren et al. |
| 2021/0016041 A1 | 1/2021 | Huddart et al. |
| 2021/0220598 A1 | 7/2021 | Felix et al. |
| 2022/0126049 A1 | 4/2022 | Amarasinghe |
| 2022/0331542 A1 | 10/2022 | McLaren et al. |
| 2023/0201510 A1 | 6/2023 | Hammer |

FOREIGN PATENT DOCUMENTS

| | | |
|---|---|---|
| CA | 2995960 | 2/2017 |
| CN | 2172538 | 7/1994 |
| CN | 1784250 | 6/2006 |
| CN | 1901963 A | 1/2007 |
| CN | 201033204 | 3/2008 |
| CN | 201171846 | 12/2008 |
| CN | 101432039 A | 5/2009 |
| CN | 100502972 C | 6/2009 |
| CN | 101516427 | 8/2009 |
| CN | 202822396 U | 3/2013 |
| DE | 895692 | 11/1953 |
| DE | 2706284 | 8/1978 |
| DE | 3122034 | 12/1982 |
| DE | 3907428 | 9/1990 |
| DE | 10254399 | 6/2004 |
| DE | 102006011151 | 9/2007 |
| EP | 0 350 322 | 1/1990 |
| EP | 0 401 307 | 8/1995 |
| EP | 0 879 565 | 11/1998 |
| EP | 0 982 049 | 3/2000 |
| EP | 1 187 650 | 12/2005 |
| EP | 2 130 563 | 12/2009 |
| EP | 2 517 757 | 10/2012 |
| EP | 2 022 528 | 3/2016 |
| FR | 2390116 | 3/1938 |
| FR | 2618340 | 11/1970 |
| FR | 825960 | 1/1989 |
| FR | 2658725 | 8/1991 |
| FR | 2749176 | 12/1997 |
| FR | 2804421 | 8/2001 |
| GB | 190224431 | 12/1902 |
| GB | 339522 | 12/1930 |
| GB | 826198 | 12/1959 |
| GB | 880824 | 10/1961 |
| GB | 1467828 | 3/1977 |
| GB | 2133275 | 7/1984 |
| GB | 2188236 | 9/1987 |
| GB | 1211268 | 4/2000 |
| GB | 2478305 | 9/2011 |
| GB | 2491227 | 11/2012 |
| GB | 2553475 | 3/2018 |
| JP | S46-12114 | 4/1971 |
| JP | 46-016719 | 6/1971 |
| JP | S55-89072 | 7/1980 |
| JP | 368861 U | 5/2000 |
| JP | 2004-016488 | 1/2004 |
| JP | 2003-053874 | 9/2004 |
| JP | 2009-125306 | 6/2009 |
| JP | 2010-090973 | 4/2010 |
| JP | 2000-102624 | 5/2013 |
| JP | 2018-127729 | 8/2018 |
| KR | 10-2011-0028950 | 3/2011 |
| NZ | 585295 | 12/2011 |
| TW | 201340900 | 1/2013 |
| WO | WO 95/12432 | 5/1995 |
| WO | WO 97/32494 | 9/1997 |
| WO | WO 98/003225 | 1/1998 |
| WO | WO 98/018514 | 5/1998 |
| WO | WO 99/04842 | 2/1999 |
| WO | WO 99/058181 | 11/1999 |
| WO | WO 00/50122 | 8/2000 |
| WO | WO 00/069497 | 11/2000 |
| WO | WO 00/074758 | 12/2000 |
| WO | WO 01/041854 | 6/2001 |
| WO | WO 01/097892 | 12/2001 |
| WO | WO 02/44749 | 6/2002 |
| WO | WO 02/047749 | 6/2002 |
| WO | WO 02/074372 | 9/2002 |
| WO | WO 04/041341 | 5/2004 |
| WO | WO 04/073778 | 9/2004 |
| WO | WO 05/021075 | 3/2005 |
| WO | WO 05/032634 | 4/2005 |
| WO | WO 05/046776 | 5/2005 |
| WO | WO 05/051468 | 6/2005 |
| WO | WO 05/063328 | 7/2005 |
| WO | WO 05/118042 | 12/2005 |
| WO | WO 05/123166 | 12/2005 |
| WO | WO 06/130903 | 12/2006 |
| WO | WO 06/138416 | 12/2006 |
| WO | WO 07/022562 | 3/2007 |
| WO | WO 07/041786 | 4/2007 |
| WO | WO 07/068044 | 6/2007 |
| WO | WO 07/125487 | 11/2007 |
| WO | WO 07/147088 | 12/2007 |
| WO | WO 08/007985 | 1/2008 |
| WO | WO 08/060295 | 5/2008 |
| WO | WO 08/070929 | 6/2008 |
| WO | WO 08/106716 | 9/2008 |
| WO | WO 08/148086 | 12/2008 |
| WO | WO 09/026627 | 3/2009 |
| WO | WO 09/038918 | 3/2009 |
| WO | WO 09/052560 | 4/2009 |
| WO | WO 09/059353 | 5/2009 |
| WO | WO 09/092057 | 7/2009 |
| WO | WO 09/108994 | 9/2009 |
| WO | WO 09/108995 | 9/2009 |
| WO | WO 09/139647 | 11/2009 |
| WO | WO 09/148956 | 12/2009 |
| WO | WO 10/066004 | 6/2010 |
| WO | WO 10/131189 | 11/2010 |
| WO | WO 10/139014 | 12/2010 |
| WO | WO 11/072739 | 6/2011 |
| WO | WO 11/077254 | 6/2011 |
| WO | WO 11/112401 | 9/2011 |
| WO | WO 12/07300 | 1/2012 |
| WO | WO 12/045127 | 4/2012 |
| WO | WO 12/069951 | 5/2012 |
| WO | WO 12/071300 | 5/2012 |
| WO | WO 12/143822 | 10/2012 |
| WO | WO 12/177152 | 12/2012 |
| WO | WO 13/006913 | 1/2013 |
| WO | WO 13/026091 | 2/2013 |
| WO | WO 13/026092 | 2/2013 |
| WO | WO 13/064930 | 5/2013 |
| WO | WO 14/020469 | 2/2014 |
| WO | WO 14/025267 | 2/2014 |
| WO | WO 14/031673 | 2/2014 |
| WO | WO 14/075141 | 5/2014 |
| WO | WO 14/077708 | 5/2014 |
| WO | WO 14/110622 | 7/2014 |
| WO | WO 14/110626 | 7/2014 |
| WO | WO 14/129913 | 8/2014 |
| WO | WO 14/175752 | 10/2014 |
| WO | WO 14/175753 | 10/2014 |
| WO | WO 15/033287 | 3/2015 |
| WO | WO 15/043229 | 4/2015 |
| WO | WO 15/070289 | 5/2015 |
| WO | WO 15/079396 | 6/2015 |

(56) References Cited

FOREIGN PATENT DOCUMENTS

| WO | WO 15/083060 | 6/2015 |
| --- | --- | --- |
| WO | WO 15/151019 | 10/2015 |
| WO | WO 15/187986 | 12/2015 |
| WO | WO 16/043603 | 3/2016 |
| WO | WO 17/030447 | 2/2017 |
| WO | WO 17/150990 | 9/2017 |
| WO | WO 17/158474 | 9/2017 |
| WO | WO 17/158544 | 9/2017 |
| WO | WO 17/160166 | 9/2017 |
| WO | WO 17/216708 | 12/2017 |
| WO | WO 19/003094 | 1/2019 |

OTHER PUBLICATIONS

Pad A Cheek, LLC, Sleep apnea can make beautiful sleep elusive, (http://web.archive.org/web/20070701000000*/http://www.padacheek.com/;Wayback Machine), downloaded Feb. 24, 2020, 3 pp.

Philips Respironics 'System One Heated Humidifier—User Manual', 2011, pp. 1-16, [retrieved on Nov. 25, 2013] from the internet: URL: http://www.cpapxchange.com/cpap-machines-biap-machines/system-one-60-series-cpap-humidifier-manual.pdf.

* cited by examiner

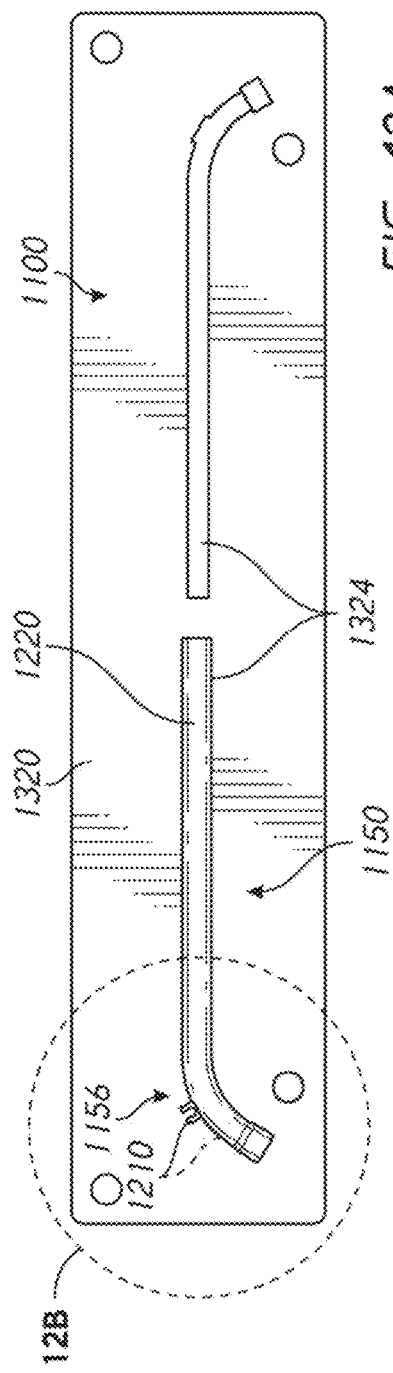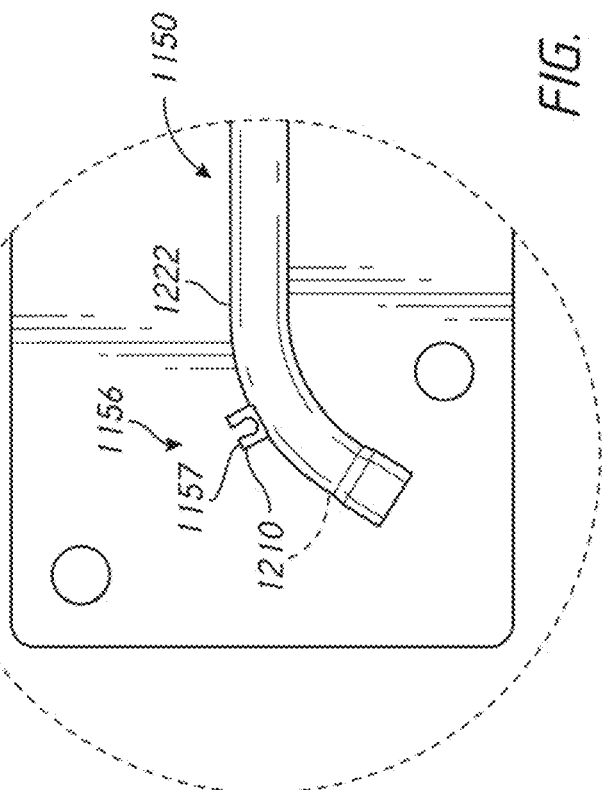

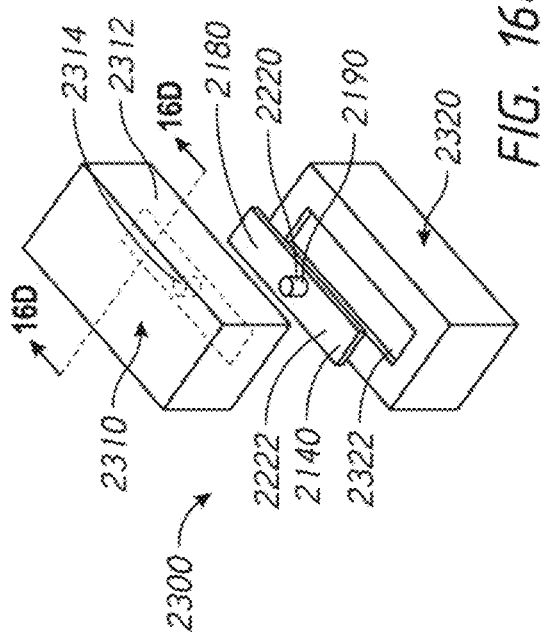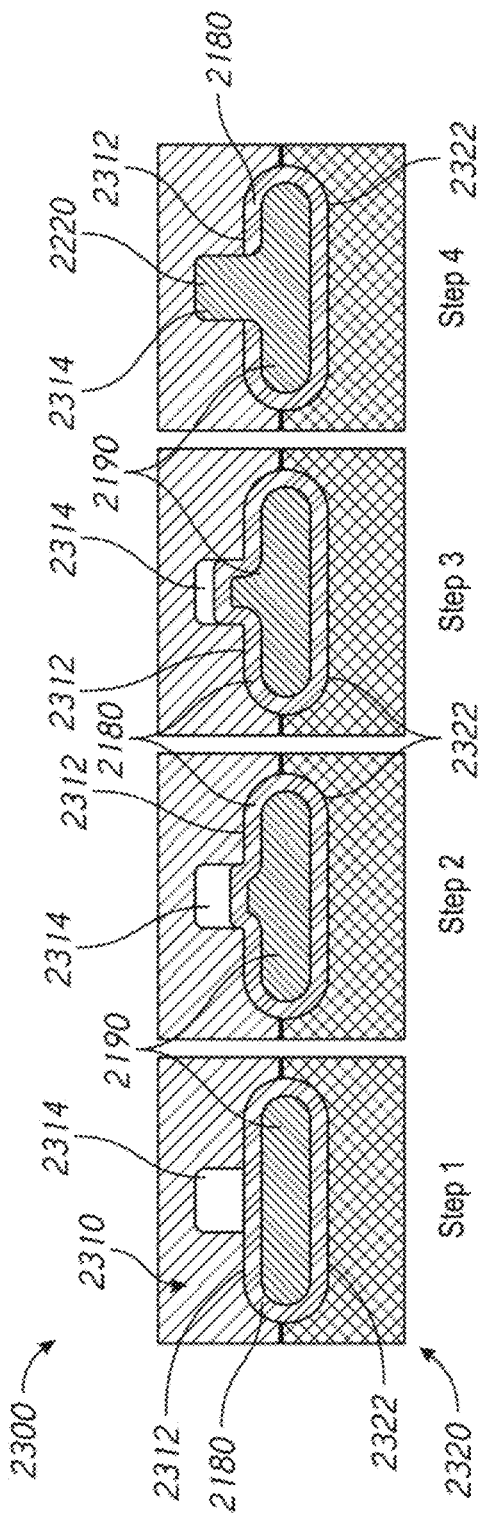

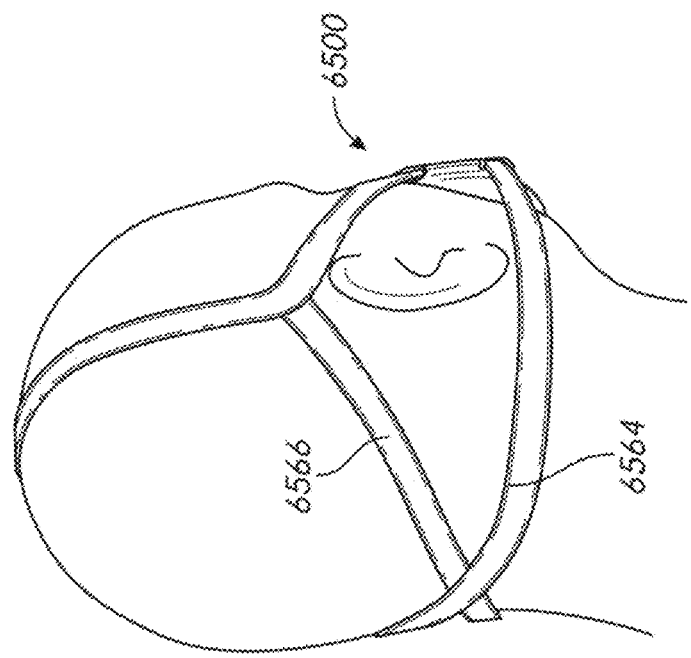
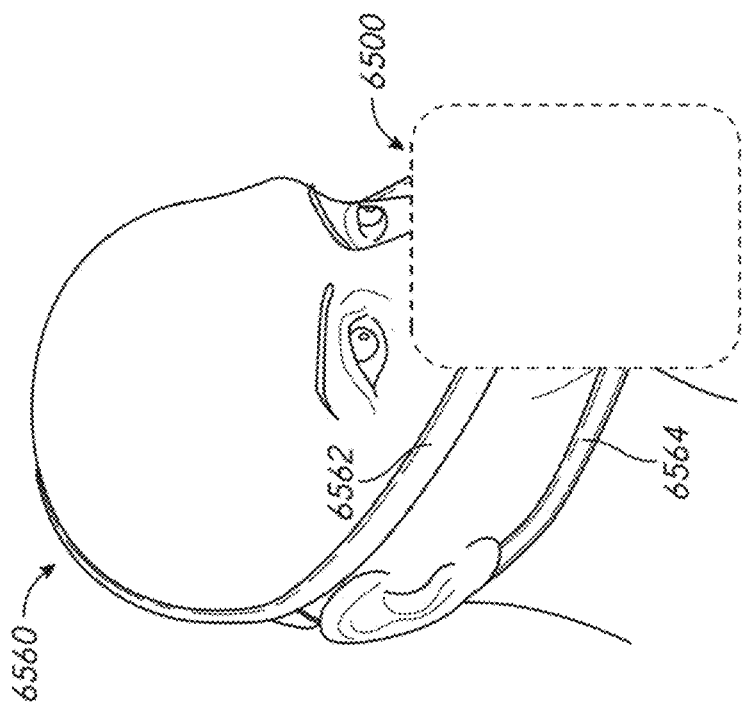
FIG. 48A
FIG. 48B

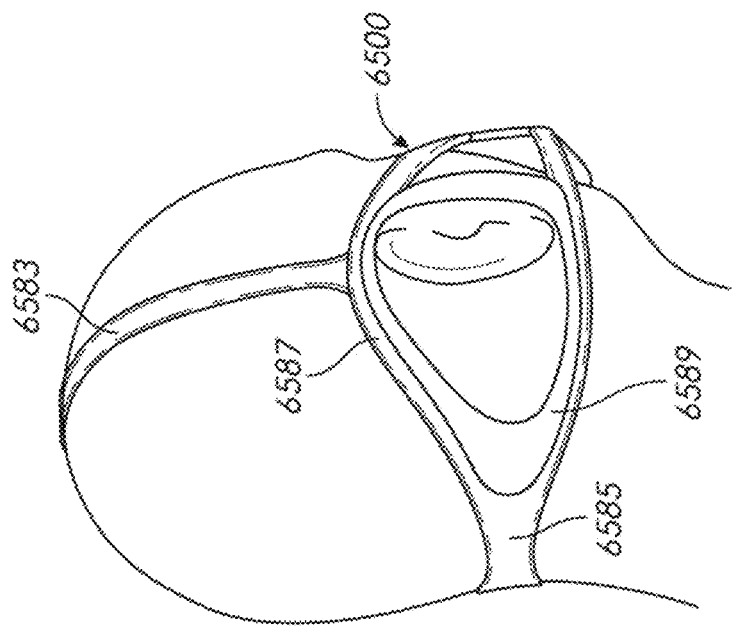
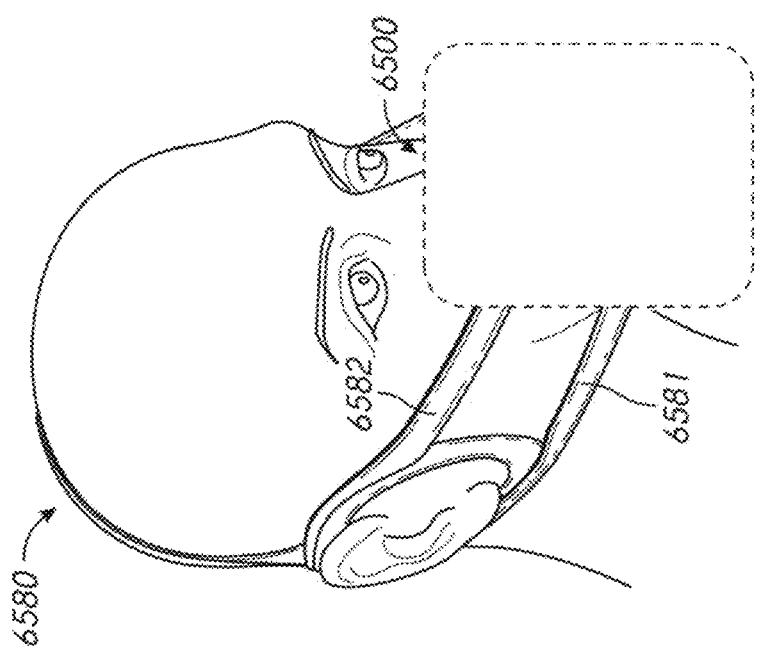
FIG. 50B
FIG. 50A

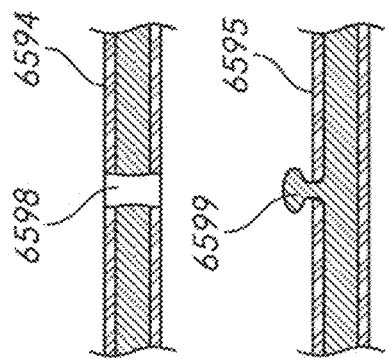
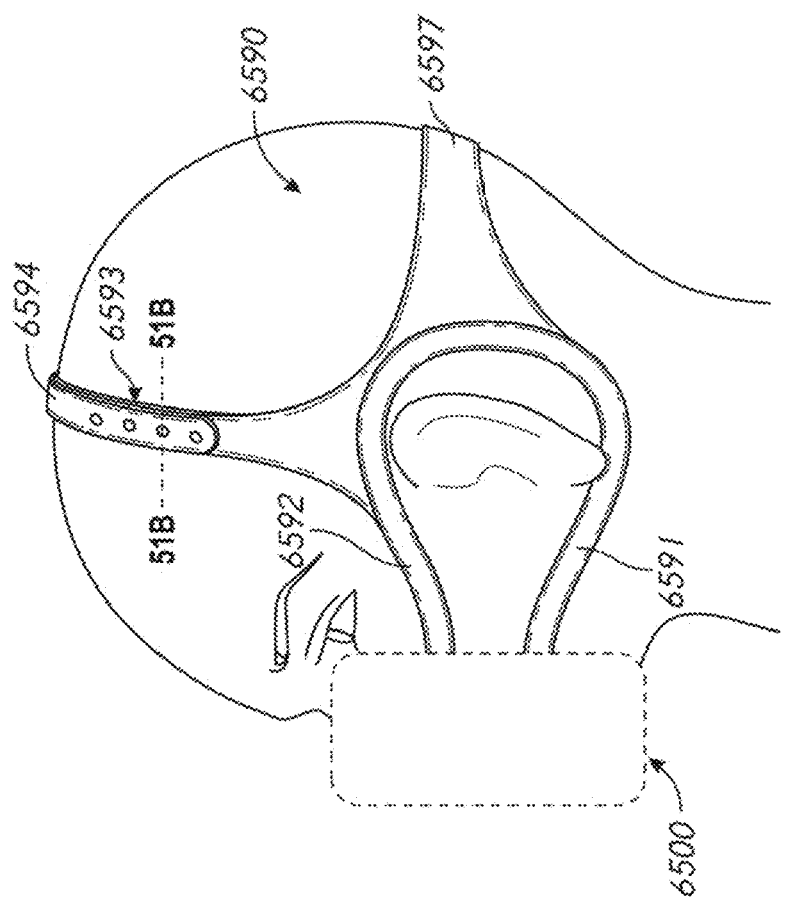

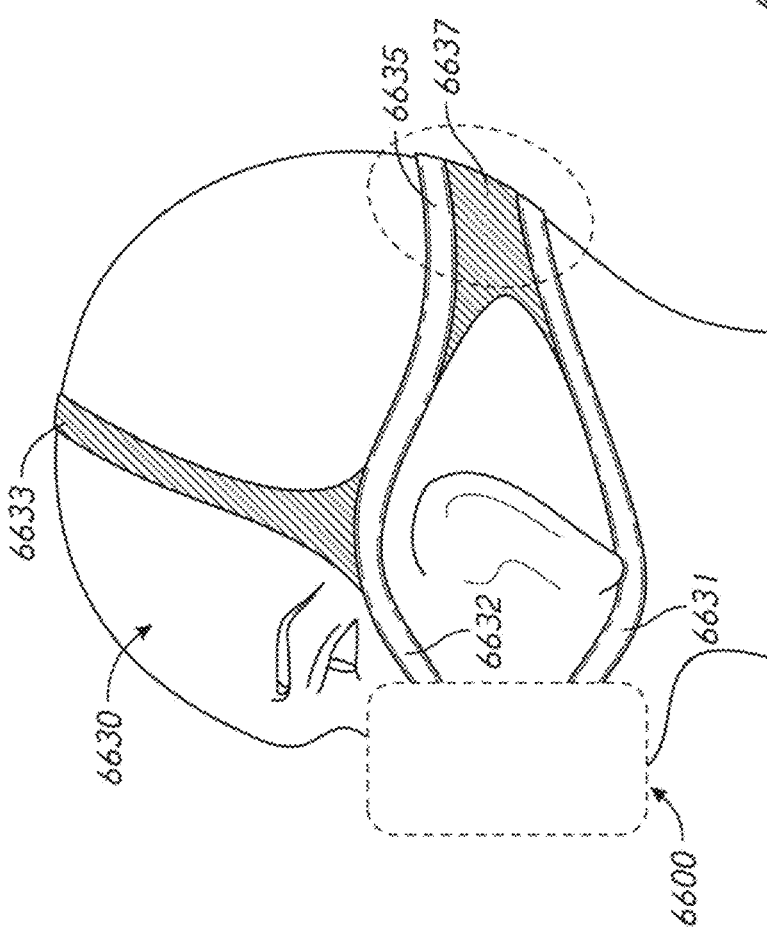
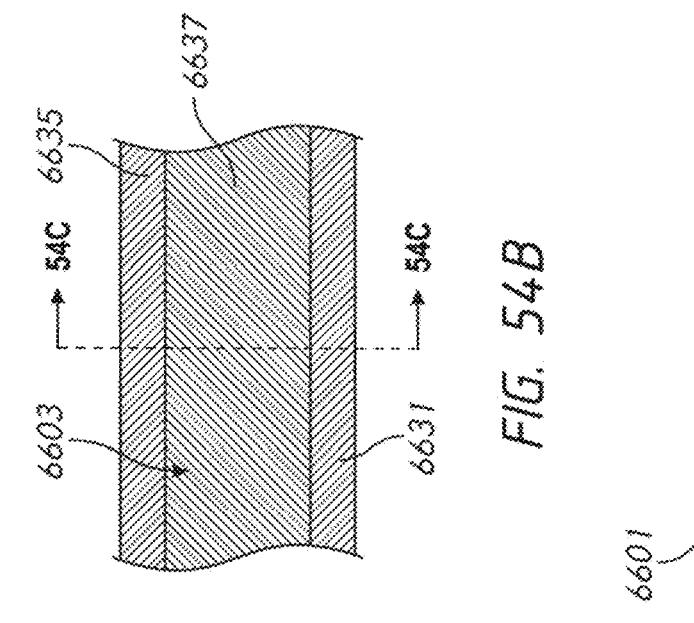
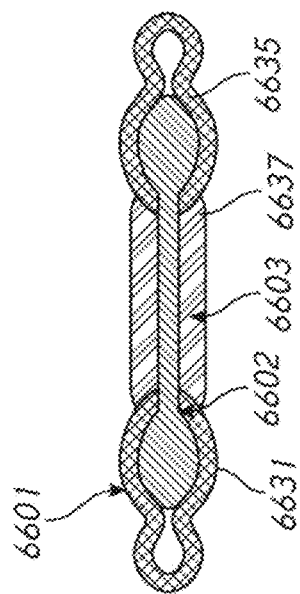

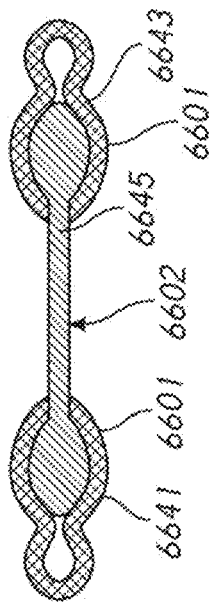
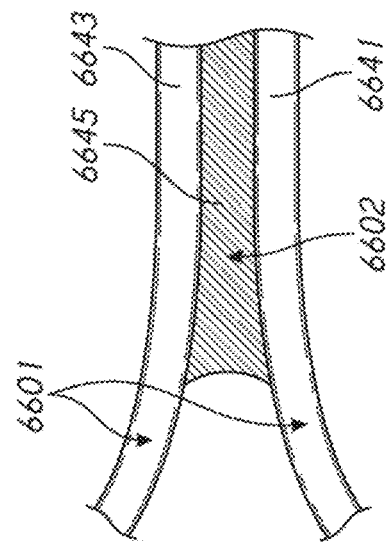
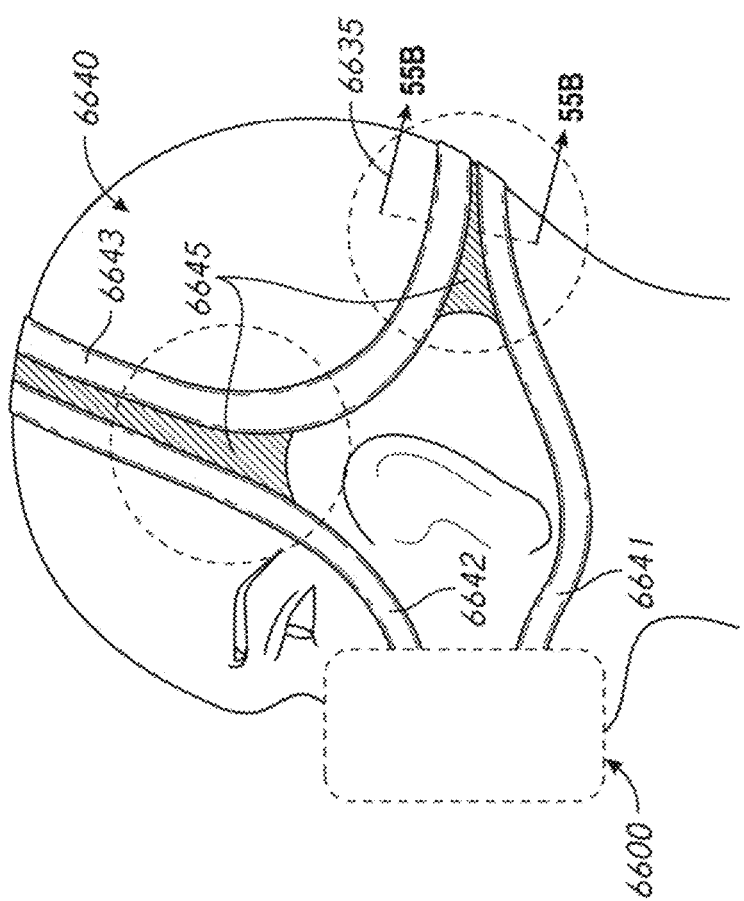

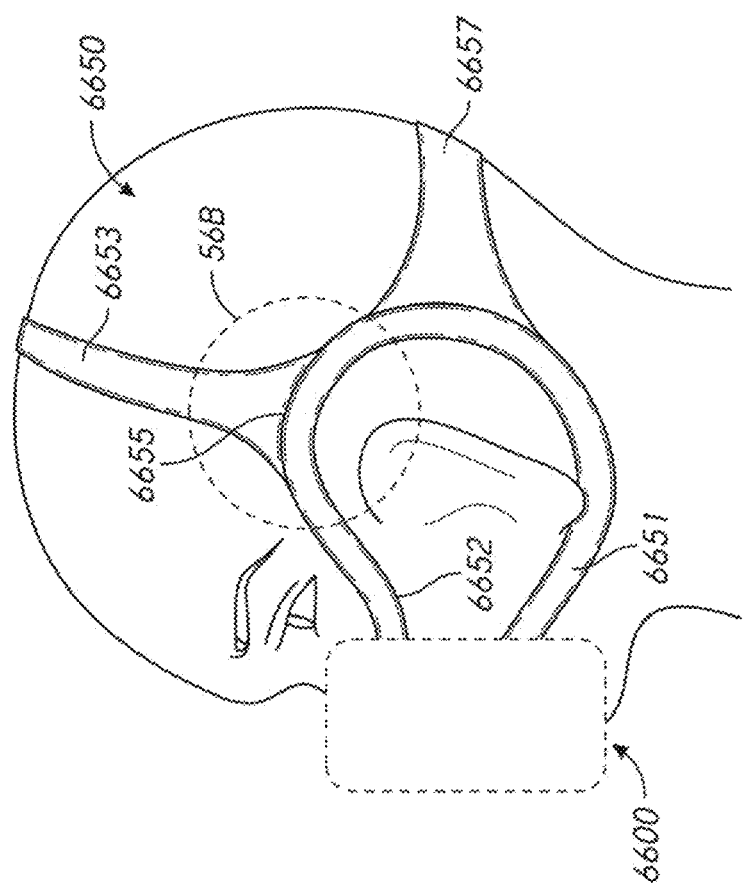
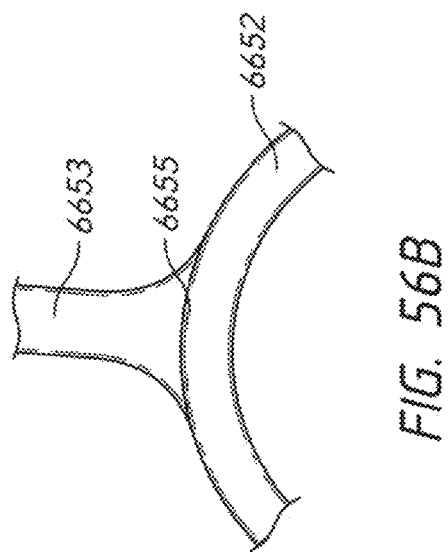
FIG. 56A
FIG. 56B

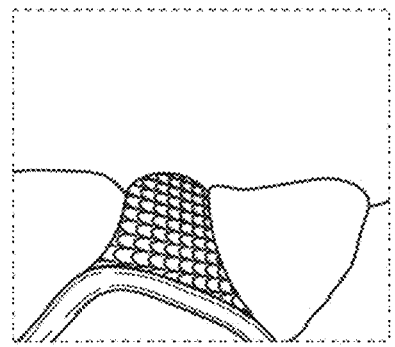
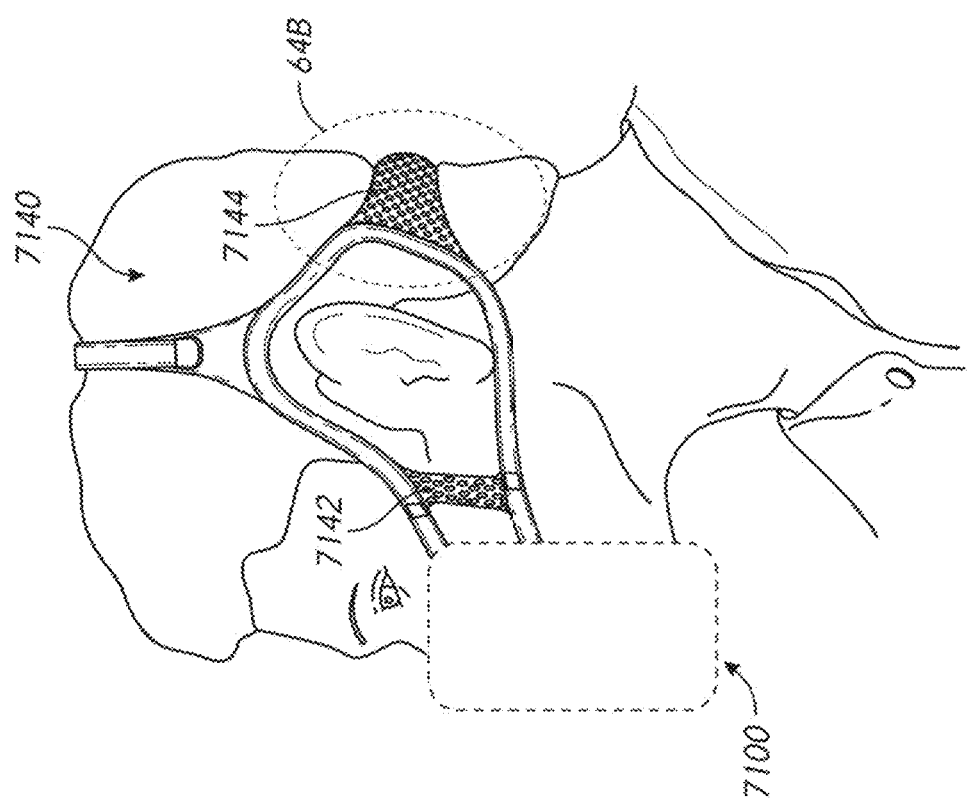
FIG. 64B
FIG. 64A

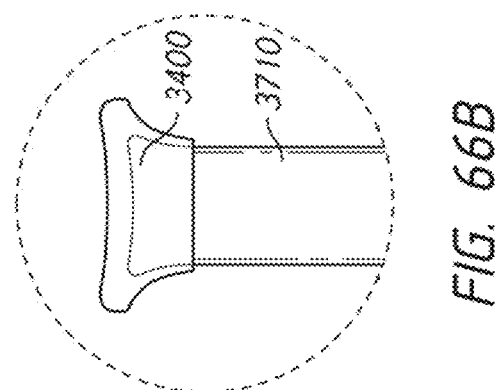
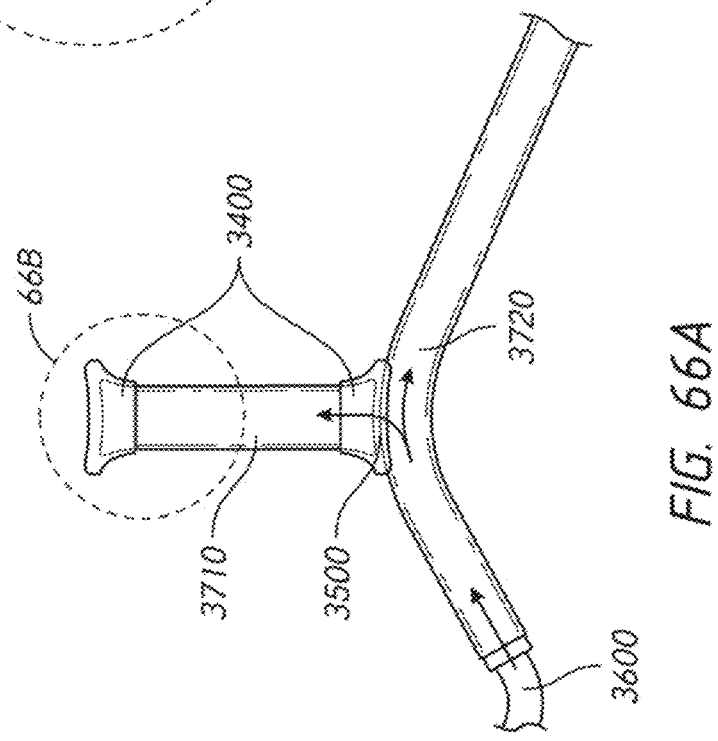
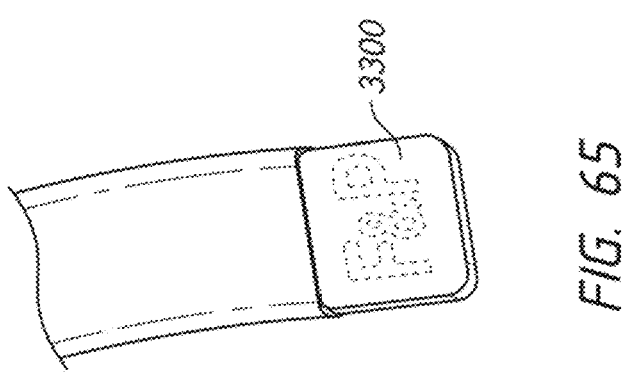

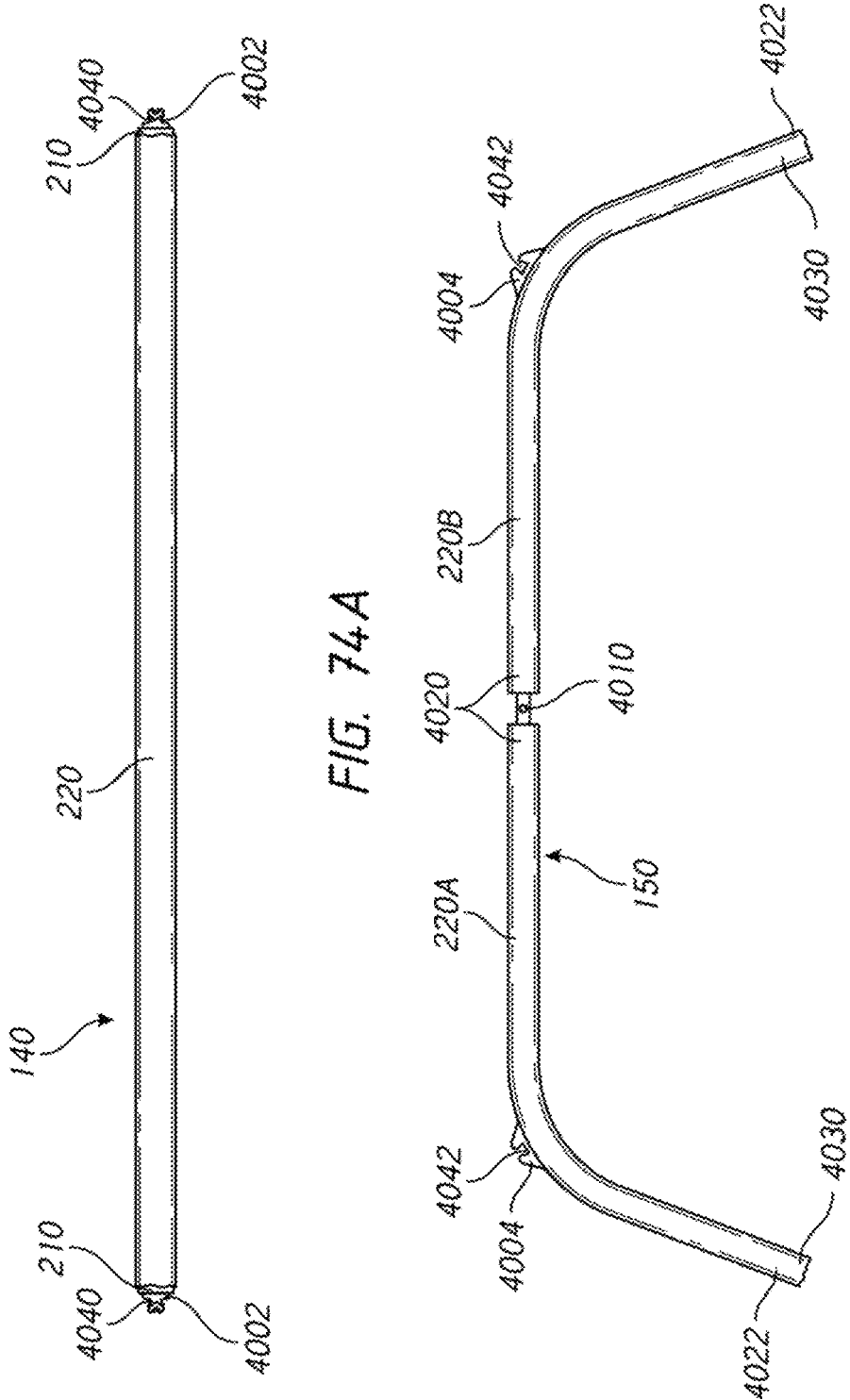

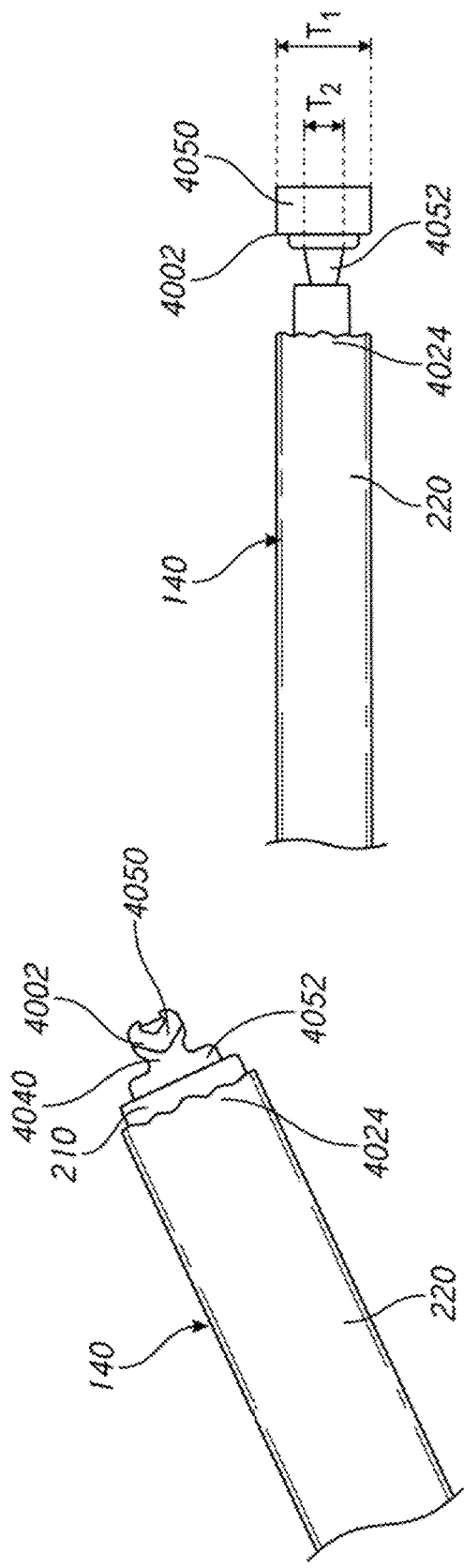

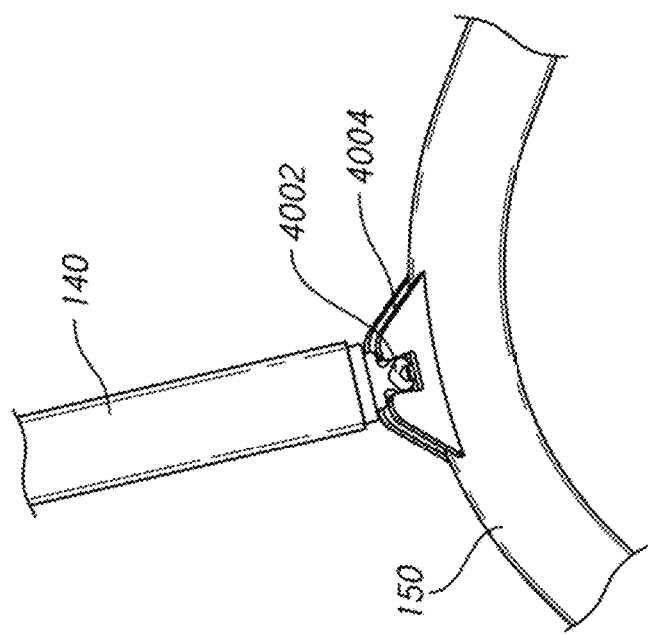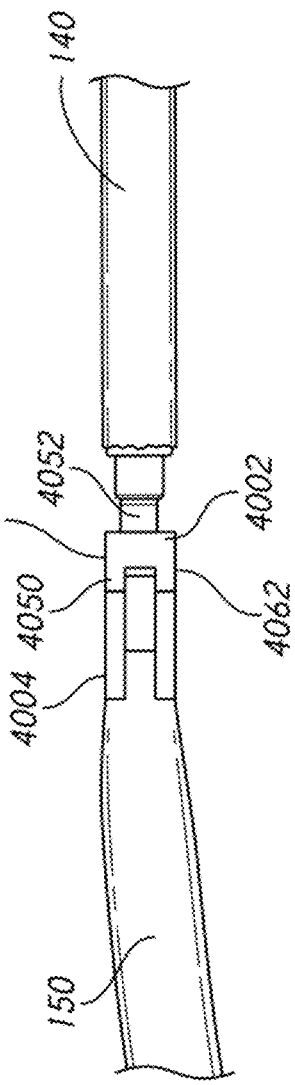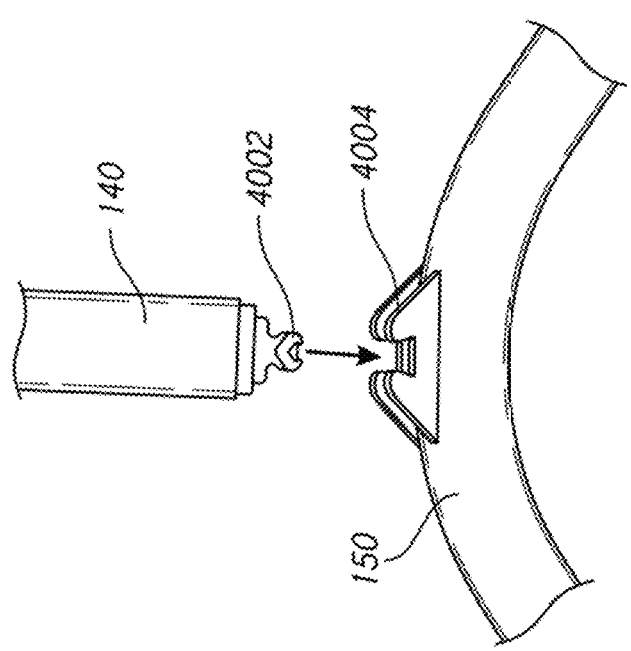

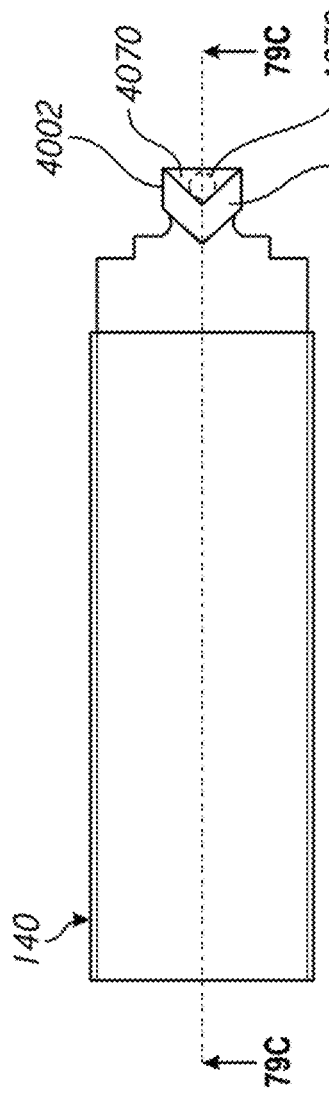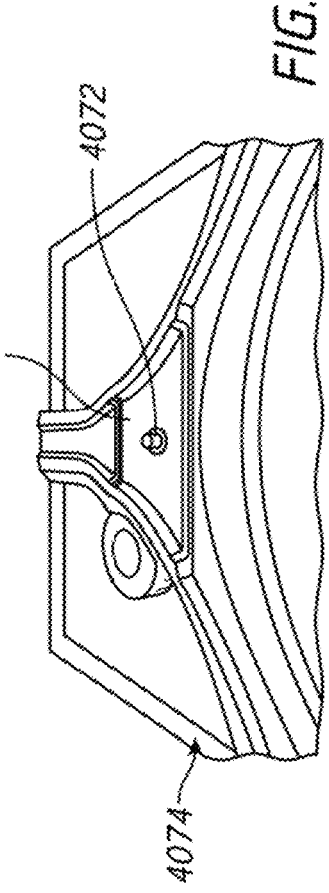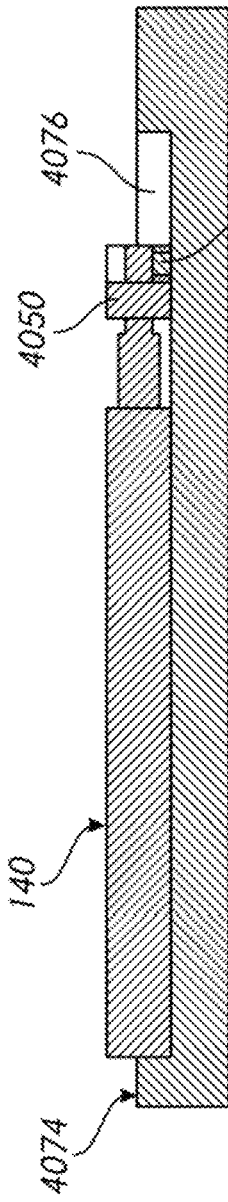

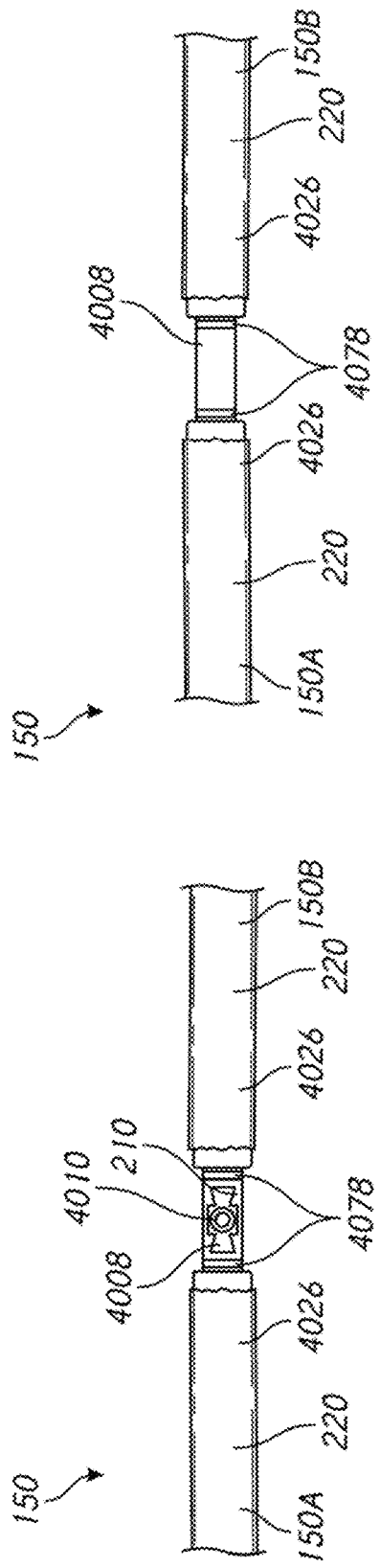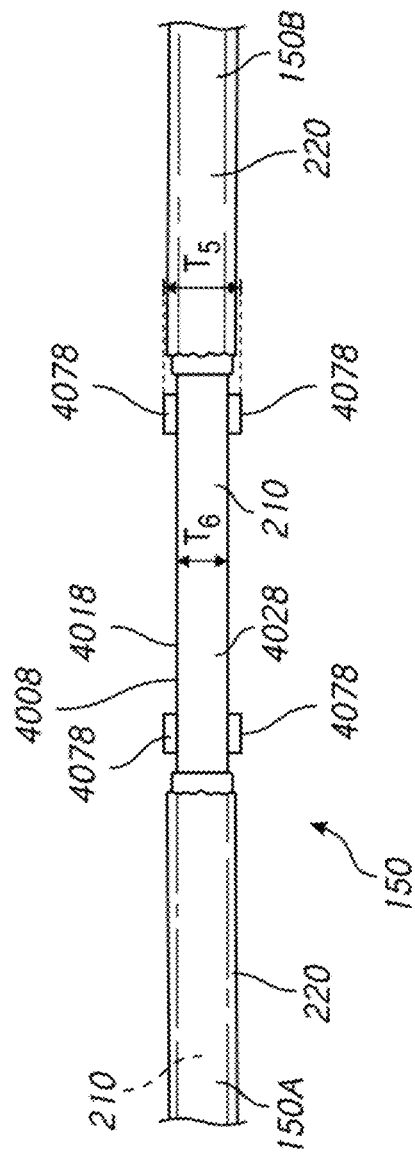

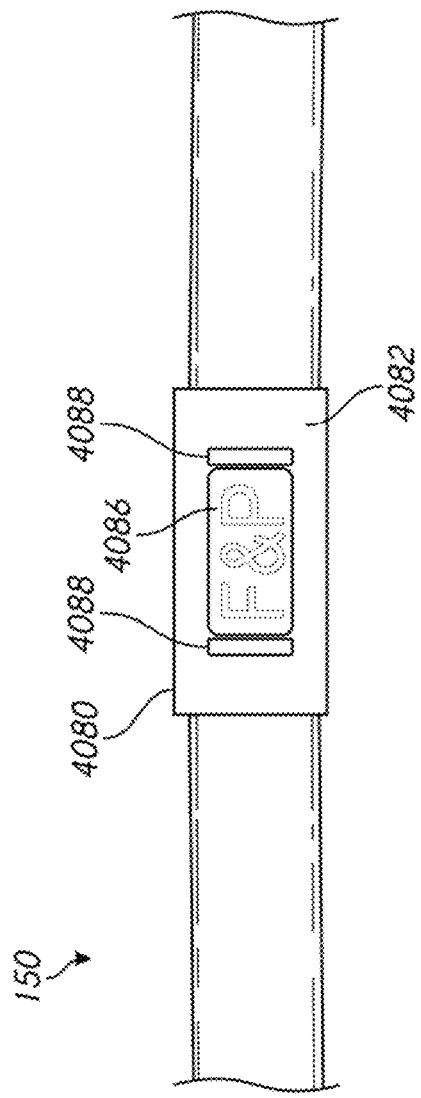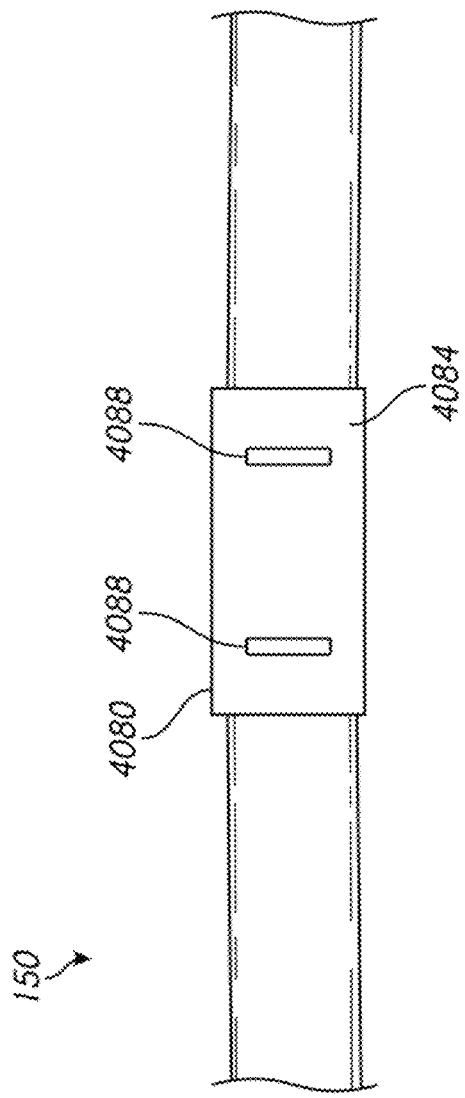

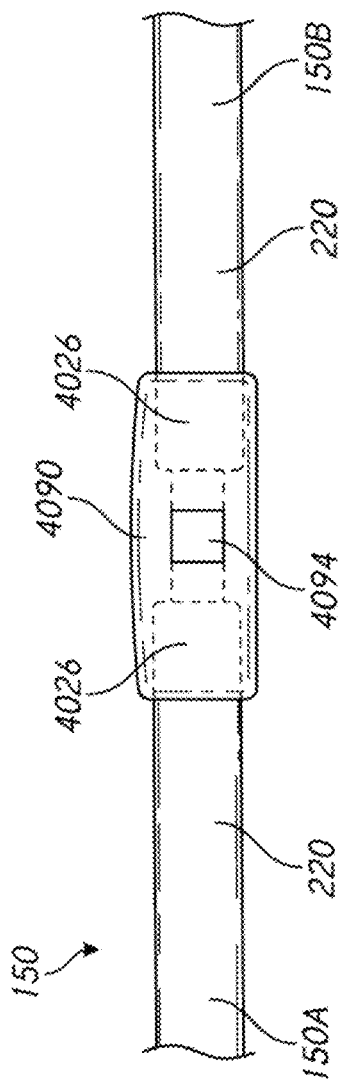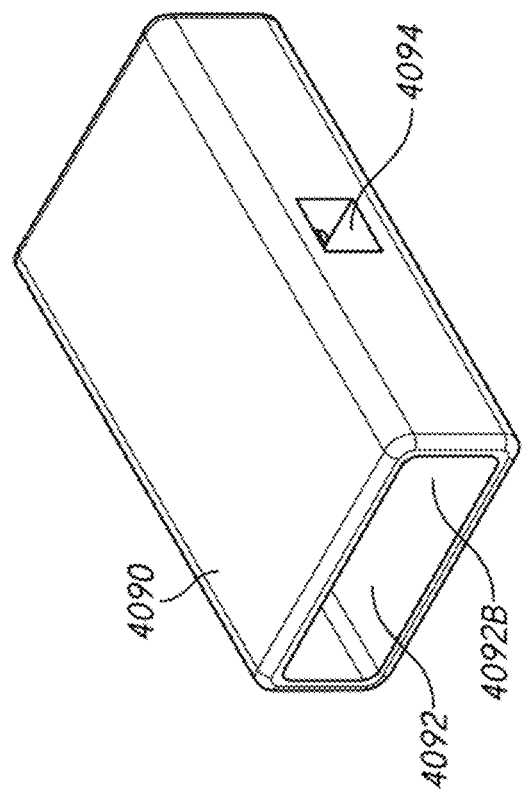

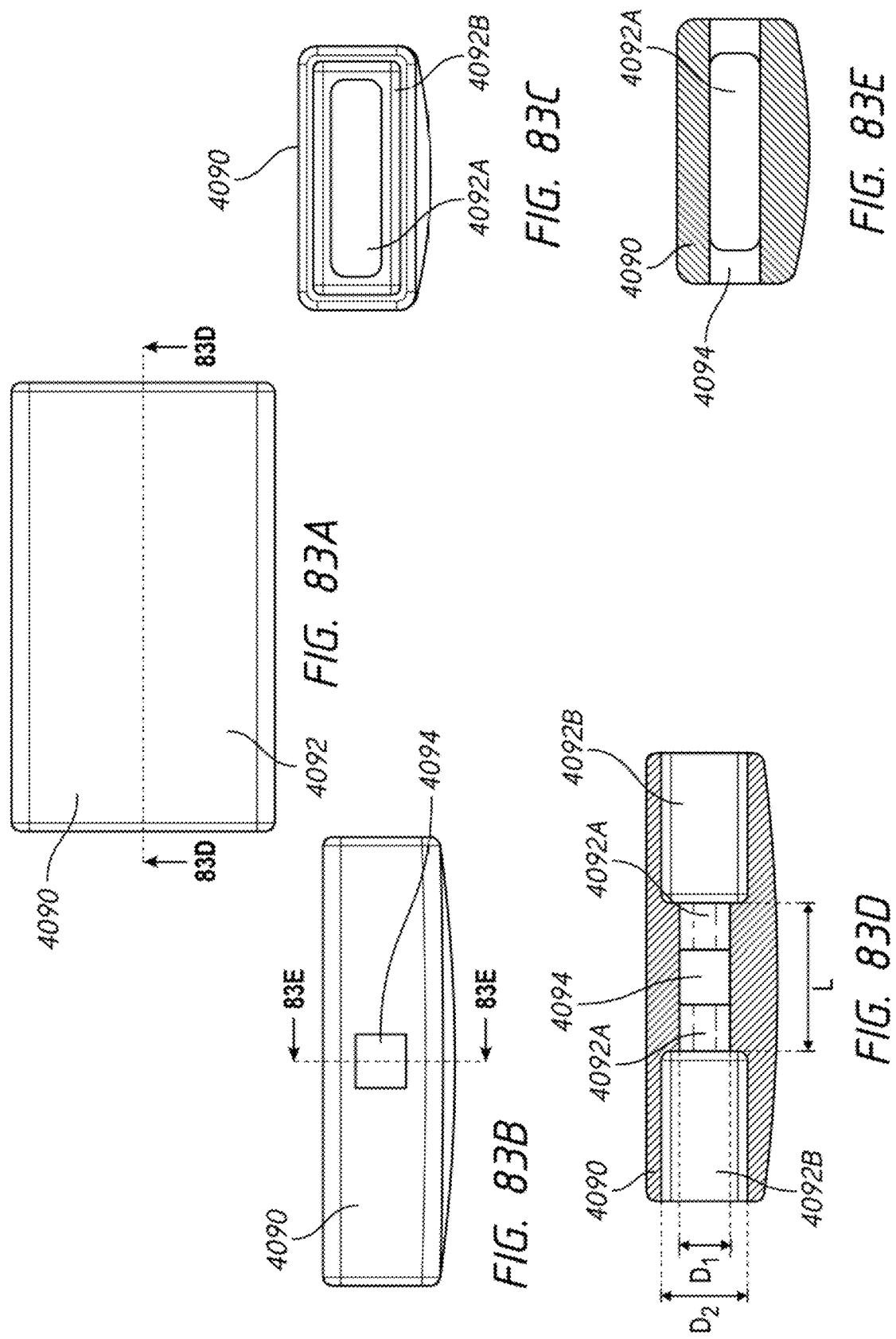

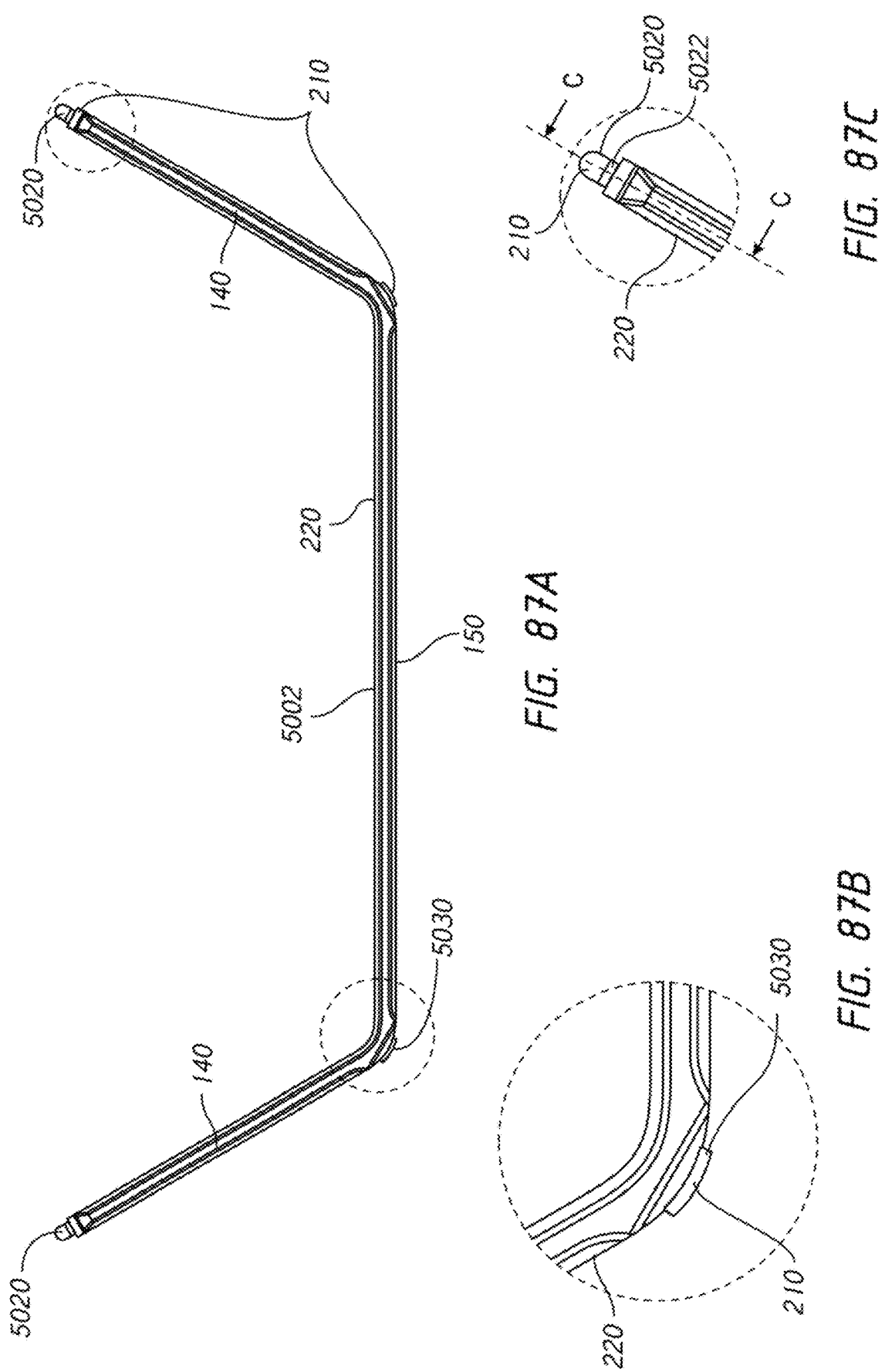

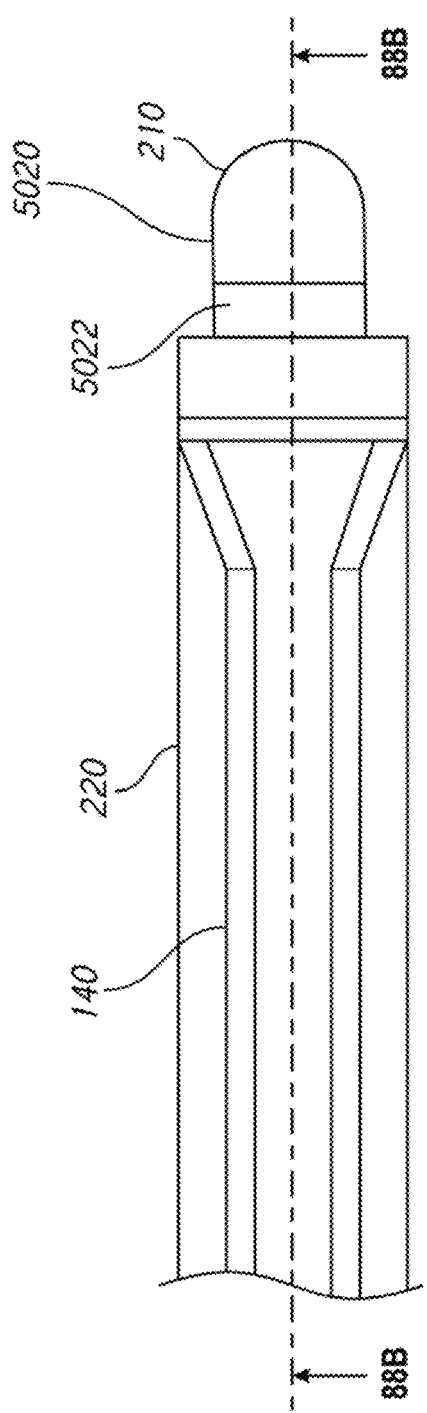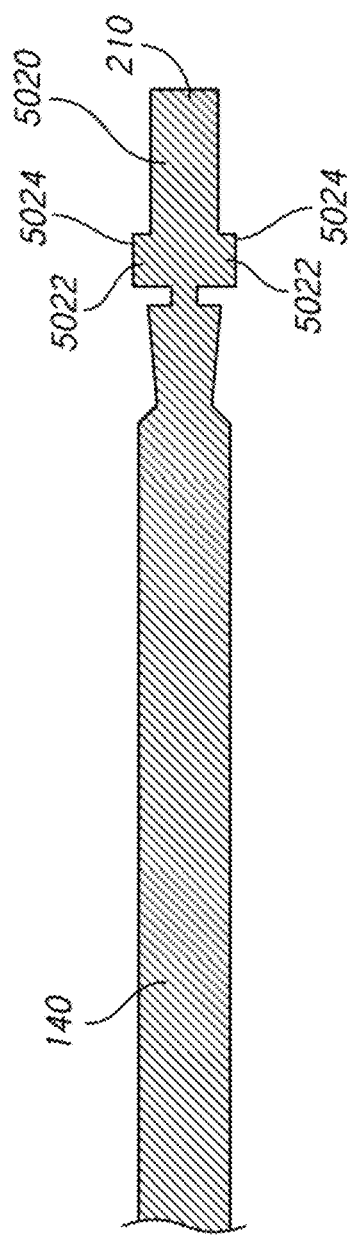
FIG. 88A
FIG. 88B

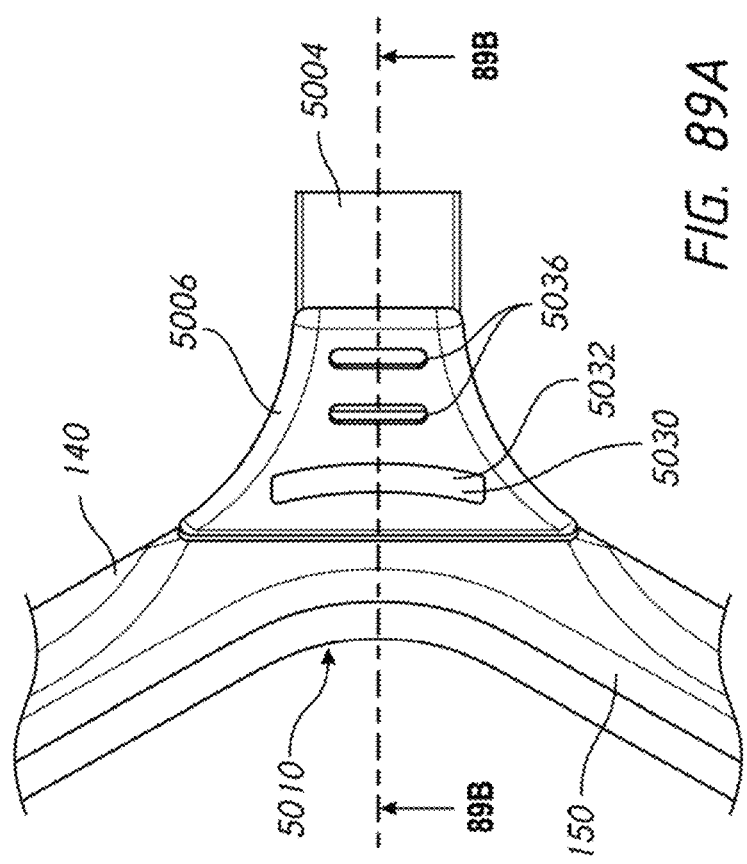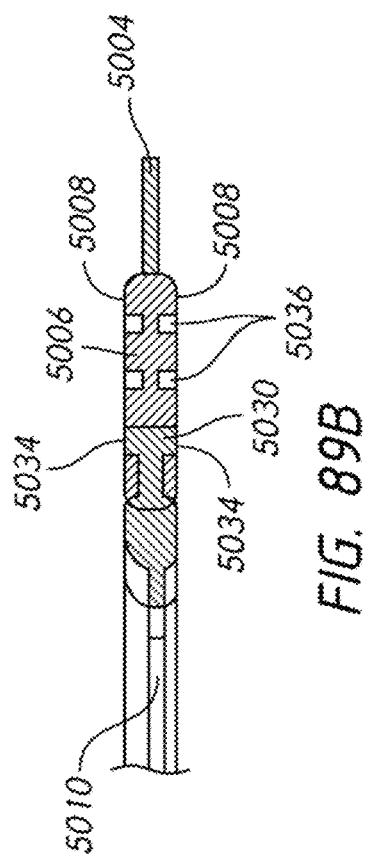

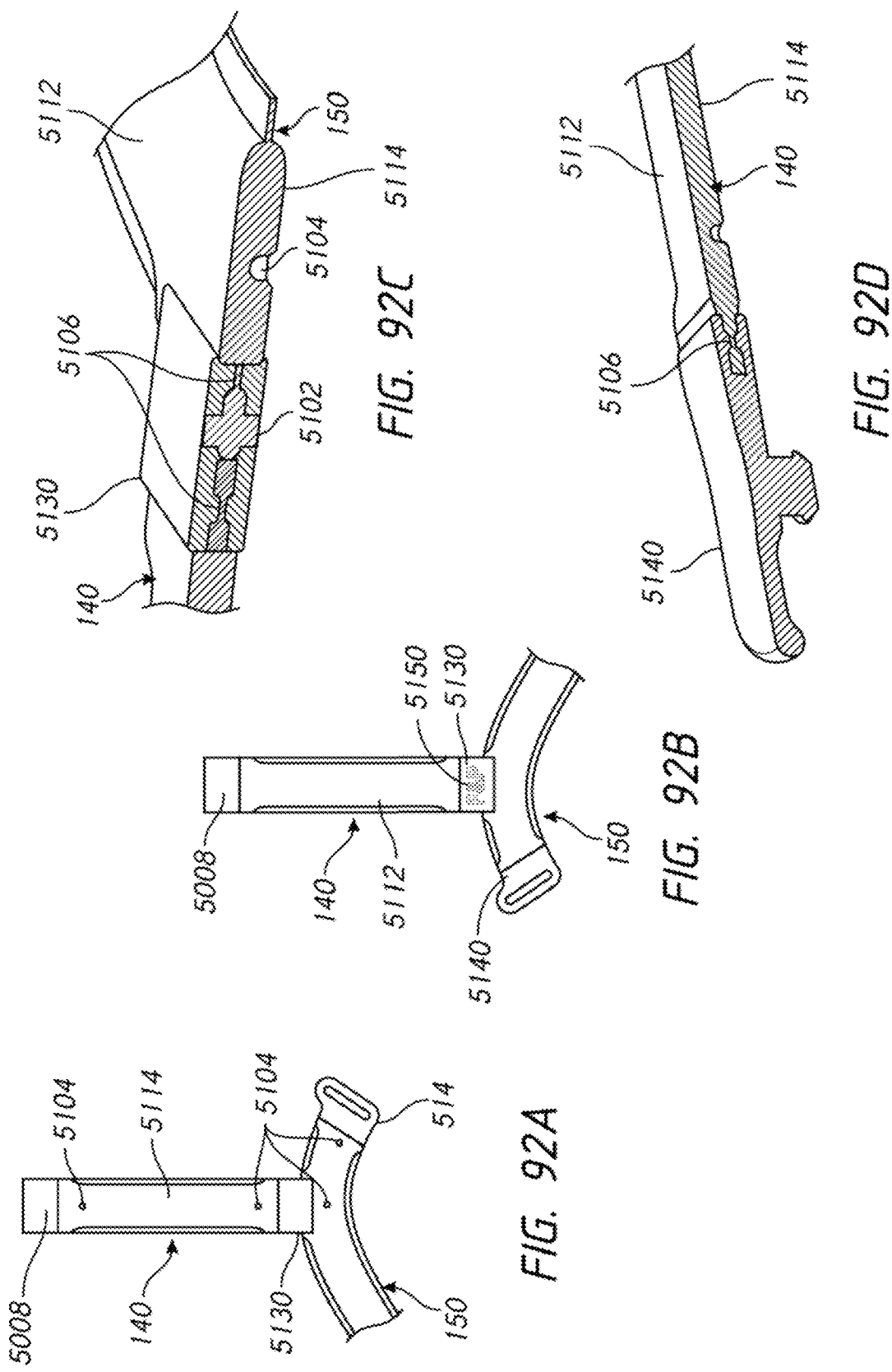

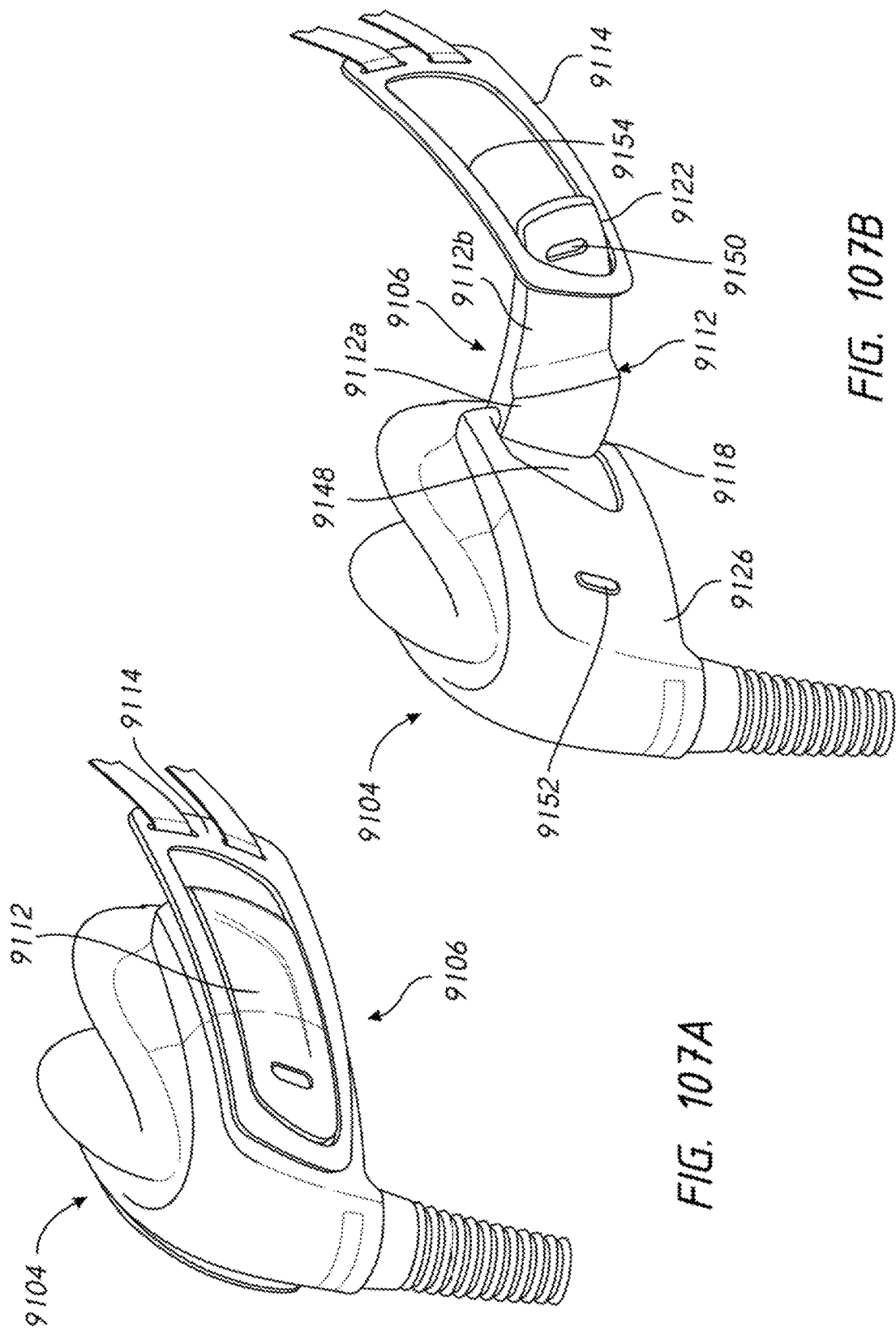

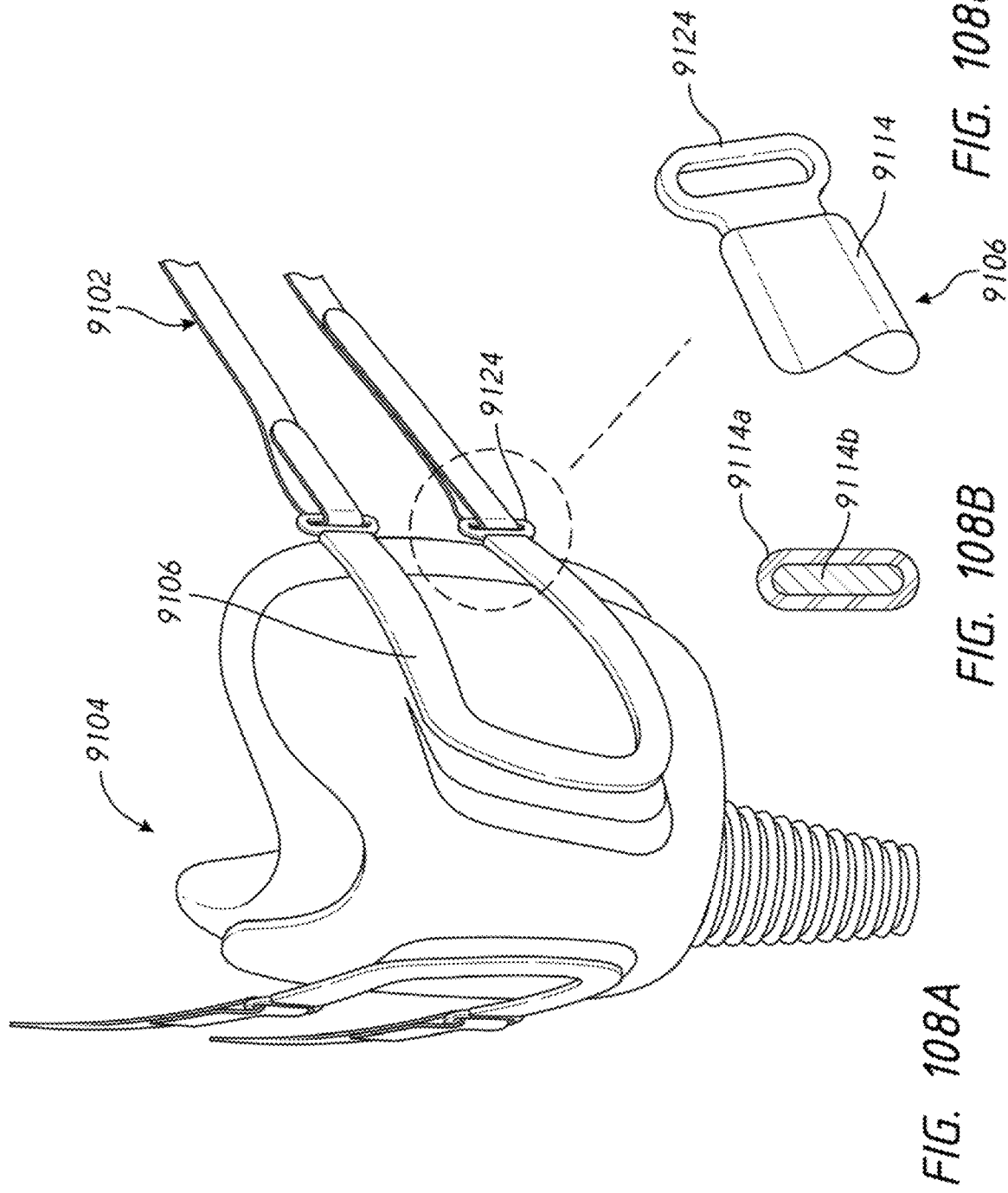

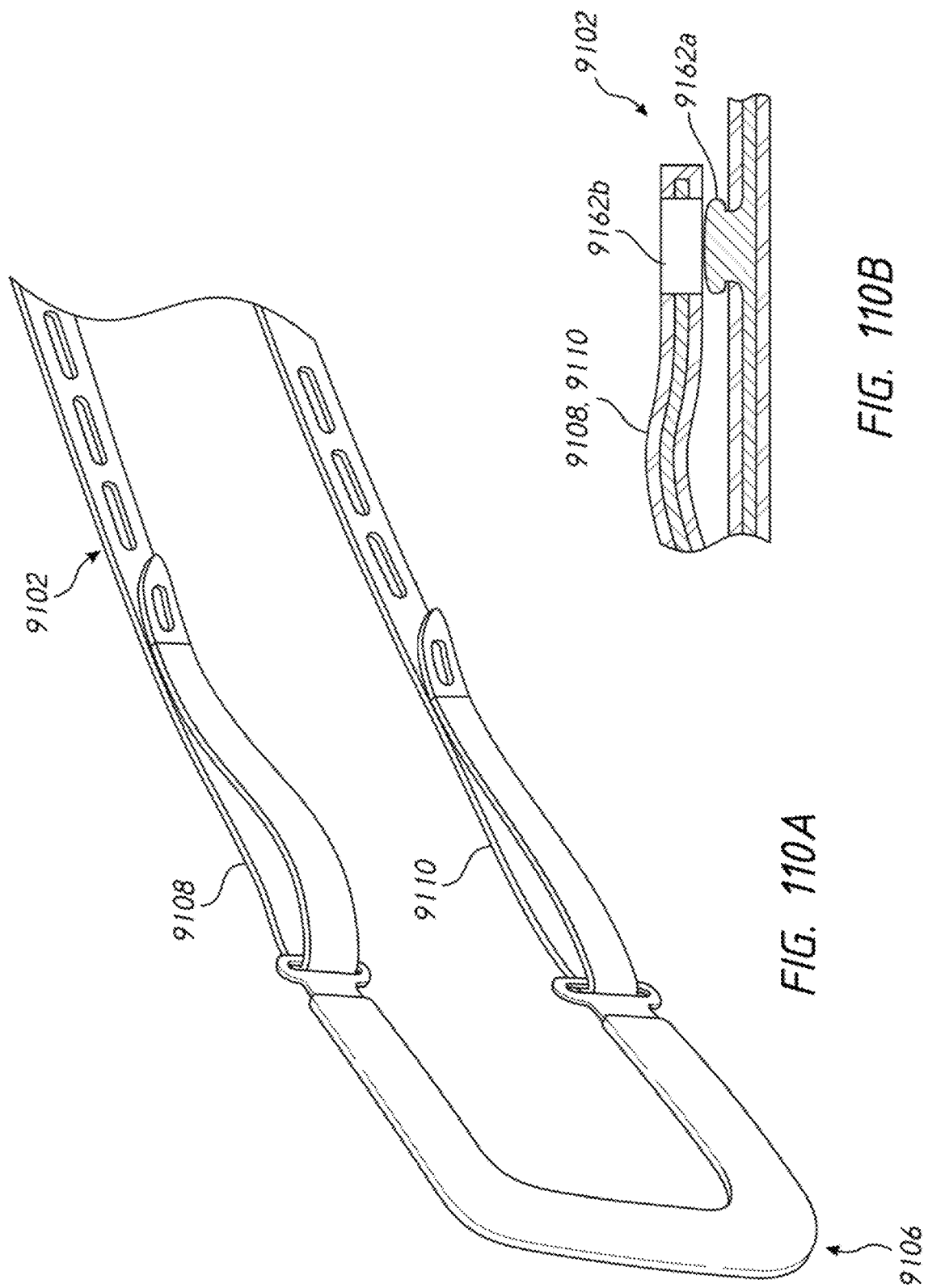

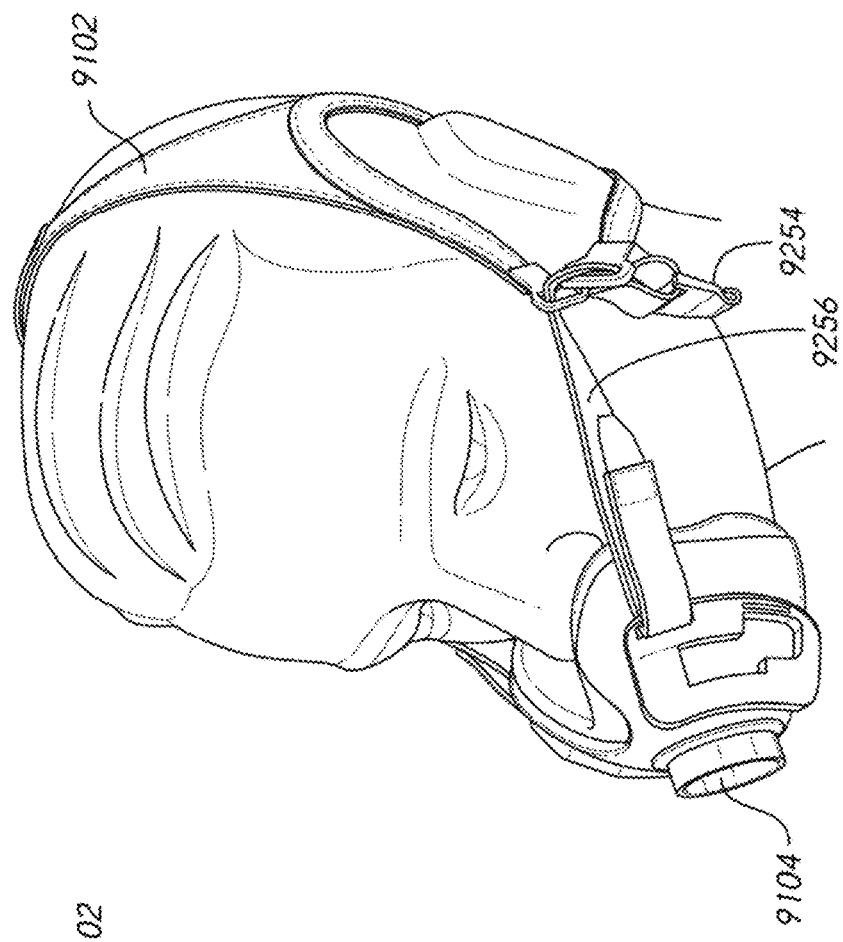
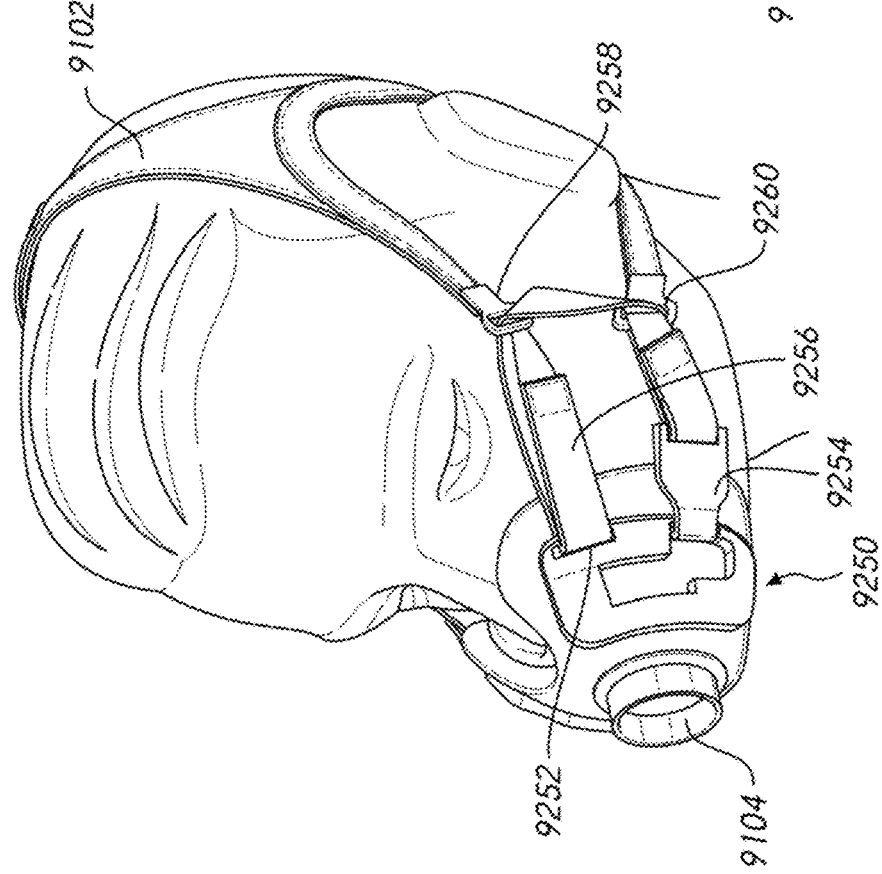
FIG. 120A
FIG. 120B

STRAP ASSEMBLY, STRAP CONNECTOR, HEADGEAR, HEADGEAR ASSEMBLY, METHOD OF FORMING HEADGEAR, TUBULAR CONNECTOR, PATIENT INTERFACE AND METHOD OF JOINING STRAPS

INCORPORATION BY REFERENCE TO PRIORITY APPLICATIONS

The present application is a continuation application of U.S. patent application Ser. No. 16/085,304, filed Sep. 14, 2018, which is a national stage application under 35U.S.C. § 371(c) of PCT Application No. PCT/IB2017/051373, filed Mar. 9, 2017, which is related to and claims priority from U.S. Provisional Patent Application No. 62/309,400, filed Mar. 16, 2016, U.S. Provisional Patent Application No. 62/323,459, filed Apr. 15, 2016, and U.S. Provisional Patent Application No. 62/364,767, filed Jul. 20, 2016, U.S. Provisional Patent Application No. 62/401,462, filed Sep. 29, 2016, U.S. Provisional Patent Application No. 62/468,915, filed Mar. 8, 2017, U.S. Provisional Patent Application No. 62/323,489, filed Apr. 15, 2016, and U.S. Provisional Patent Application No. 62/327,942, filed Apr. 26, 2016, the entireties of which are hereby incorporated by reference herein and made a part of the present disclosure.

BACKGROUND

Technical Field

The present disclosure generally relates to headgear for use in combination with a breathing apparatus. More particularly, the present disclosure relates to the forming of a three-dimensional headgear, portions thereof and a process for moulding such headgear. Further applications of the moulding process are also disclosed. The present disclosure also generally relates to a full face under nose patient interface having a closed-loop headgear and various components of a patient interface.

Description of the Related Art

Patient interfaces are used to provide respiratory therapy to the airways of a person suffering from any of a number of respiratory illnesses or conditions. Such therapies may include but are not limited to continuous positive airway pressure (CPAP) therapy and non-invasive ventilation (NIV) therapy.

CPAP therapy can be used to treat obstructive sleep apnea (OSA), which is a condition in which a patient's airway intermittently collapses, during sleep, preventing the patient from breathing for a period of time. The cessation of breathing, or apnea, results in the patient awakening. Repetitive and frequent apneas may result in the patient rarely achieving a full and restorative night's sleep.

CPAP therapy involves the delivery of a supply of continuous positive air pressure to the airway of the patient via a patient interface. The continuous positive pressure acts as a splint within the patient's airway, which secures the airway in an open position such that the patient's breathing and sleep are not interrupted.

Patient interfaces typically comprise a mask assembly and a headgear assembly, wherein the mask assembly is configured to deliver the supply of continuous positive air pressure to the patient's airway via a seal or cushion that forms a substantially airtight seal in or around the patient's nose and/or mouth. Mask assemblies are available in a range of styles including full-face, nasal, direct nasal and oral masks, which create a substantially airtight seal with the nose and/or mouth. The seal or cushion is held in place on the patient's face by the headgear assembly. In order to maintain a substantially airtight seal the headgear assembly should provide support to the mask assembly such that it is held in a stable position relative to the patient's face during use. Such patient interfaces may also be used to deliver NIV and other therapies.

A patient interface creates at least a substantial "seal" on or around the nose and/or the mouth of a user while a cannula does not provide a seal but provides a delivery pathway for supplemental respiratory gas delivery. A result of creating this "seal" is that the combination of the enclosure area of the breathing apparatus and its internal pressure creates a resulting force that attempts to push the breathing apparatus off of the face. To counteract this force, it is normal to use a headgear comprising a series of straps that pass around the back and/or top of a user's head.

A common issue with an adjustable headgear or a headgear that requires left and right side connections to be made with the under nose type of mask is that the user can overtighten one side of the headgear which pulls the mask off-center. In other instances, the user may simply pull the mask off-center as a result of connecting one side of the mask first. An under nose-style mask may be more susceptible to being pulled off-center than a mask that goes over the bridge of the nose because the nose portion may collapse while an over the nose bridge mask centers itself with the apex of the mask seal. Therefore, it is desirable to form a closed-loop headgear design having a connection mechanism with a mask assembly which ensures that the patient interface seal remains centered on the user's face when donning and doffing the headgear.

SUMMARY

The systems, methods and devices described herein have innovative aspects, no single one of which is indispensable or solely responsible for their desirable attributes. Without limiting the scope of the claims, some of the advantageous features will now be summarized.

In accordance with at least one of the embodiments disclosed herein, a headgear is provided. The headgear includes a top strap, and a bottom strap connected to the top strap at a position between end portions of the bottom strap. A unitary plastic core material is integrally formed within textile casings of both the top strap and the bottom strap.

According to a further aspect, the unitary plastic core material extends through at least one of the textile casings of the top strap and the bottom strap.

According to a further aspect, the textile casings have a seamless tubular shape.

According to a further aspect, the textile casings are knitted, woven, braided or crocheted.

According to a further aspect, an end portion of the textile casing of the top strap is in abutting contact with the textile casing of the bottom strap.

According to a further aspect, the textile casing of the top strap expands radially outward along the length of the top in a direction toward the end portion of the top strap.

According to a further aspect, an end portion of the textile casing of the top strap has a sealed portion, wherein the sealed portion is formed by cutting with a hot knife.

According to a further aspect, the headgear further includes a filament core bonded to the unitary plastic core material within the bottom strap.

According to a further aspect, the headgear further includes strap connectors positioned on an outer surface of at least one of the top strap and the bottom strap, wherein the strap connectors are formed from the unitary plastic core material.

In accordance with at least one of the embodiments disclosed herein, a method for forming a headgear within a moulding tool is provided. The method includes placing a first tubular textile casing and a second tubular textile casing within cavities of the moulding tool, introducing a molten plastic material into the moulding tool and into the first tubular textile casing, pushing the molten plastic material into the second tubular textile casing through the first tubular textile casing, and allowing the molten plastic material to solidify within the first and second textile casings to form an integral plastic core.

According to a further aspect, pushing the molten plastic material into the second tubular textile casing through the first tubular textile casing further includes displacing threads of the first tubular textile casing to form gaps in a wall of the first tubular textile casings through which the molten plastic material flows into the second tubular textile casing.

According to a further aspect, pushing the molten plastic material into the second tubular textile casing through the first tubular textile casing further includes tearing threads of the first tubular textile casing to form a hole in a wall of the first tubular textile casings through which the molten plastic material flows into the second tubular textile casing.

According to a further aspect, placing a first tubular textile casing and a second tubular textile casing within cavities of the moulding tool further includes positioning the first tubular textile casing to be in contact with the second tubular textile casing.

According to a further aspect, an open end portion of the first tubular textile casing is in abutting contact with the second tubular textile casing at a position between end portions of the second tubular textile casing.

According to a further aspect, the first tubular textile casing and the second tubular textile casing contact each other at positions between their end portions.

According to a further aspect, outer edges of the cavities narrow relative to center portions of the cavities such that outer edges of the first and second tubular textile casings are clamped to prevent molten plastic material from flowing between the outer edges of the first and second tubular textile casings.

According to a further aspect, center portions of the cavities include protrusions that depress a surface of at least one of the first and second tubular textile casings such that indentations are integrally formed on the surface of the at least one of the first and second tubular textile casings.

In accordance with at least one of the embodiments disclosed herein, a method for forming a headgear within a moulding tool is provided. The method includes placing a first tubular textile casing into a cavity of a first moulding tool, positioning a portion of the first tubular textile casing in contact with an adjacent cavity having a shape of a connector portion, introducing molten plastic material into the first moulding tool and into the first tubular textile casing, pushing the molten plastic material into the adjacent cavity through the first tubular textile casing, and allowing the molten plastic material to solidify within the first tubular textile casing to form a first strap portion having an inner core and a connector portion formed from unitary plastic material.

According to a further aspect, the method further includes placing the first strap portion into a second moulding tool, positioning an end portion of a second tubular textile casing over the connector portion and in contact with the first tubular textile casing of the first strap portion, introducing molten plastic material into the second moulding tool and into the second tubular textile casing, and allowing the molten plastic material to solidify within the second tubular textile casing to form a second strap portion having an inner core formed from unitary plastic material that is connected to the connector portion of the first strap portion.

In accordance with at least one of the embodiments disclosed herein, a headgear assembly is provided. The headgear assembly includes a top strap, an upper side strap connected to the top strap, and a lower side strap connected to the upper side strap. The upper side strap and the lower side strap are formed unitarily as an integral structure.

According to a further aspect, the upper side strap and the lower side strap are formed as a closed loop structure.

According to a further aspect, the top strap, the upper side strap and the lower side strap are formed unitarily as an integral structure.

According to a further aspect, the top strap, the upper side strap and the lower side strap are formed as a closed loop structure.

According to a further aspect, the upper side strap and the lower side strap are joined by an intra-moulded webbing.

According to a further aspect, the headgear assembly further includes a neck panel attached to at least one of the top strap and lower side strap.

According to a further aspect, at least one of the top strap and the neck panel comprises a breathable moisture-wicking material.

According to a further aspect, the top strap comprises a quilted textile material.

According to a further aspect, a unitary plastic core material is integrally formed within the upper side strap and the lower side strap.

According to a further aspect, a unitary plastic core material is integrally formed within the top strap, the upper side strap and the lower side strap.

In accordance with at least one of the embodiments disclosed herein, a tubular connector for adjoining an end of a first strap to a sidewall of a second strap is provided. The connector includes a first end having a shape corresponding to a shape of the end of the first strap, wherein the first end contacts or is positioned over the end of the first strap; a second end positioned opposite of the first end and having a shape corresponding to the sidewall of the second strap, wherein the second end contacts or is positioned over the sidewall of the second strap; a cavity positioned between the first and second ends; and a plastic core material positioned within the cavity, wherein the plastic core material unit unitarily bonds the first and second straps to form an integral structure.

According to a further aspect, the first end overlaps the end of the first strap.

According to a further aspect, the end of the first strap abuts the second strap.

According to a further aspect, the second end overlaps the sidewall of the second strap.

In accordance with at least one of the embodiments disclosed herein, a method for joining an end of a first strap to a sidewall of a second strap within a moulding tool is provided. The method includes positioning an end of first tubular textile casing into a cavity of a tubular connector and a portion of a sidewall of a second tubular textile casing adjacent or into the cavity of a tubular connector; placing the first and second tubular textile casings and tubular connector into a cavity of a moulding tool; introducing molten plastic material into the moulding tool and into the first tubular textile casing; injecting the molten plastic material into the second tubular textile casing through the first tubular textile casing and the tubular connector; and allowing the molten plastic material to solidify within the first and second tubular textile casings and tubular connector to form a unitary inner core within the first and second tubular textile casings and tubular connector from the plastic material.

According to a further aspect, the positioning comprises abutting the end of the first tubular textile casing against the second tubular textile casing.

In accordance with at least one of the embodiments disclosed herein, disclosed is a strap connector assembly for connecting first and second straps, each of the straps comprising a unitary plastic core within a textile casing, the strap connector assembly comprising: a first connector portion positioned at an end portion of the first strap; a second connector portion positioned between end portions of the second strap, the second connector portion comprising a projection of the unitary plastic core protruding through the textile casing of the second strap, the second connector portion configured to align with the first connector portion to facilitate connection of the first and second straps. According to a further aspect, a thickness of the first connector portion is equal to a thickness of the second connector portion. According to a further aspect, the first and second connector portions are configured to have a clearance gap disposed therebetween when the first and second connector portions are in alignment to facilitate connection of the first and second straps. According to a further aspect, the strap connector assembly further comprises an alignment recess disposed on the first connector portion, the alignment recess being configured to engage a protrusion disposed on an internal surface of a moulding tool to maintain a position of the first connector portion relative to the moulding tool. According to a further aspect, the strap connector assembly further comprises an overmoulded joint that is overmoulded over the first and second connector portions. According to a further aspect, a thickness of the overmoulded joint is equal to a thickness of the first connector portion and a thickness of the second connector portion. According to a further aspect, the overmoulded joint contacts the textile casings of the first and second straps. According to a further aspect, the first and second connector portions are shaped to inter-fit with each other. According to a further aspect, the first connector portion comprises an extension of the unitary plastic core beyond the textile casing. According to a further aspect, the first connector portion extends beyond an end of the textile casing. According to a further aspect, the first and second connector portions are male and female connector portions respectively. According to a further aspect, each of the first and/or second connector portions comprise tabs. According to a further aspect, the first and/or second connector portions have a width that is equal to the width of the unitary plastic core of respective first and second straps.

In accordance with at least one of the embodiments disclosed herein, disclosed is a strap connector assembly for connecting first and second strap portions, each of the strap portions comprising a unitary plastic core within a textile casing, the strap connector assembly comprising: a joining tab comprising a portion of the unitary plastic core of one of the straps and configured to connect the first and second strap portions; an alignment post protruding from a surface of the joining tab; and an overmoulded joint that is overmoulded over the joining tab. According to a further aspect, a thickness of the alignment post is greater that a thickness of the joining tab. According to a further aspect, a thickness of the alignment post is equal to a thickness of the overmoulded joint. According to a further aspect, the overmoulded joint is formed from an elastomeric material. According to a further aspect, the strap connector assembly further comprises a label formed into a surface of the overmoulded joint.

In accordance with at least one of the embodiments disclosed herein, disclosed is a strap connector for connecting first and second strap portions, the strap portions comprising a unitary plastic core within a textile casing, the strap connector comprising: a housing having outer cavities disposed at end portions of the housing and configured to receive end portions of the first and second strap portions, an inner cavity positioned between the outer cavities, and an injection aperture extending between the inner and outer cavities, wherein the unitary plastic core of the strap portions extends through the injection aperture. According to a further aspect, a height of the outer cavities is greater than a height of the inner cavity. According to a further aspect, a height of the inner cavity is equal to a thickness of the unitary plastic core within the textile casing.

In accordance with at least one of the embodiments disclosed herein, disclosed is a strap assembly for a headgear comprising: a textile casing including an outer surface facing away from a user, an inner surface facing toward the user and a cavity disposed between the outer and inner surfaces; and a plastic core material positioned within the cavity of the textile casing, wherein the outer surface of the textile casing has a convex shape. According to a further aspect, the inner surface of the textile casing has a substantially planar shape. According to a further aspect, the inner surface of the textile casing has concave shape.

In accordance with at least one of the embodiments disclosed herein, disclosed is a strap assembly for a headgear comprising: a textile casing including an ear arch region configured to be positioned above a user's ear; and a plastic core positioned within a cavity of the textile tubular casing, wherein a distance between the plastic core and an edge of the textile casing is greater in the ear arch region than in remaining portions of the strap assembly.

In accordance with at least one of the embodiments disclosed herein, disclosed is a headgear assembly comprising: a headgear loop strap configured to receive top and rear portions of a user's head, the headgear loop strap comprising: a unitary plastic core integrally formed with a textile casing, and a connector tab portion formed from the unitary plastic core and protruding through the textile casing between end portions of the headgear loop strap; a front strap; and a connector positioned over the connector tab portion of the headgear loop strap and an end portion of the front strap. According to a further aspect, the connector is overmoulded onto the end portions of the headgear loop strap and the front strap. According to a further aspect, a thickness of the connector is equal to a thickness of the connector tab portion. According to a further aspect, a thickness of the connector is equal to a thickness of the headgear loop strap. According to a further aspect, the headgear loop strap further comprises: an alignment tab extending from end portions of the headgear loop strap, the alignment tab comprising a portion of the unitary plastic core of the headgear loop strap; and an alignment post protruding from a surface of the joining tab.

In accordance with at least one of the embodiments disclosed herein, disclosed is a strap connector assembly for connecting first and second strap portions, each of the strap portions comprising a unitary plastic core within a textile casing, the strap connector assembly comprising: a first connector portion positioned at an end portion of the first strap; a second connector portion positioned between end portions of the second strap and protruding through the textile casing of the second strap; and an overmoulded joint that is overmoulded over the first and second connector portions. According to a further aspect, at least one of the first and second connector portions further comprising an alignment post protruding from a surface of the first strap, wherein the overmoulded joint surrounds the alignment post. According to a further aspect, at least one of the first and second connector portions further comprising an indent region recessed within a surface of the first strap, wherein the indent region receives overmould material of the overmoulded joint. According to a further aspect, the strap connector assembly further comprises an alignment recess that is recessed into a surface of at least one of the first and second straps, wherein the alignment recess is configured to engage a protrusion disposed on an internal surface of a moulding tool to maintain a position of the at least one of the first and second straps relative to the moulding tool.

In accordance with at least one of the embodiments disclosed herein, a strap connector assembly for connecting first and second straps within a moulding tool is provided. The straps are formed from unitary plastic core material injected into tubular textile casings. The strap connector assembly includes a male connector portion positioned at an end portion of the first strap, and a female connector portion positioned between end portions of the second strap and protruding through the tubular textile casing of the second strap. The female connector portion is configured to engage the male connector portion such that the first and second straps are connected. The male and female connector portions are formed from the molten unitary plastic core material. According to a further aspect, a thickness of the male connector portion is equal to a thickness of the female connector portion. According to a further aspect, the strap connector assembly further includes a clearance gap disposed between the male and female connector portions. According to a further aspect, the strap connector assembly further includes an alignment recess disposed on the male connector portion, the alignment recess being configured to engage a protrusion disposed on an internal surface of a moulding tool to maintain a position of the male connector portion relative to the moulding tool. According to a further aspect, the strap connector assembly further includes an overmoulded joint that is overmoulded over the male and female connector portions. According to a further aspect, a thickness of the overmoulded joint is equal to a thickness of the male connector portion and a thickness of the female connector portion. According to a further aspect, the overmoulded joint contacts the tubular textile casings of the first and second straps.

In accordance with at least one of the embodiments disclosed herein, a strap connector assembly for connecting first and second strap portions within a moulding tool is provided. The strap portions are formed from unitary plastic core material injected into tubular textile casings. The strap connector assembly includes a joining tab formed from the unitary plastic core material and configured to connect end portions of the first and second strap portions; an alignment post protruding from a surface of the joining tab; and an overmoulded joint that is overmoulded over the joining tab. According to a further aspect, a thickness of the alignment post is greater that a thickness of the joining tab.

According to a further aspect, a thickness of the alignment post is equal to a thickness of the overmoulded joint.

According to a further aspect, the overmoulded joint is formed from an elastomeric material.

According to a further aspect, the strap connector assembly further includes a label formed into a surface of the overmoulded joint.

In accordance with at least one of the embodiments disclosed herein, a strap connector for connecting first and second strap portions within a moulding tool is provided. The strap portions are formed from unitary plastic core material injected into tubular textile casings. The strap connector includes outer cavities disposed at end portions of the housing and configured to receive end portions of the first and second strap portions, an inner cavity positioned between the outer cavities, and an injection aperture in fluid communication with the inner and outer cavities and configured to receive the unitary plastic core material.

According to a further aspect, a height of the outer cavities is greater than a height of the inner cavity.

According to a further aspect, a height of the inner cavity is equal to a thickness of the unitary plastic core material within the tubular textile casings.

In accordance with at least one of the embodiments disclosed herein, a strap assembly for a headgear is provided. The strap assembly includes a textile tubular casing including an outer surface facing away from a user and an inner surface facing toward the user, and a plastic core material positioned within a cavity of the textile tubular casing. The outer surface of the textile tubular casing has a convex shape.

According to a further aspect, the inner surface of the textile tubular has substantially planar shape.

According to a further aspect, the inner surface of the textile tubular has concave shape.

In accordance with at least one of the embodiments disclosed herein, a headgear assembly is provided. The headgear assembly includes a headgear loop strap configured to receive top and rear portions of a user's head. The headgear loop strap includes a unitary plastic core material is integrally formed within textile casing of the headgear loop strap, and a connector tab portion positioned formed from the unitary plastic core material and protruding through a tubular textile casing of the headgear loop strap between end portions of the headgear loop strap. The headgear assembly further includes a front strap, and a connector positioned over the connector tab portion of the headgear loop strap and an end portion of the front strap.

According to a further aspect, the connector is overmoulded onto the end portions of the headgear loop strap and the front strap.

According to a further aspect, a thickness of the connector is equal to a thickness of the connector tab portion.

According to a further aspect, a thickness of the connector is equal to a thickness of the headgear loop strap.

According to a further aspect, the headgear loop strap further includes an alignment tab extending from end portions of the headgear loop strap, the alignment tab formed from the unitary plastic core material, an alignment post protruding from a surface of the joining tab, and an overmoulded joint that is overmoulded over the alignment tab and configured to connect the end portions of the headgear loop strap.

In accordance with at least one of the embodiments disclosed herein, a strap connector assembly for connecting first and second strap portions within a moulding tool is provided. The strap portions are formed from unitary plastic core material injected into tubular textile casings. The strap connector assembly includes a first connector portion positioned at an end portion of the first strap, a second connector portion positioned between end portions of the second strap and protruding through the tubular textile casing of the second strap, and an overmoulded joint that is overmoulded over the first and second first connector portions.

According to a further aspect, at least one of the first and second connector portions further comprising an alignment post protruding from a surface of the first strap, wherein the overmoulded joint surrounds the alignment post.

According to a further aspect, at least one of the first and second connector portions further comprising an indent region recessed within a surface of the first strap, wherein the indent region receives overmould material of the overmoulded joint.

According to a further aspect, the strap connector assembly further includes an alignment recess that is recessed into a surface of at least one of the first and second straps, wherein the alignment recess is configured to engage a protrusion disposed on an internal surface of a moulding tool to maintain a position of the at least one of the first and second straps relative to the moulding tool.

In some configurations, a headgear assembly for a patient interface comprises a headpiece and at least one connector. The headpiece comprises a top strap, a forward strap and a rear strap. The connector includes a first strap and a second strap. The first strap is configured to extend from a mask assembly, above and behind a user's ear. The second strap is configured to extend from the mask assembly below and behind the user's ear. The first strap meets the second strap at a rear connector portion. The connector includes at least one headpiece connecting surface configured to connect to the headpiece. The headpiece includes at least one connector connecting surface configured to connect to the at least one headpiece connecting surface of the connector.

In some configurations, one or more of the top strap, rear strap and the forward strap of the headpiece comprises separate left and right portions, each having a free end. The free ends of the left and right portions are adjustably connected to each other.

In some configurations, the top strap and the forward strap converge at a junction.

In some configurations, the junction forms a portion of an ear loop.

In some configurations, the rear strap forms a portion of an ear loop.

In some configurations, the ear loop is configured to surround the user's ear without contacting the ear.

In some configurations, the at least one connector connecting surface is configured to connect to the at least one headpiece connecting surface along a C-shaped connection area, which extends from above to below the ear of the user.

In some configurations, the at least one connector connecting surface is configured to connect to the at least one headpiece connecting surface along a connection line, which extends from behind to above the ear of the user, wherein an entirety of the connection line is configured to be located above a lowermost extent of the ear of the user.

In some configurations, a patient interface comprises a mask assembly and a headgear assembly as described above.

In some configurations, a headgear assembly for a patient interface comprises a headpiece and at least one connector. The headpiece comprises a top strap, a forward strap and a rear strap. The connector includes a middle strap and a lower strap. The middle strap is configured to extend from a mask assembly, above and behind a user's ear. The lower strap is configured to extend from the mask assembly below and behind the user's ear. The middle strap meets the lower strap at a rear connector portion. The connector includes at least one headpiece connecting surface configured to connect to the headpiece. The headpiece includes at least one connector connecting surface configured to connect to the connector.

In accordance with at least one of the embodiments disclosed herein, a patient interface is provided. The patient interface includes a headgear assembly, a mask assembly, and a connector portion connecting the headgear assembly to the mask assembly. The headgear assembly, the mask assembly and the connector portion form a closed-loop when the connector is disengaged with the mask assembly.

According to a further aspect, an effective length of the closed-loop increases when the connector portion is disengaged with the mask assembly compared to an effective length of the closed-loop when the connector portion is engaged with the mask assembly.

According to a further aspect, the connector portion is attached to the mask assembly by a hinge portion.

According to a further aspect, the connector portion is attached to the mask assembly by a tether.

According to a further aspect, the hinge portion is a living hinge.

According to a further aspect, the hinge portion is formed from silicone.

According to a further aspect, the living hinge is formed from fabric.

According to a further aspect, the patient interface further includes a hook is disposed on the mask assembly, and a post is disposed on the connector portion. The hook receives the post receives the hook to engage the with the mask assembly.

According to a further aspect, the connector portion engages the mask assembly via a snap-fit or interference fit.

According to a further aspect, the headgear assembly has straps formed from textile casings having a unitary plastic core material integrally formed therein.

According to a further aspect, a difference between the effective length of the closed-loop when the connector portion is disengaged with the mask assembly and the effective length of the closed-loop when the connector portion is engaged with the mask assembly is at least 40 millimetres.

Further aspects of one or more embodiments of the invention, which should be considered in all its novel aspects, will become apparent from the following description.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 12A illustrates a top-down view of a first moulding tool for forming a bottom strap with an attachment member for an intra-moulded bifurcated headgear.

FIG. 12B illustrates a close-up top-down view of the first moulding tool showing the bottom strap and the attachment member.

FIG. 16C a side perspective view of an injection moulding tool for forming a button of the button and hole size adjustment system.

FIG. 16D illustrates cross-sectional views of first and second moulding tool halves during the process of burst-through intra-moulding the button of the button and hole size adjustment system.

FIG. 48A is a front perspective view of an exemplary headgear that can be used with a patient interface.

FIG. 48B is a rear perspective view of the exemplary headgear in FIG. 48A.

FIG. 50A is a front perspective view of an exemplary headgear that can be used with a patient interface.

FIG. 50B is a rear perspective view of the exemplary headgear in FIG. 50A.

FIG. 51A is a side view of an exemplary headgear that can be used with a patient interface.

FIG. 51B is a cross-sectional view of the strap portions of the exemplary headgear in FIG. 51A.

FIG. 54A is a side view of an exemplary headgear that can be used with a patient interface and having lower and middle straps that are formed from a continuous casing.

FIG. 54B is a close-up view of a web portion of the exemplary headgear in FIG. 54A.

FIG. 54C is a cross-sectional view of the web portion along a line 54C-54C in FIG. 54B.

FIG. 55A is a side view of an exemplary headgear that can be used with a patient interface and having a continuous lower strap and a combination continuous middle and vertical strap.

FIG. 55B is a cross-sectional view of the web portion of the exemplary headgear along a line 55B-55B in FIG. 55A.

FIG. 55C is a close-up view of the web portion of the exemplary headgear in FIG. 55A.

FIG. 56A is a side view of an exemplary headgear that can be used with a patient interface and lower and middle straps that are formed from a continuous casing in the form of a closed loop structure.

FIG. 56B is a close-up view of a junction of the exemplary headgear in FIG. 56A.

FIG. 64A is a side view of an exemplary headgear that can be used with a patient interface, and having a fabric or textile material provided attached to portions of the headgear in direct contact with the user's skin or hair.

FIG. 64B is a close-up view of the fabric or textile material of the exemplary headgear in FIG. 64A.

FIG. 65 is a close-up view of a branded grip that can be used with an embodiment of the disclosed headgear.

FIG. 66A is a side view of a T-shaped junction between an end of a first strap and a central or intermediate portion of a second strap.

FIG. 66B is a close-up view of a connector for forming the T-shaped junction in FIG. 66A.

FIG. 67 is a perspective view of a T-shaped junction.

FIG. 68A is a bottom view of the connector.

FIG. 68B is a side view of the connector.

FIG. 68C is a top view of the connector.

FIG. 68D is a perspective view of the connector.

FIG. 69 is a side view of the T-shaped junction illustrating the connector positioned over the first strap so that the end of the first strap is positioned inside of the connector.

FIG. 70 is a perspective view of the connector and the T-shaped junction.

FIG. 71 is a close-up side view of the filled connector and the T-shaped junction.

FIG. 72 is a cross-sectional view of the filled connector and the T-shaped junction.

FIG. 73 is a side view of the filled connector and the T-shaped junction.

FIG. 74A illustrates a top view of a top strap of an exemplary head gear arrangement having male connectors for forming an overmoulded joint.

FIG. 74B illustrates a top view of a bottom strap of the exemplary head gear arrangement having female connectors for forming the overmoulded joint.

FIG. 75A illustrates a close-up top view of the male connector of the top strap.

FIG. 75B illustrates a close-up cross-sectional view of the male connector of the top strap.

Figure 76C:
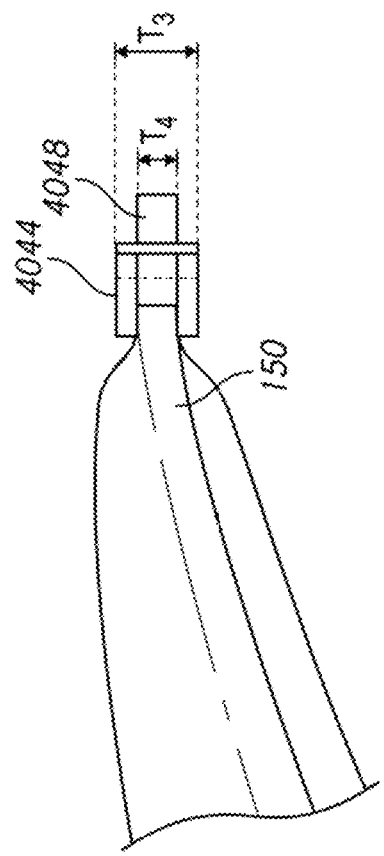
Figure 76A:
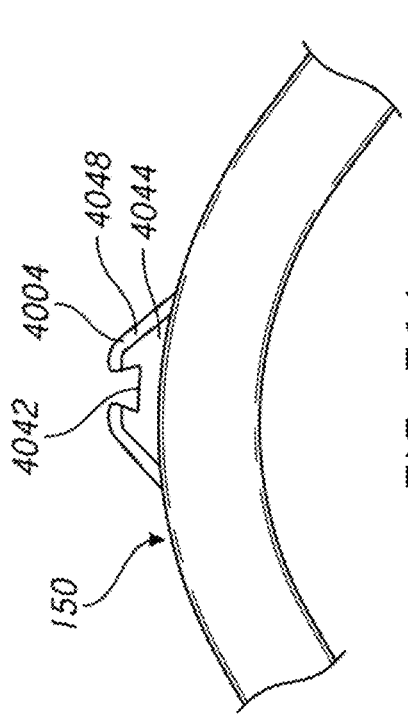

FIG. 76A illustrates a close-up top view of the female connector of the bottom strap.

Figure 76B:
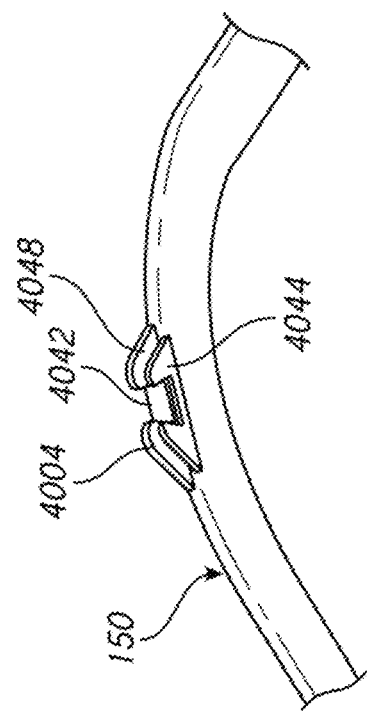

FIG. 76B illustrates a close-up cross-sectional view of the female connector of the bottom strap.

FIG. 76C illustrates a close-up perspective view of the female connector of the bottom strap.

FIG. 77A illustrates a close-up top view of the male and female connectors in alignment.

FIG. 77B illustrates a close-up top view of the male connector inserted into and received by the female connector.

FIG. 77C illustrates a close-up cross-sectional view of the male connector inserted into and received by the female connector.

Figure 78B:
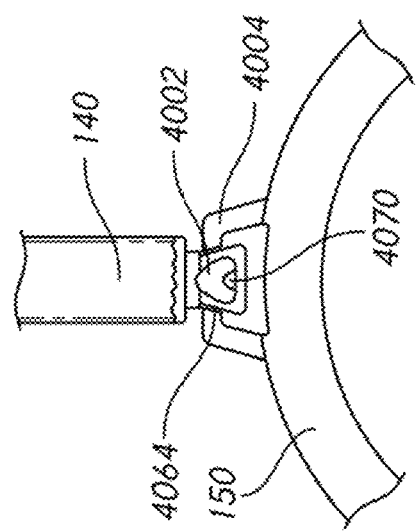
Figure 78A:
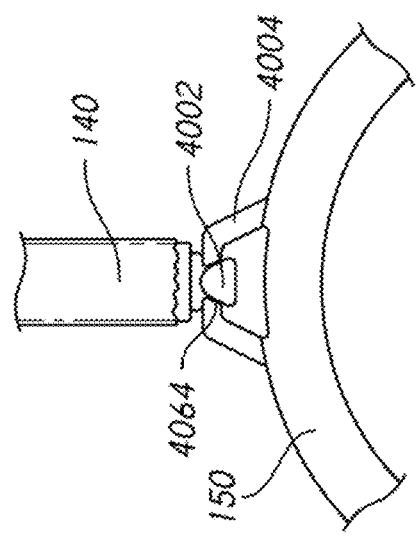

FIG. 78A illustrates a close-up side view of the male and female connectors illustrating a smaller clearance gap between the male and female connectors.

FIG. 78B illustrates a close-up side view of the male and female connectors illustrating a larger clearance gap between the male and female connectors.

FIG. 79A illustrates a close-up top view of the male connector.

FIG. 79B illustrates a perspective view of the overmoulding cavity of the overmoulding tool.

FIG. 79C illustrates a cross-section view of the male connector inserted into the overmoulding cavity of the overmoulding tool.

Figure 80B:
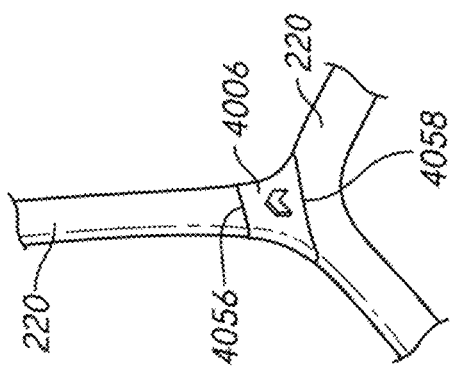
Figure 80C:
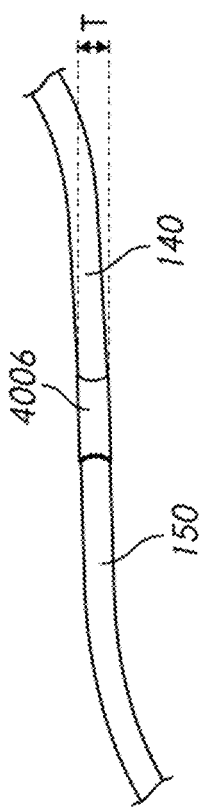
Figure 80A:
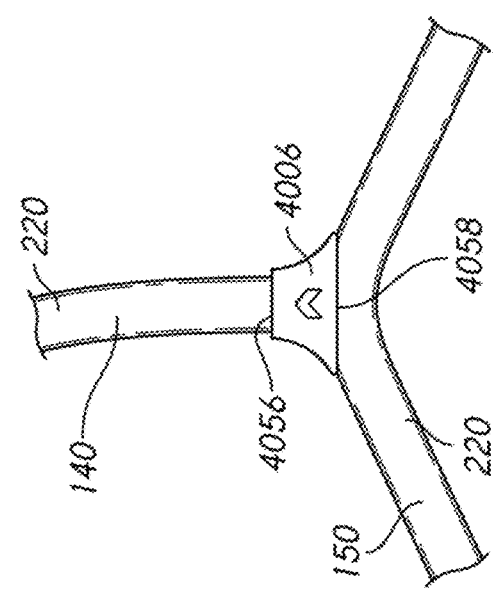

FIG. 80A illustrates a close-up top view of an overmoulded joint bonding the top and bottom straps.

FIG. 80B illustrates a perspective view of an overmoulded joint bonding the top and bottom straps.

FIG. 80C illustrates a cross-section bottom view of the view of the overmoulded joint bonding the top and bottom straps.

FIG. 81A illustrates a close-up top view of a joining tab and alignment posts prior to overmoulding for joining two halves of a bottom strap.

FIG. 81B illustrates a close-up bottom view of the joining tab and alignment posts in FIG. 81A.

FIG. 81C illustrates a close-up cross-section view of the joining tab and alignment posts in FIG. 81A.

FIG. 81D illustrates a close-up top view of an overmould formed over the joining tab and alignment posts in FIG. 81A.

FIG. 81E illustrates a close-up bottom view of the overmould in FIG. 81D.

FIG. 82A illustrates a side view of a strap end joint housing.

FIG. 82B illustrates a perspective view of the strap end joint housing in FIG. 82A.

FIG. 83A illustrates a top view of the strap end joint housing in FIG. 82A.

FIG. 83B illustrates a side view of the strap end joint housing in FIG. 82A.

FIG. 83C illustrates an end view of the strap end joint housing in FIG. 82A.

FIG. 83D illustrates a side cross-section view of the strap end joint housing along a line 83D-83D in FIG. 83A.

FIG. 83E illustrates an end cross-sectional view of the strap end joint housing along a line 83E-83E in FIG. 83B.

Figure 84A:
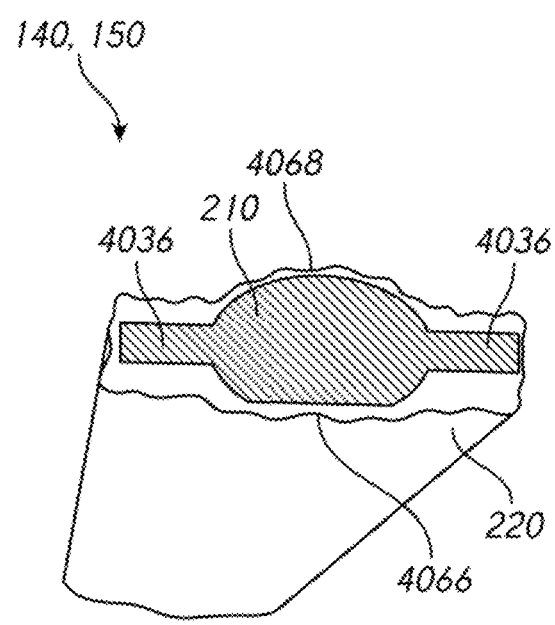

FIG. 84A illustrates a side cross-section view of a strap having a D-shaped cross-section with flange portions formed along edges of the strap.

Figure 84B:
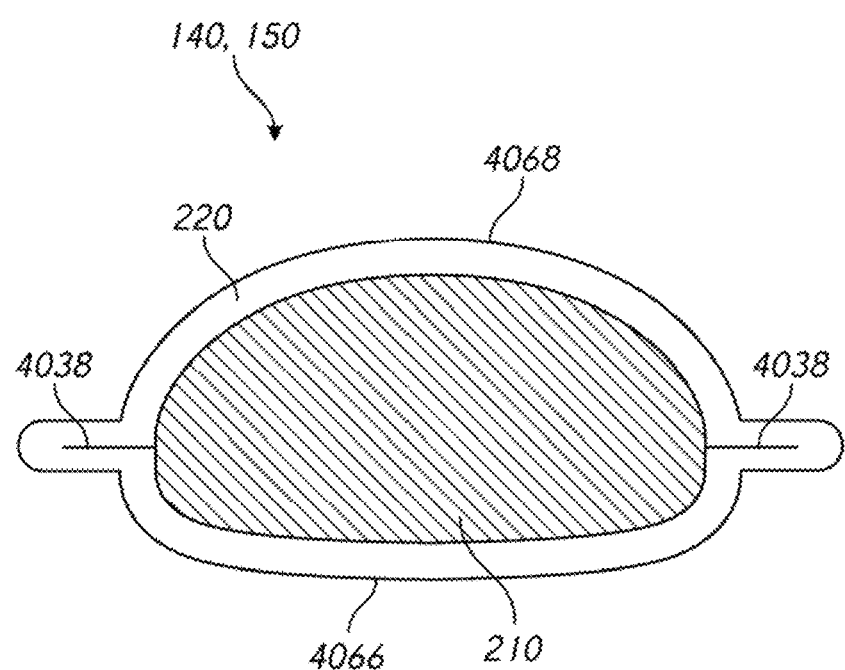

FIG. 84B illustrates a side cross-section view of a strap having a D-shaped cross-section without flange portions formed along edges of the strap.

Figure 85:
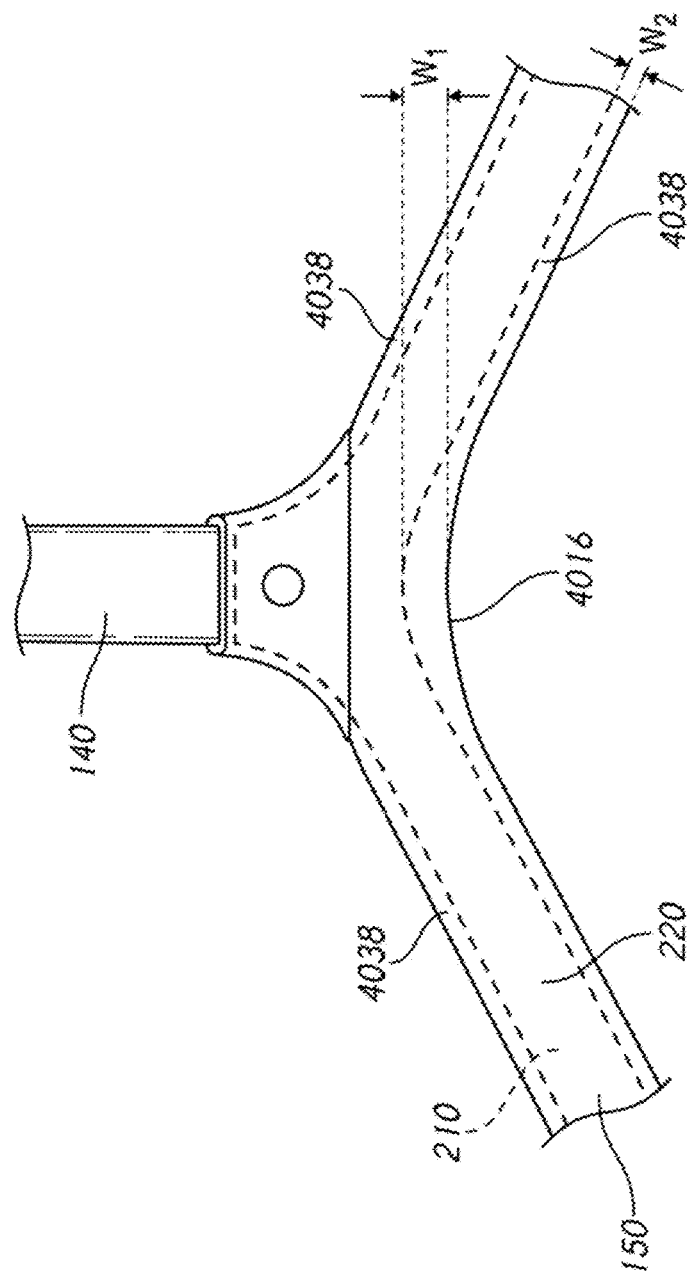

FIG. 85 illustrates a top view of a strap having a bottom strap having a soft edge positioned above a user's ear.

Figure 86:
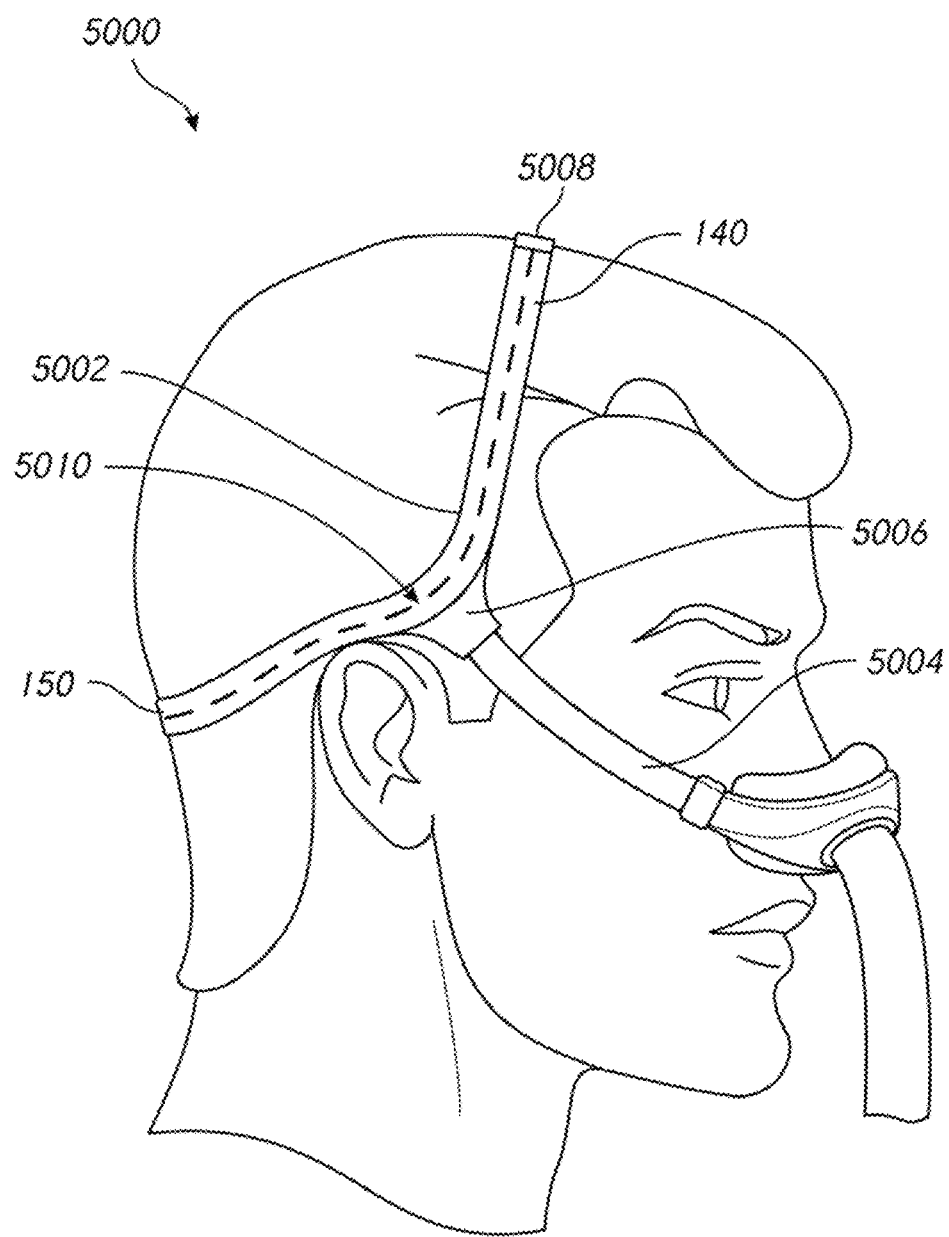

FIG. 86 illustrates a side view of a bifurcated headgear arrangement formed by the burst-through intra-moulding arrangement having a rear headgear loop strap.

FIG. 87A illustrates a top view of the rear headgear loop strap in FIG. 86.

FIG. 87B illustrates a close-up top view of a burst-through tab of the rear headgear loop strap in FIG. 86.

FIG. 87C illustrates a close-up top view of an alignment tab of the rear headgear loop strap in FIG. 86.

FIG. 88A illustrates a top view of the alignment tab of the rear headgear loop strap in FIG. 86.

FIG. 88B illustrates a close-up cross-sectional view of the alignment tab of the rear headgear loop strap along a line 88B-88B in FIG. 87C.

FIG. 89A illustrates a top view of an overmoulded joint bonding the rear headgear loop strap to a front strap.

FIG. 89B illustrates a close-up cross-sectional view of the overmoulded joint in FIG. 89A along a line 89B-89B.

Figure 90A:
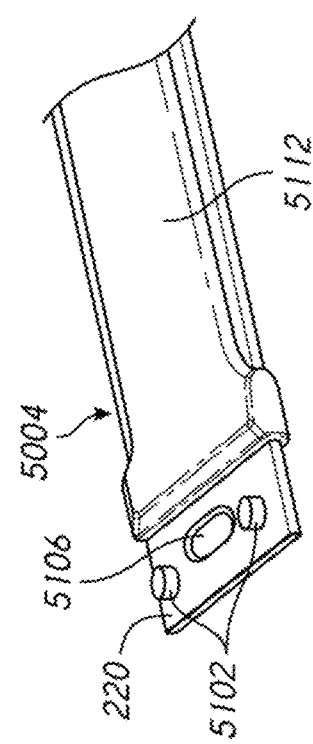

FIG. 90A illustrates a perspective view of a top strap having alignment posts and an indent.

Figure 90B:
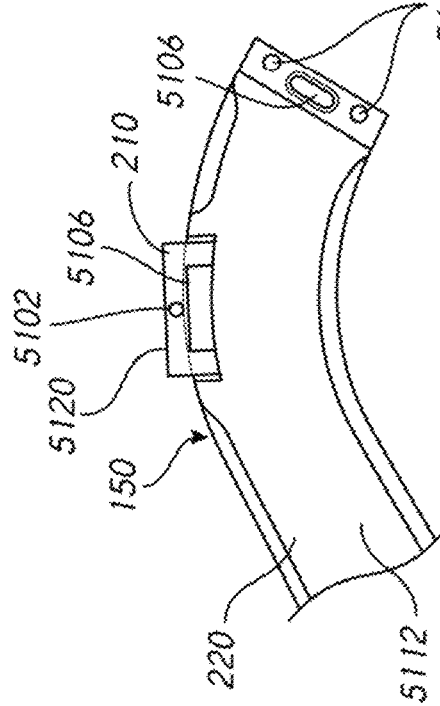

FIG. 90B illustrates a bottom view of the top strap in FIG. 90A.

Figure 90C:
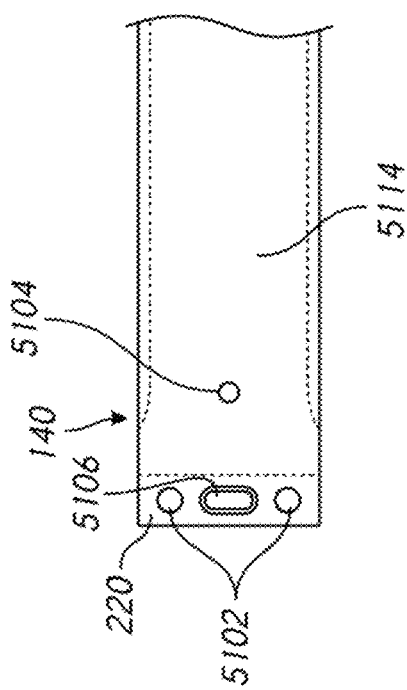

FIG. 90C illustrates a top view of a bottom strap having alignment posts and an indent.

Figure 90D:
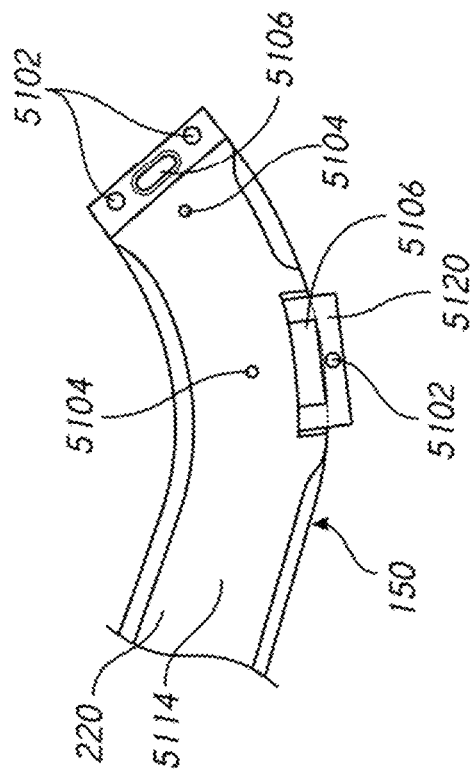

FIG. 90D illustrates a top view of the bottom strap in FIG. 90C having alignment posts, post holes and an indent.

Figure 91B:
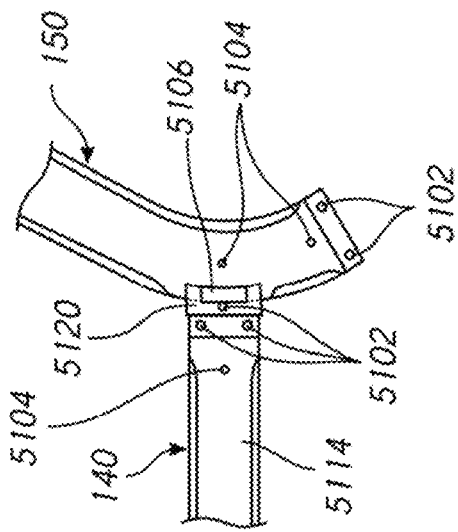
Figure 91D:
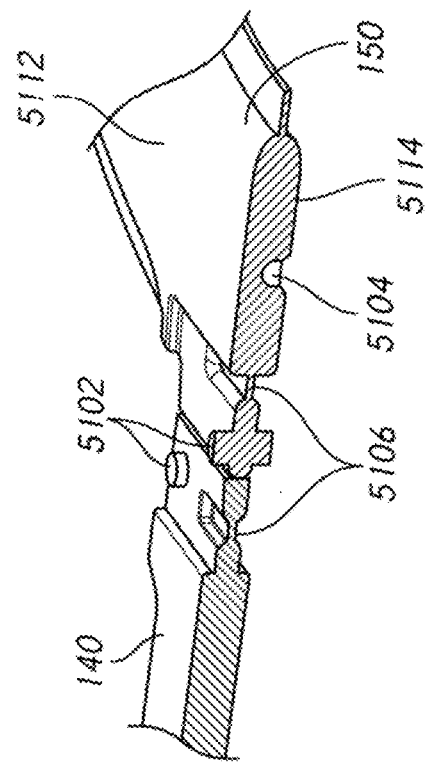
Figure 91A:
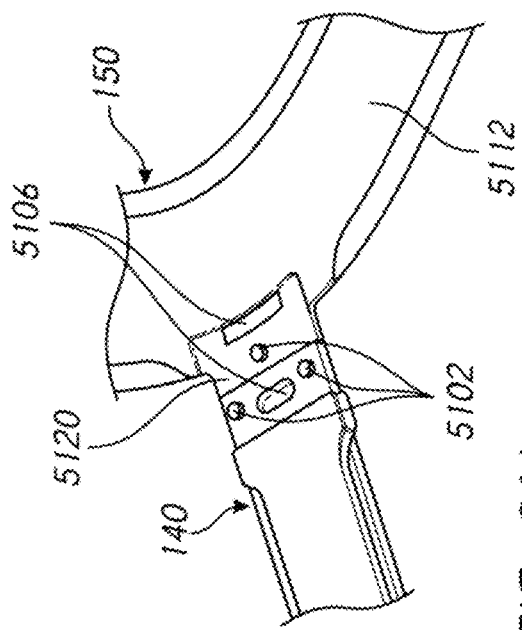

FIG. 91A illustrates a perspective view of the top strap in FIG. 90A aligned with the bottom strap in FIG. 90C.

FIG. 91B illustrates a bottom view of the top strap in FIG. 90A aligned with the bottom strap in FIG. 90C.

Figure 91C:
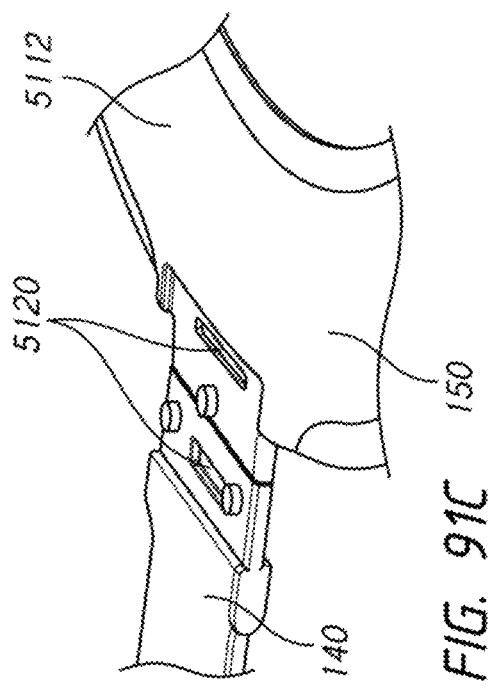

FIG. 91C illustrates a perspective view of the top strap in FIG. 90A aligned with the bottom strap in FIG. 90C.

FIG. 91D illustrates perspective cross-sectional view of the top strap in FIG. 90A aligned with the bottom strap in FIG. 90C.

FIG. 92A illustrates bottom view of an overmoulded joint bonding the top strap in FIG. 90A and the bottom strap in FIG. 90C.

FIG. 92B illustrates a top view of the overmoulded joint in FIG. 92A.

FIG. 92C illustrates a perspective cross-sectional view of the overmoulded joint in FIG. 92A.

FIG. 92D illustrates a perspective cross-sectional view of an overmoulded connector.

Figure 93A:
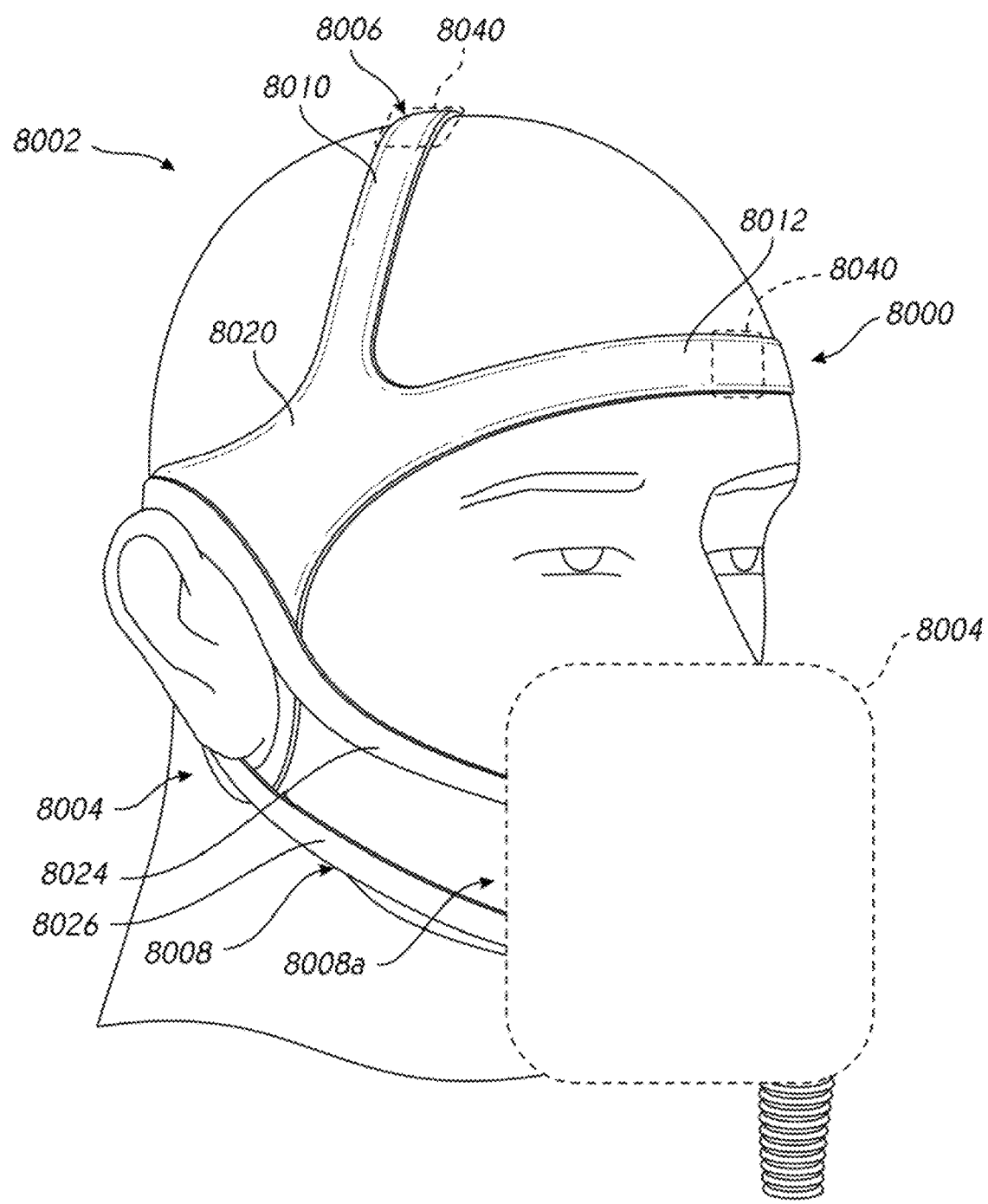

FIG. 93A is a perspective view of a non-limiting exemplary embodiment of a patient interface having a headgear assembly and a mask assembly according to the present disclosure. The headgear assembly includes a headpiece and one or more connectors between the headpiece and the mask assembly.

Figure 93B:
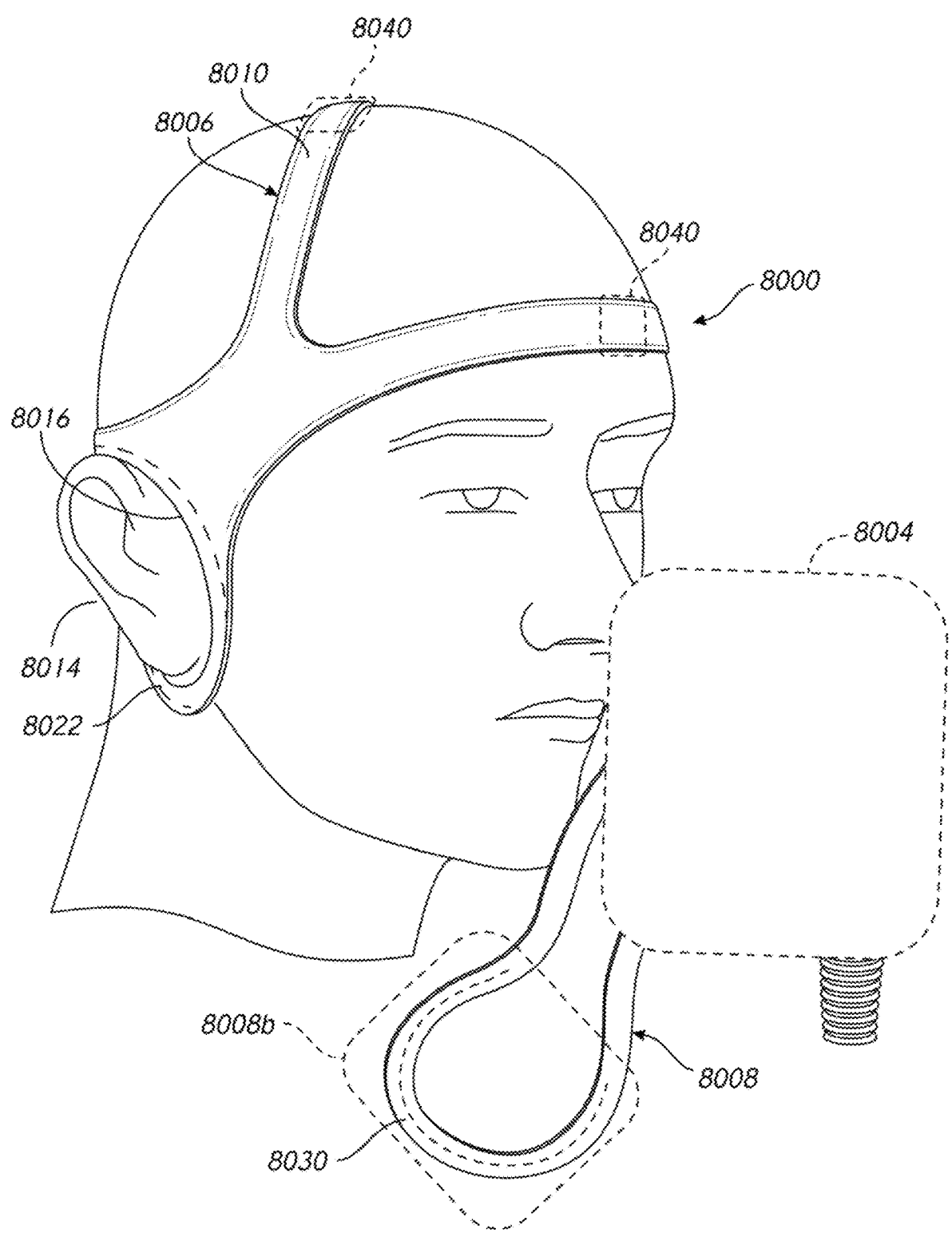

FIG. 93B is a perspective view of the patient interface of FIG. 93A with the connector disconnected from the headpiece.

Figure 93C:
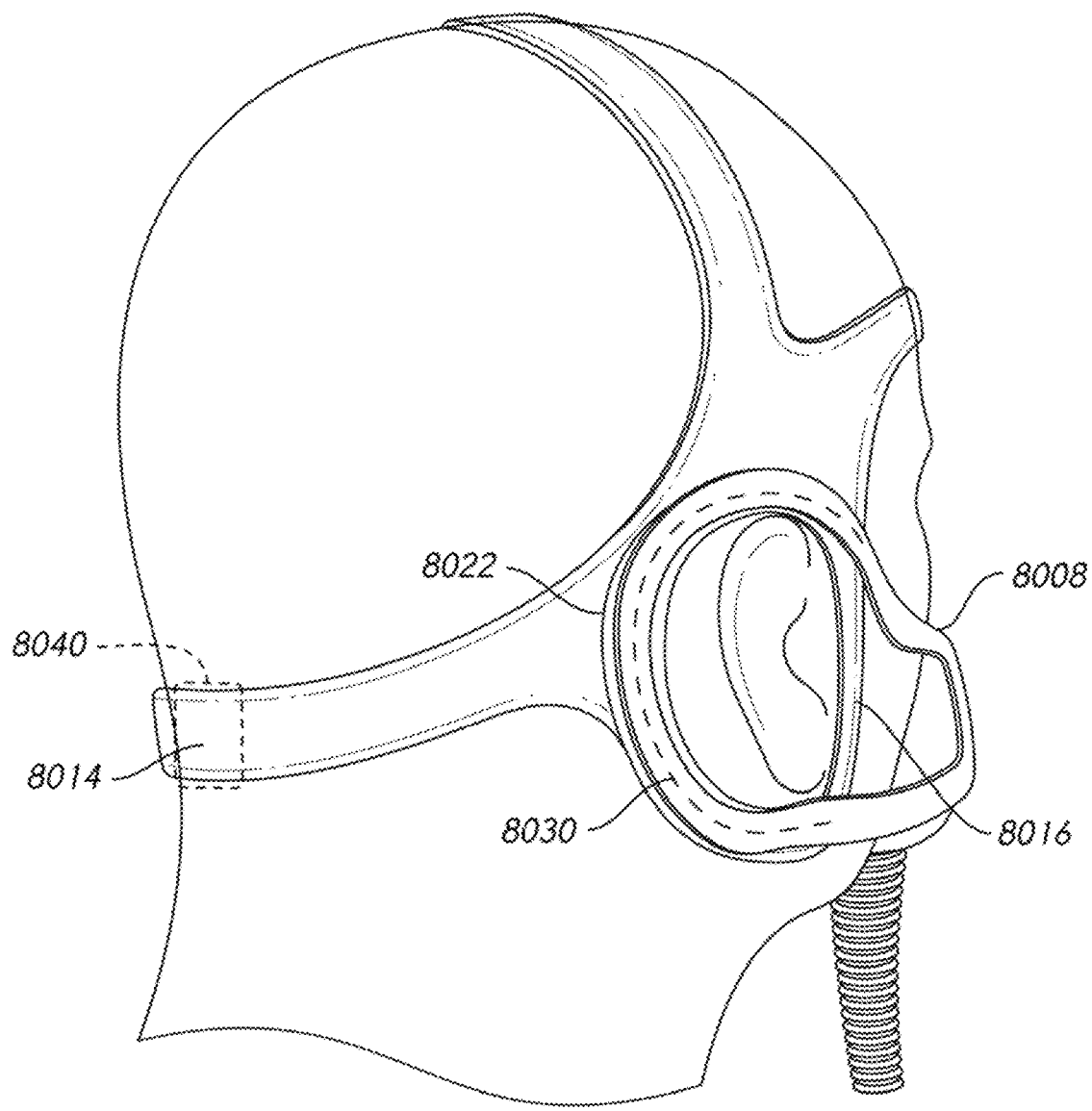

FIG. 93C is a rear perspective view of the patient interface of FIG. 93A.

Figure 94A:
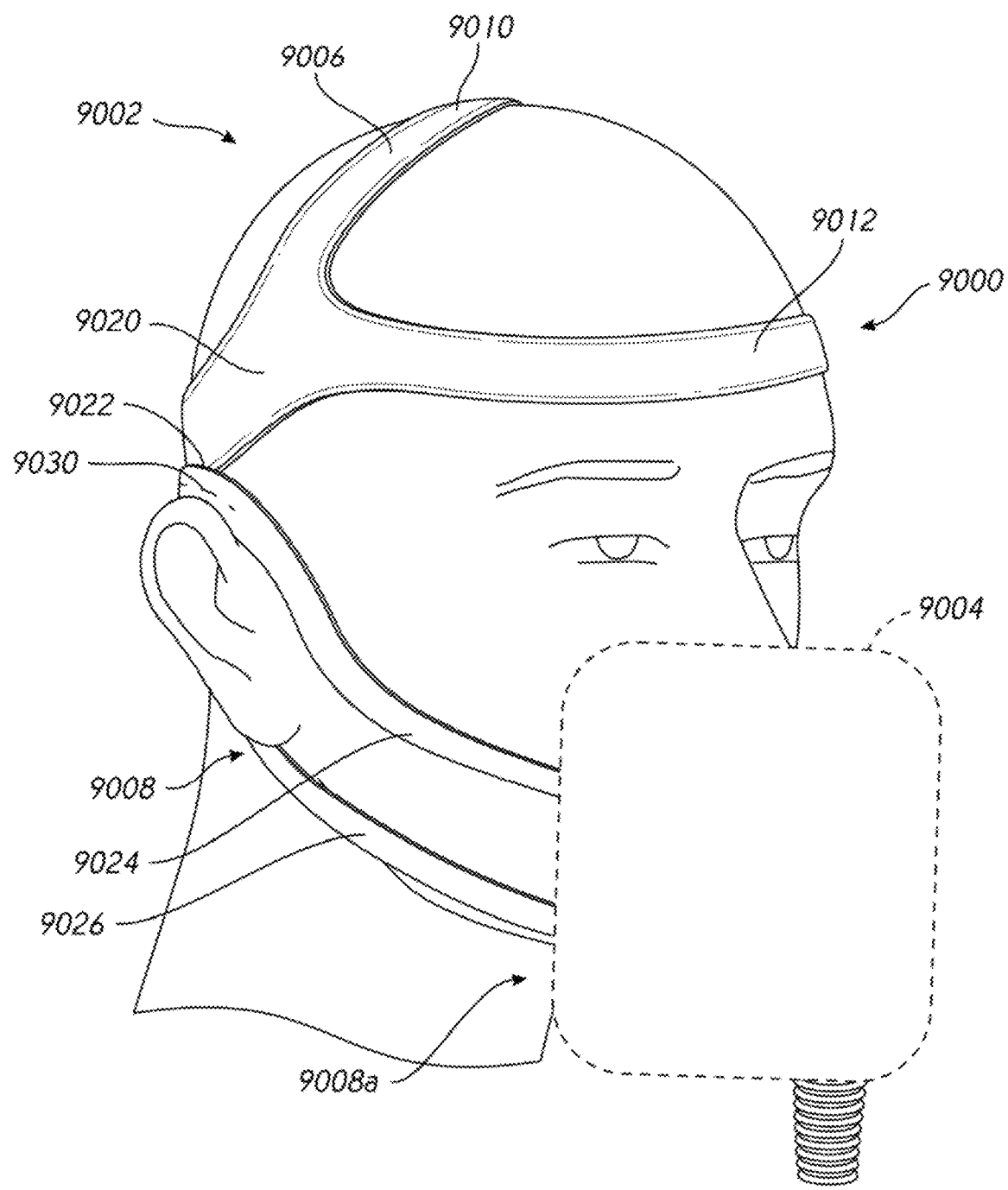

FIG. 94A is a perspective view of another non-limiting exemplary embodiment of a patient interface having a headgear assembly and a mask assembly according to the present disclosure. The headgear assembly includes a headpiece and one or more connectors between the headpiece and the mask assembly.

Figure 94B:
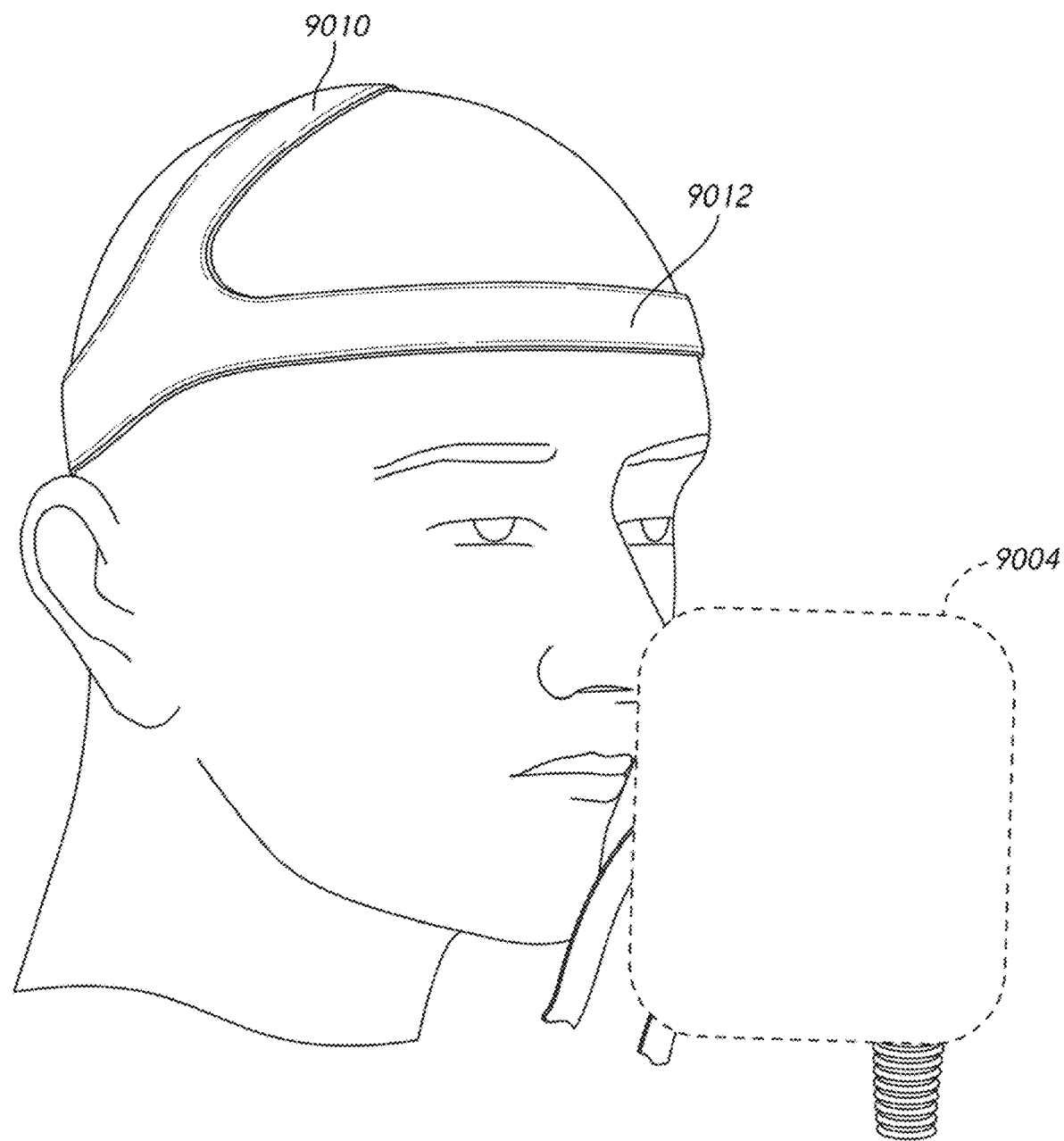

FIG. 94B is a perspective view of the patient interface of FIG. 94A with the connector disconnected from the headpiece.

Figure 94C:
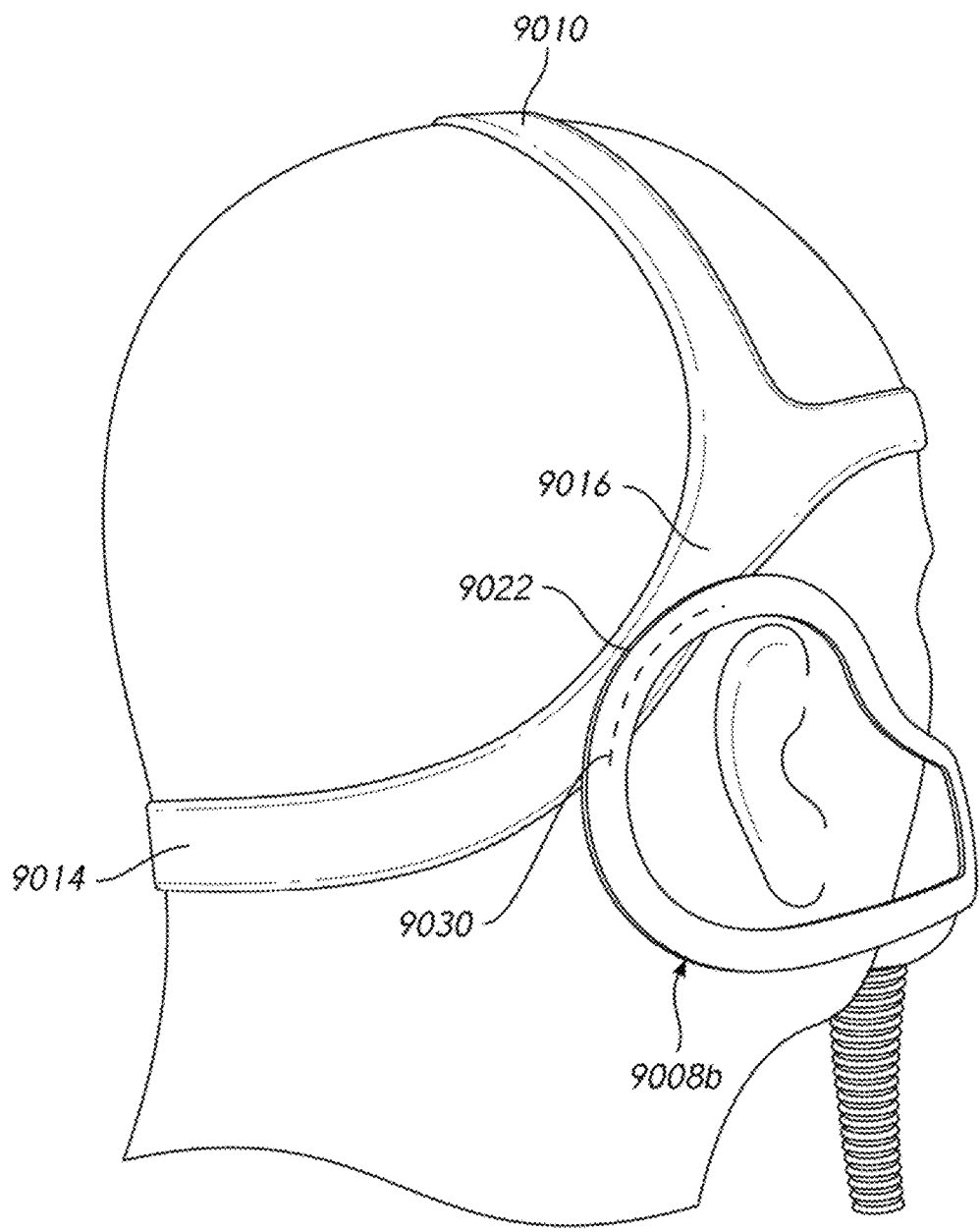

FIG. 94C is a rear perspective view of the patient interface of FIG. 94A.

Figure 95:
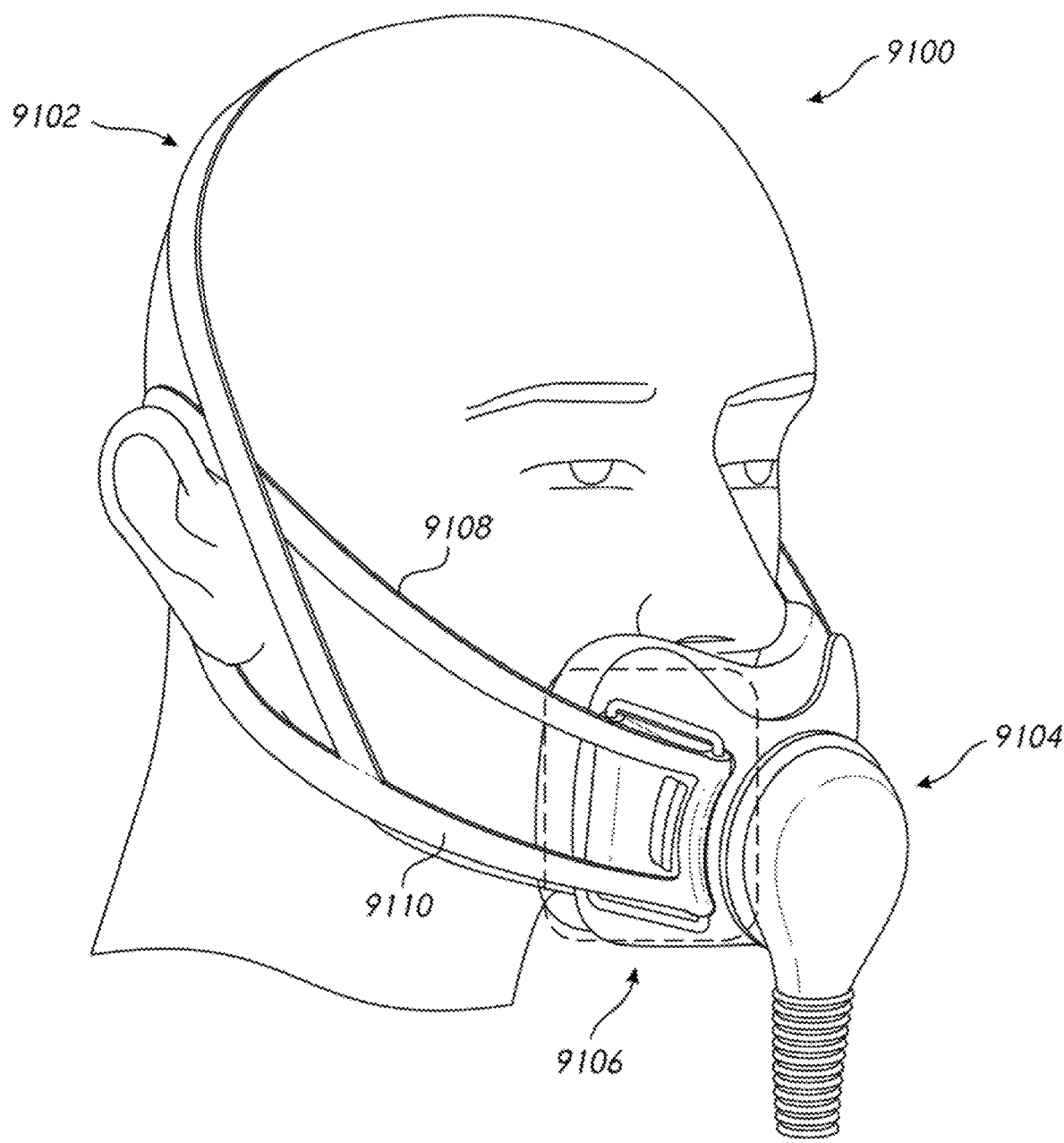

FIG. 95 shows an isometric view of a patient interface of the present disclosure including a headgear, a mask assembly and a connector.

Figure 96:
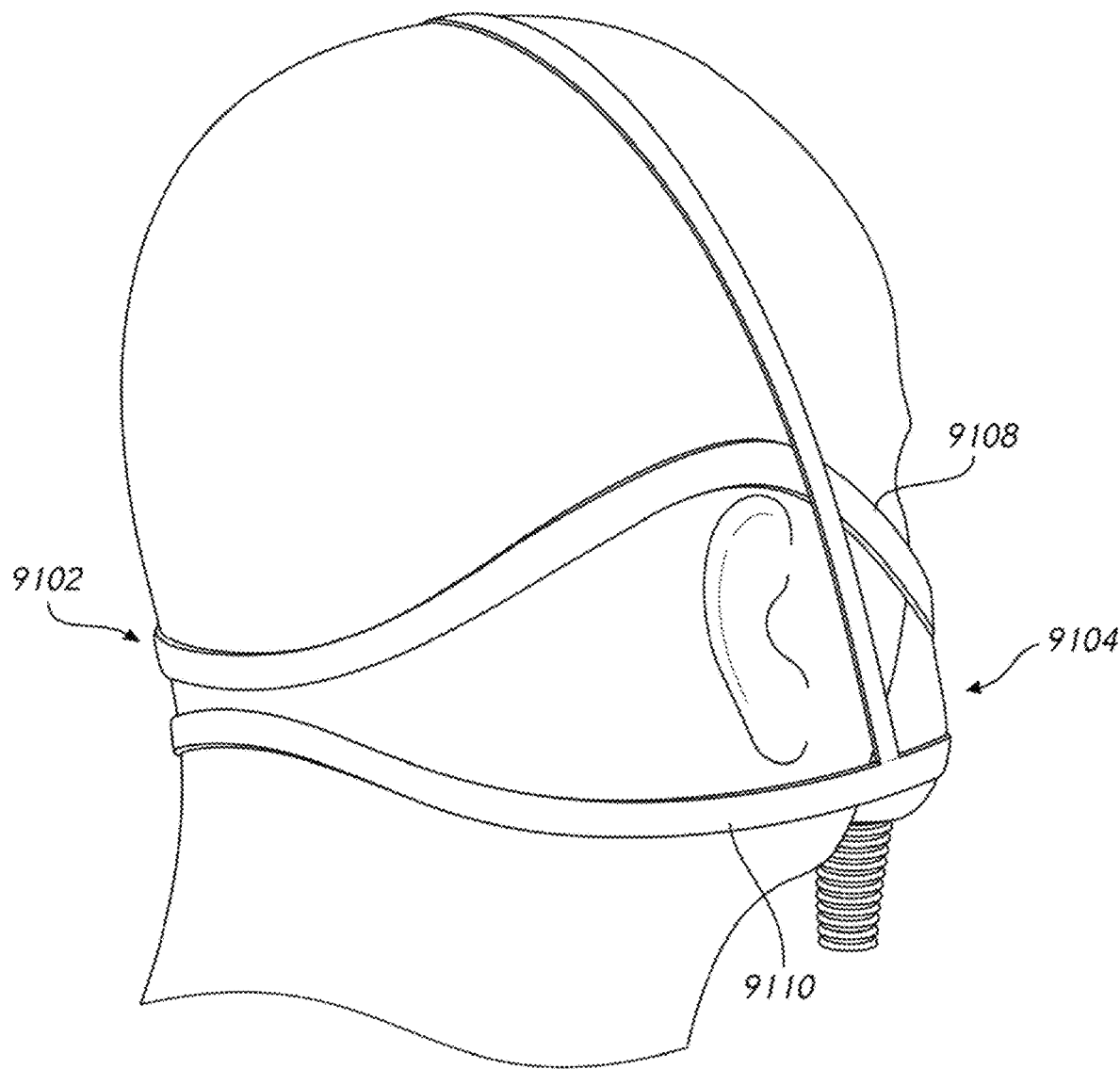

FIG. 96 shows a rear isometric view of the patient interface of FIG. 95.

Figure 97:
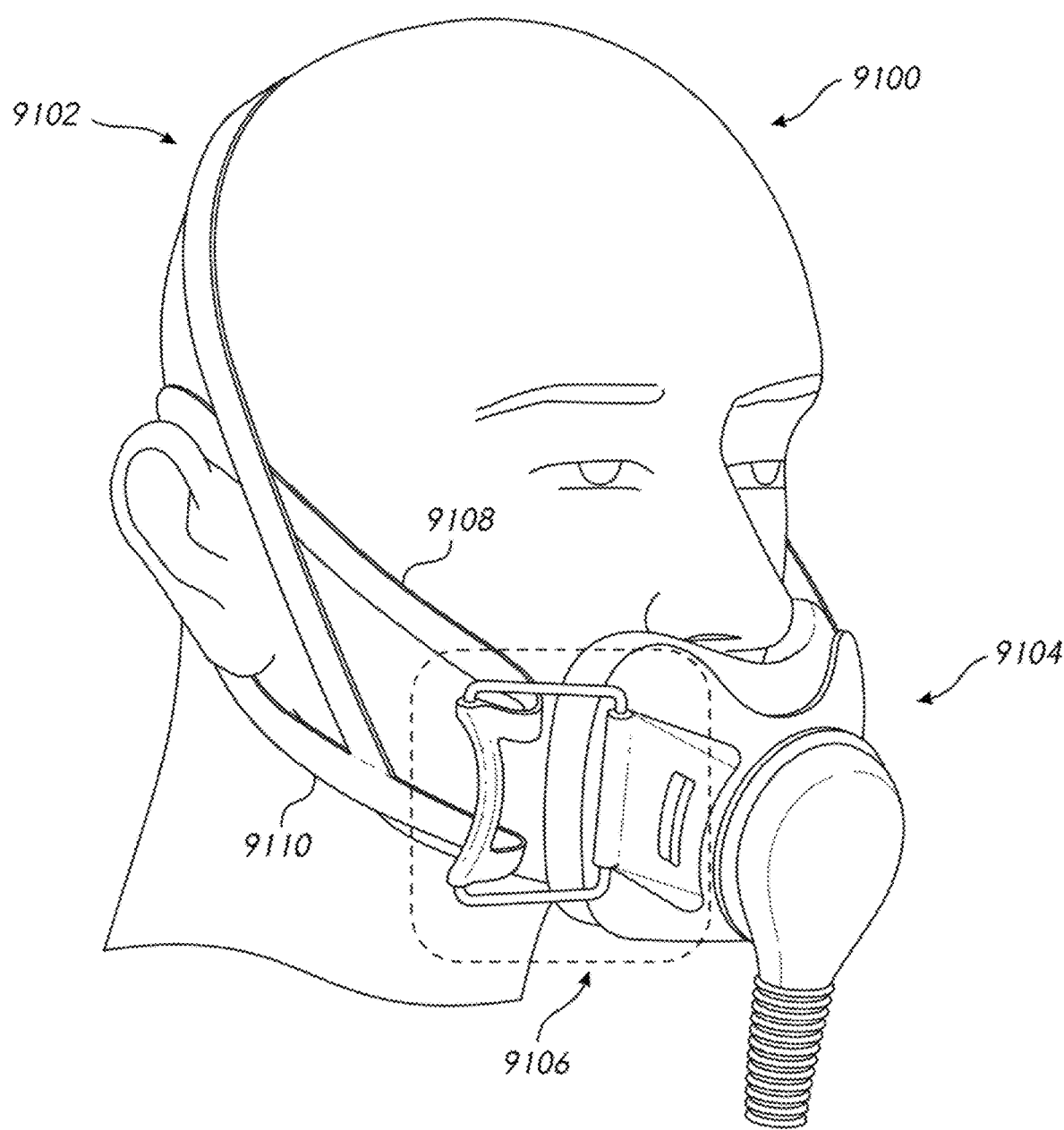

FIG. 97 shows an isometric view of the patient interface showing the connector disengaged from the mask assembly.

Figure 98:
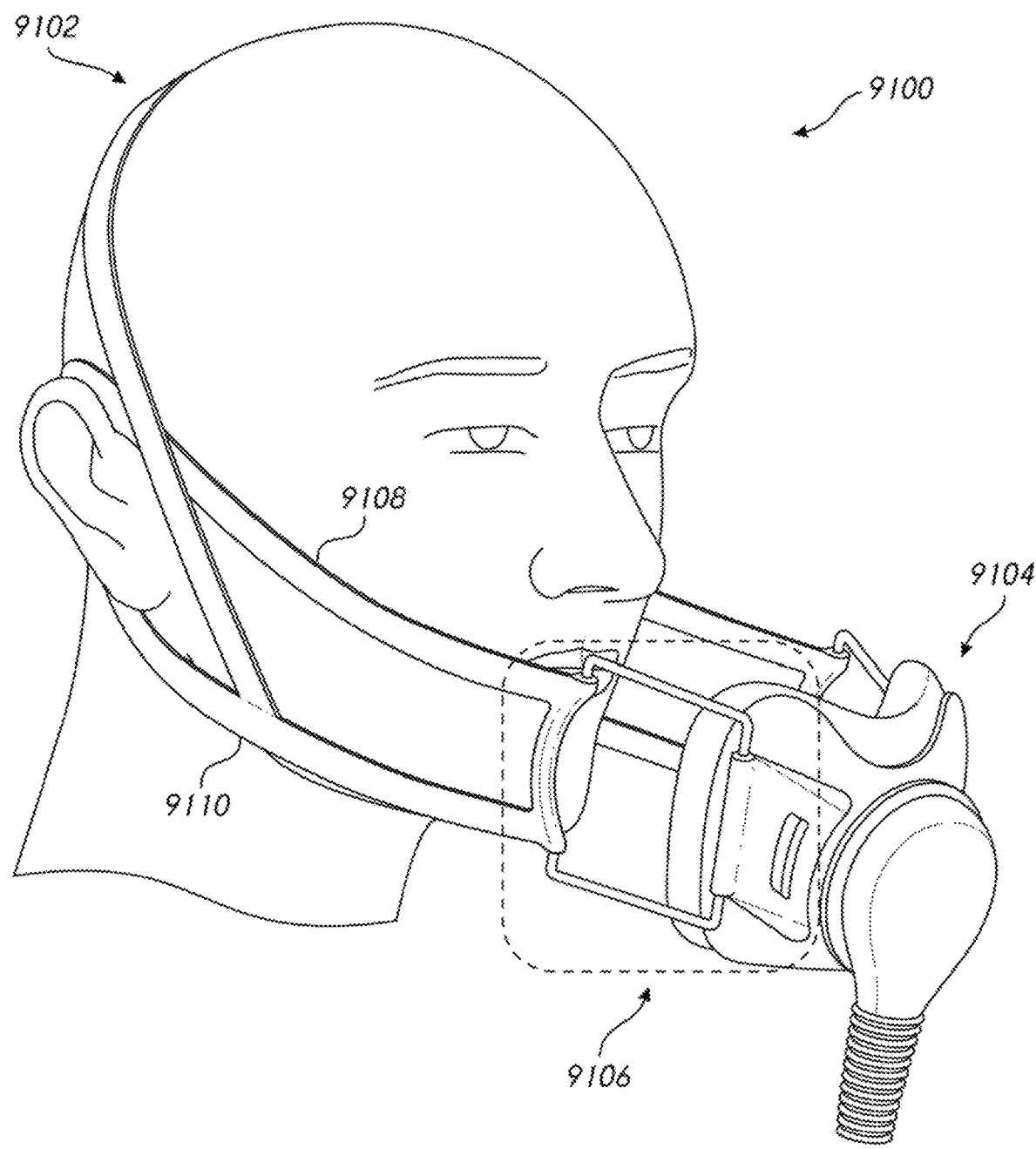

FIG. 98 shows an isometric view of the patient interface of FIG. 97 showing the connector fully extended away from the mask assembly.

Figure 99A:
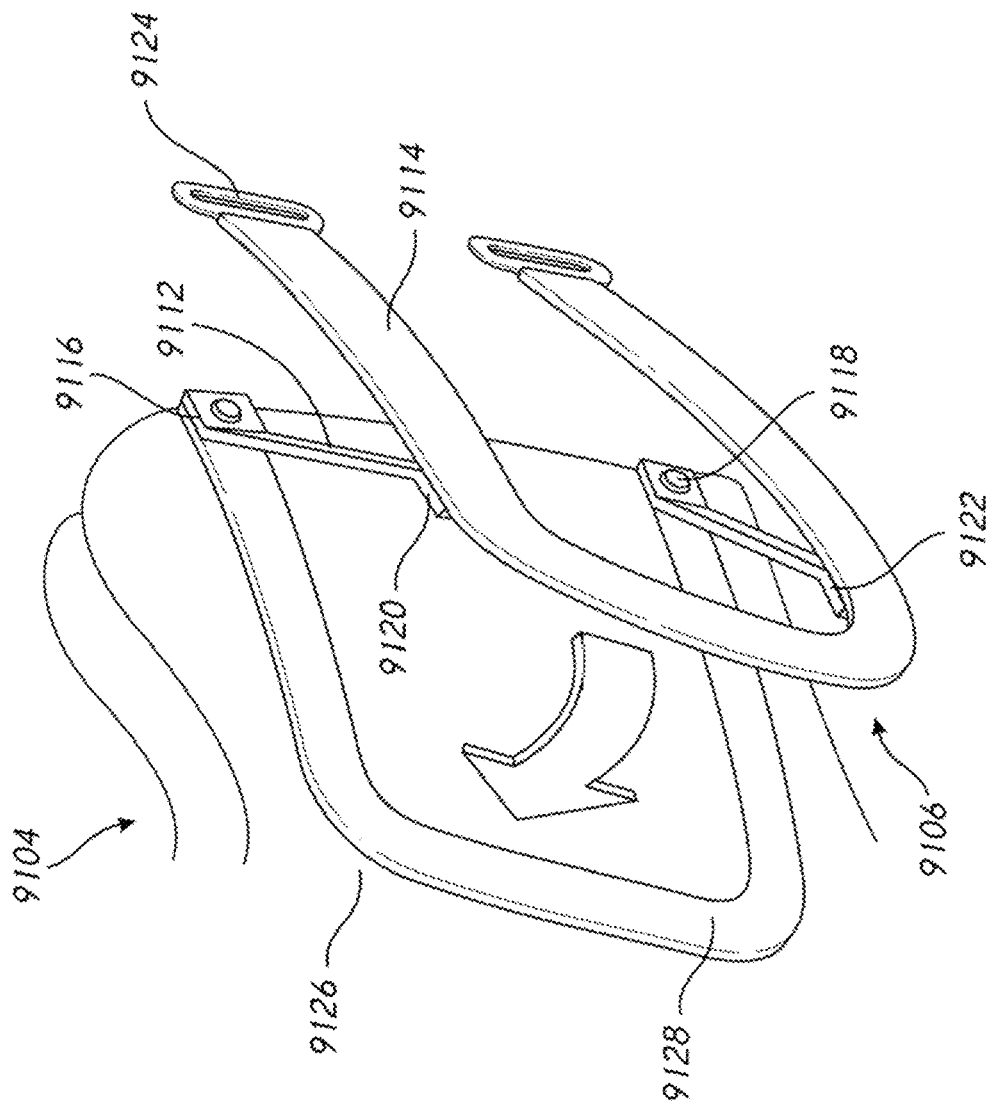

FIG. 99A shows an isometric view of a living hinge connector.

Figure 99B:
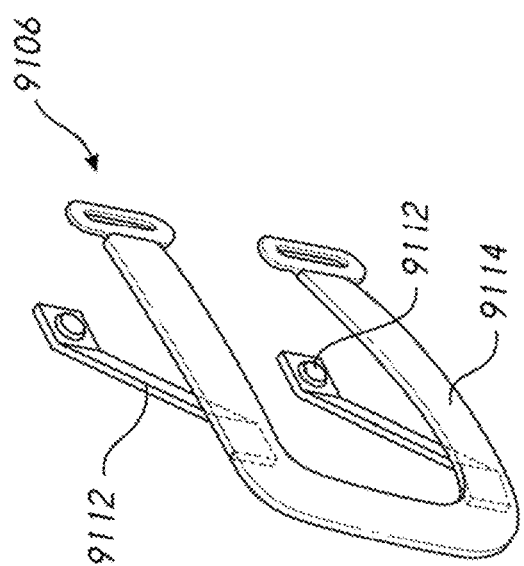

FIG. 99B shows an isometric view of an alternative living hinge connector.

Figure 100:
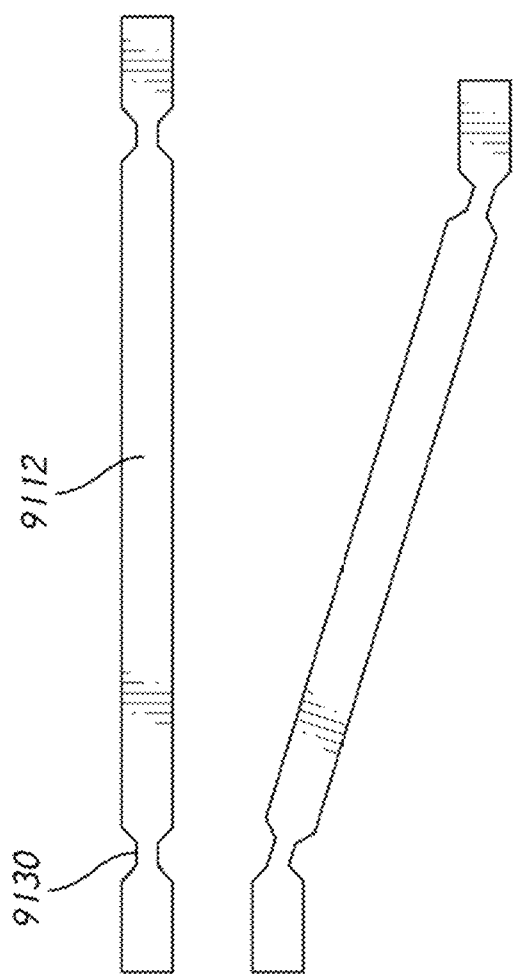

FIG. 100 shows a top view of a living hinge connector having sections of reduced thickness.

Figure 101B:
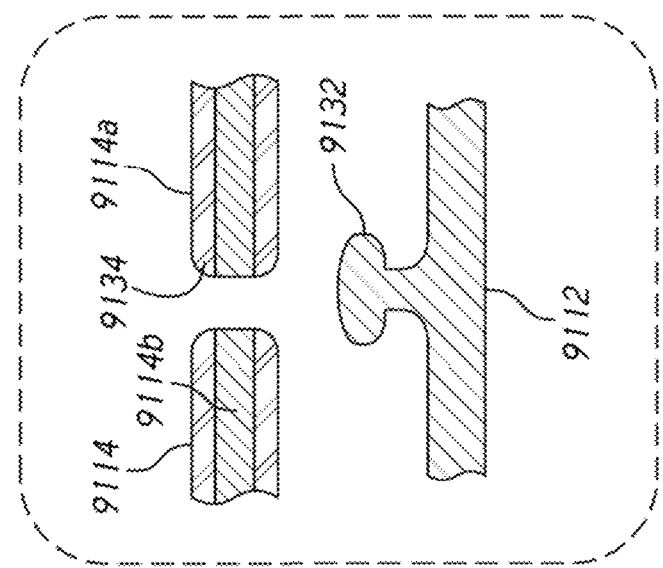
Figure 101A:
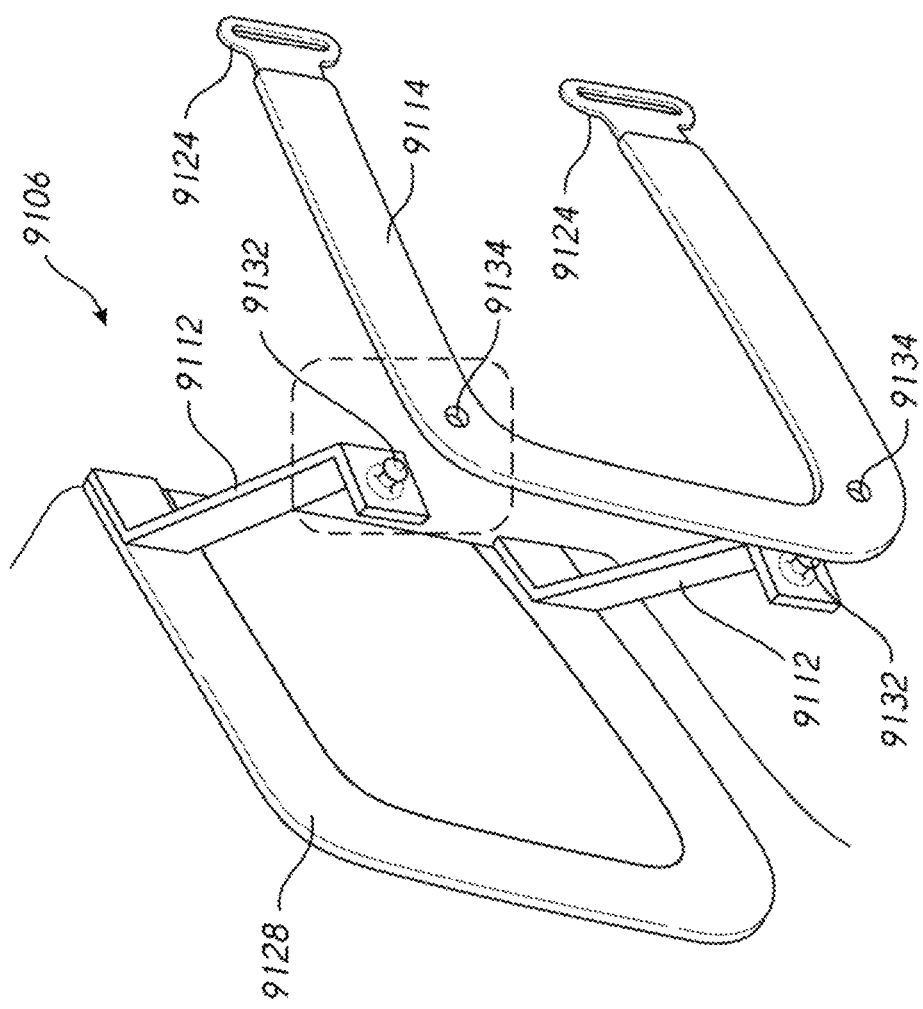

FIG. 101A shows an isometric exploded view of a living hinge connector.

FIG. 101B shows a cross-sectional view of a headgear connector member and a mask connector member of the living hinge connector of FIG. 101A.

Figure 102B:
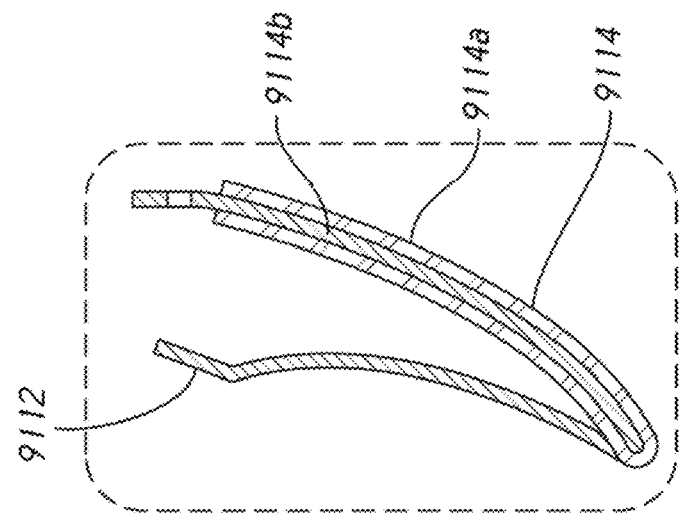
Figure 102A:
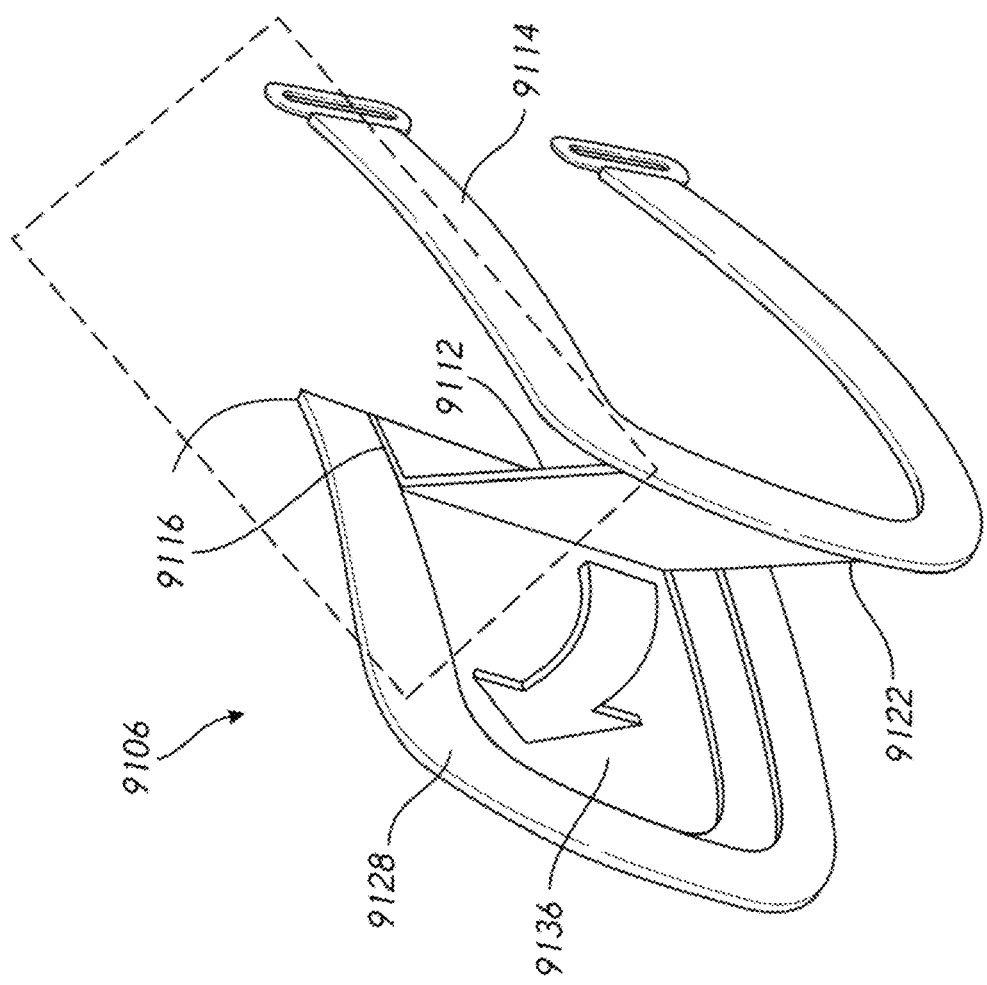

FIG. 102A shows an isometric view of a living hinge connector having a single mask hinge and a single connector hinge.

FIG. 102B shows a top cross-sectional view of a headgear connector member and a mask connector member of the living hinge connector of FIG. 102A.

Figure 103B:
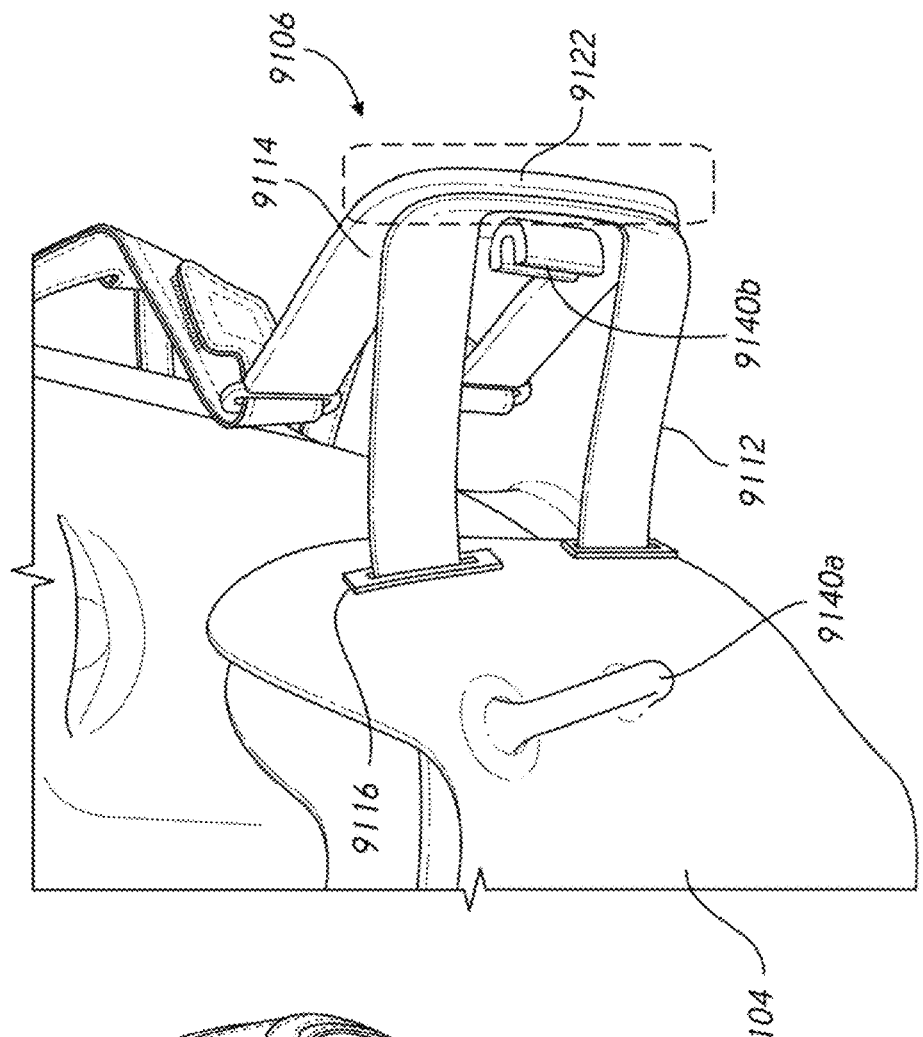
Figure 103A:
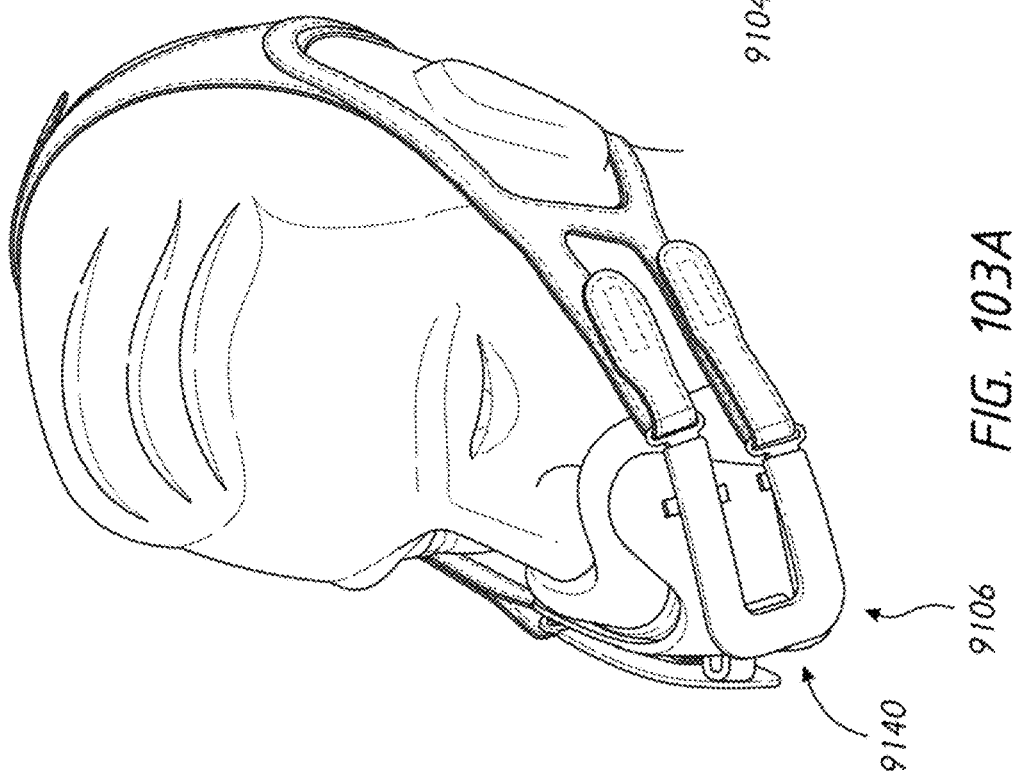

FIG. 103A shows an isometric view of a patient interface having a living hinge connector with a hook and post retaining system.

FIG. 103B shows a front view of the living hinge connector of FIG. 103A in an open position.

Figure 104B:
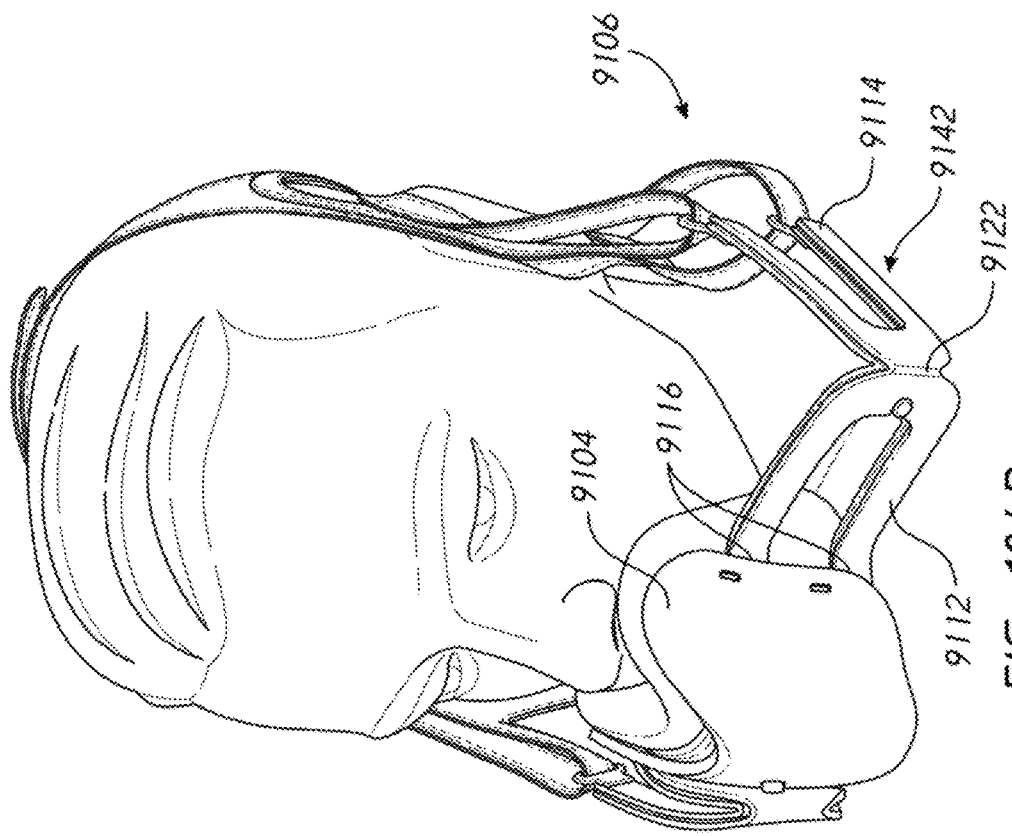
Figure 104A:
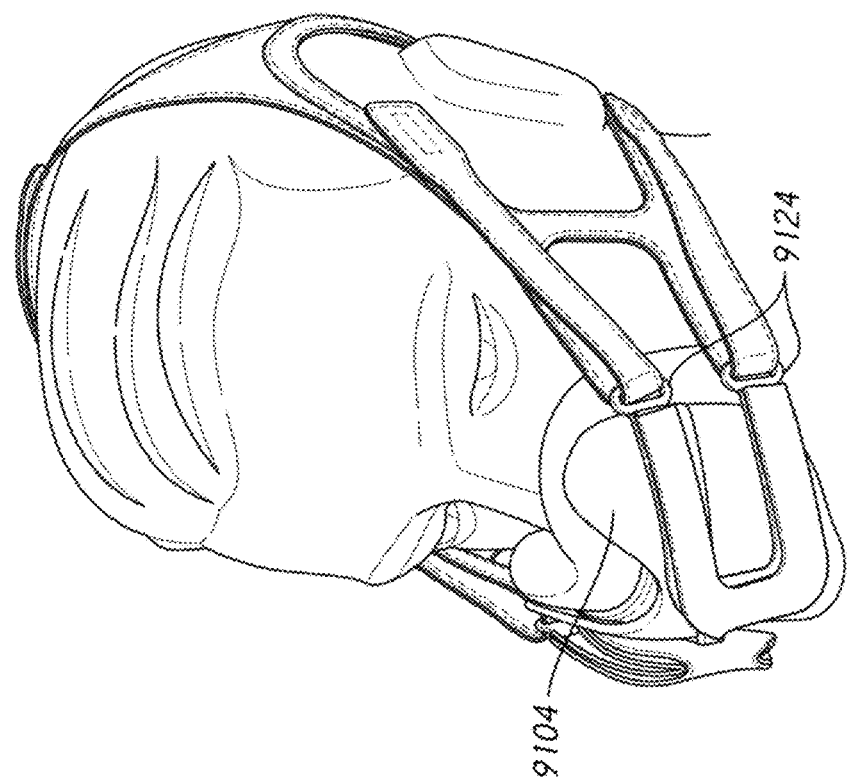

FIG. 104A shows an isometric view of a patient interface having a fabric living hinge connector in a closed position.

FIG. 104B shows an isometric view of the patient interface of FIG. 104A showing the fabric living hinge connector in an open position.

Figure 105B:
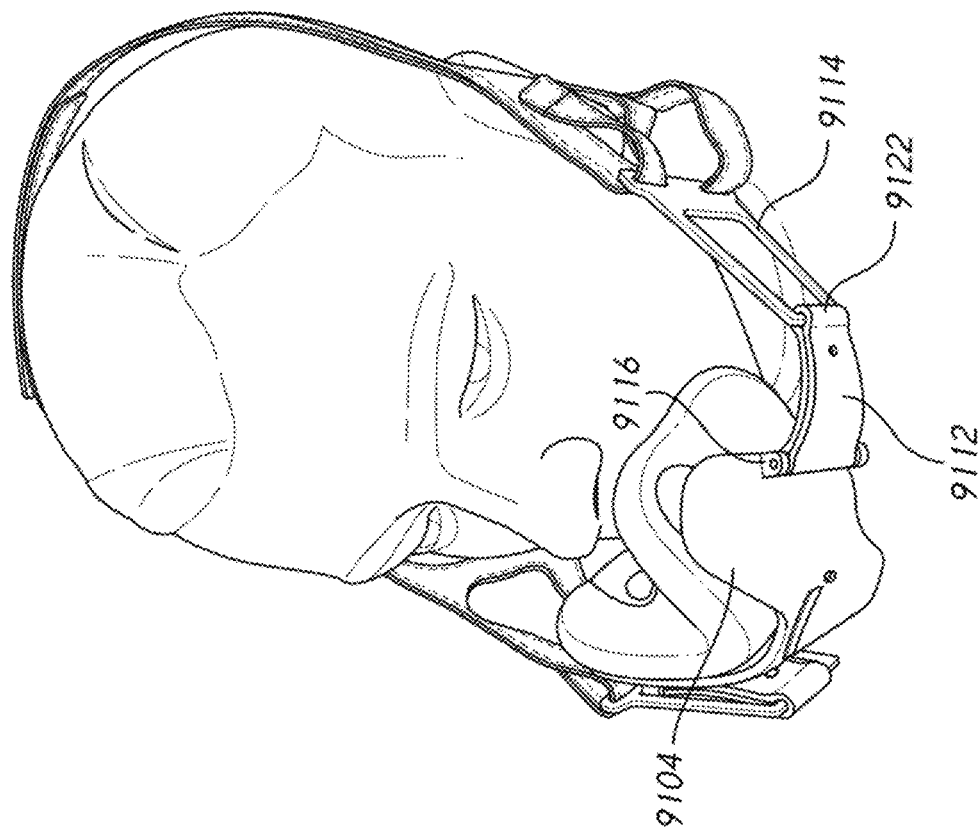
Figure 105A:
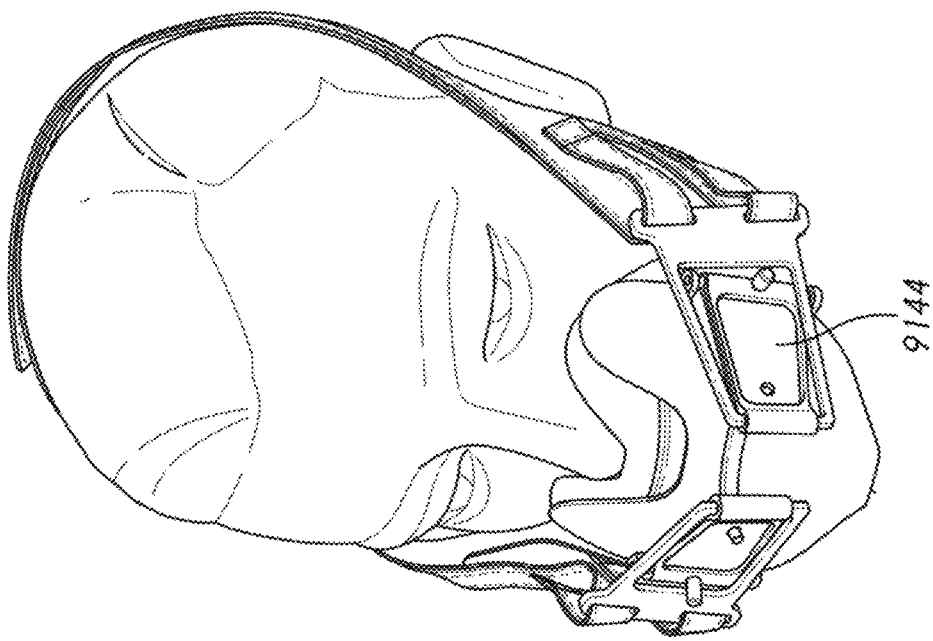

FIG. 105A shows an isometric view of a patient interface having a silicon hinge connector in a closed position.

FIG. 105B shows an isometric view of the patient interface of FIG. 105A showing the silicon hinge connector in an open position.

Figure 106B:
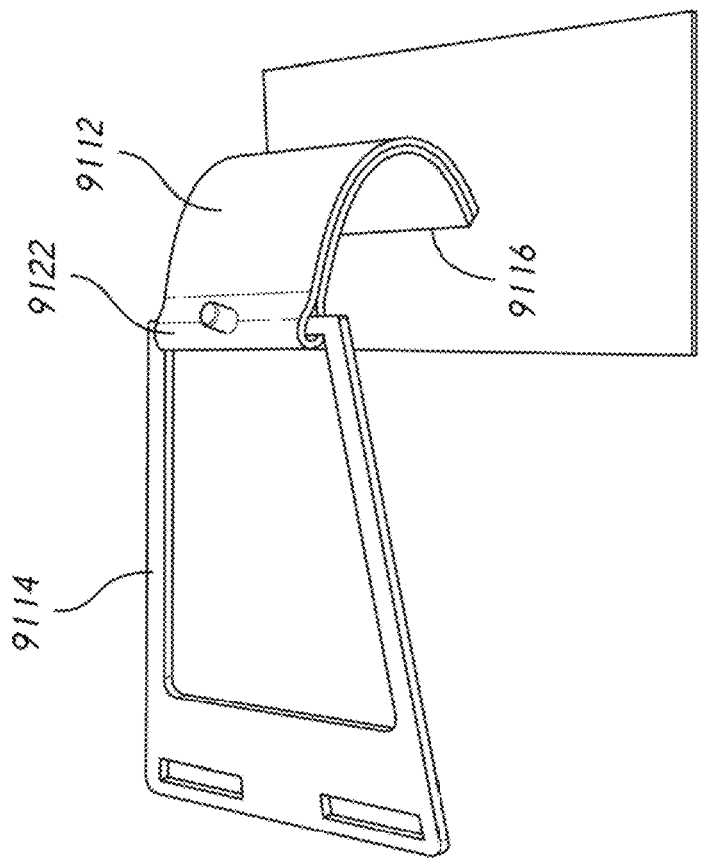
Figure 106A:
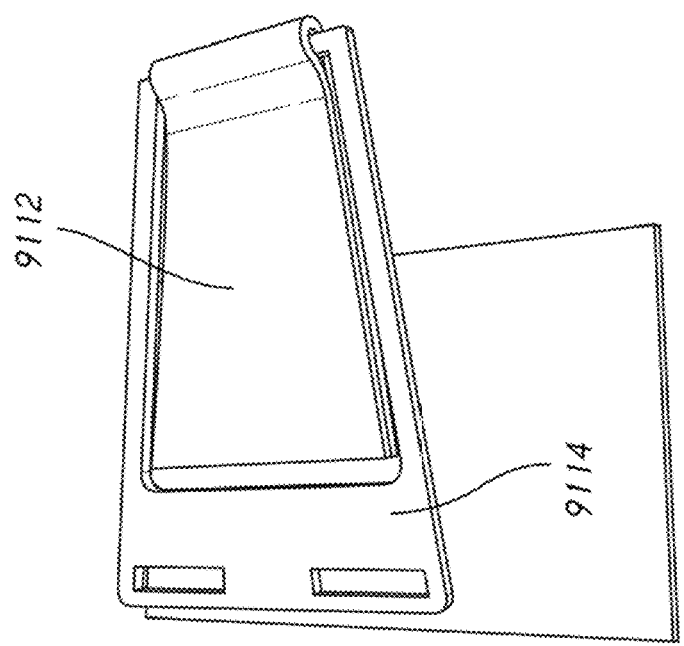

FIG. 106A shows a top-down view of an alternative silicon hinge with the connector in a closed position.

FIG. 106B shows a top-down view of the silicon hinge of FIG. 106A with the connector in open position.

FIG. 107A shows an isometric view of a patient interface having an alternative silicon hinge connector in a closed position.

FIG. 107B shows an isometric view of the silicon hinge connector of FIG. 107A in an open position.

FIG. 108A shows an isometric view of a patient interface showing a headgear connection of the present disclosure.

FIG. 108B shows a close-up perspective view of a lateral end of a connector of the headgear connection in FIG. 108A.

FIG. 108C shows a cross-sectional view of the connector of the headgear connection in FIG. 108A.

Figures 109A, 109B:
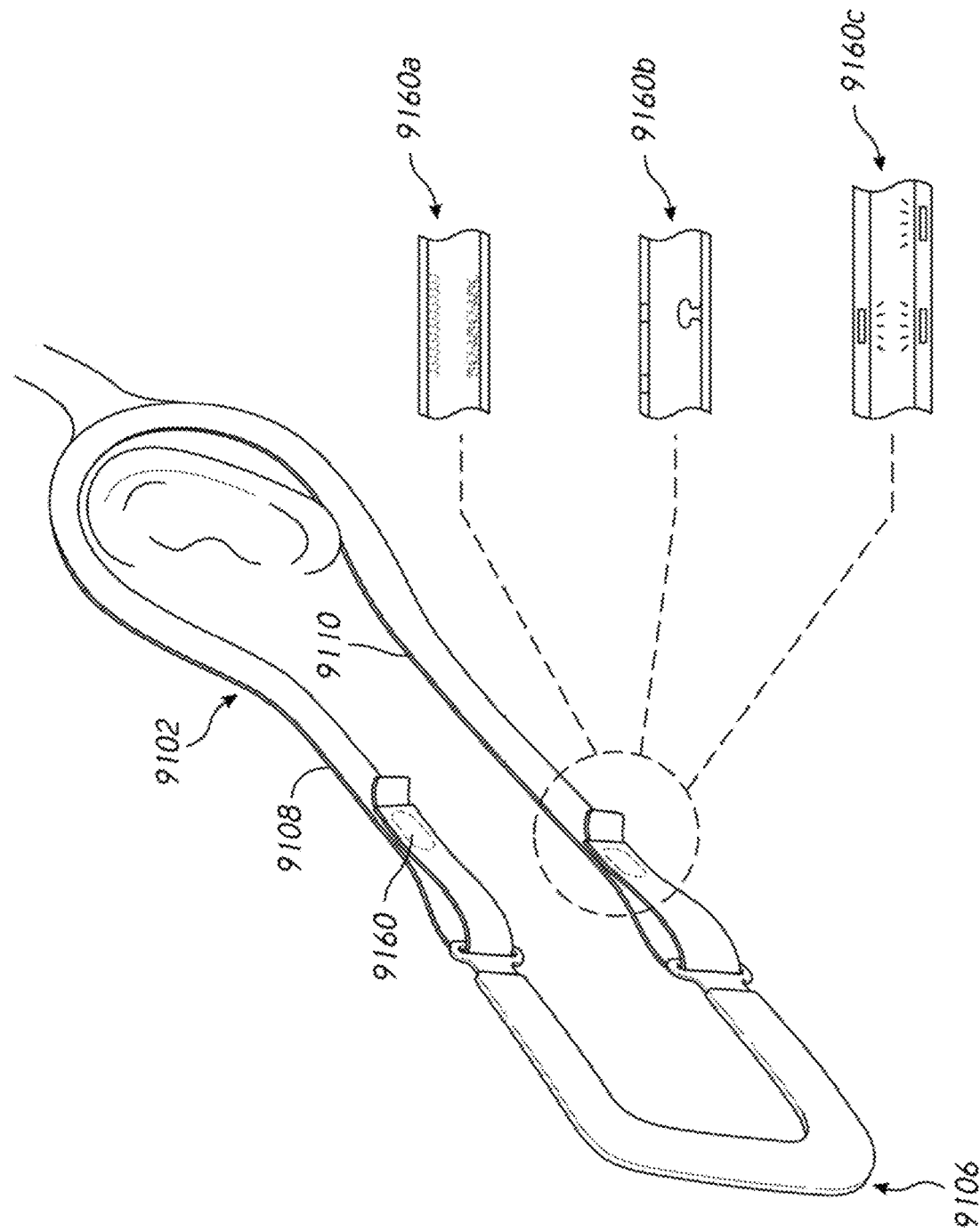

FIG. 109A shows an isometric view of a headgear securement mechanism.

FIG. 109B shows a top view of alternative headgear securement mechanisms.

FIG. 110A shows an isometric view of a push-fit headgear securement mechanism.

FIG. 110B shows a cross-sectional view of the push-fit headgear securement mechanism.

Figure 111B:
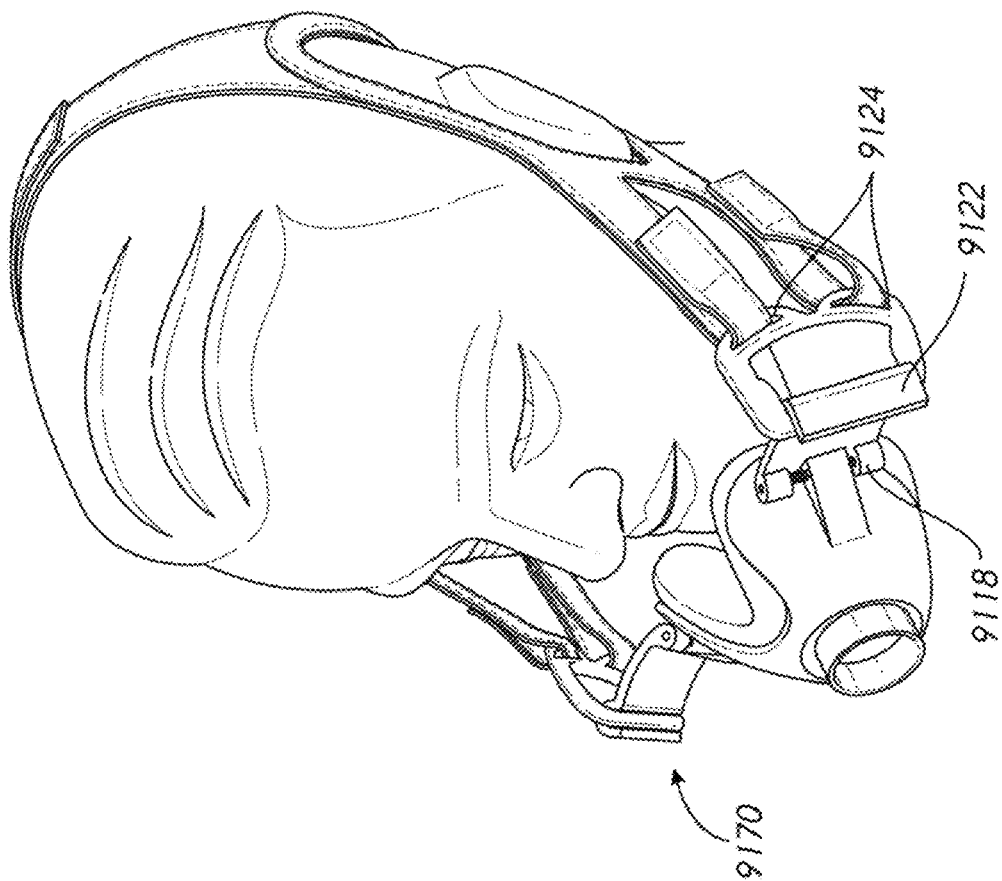
Figure 111A:
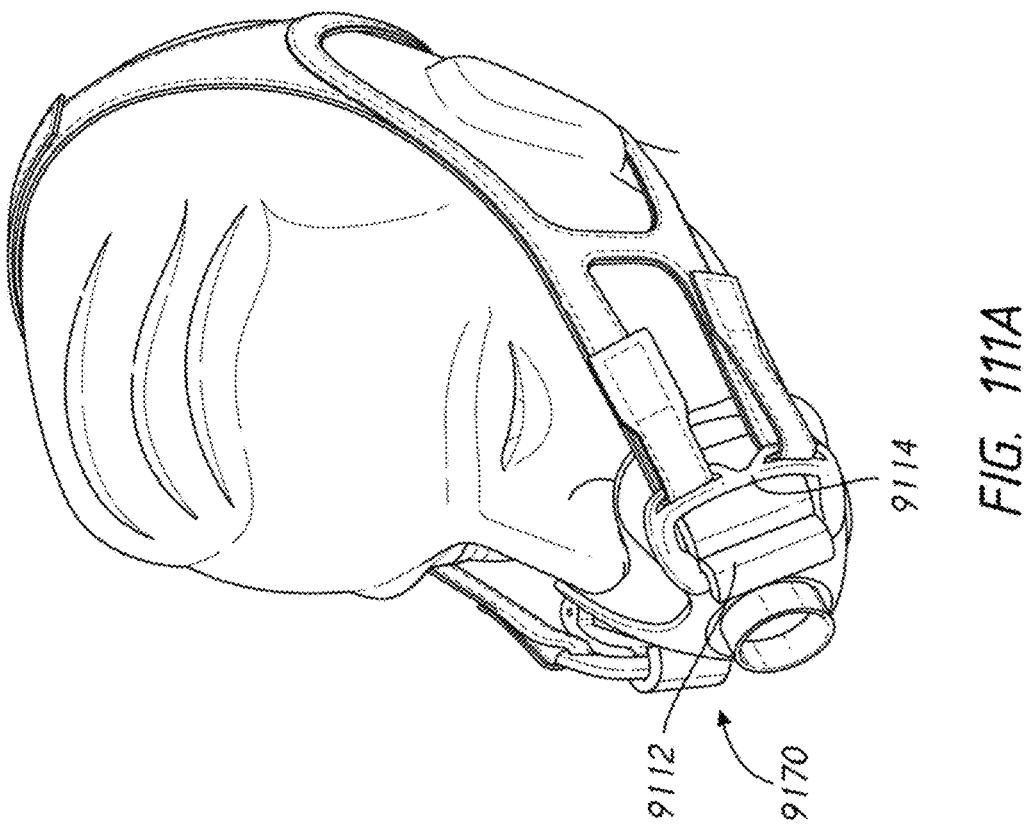

FIG. 111A shows an isometric view of a patient interface having an over-centered clip design connector in a closed position.

FIG. 111B shows an isometric view of the patient interface of FIG. 111A showing the over-centered clip design connector in an open position.

Figure 112B:
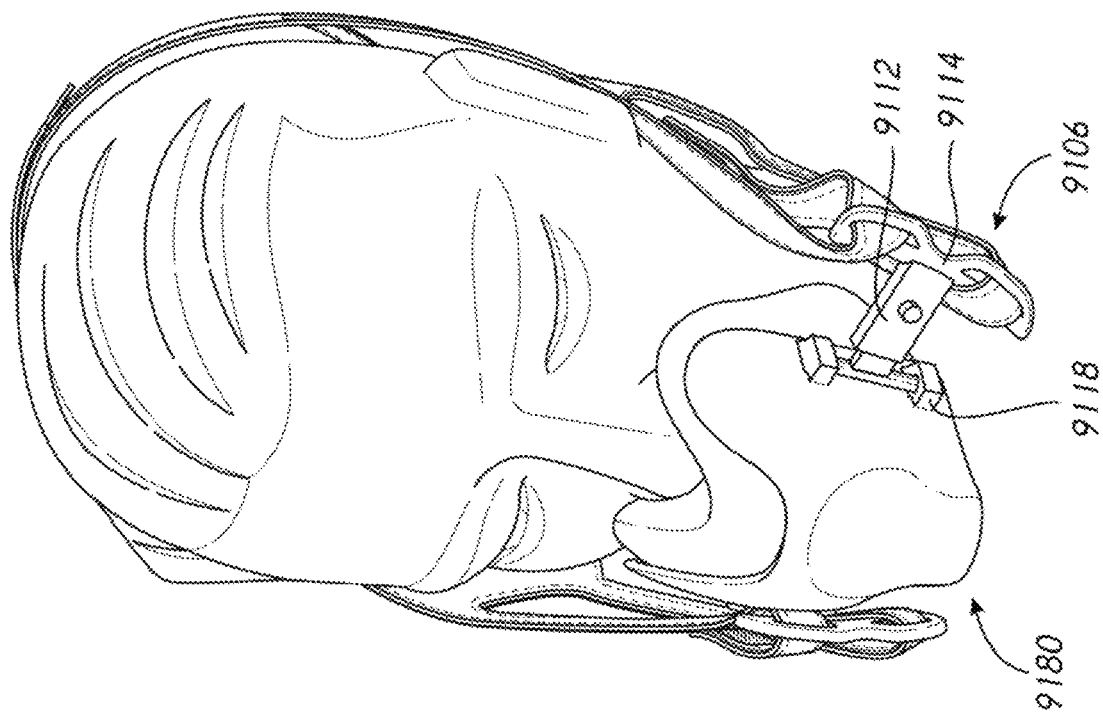
Figure 112A:
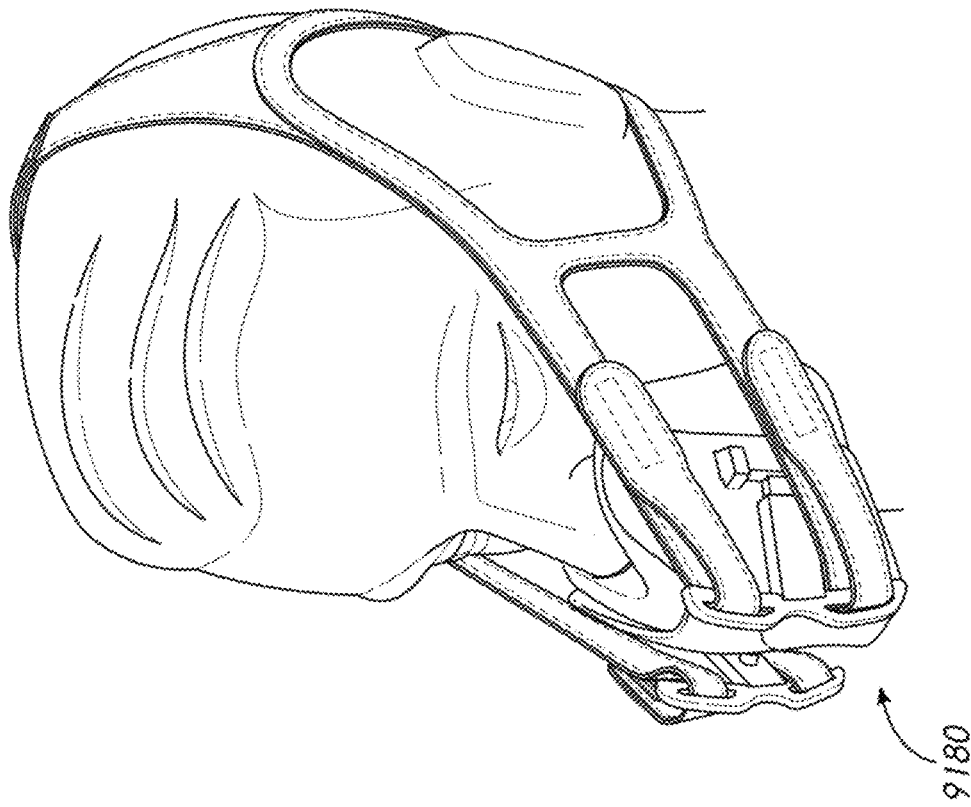

FIG. 112A shows an isometric view of a patient interface having an extendable pivot connector in a closed position.

FIG. 112B shows an isometric view of the patient interface of FIG. 112A showing the extendable pivot connector in an open position.

Figure 112C:
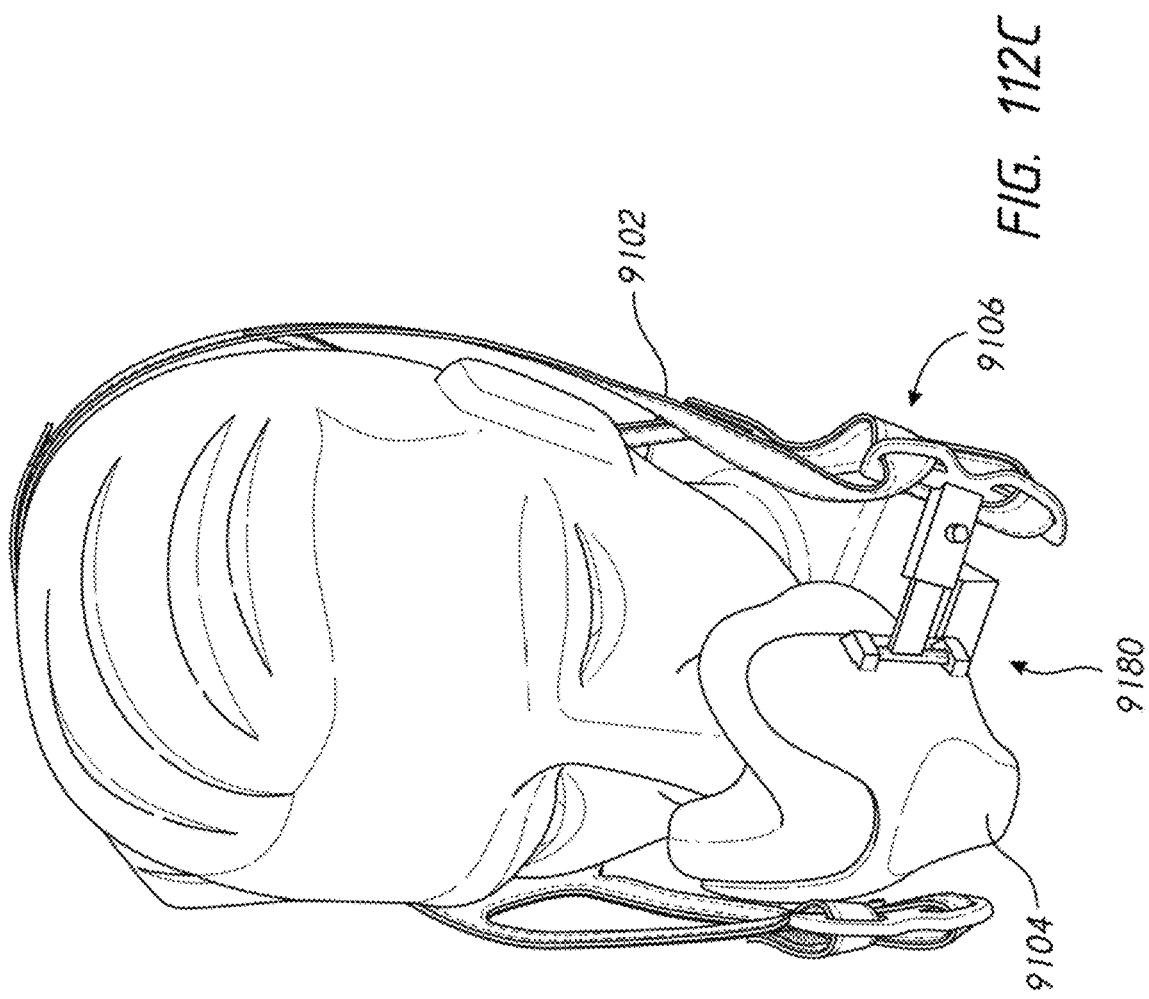

FIG. 112C shows an isometric view of the patient interface of FIG. 112A showing the extendable pivot connector in an open and extended position.

Figure 113B:
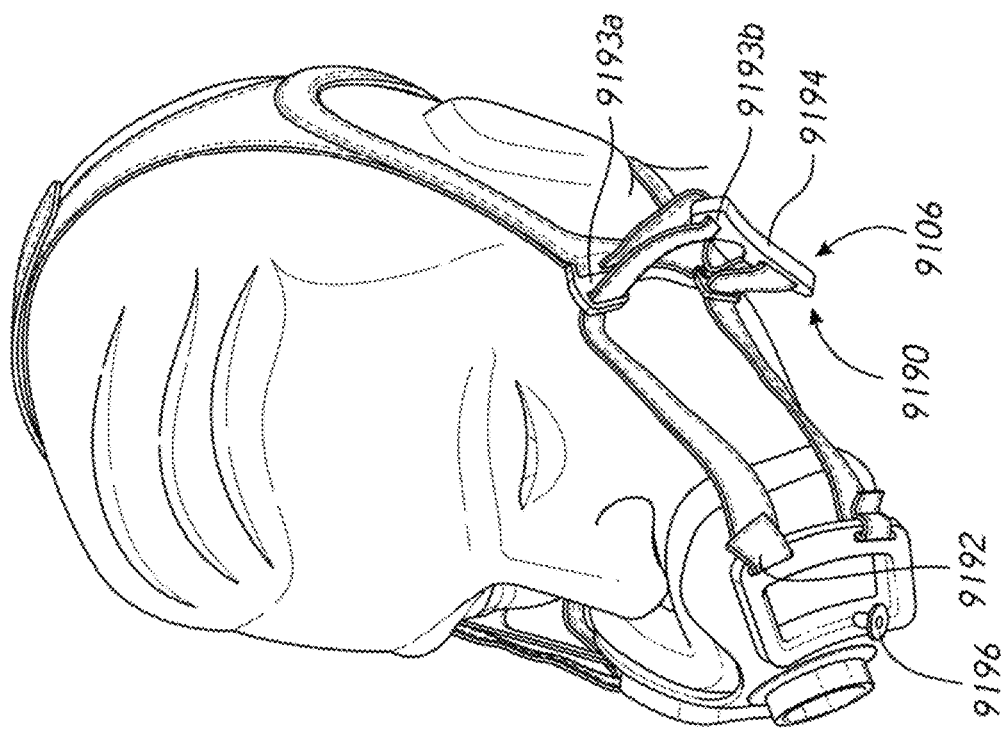
Figure 113A:
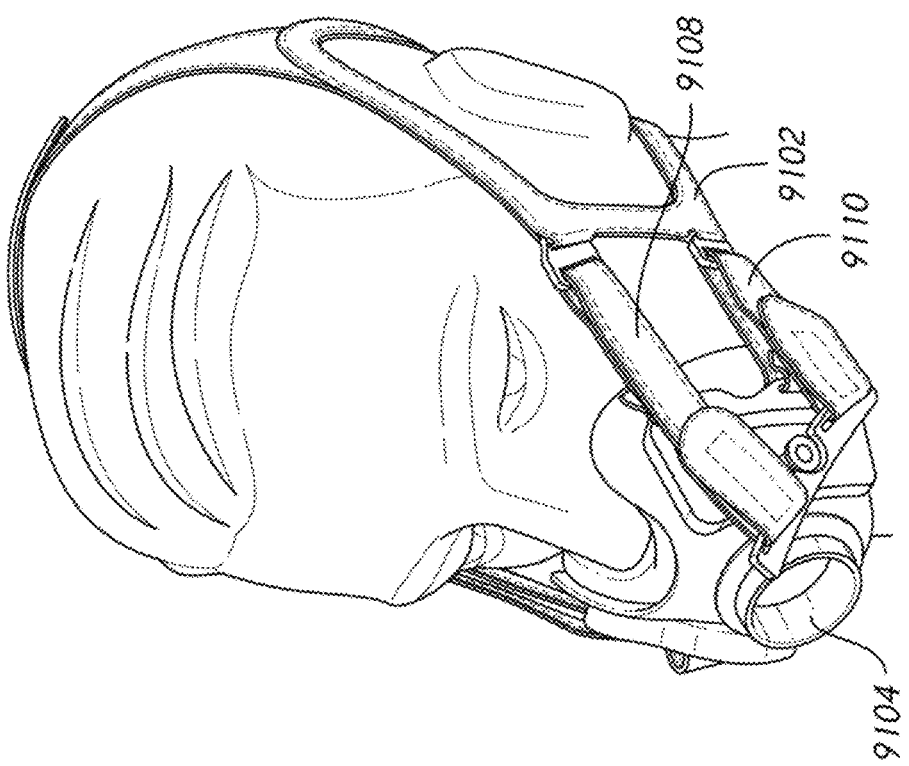

FIG. 113A shows an isometric view of a patient interface having a hard stop sliding strap connector in a closed position.

FIG. 113B shows an isometric view of the patient interface of FIG. 113A showing the hard stop sliding strap connector in an open position.

Figure 114B:
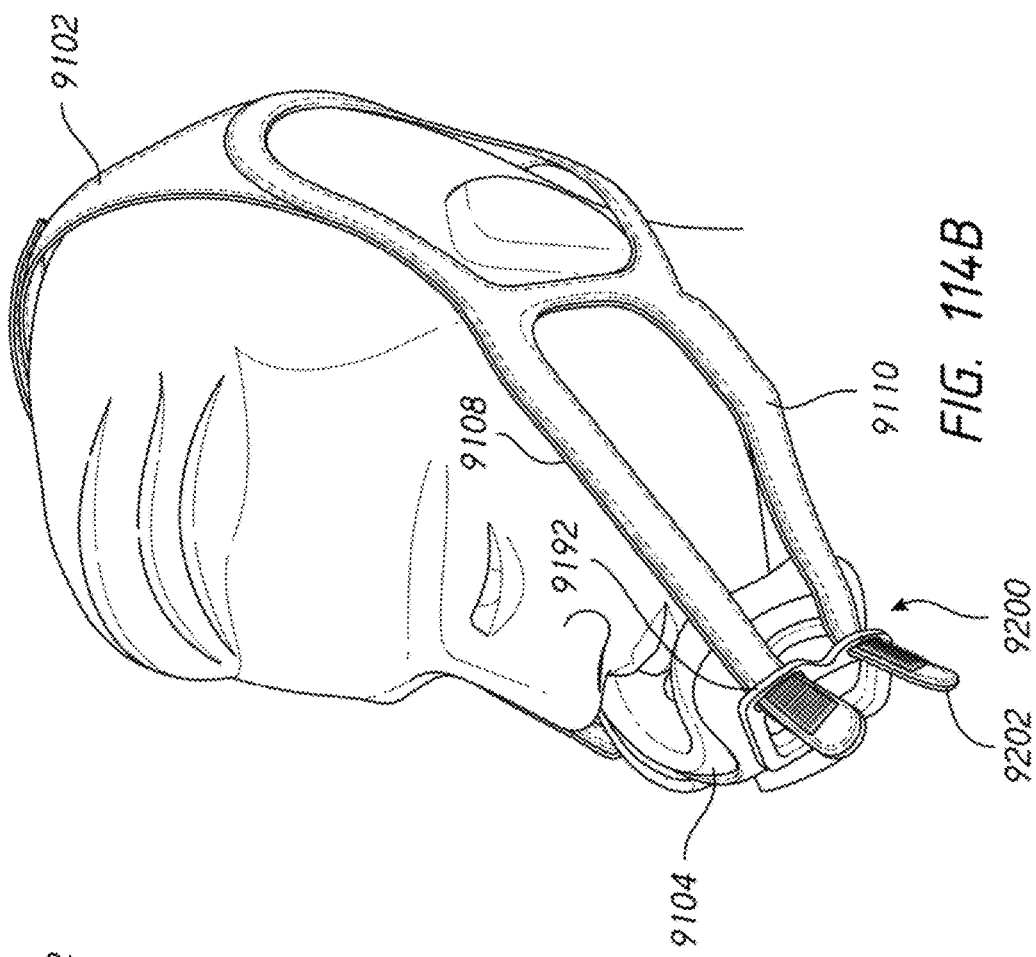
Figure 114A:
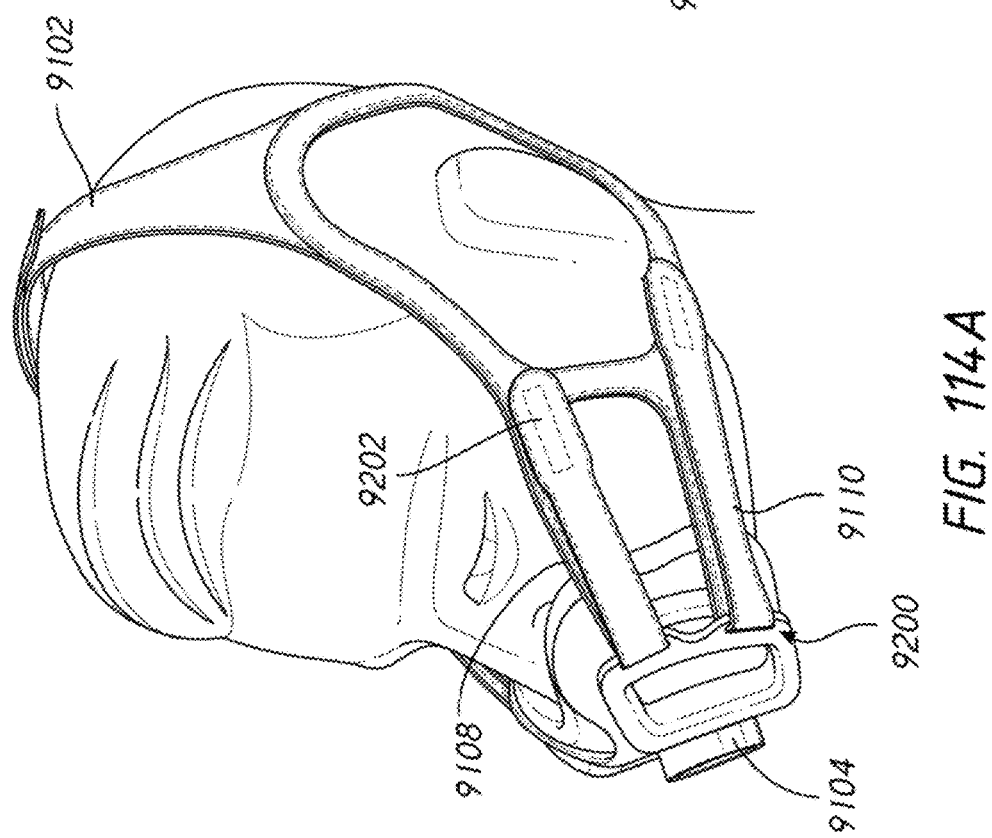

FIG. 114A shows an isometric view of a patient interface having a strap end hard stop connector in a closed position.

FIG. 114B shows an isometric view of the patient interface of FIG. 114A showing the strap end hard stop connector in an open position.

Figure 115B:
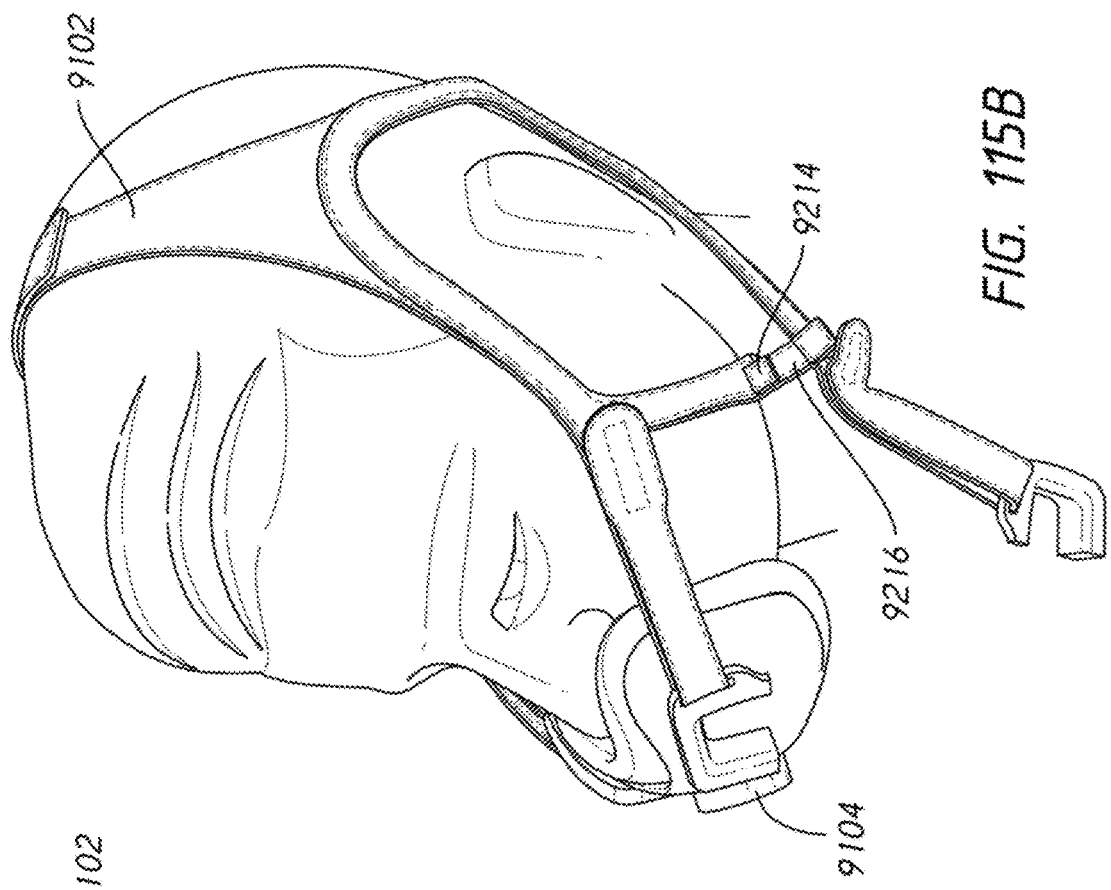
Figure 115A:
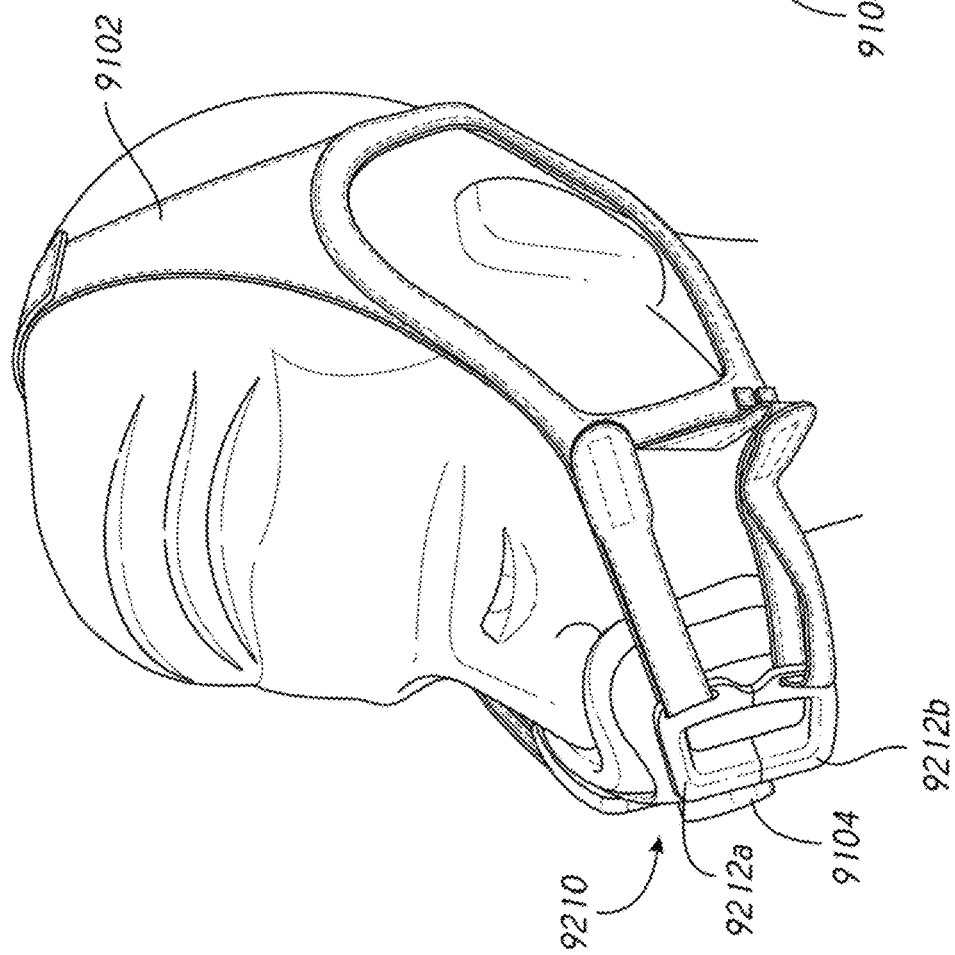

FIG. 115A shows an isometric view of a patient interface having break-fit magnets and tether connector in a closed position.

FIG. 115B shows an isometric view of the patient interface of FIG. 115A showing the break-fit magnets and tether connector in an open position.

Figure 116B:
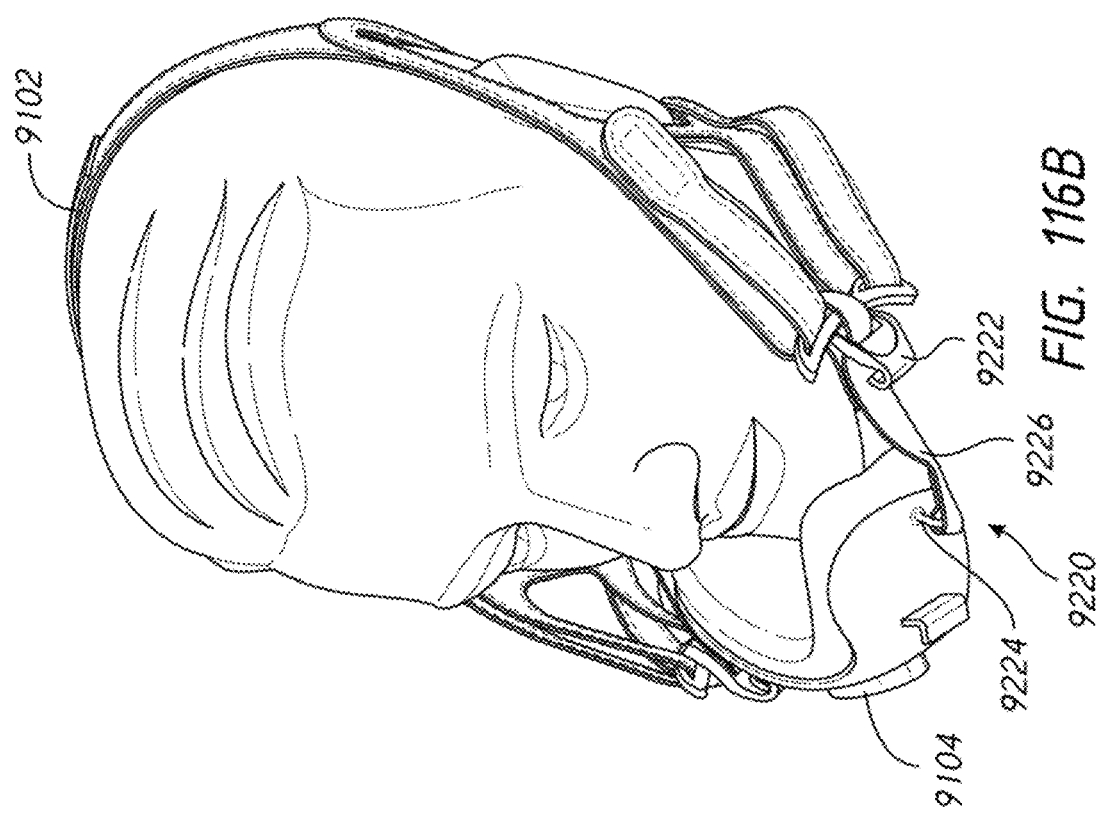
Figure 116A:
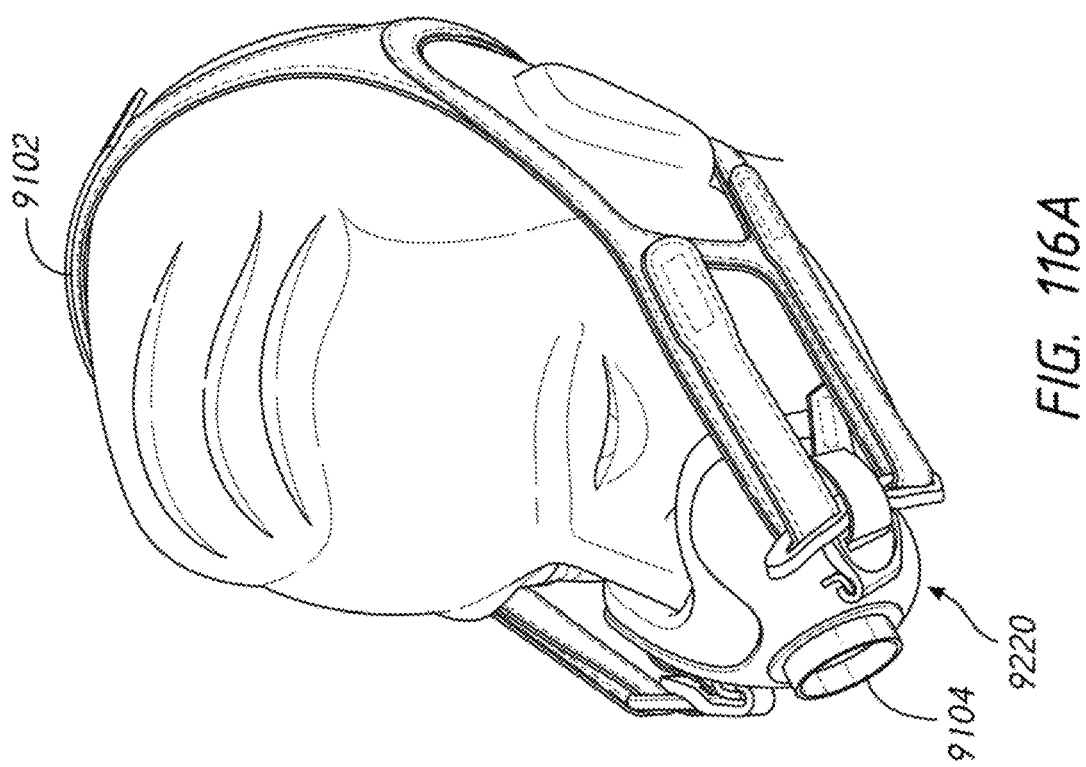

FIG. 116A shows an isometric view of a patient interface having a break-fit clip and tether connector in a closed position.

FIG. 116B shows an isometric view of the patient interface of FIG. 116A showing the break-fit clip and tether connector in an open position.

Figure 117B:
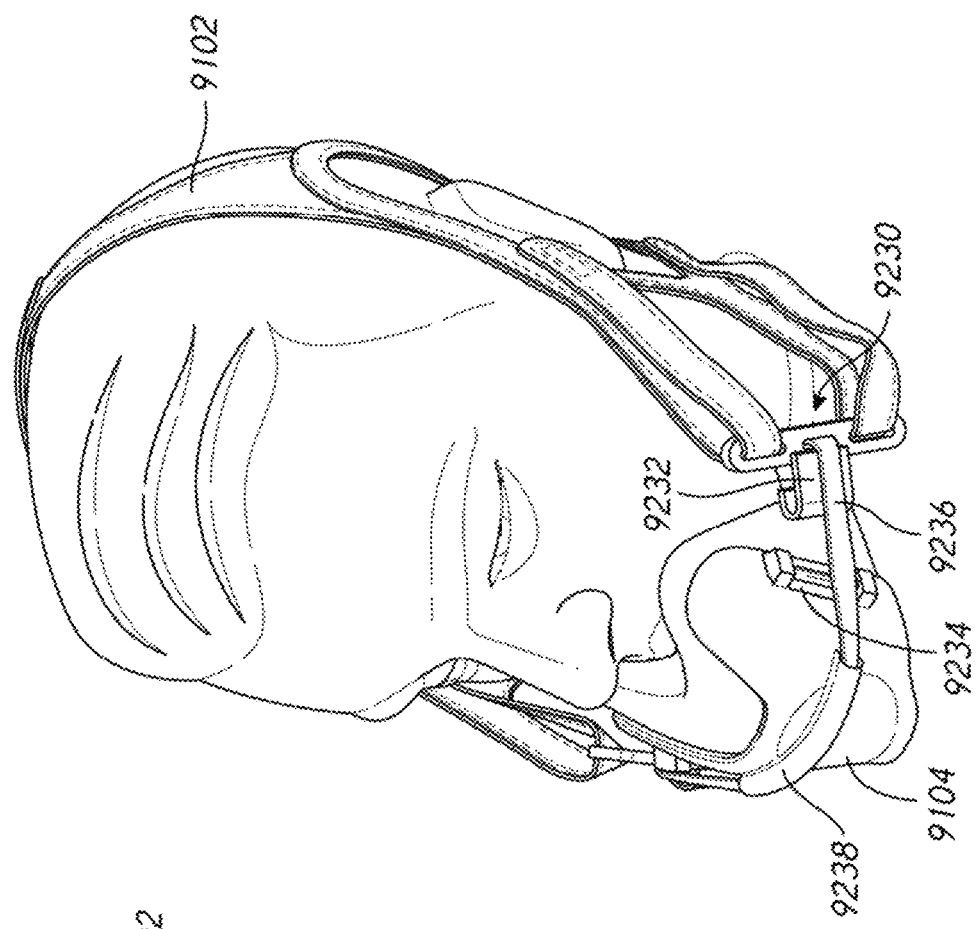
Figure 117A:
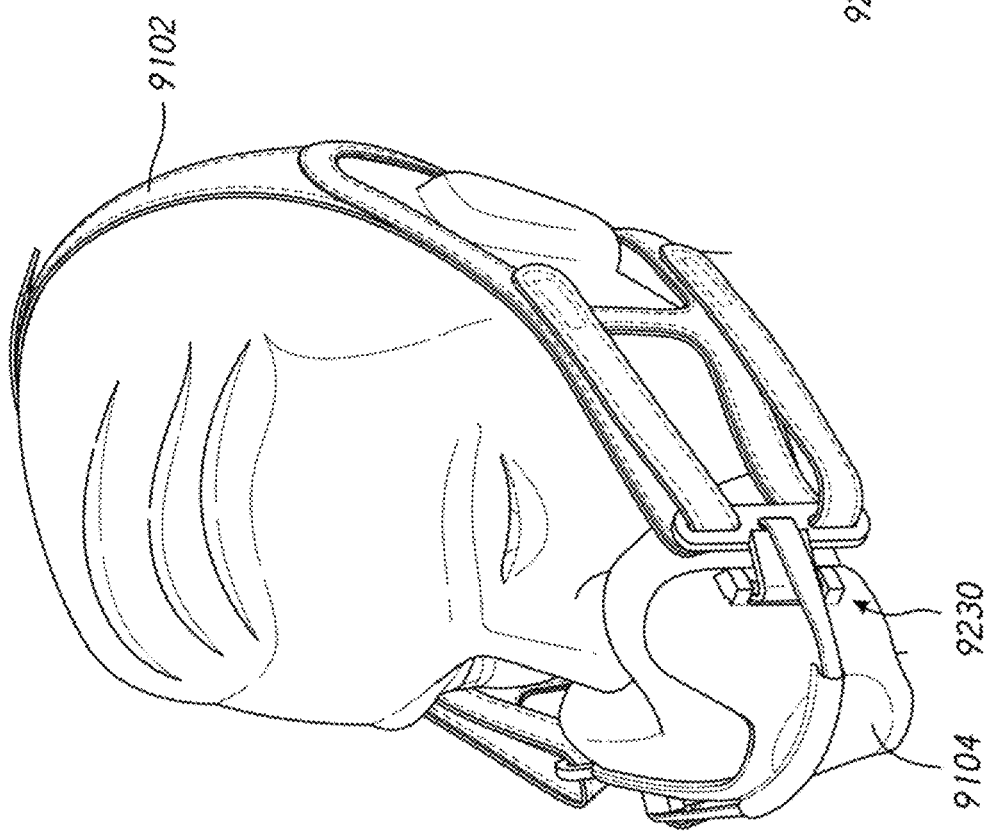

FIG. 117A shows an isometric view of a patient interface having a clip and continuous tether connector in a closed position.

FIG. 117B shows an isometric view of the patient interface showing the clip and continuous tether connector of FIG. 117A in an open position.

Figure 118B:
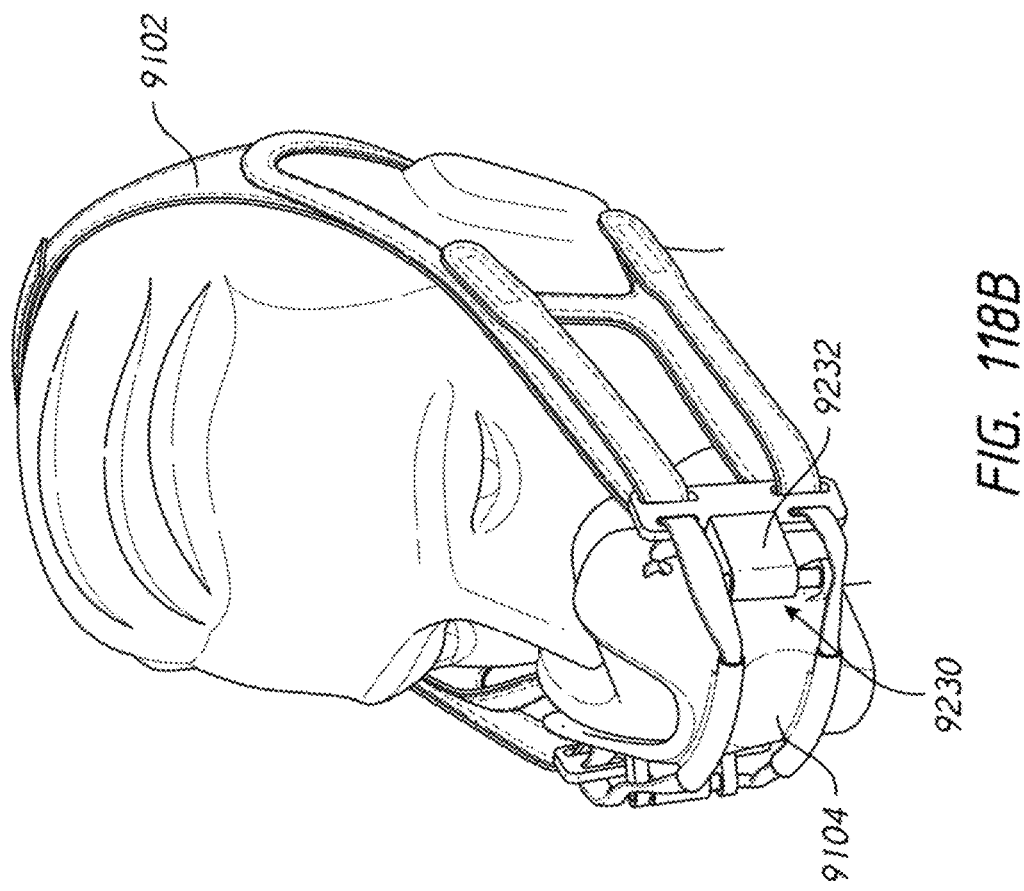
Figure 118A:
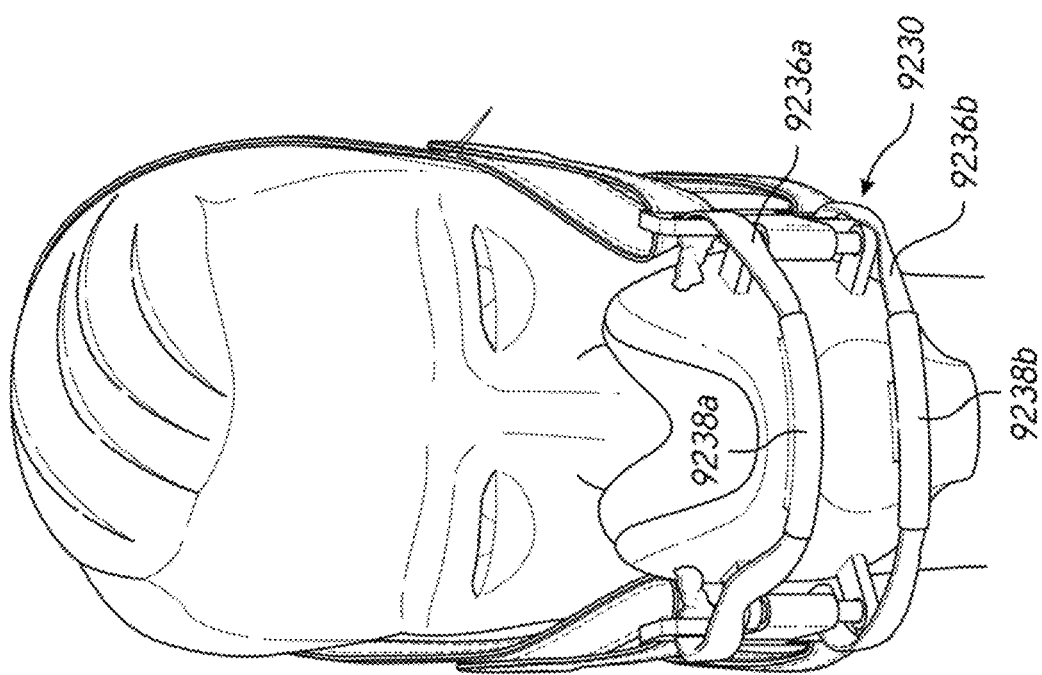

FIG. 118A shows a front view of a patient interface having dual clip and continuous tether connectors in closed positions.

FIG. 118B shows an isometric view of the patient interface of FIG. 118A showing the dual clip and continuous tether connectors in closed positions.

Figure 119B:
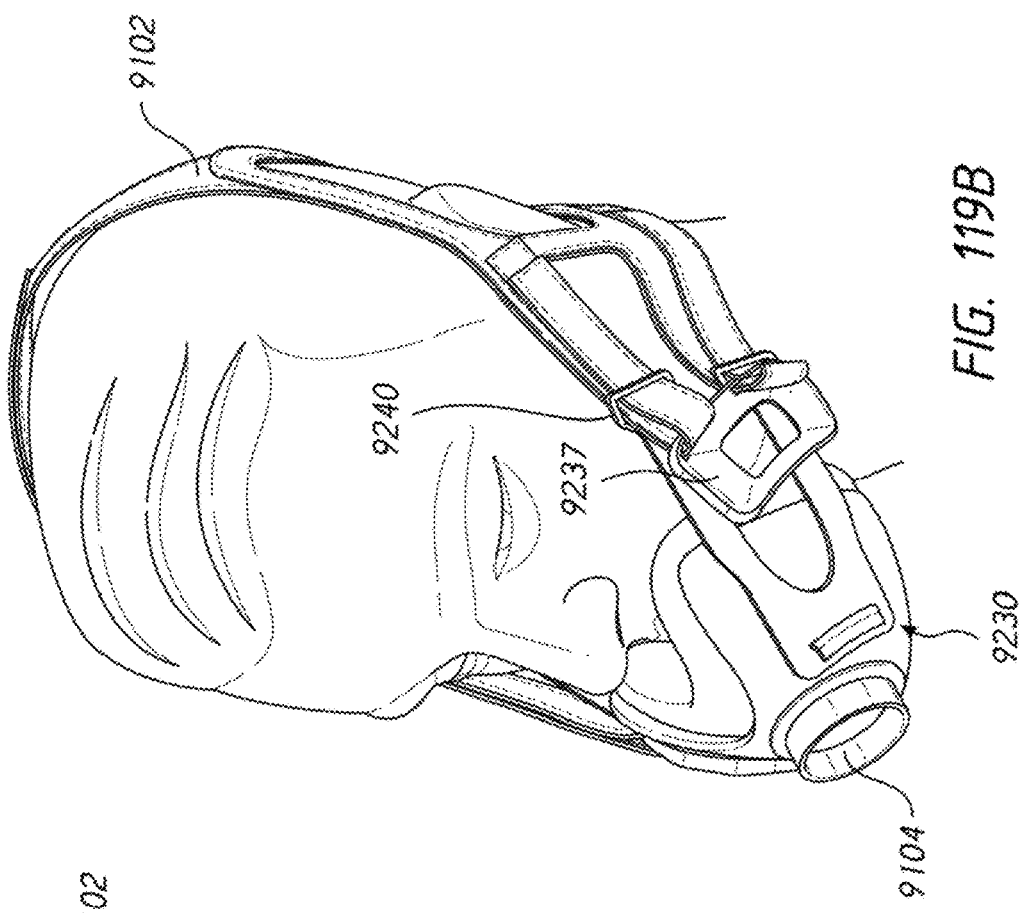
Figure 119A:
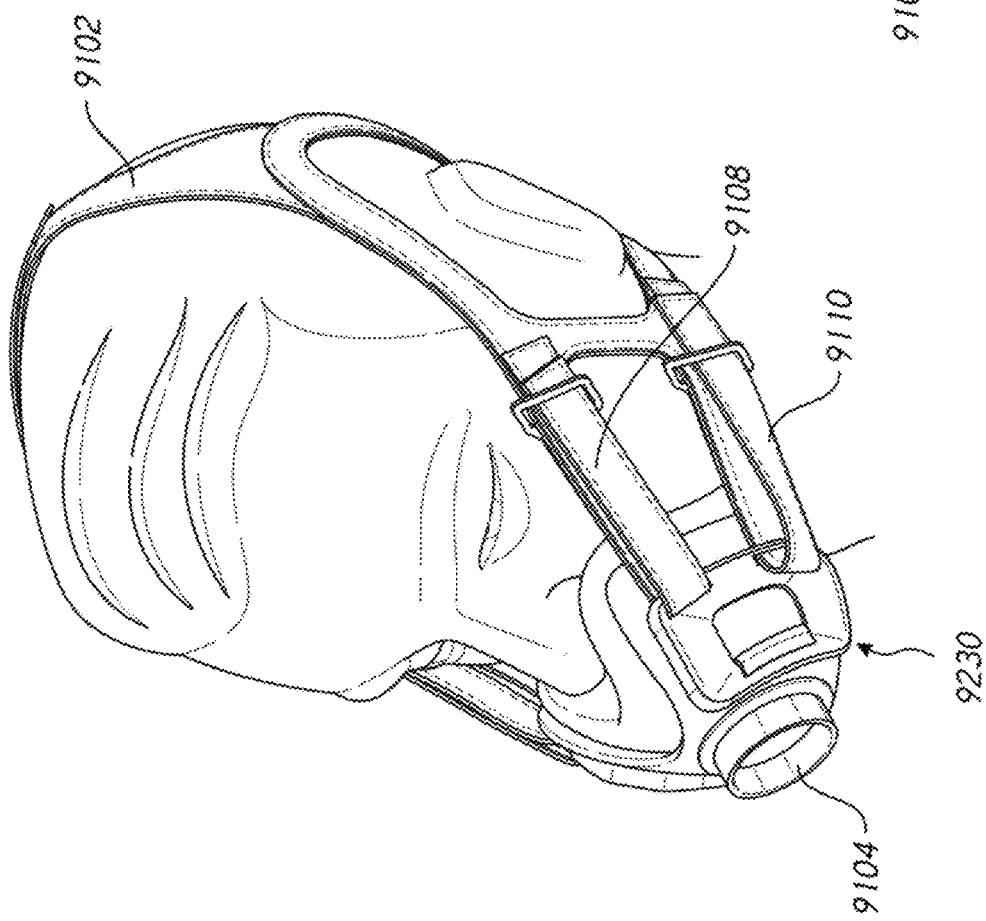

FIG. 119A shows an isometric view of a patient interface having a clip and rigid tether connector in a closed position.

FIG. 119B shows an isometric view of the patient interface showing the clip and rigid tether connector of FIG. 119A in an open position.

FIG. 120A shows an isometric view of a patient interface having a hook and post loop connector in a closed position.

FIG. 120B shows an isometric view of the patient interface showing the hook and post loop connector of FIG. 120A in an open position.

Figure 121B:
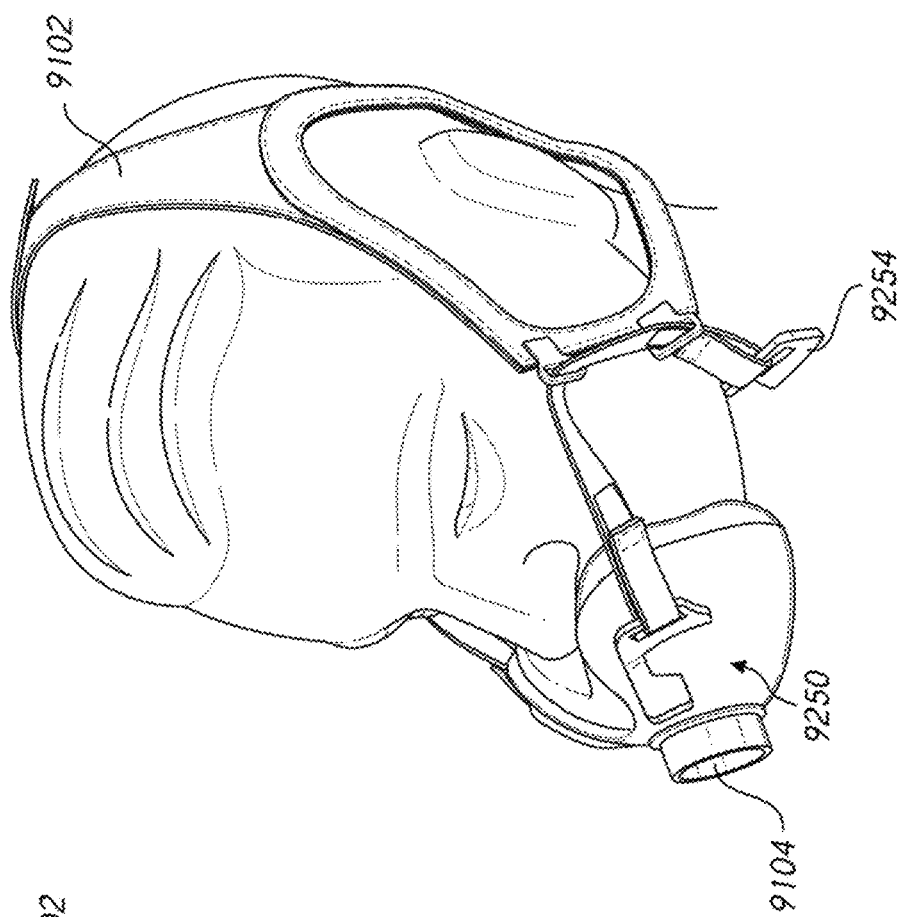
Figure 121A:
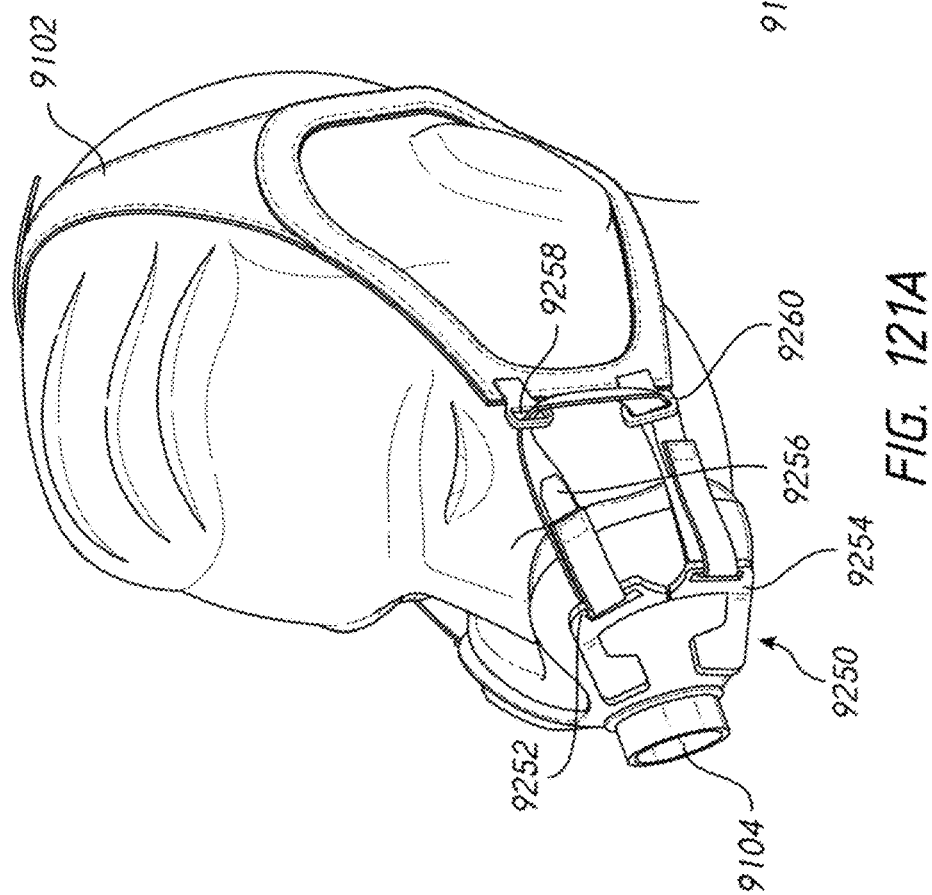

FIG. 121A shows an isometric view of a patient interface having an alternative hook and post loop connector in a closed position.

FIG. 121B shows an isometric view of the patient interface showing the alternative hook and post loop connector of FIG. 121A in an open position.

DETAILED DESCRIPTION

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

As used herein the term 'substantially inelastic' shall refer to the ability of a headgear or material to resist stretching relative to the loads to which it may be subjected. Thus, a headgear or material may be substantially inelastic in one direction and may be somewhat elastic in another direction. In some configurations, the headgear or material is configured to be substantially inelastic in a direction in which loads are applied by therapy with which the headgear or material is intended for use. A substantially inelastic headgear or material, for example, can resist stretching that would compromise a seal of a respiratory mask in a sealed system under normal or expected conditions. In an unsealed system, a substantially inelastic headgear or material, for example, can resist stretching that would compromise the appropriate placement of the respiratory interface in response to normal or expected conditions, such as hose pull forces or movement of the user. When the expected loading forces are relatively low, the headgear or material may have greater elasticity because the load will not be sufficient to cause stretching. Conversely, if it is expected that the headgear and/or material will be subjected to high loading forces, then greater inelasticity will be required to resist stretching.

Throughout this specification, reference is made to "burst-through" moulding, processes, techniques and components made by such moulding, processes and techniques. Reference is also made to "burst-through intra-moulding" and "intra-moulding burst-through". It is to be appreciated that all such references are general references to embodiments of the present disclosure and are not intended to be specifically limiting.

Headgear

Figure 1A:
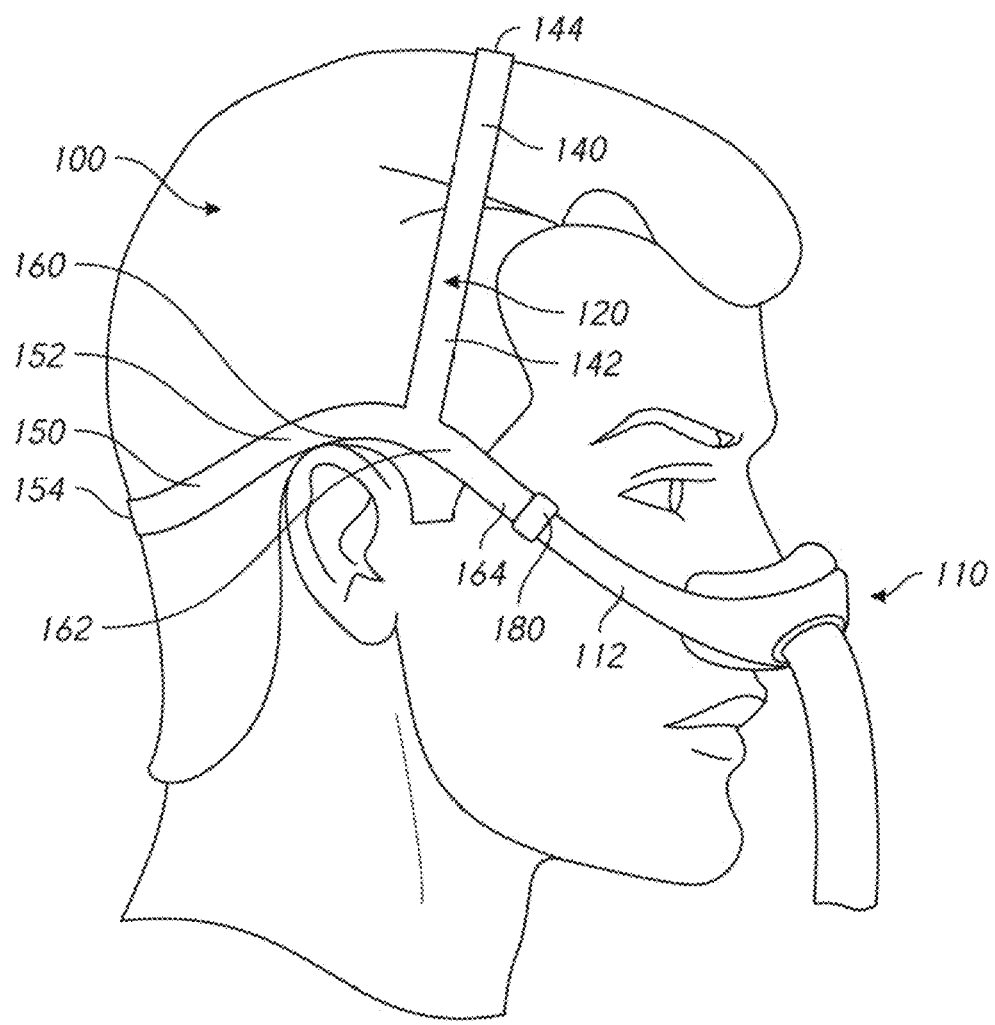
FIG. 1A illustrates a side view of a bifurcated headgear arrangement formed by the burst-through intra-moulding arrangement of the present disclosure.

FIG. 1A shows a non-limiting exemplary embodiment of an intra-moulded bifurcated headgear 100 of the present disclosure in use in combination with a breathing apparatus 110. "Intra-moulding" comprises forming a component as a plastic core and a textile casing as an integral structure by the application of molten plastic into the textile casing. A strap or any other component that has been "intra-moulded" is a component formed by the application of molten plastic into the textile casing.

Figure 1B:
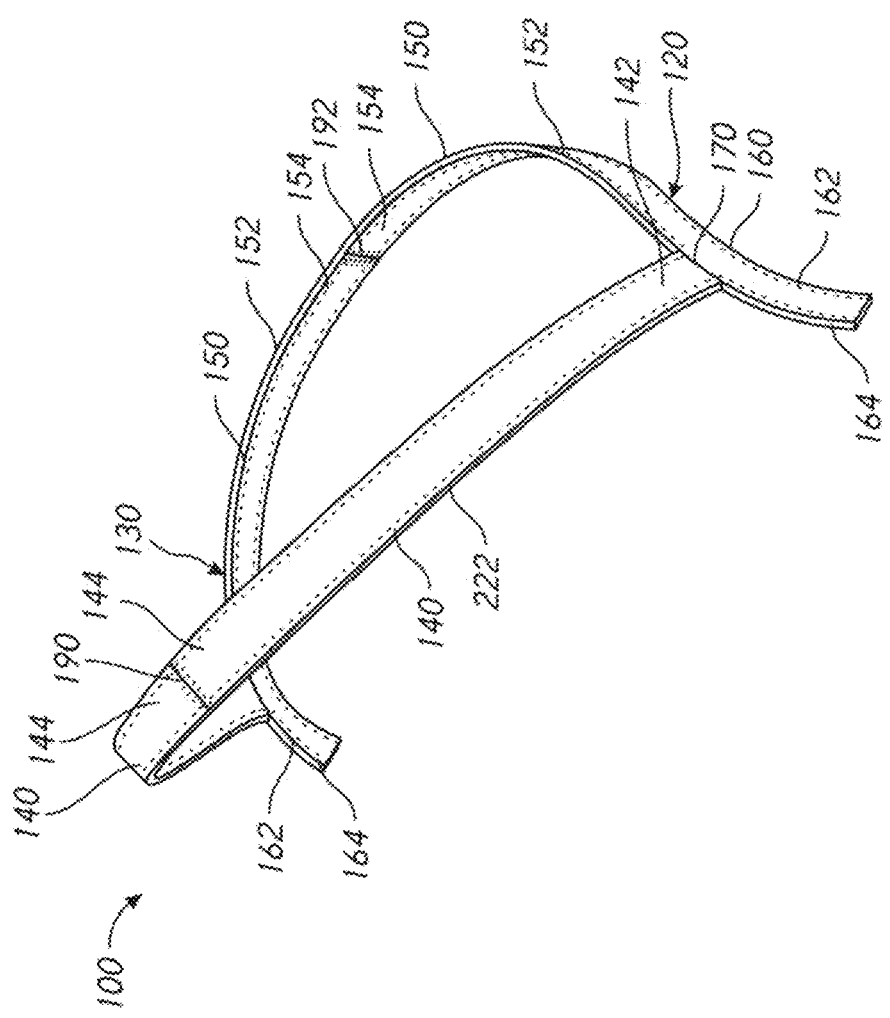
FIG. 1B illustrates a top perspective view of the bifurcated headgear arrangement of the present disclosure.

FIGS. 1A and 1B show that the bifurcated headgear 100 is configured to be substantially inelastic and three-dimensional (3D) in structure. Bifurcated headgear designs are preferred over single strap designs as they have improved stability on the patient's head since the headgear is supported at multiple locations on the user's head. As used herein, a three-dimensional structure is one that doesn't lie in a single plane, but is shaped to extend in multiple planes. In other words, the three-dimensional structure is not flat. The illustrated headgear 100 comprises a right side 120 and a left side 130. Both the right and left sides 120, 130 comprise a top strap 140, a bottom strap 150 and a mask connector 180.

The top straps 140 have an elongate shape and include a top strap lateral end portion 142 and a top strap central end portion 144. The top strap 140 is configured to extend upwardly from the lateral end portion 142 at a location generally above each ear of the user and over the parietal or frontal region of a user's head before terminating at the top strap central end portion 144. The top strap central end portion 144 is configured to be positioned at or near a central point or location on the top of the user's head. The top strap central end portions 144 of the right and left sides 120, 130 are configured to be joined together by a top joint 190 at a position over the top of the user's head. The top joint 190 may comprise stitching, welding, bonding, overmoulding, or any other fastening arrangement, which can be permanent or removable/disconnectable. In some arrangements, the top joint 190 may include an adjustment mechanism (not shown) such as hook-and-loop fasteners, snap-fit connectors, etc., to allow the combined length of the top straps 140 to be varied to accommodate different user head sizes. Each top strap lateral end portion 142 is configured to be integrally formed with the bottom strap 150 at a casing or strap junction 170, as will be discussed in further detail below. The junction 170 is located either above or just behind the user's ear in use.

The bottom strap 150 have an elongate shape and include a rear bottom strap portion 152 and a front bottom strap portion 162. The rear bottom strap portion 152 and the front bottom strap portion 162 are unitary and integral with each other. The rear bottom strap portion 152 comprises a portion of the bottom strap 150 extending rearward from the junction 170 and around the occipital region of the user's head before terminating at a bottom strap rear end portion 154. An ear arch 160 in the bottom strap 150 curves over the top of the patient's ears, when in use, so that the strap 150 avoids contact with the ears. The bottom strap rear end portion 154 is configured to be positioned at or near a central point or location on the rear of the user's head. The bottom strap rear end portions 154 of the right and left sides 120, 130 are configured to be joined together by a bottom joint 192. The bottom joint 192 may comprise stitching, welding, bonding, overmoulding, or any other fastening arrangement, which can be permanent or removable/disconnectable. In some arrangements, the bottom joint 192 may include an adjustment mechanism (not shown) such as hook-and-loop fasteners, snap-fit connectors, etc., to allow the combined length of the rear bottom strap portion 152 of the bottom strap 150 to be varied to accommodate different user head sizes.

The front bottom strap portion 162 comprises a portion of the bottom strap 150 extending forward from the junction 170 and across the user's temples towards the user's nose. In some configurations, the front bottom strap portions 162 are shorter than one or both of the top straps 140 or the bottom strap portions 152 and terminate at a bottom strap front end portion 164. The bottom strap front end portions 164 are configured to comprise, or at least attach to, a mask connector 180. The bottom strap front end portions 164 include a female recessed portion 166 which engages the mask connector 180. In some configurations, the mask connector 180 may be pressed or overmoulded onto the bottom strap front end portion 164 and into the female recessed portion 166. The mask connector 180 can include a clip or retaining feature configured to join to the breathing apparatus 110. The mask connector 180 may include a push fit, snap fit or other suitable connector that is configured to provide a detachable connection to a mask frame 112 of the breathing apparatus 110. In some embodiments, the mask connector 180 may be configured to connect to an adjustment mechanism, wherein the adjustment mechanism provides a means for automatically or manually adjusting the size of the bifurcated headgear 100. In some configurations, the mask connector 180 may be permanently connected to a mask frame or yoke to form a continuous loop between the headgear 100 and the breathing apparatus 110.

The right and left sides 120, 130 of the bifurcated headgear 100 are formed as substantially two-dimensional (2D) pieces, i.e., they are formed in a flat structure. When the top straps 140 and the bottom straps 150 of the right and left sides 120, 130 are joined together, a 3D bifurcated structure is formed (as shown in FIG. 1B). In some configurations, the composition of the bifurcated headgear 100 is such that the 3D bifurcated structure is maintained at all times, at least when the right and left sides 120, 130 are connected. This 3D structure may improve the ease with which a user interacts with and fits or dons the bifurcated headgear 100 and the associated breathing apparatus 110. Because the bifurcated headgear 100 holds its shape, the straps are less likely to get tangled and it should be easier for a user to grasp and orient the bifurcated headgear 100. In some configurations, the bifurcated headgear 100 at least maintains partial or complete separation of the sides 120, 130. In some configurations, the bifurcated headgear 100 at least maintains partial or complete separation at the junctions 170 and/or the front bottom strap portions 162 of the opposite sides 120, 130.

The top strap 140 and the bottom strap 150 are each comprised of a unitary plastic core material 210 surrounded by and bonded to an outer casing 220. The casing 220 may be knitted, woven, braided, crocheted, etc. The unitary plastic core material 210 forms both the top strap 140 and the bottom strap 150. That is, the plastic core material 210 is unitary between the top strap 140 and the bottom strap 150 and throughout the bifurcated headgear 100. The casing 220 of both the top strap 140 and the bottom strap 150 may be knitted, woven, braided crocheted, etc. into a seamless, continuous and uninterrupted tube. That is, the casing 220 may have a seamless and uniform outer surface along the length of the top strap 140 and the bottom strap 150. The casing 220 may be woven from spools of thread containing wool, cotton, nylon, lycra, spandex or a blend of natural and/or synthetic materials. In some configurations, the casing 220 may be loosely woven such that the casing 220 is capable of extending in length without stretching or tearing of the threads. The amount of lycra within the thread may be varied to vary the elasticity of the strap.

The casing 220 provides a clean and tidy edge finish to the intra-moulded bifurcated headgear 100. That is, the top strap 140 and the bottom strap 150 have a uniform shape and form that is devoid of seams to provide an aesthetically pleasing appearance. Further, straps 140, 150 that are formed from the casing 220 are easier to manufacture. A seamless circular woven tube does not require an additional step of sewing or bonding which reduces manufacturing time and cost. Further, it is easy to produce and form long lengths of straight woven tubes which can then be cut to length and shaped during a burst-through intra-moulding process as described herein. Even further, the casing 220 is easy to locate and position within a moulding tool. The tubular shape and circular cross-section of the casing 220 is self-supporting and remains open within the moulding tool to provide an open flow path for the injected material through the casing.

The casing 220 is flexible prior to having plastic core material 210 inserted therein such that the casing 220 may be easily positioned with the cavity of the moulding tool. The casing 220 may be knit from a material having a soft texture such that the top strap 140 and the bottom strap 150 are comfortable when in contact with the user's skin. Similarly, the casing 220 may have a thickness and ply such that the top strap 140 and the bottom strap 150 are comfortable when in contact with the user's skin. Further, in some configurations, the casing 220 may be knit from a material having moisture wicking properties to improve the comfort of the bifurcated headgear 100. Even further, in some configurations, the casing 220 may be knit from a material having tactile properties to reduce or inhibit the bifurcated headgear 100 from sliding against the user's skin or hair. In some configurations, the casings 220 may be different between the top strap 140 and the bottom strap 150. For example, the bottom strap 150 may be constructed from a material having moisture wicking properties while the top strap 140 is constructed from a material having tactile properties. Still further, in some configurations, the casings 220 may be constructed from different materials along the lengths of the top strap 140 and the bottom strap 150 such that different regions along the length of the straps 140, 150 have different properties. For example, the top strap 140 and bottom strap 150 may have different colors.

The casings 220 of the top strap 140 and the bottom strap 150 are filled with a unitary plastic core material 210. In some configurations, the plastic core material 210 comprises a relatively rectangular cross-section of a thermoform or thermoset plastic material that is configured to provide the bifurcated headgear 100 with the aforementioned 3D structure. The plastic core material 210 provides the foundation for the overall structure of the bifurcated headgear 100. The plastic composition of the plastic core material 210 offers the benefits of a resilient structure that is capable of maintaining a preformed shape while conforming somewhat to the individual cranial geometry of the user. The plastic core material 210 has a width and that is substantially greater than its depth. The illustrated cross-sectional geometry in combination with the material selection allows the bifurcated headgear 100 to be flexible in a direction that is normal to the width (the vertical direction in FIG. 1A) and relatively inflexible in a direction that is normal to the depth (the horizontal direction in FIG. 1A). This flexibility in one direction allows the bifurcated headgear 100 to conform to a user's head while providing rigidity in another direction that stabilizes and minimizes dislodging of the breathing apparatus 110 on a user's face.

The bifurcated headgear 100 can be configured to be substantially inelastic as a result of material selection, for example. One or more elements of the composite material may provide the bifurcated headgear 100 with substantially inelastic qualities. In the first non-limiting exemplary embodiment of this disclosure, the plastic core material 210 is made from a substantially inelastic material, such as polypropylene or nylon, for example but without limitation. In embodiments where the bifurcated headgear 100 is expected be subjected to low loading forces, the plastic core material 210 may be made of other materials, such as, but not limited to, thermoplastic elastomers (TPE) or silicone. In some embodiments, the plastic core material 210 may have a degree of elasticity and one or both of the casings 220 of the top strap 140 and the bottom strap 150 can be substantially inelastic. The inclusion of a substantially inelastic material in the bifurcated headgear 100 is advantageous because the material reduces or eliminates the likelihood of the headgear being stretched or pulled too far over the user's head. If the bifurcated headgear 100 is pulled too far over the user's head, the breathing apparatus may not be effectively positioned to provide therapy and uncomfortable forces may be applied to the user's head, which can result in reduced compliance with therapy.

Junction

Figure 2B:
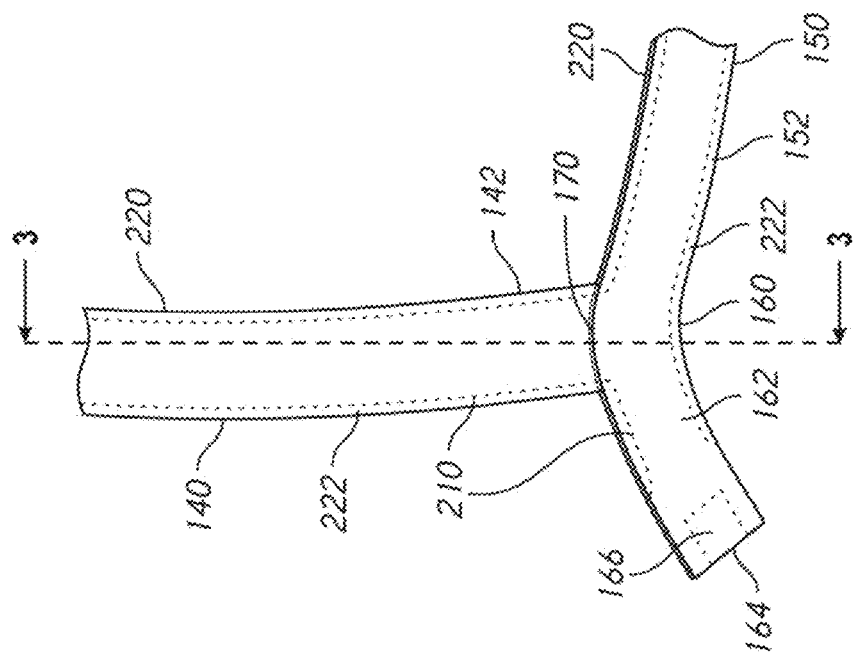
FIG. 2B illustrates a close-up side view of a junction between top and bottom straps of the bifurcated headgear arrangement of the present disclosure.
Figure 2A:
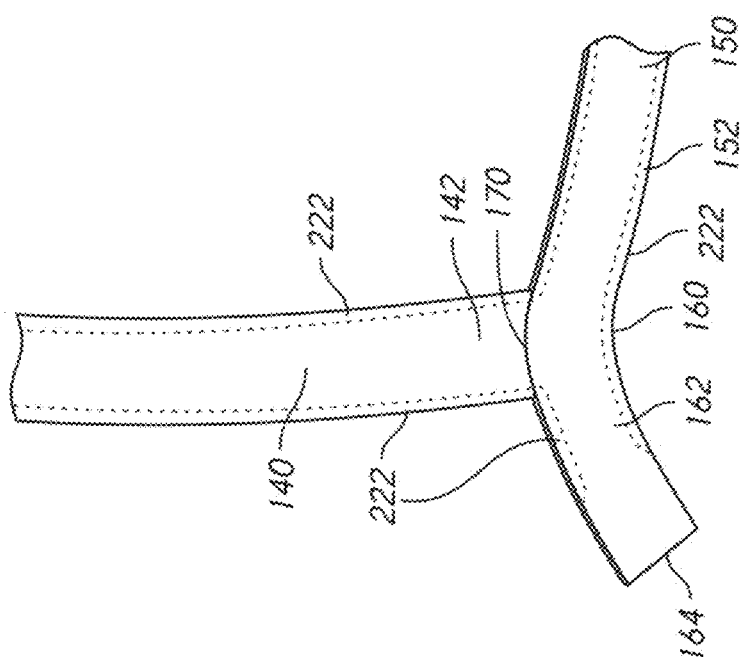
FIG. 2A illustrates a close-up side view of a junction between top and bottom straps of the bifurcated headgear arrangement of the present disclosure.
Figure 3:
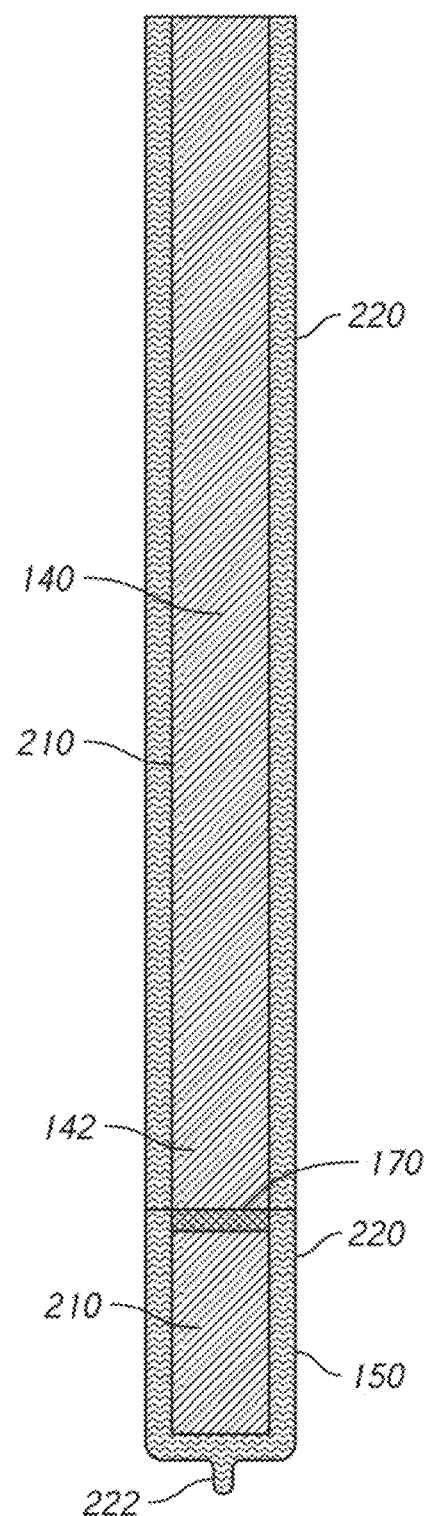
FIG. 3 illustrates a cross-sectional view of the junction between top and bottom straps of the bifurcated headgear arrangement of the present disclosure.

FIGS. 2A and 2B are close-up views of the connection between the top strap 140 and the bottom strap 150 at the junction 170. As stated above, the plastic core material 210 is unitary and is positioned within the casings 220 of both the top strap 140 and the bottom strap 150. FIG. 3 is a cross-sectional view of the top strap 140 and the bottom strap 150 along a line 3-3 in FIG. 2B. As illustrated, the bottom strap 150 is filled with the plastic core material 210 which extends through casing 220 of the bottom strap 150 at the junction 170 and into top strap lateral end portion 142 to fill the top strap 140. As a result, the casings 220 of the top and bottom straps 140, 150 are bonded together by the plastic core material 210.

As shown in FIGS. 2A to 3, the top and bottom straps 140, 150 may have a soft edge portion 222 that extends along the edges of portions of the top and bottom straps 140, 150 in a lengthwise direction. The soft edge portion 222 is a portion of the casing 220 that is not filled with plastic core material 210. As a result, the soft edge portion 222 provides the top and bottom straps 140, 150 with a soft or cushioned edge that is comfortable against the user's skin and that is also aesthetically pleasing. As will be described in further detail below, the soft edge portion 222 is formed by crimping the edges of the casing 220 prior to injecting of the plastic core material 210 such that the plastic core material 210 is inhibited or restricted from flowing into the portions of the casing 220. The edges of the casing 220 are crimped by a portion of the moulding tool adjacent a mould cavity of the moulding tool. The depth of crimping of the edges of the top and bottom straps 140, 150 by the moulding tool may vary along the length of the top and bottom straps 140, 150 such that the width (the vertical direction in FIG. 1A) of the plastic core material 210 may vary along the length of the top and bottom straps 140, 150. As such, the width of plastic core material 210 may be wider at different regions of the top and bottom straps 140, 150 such as the junction 170 and the bottom strap front end portion 164 to reinforce and provide additional strength to those regions. Similarly, in some configurations, the width of the plastic core material 210 may be narrower at certain regions along the length of the top and bottom straps 140, 150 to provide flexibility to those narrower regions. It should be understood to one of ordinary skill in the art that the shape and geometry of the plastic core material may vary to provide strength and stiffness to the top and bottom straps 140, 150 in the desired directions.

Mould Tool

Figure 4:
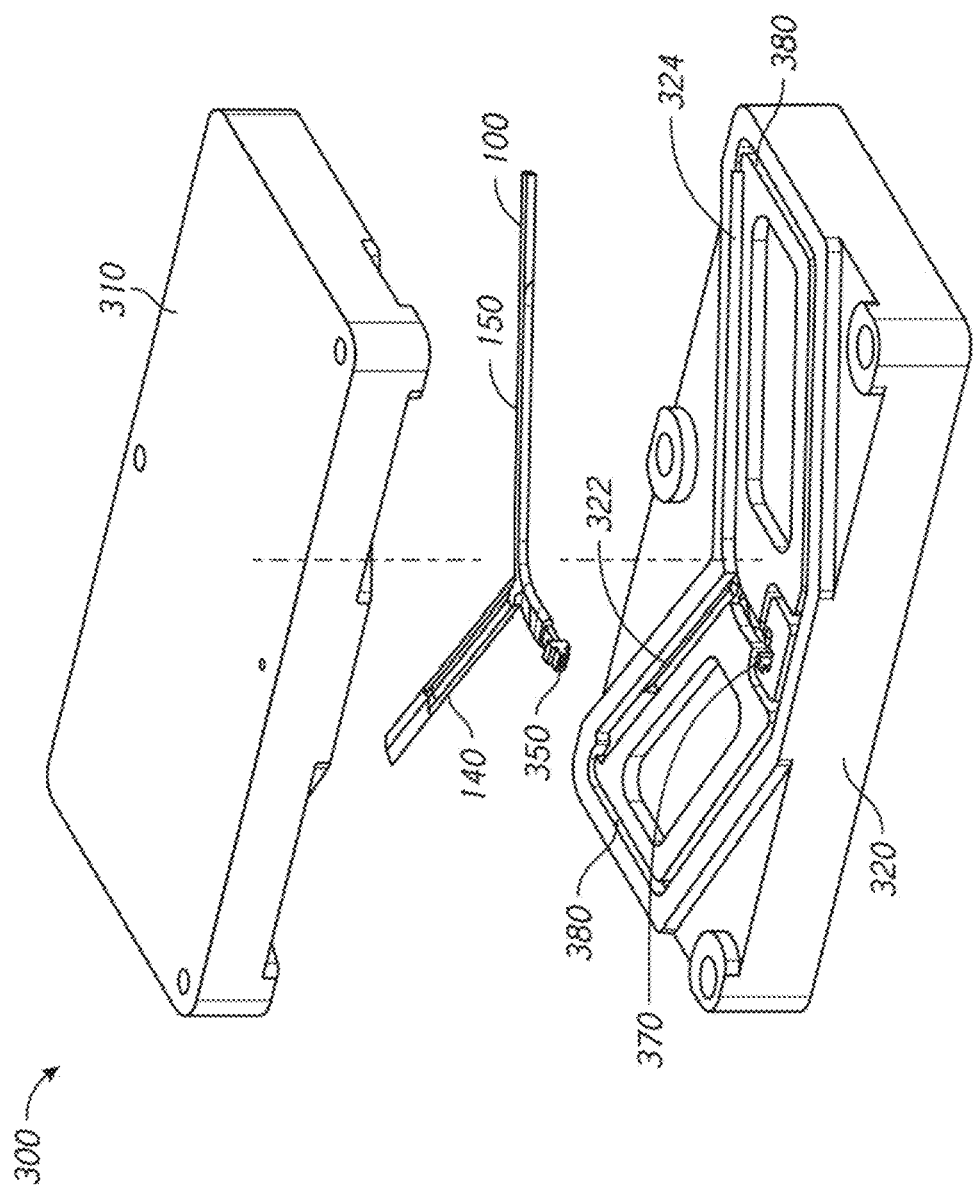
FIG. 4 illustrates a perspective of an injection moulding tool for forming the bifurcated headgear arrangement of the present disclosure.
Figure 5:
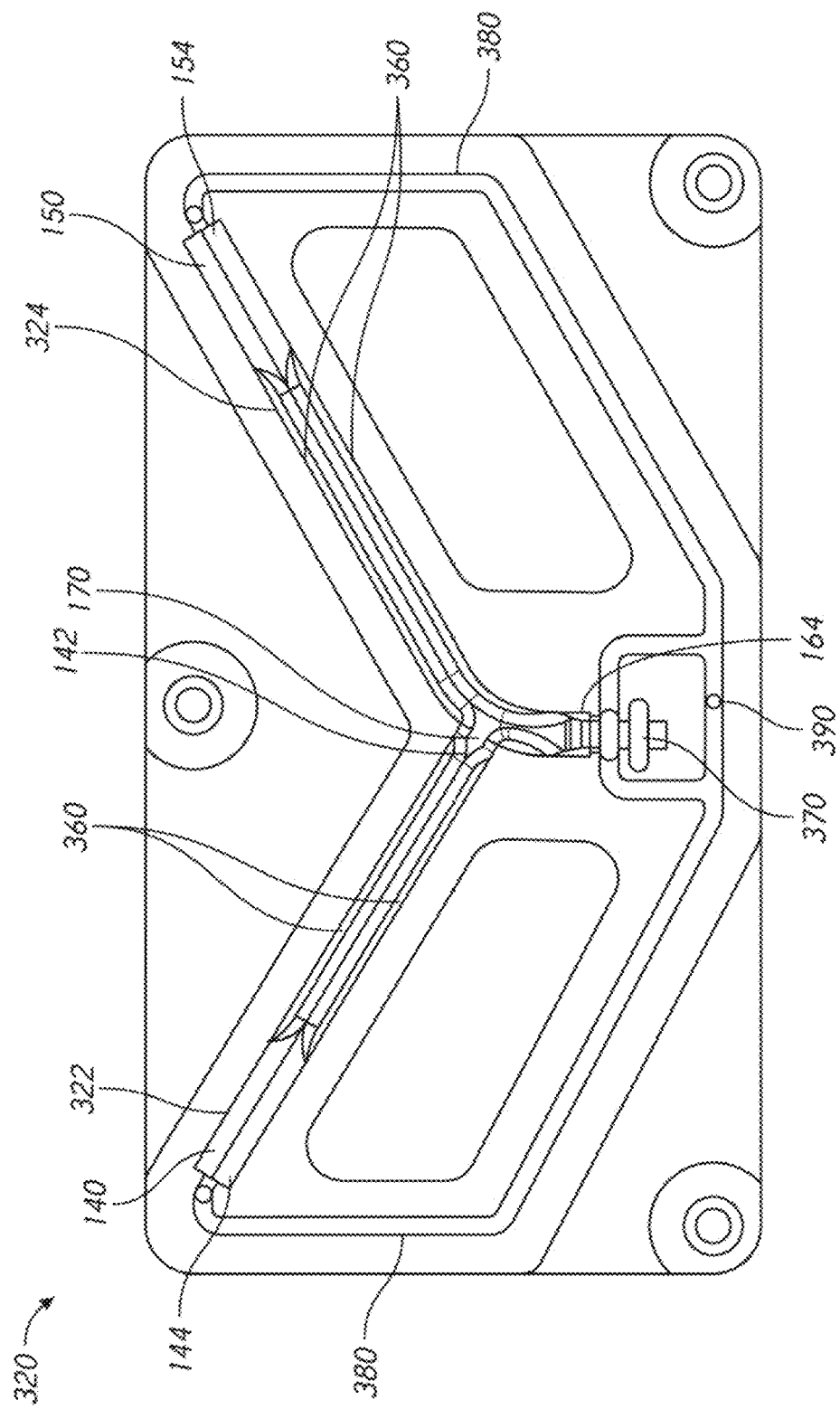
FIG. 5 illustrates a top down view of a second tool half of the injection moulding tool.

FIG. 4 shows an open/shut injection moulding tool 300 configured to form a right side 120 or a left side 130 of the bifurcated headgear 100 in a single injection moulding process. In some configurations, the right and left sides 120, 130 are identical in which the injection moulding tool 300 may be used to form both sides 120, 130. FIG. 4 shows a fully formed bifurcated headgear 100 after the completion of the injection moulding process. The injection moulding tool 300 comprises a first tool half 310 and a second tool half 320. The first tool half 310 is configured to be aligned with and placed on top of the second tool half 320 to close the injection moulding tool 300. The first and second tool halves 310, 320 are substantially symmetrical (i.e., mirror images) and, therefore, for the sake of brevity, the following discussion will refer to the second tool half 320. As illustrated in FIG. 5, the second tool half 320 includes a top strap cavity 322 and bottom strap cavity 324. The top and bottom strap cavities 322, 324 are configured to receive the casings 220 for both the top and bottom straps 140, 150. Accordingly, top and bottom strap cavities 322, 324 are arranged in a shape corresponding to the desired shape of the left and/or right sides of the bifurcated headgear 100. In some configurations, injection moulding tool 300 may be used to form both the right and left sides 120, 130 of the bifurcated headgear 100. In some configurations, the casings 220 are cut to length to fit within the strap cavities 322, 324 prior to closing the moulding tool 300.

Figure 7:
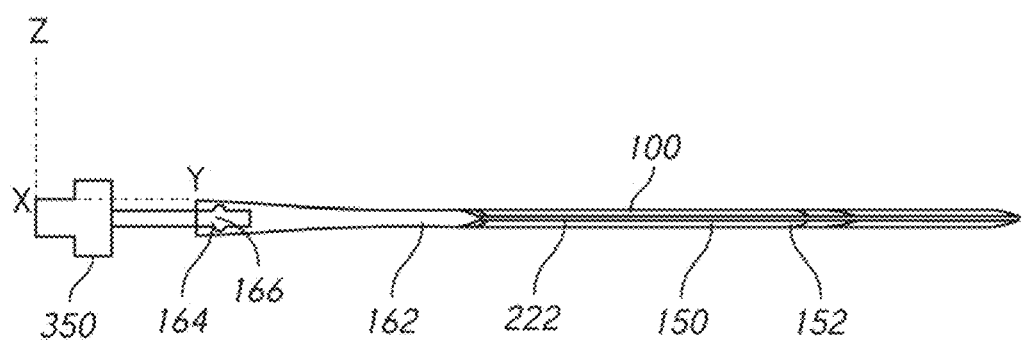
FIG. 7 illustrates a cross-section bottom view of a fully formed bifurcated headgear portion.

A connector insert 350 is inserted into the bottom strap front end portion 164 of the casing 220. A connector insert cavity 370 is positioned within the second tool half 320 and has a corresponding shape as the connector insert 350. Both the connector insert 350 and the casing 220 are positioned within the connector insert cavity 370 and the strap cavities 322, 324, respectively. When using a casing 220 to form the straps 140, 150 of a bifurcated headgear 100, the end of the casing 220 is open or formed as a hollow tube which provides a passage for the plastic core material 210 to be injected within the casing 220. Accordingly, the connector insert 350 positioned within an open end of the bottom strap 150 reduces or inhibits narrowing or closing of the open end of the casing 220. The connector insert 350 comprises a pre-made component that fits inside the open end of the casing 220 and pushes the opening of the casing 220 outwards towards the walls of the strap cavities 322, 324 in the first and second tool halves 310, 320. The connector insert 350 has openings (not shown) that are aligned with runners 380 through which a direct flow path is provided for plastic core material to be injected into the casing 220. The connector insert 350 is also configured to form an internal (female) connection geometry within the bottom strap front end portion 164 (see FIG. 7) that connects with an opposing male connector geometry (not shown) on the mask frame or other mask component. The connector insert 350 may be made of plastic or metal. If made of plastic, in some configurations, the connector insert 350 may be made of the same plastic as that of the core so that a chemical bond can be formed between the connector insert 350 and the plastic core material during the burst-through intra-moulding process. Further, the connector insert 350 may be formed in a shape that can have additional function as a connector between headgear components, adjustment mechanisms or between the headgear and mask (e.g., connector 180).

As shown in FIGS. 4 and 5, the runners 380 fluidly connect the sprue injection point 390, the bottom strap front and rear end portions 154, 164 and the top strap central end portion 144. Accordingly, when plastic core material 210 is injected into the first and second tool halves 310, 320, the plastic core material 210 is injected into the casings 220 through each of the bottom strap front and rear end portions 154, 164 and the top strap central end portion 144.

The top and bottom strap cavities 322, 324 have soft edge clamps 360 that are formed along one or both of the outer edges of the cavities 322, 324 in a lengthwise direction. The soft edge clamps 360 are raised regions that protrude into the top and bottom strap cavities 322, 324 in a direction substantially parallel with the closing direction of the injection moulding tool 300 such that the top and bottom strap cavities 322, 324 narrow along one or both of the outer edges of the cavities 322, 324 in a lengthwise direction (i.e., narrowing of outer edges relative to a center region of the cavities 322, 324) when the injection moulding tool 300 is closed. Accordingly, the soft edge clamps 360 clamp or crimp the outer edges of the casings 220 for both the top and bottom straps 140, 150 such that the soft edge portion 222 are formed. More specifically, the soft edge clamps 360 press the edges of the casings 220 together such that the edges are fully crimped. As a result, the plastic core material 210 is unable to flow between the crimped edges when the plastic core material 210 is injected into the casings 220. This creates a soft or cushioned edge finish on the intra-moulded bifurcated headgear 100 by preventing intra-moulded plastic core material 210 from filling the casing 220. A portion on each edge of the straps 140, 150 remains empty and soft to touch, to improve patient comfort. In some configurations, the edges of the casings 220 may be narrowed but not fully crimped such that a reduced amount of plastic core material 210 (relative to uncrimped portions of the casing 220) may flow between the edges of the casings 220.

Figure 6:
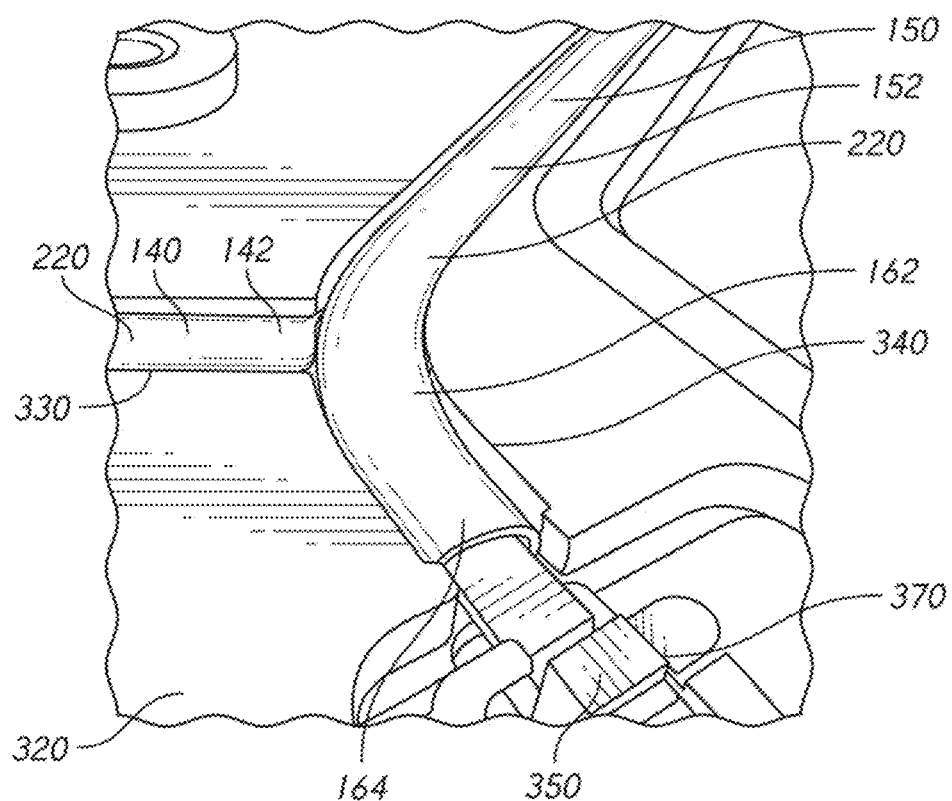
FIG. 6 illustrates a close-up top perspective view of the top and bottom straps positioned within the second tool half of the injection moulding tool.

FIG. 6 is a close-up view of the second tool half 320 illustrating the positioning of the top and bottom straps 140, 150 relative to each other. As shown, the top strap lateral end portion 142 is positioned against or in contact with the casing 220 of the bottom strap 150. That is, the casing 220 of the top strap 140 is placed within the top strap cavity 330 such that the top strap lateral end portion 142 abuts against an edge of the casing 220 of the bottom strap 150. As will be described in greater detail below, the arrangement of the straps is not limited to having an open end of one strap in contact with an edge of another strap. In some configurations, the straps may have middle or non-end portions in abutting contact with each other, through which the straps are bonded.

Moulding Process

A process of moulding the left or right sides 120, 130 of the bifurcated headgear 100 using the injection moulding tool 300 comprises the following steps: inserting the casings, closing the tool; injecting plastic; and opening the tool to release part. In some configurations, the steps are accomplished in this order; however, in other configurations the order may be changed and/or additional steps may be included. Such additional steps may be interposed within the above-identified steps.

In at least some embodiments, the process of moulding the left or right sides 120, 130 of the bifurcated headgear 100 comprises a "burst-through" moulding process as described below.

A first length of the casing 220 is inserted into the bottom strap cavity 324 of the second tool half 320 of the injection moulding tool 300, which is configured to form the bottom strap 150. Similarly, a second length of the casing 220 is inserted into the top strap cavity 322, which is configured to form the top strap 140. The casing 220 can be cut to length such that it fits snuggly within the strap cavities 322, 324. The connector insert 350 is positioned inside an open end of the second length of the casing 220 (i.e., the bottom strap front end portion 164) and the connector insert 350 is aligned with and inserted into the connector insert cavity 370.

Once the casings 220 are aligned within the second tool half 320, the injection moulding tool 300 is shut such that the strap cavities 322, 324 become fully enclosed. Thermoset or thermoform plastic core material 210 is then injected into the mould cavity strap cavities 322, 324 via the sprue 390 and the runner 380. More specifically, the plastic core material 210 is injected into the injection moulding tool 300 through the sprue 390. Generally, the plastic core material 210 follows the path of least resistance in order to fill the strap cavities 322, 324. The plastic core material 210 travels through the runners 380 until reaching the open ends of the casings 220. The plastic core material 210 enters the top strap central end portion 144, the bottom strap rear end portion 154, and the bottom strap front end portion 164 (via the connector insert 350). With reference to FIG. 6, when the casing 220 in the bottom strap cavity 324 is full of plastic core material 210 (i.e., since it is being filled from both open ends as opposed to the casing 220 in the top strap cavity 322 which initially is filled at one end), the plastic core material 210 will burst through, penetrate through, and push through the wall of the casing 220 of the bottom strap 150 at the junction 170. The plastic core material 210 that penetrates the wall of the bottom strap 150 enters the open end of the casing 220 of the top strap 140 (i.e., the top strap lateral end portion 142) and joins the plastic core material 210 entering the opposite end of the casing 220 of the top strap 140 (i.e., from the top strap central end portion) until the casing 220 of the top strap 140 is filled with plastic core material 210. Once the casings 220 of the straps 140, 150 are filled, the plastic core material 210 is provided time to set, cool and solidify. Once set, the injection moulding tool 300 is opened and the part is removed. Accordingly, a unitary plastic core material 210 may be formed within the top and bottom straps 140, 150 with seamless and uniform casings 220 of the top and bottom straps 140, 150. That is, the unitary plastic core material 210 of the top and bottom straps 140 may be formed by pushing the plastic core material 210 into the top strap 140 through the casing 220 of the bottom strap 150. In other words, forming a unitary plastic core material 210 within the top and bottom straps 140 when both straps have seamless and uniform casings 220 and one strap is attached to a middle or non-end portion of the seamless adjoining strap is an advantageous effect of the burst-through intra-moulding process. In other embodiments, the plastic core material 210 penetrates and bursts through the casing 220 prior to the casing 220 and strap cavity being filled with plastic core material 210. This may occur, for example where the unsupported location of the casing 220 is closer to the injection point, the plastic core material 210 is of a low density or viscosity, the casing 220 has a low thread density, and/or the unsupported portion is large with respect to the supported area.

The plastic core material 210 penetrates and bursts through the wall of the casing 220 of the bottom strap 150 because the plastic core material 210 follows the path of least resistance in order to fill the strap cavity. Where the casing 220 is supported by, in abutting contact with, or pressed against a surface of the injection moulding tool 300, the injected plastic core material 210 will flow in lesser restrictive direction until the cavities within the injection moulding tool 300 are filled. With reference to FIG. 5, once the bottom strap cavity 324 is full of plastic core material 210, the least restrictive direction of flow is into the top strap cavity 322 since the casing 220 of the bottom strap 150 is not supported by, in abutting contact with, or pressed against a surface of the bottom strap cavity 324. Where the casing 220 is not pressed (i.e., unsupported) against a surface of the injection moulding tool 300, the injected plastic core material 210 will fill the cavity by penetrating through the casing 220. Penetration of the casing 220 may occur by the plastic core material 210 flowing through the casing 220. That is, the threads of the casing 220 are being displaced or elastically deformed (i.e., depending upon the material of the casing 220) when under pressure of the injected plastic core material 220 (i.e., when unsupported). As a result, the plastic core material 220 will flow and push through gaps created between the displaced or elastically deformed threads of the casing 220. In some configurations, pressure of the plastic core material 220 within the casing 220 may cause the threads of the casing 220 to tear or break at an unsupported portion of the casing 220. Tearing or breaking of the casing 220 may cause a hole to be formed within the casing 220 through which the plastic core material 210 may penetrate and burst through to flow and push into the adjoining strap.

Bursting through or penetration of the plastic core material 210 through the casing 220 may depend on injection moulding parameters and textile properties of the casing 220. With regard to injection moulding parameters, whether bursting or penetration through occurs may depend on the pressure, injection speed, location of injection points and length of injection path, location of unsupported regions and relative size of unsupported areas with respect to supported areas, and material properties of the injected plastic core materials 210. With regard to textile properties of the casing 220, whether penetration occurs may depend on the thread count, thread size, elasticity, thread density, denier, thread strength, etc. of the casing 220. Bursting or penetration through the casing 220 may occur at higher pressures. In at least some embodiments, elasticity alone may or may not affect penetration. By way of non-limiting example, a high elasticity casing combined with a high thread count may deform/stretch (i.e., as opposed to allowing penetration) when not supported by the moulding tool 300. However, as the casing 220 stretches, gaps or spaces between threads would begin to form to provide paths for the plastic core material to penetrate through the casing 220. Accordingly, the injection moulding parameters and textile properties may be varied according to the desired properties of the bifurcated headgear 100 and the manufacturability of the bifurcated headgear 100 using the burst-through intra-moulding process.

Alternative Arrangements

Figure 8B:
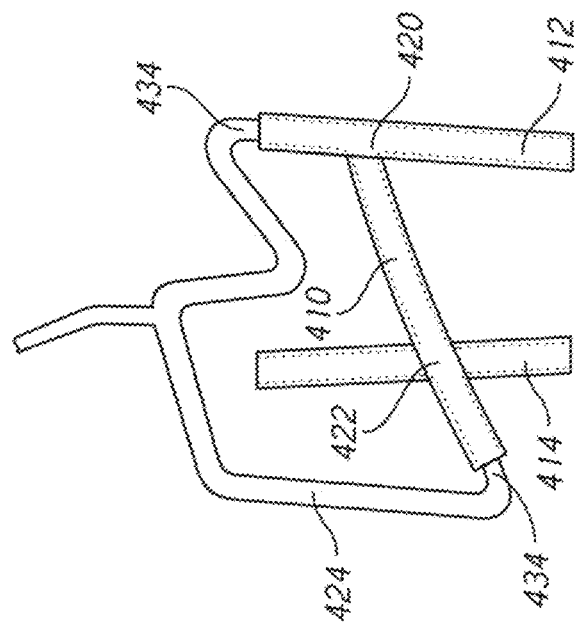
FIG. 8B illustrates a top-down view of the strap arrangement having the X-shaped junction and the T-shaped junction.
Figure 8A:
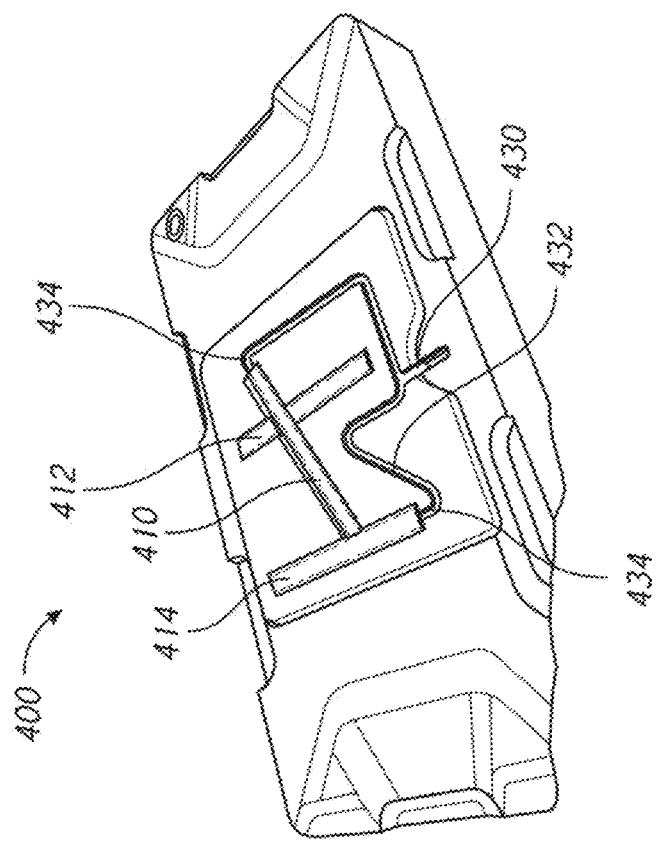
FIG. 8A illustrates a perspective view of a second tool half of an alternative intra-moulded strap cavity arrangement for forming an X-shaped junction and a T-shaped junction.

FIG. 8A illustrates a second tool half of an injection molding tool 400 having an alternative intra-moulded strap cavity arrangement for bonding multiple straps 410, 412, 414 in the junction configurations illustrated in FIG. 8B. For comparison, FIG. 8B illustrates a T-shaped junction 420 that is similar to the junction 170 in FIGS. 1A-7. FIG. 8B also illustrates an alternatively shaped junction in the form of an X-shaped junction 422. As described above and illustrated in FIG. 8B, a T-shaped junction 420 is formed by positioning an open end of a casing of strap 410 in contact with an edge of a casing of strap 412 (i.e., with a moulding tool providing strap cavities with a corresponding arrangement). In contrast, the X-shaped junction 422 is formed by overlapping non-open end portions of the casings of the straps 410, 414. In other words, the straps 410, 414 are positioned in an overlapping orientation such that the straps 410, 414 are in abutting contact at a position between their open ends and form an X-shaped junction 422. In an alternative embodiment, one of the straps 414 is formed from two strap portions that is joined to the other strap 410 by joining respective ends of each of the strap portions to the other strap 410 form an X-shaped junction. In these embodiments, the injection molding tool 400 includes correspondingly shaped strap cavities for supporting the straps 410, 414. FIGS. 8A and 8B illustrate the positioning of the sprue 430, runners 432 and injection points 434 through which plastic core material 424 is injected into injection molding tool 400 to fill the straps 410, 412, 414. An injection point 434 is positioned on one open end of the strap 410 and effectively on the opposite open end of the strap 410 (i.e., via the injection point 434 through strap 412). In the illustrated configuration, the open ends of strap 414 are not fluidly connected to injection points 430 except through the X-shaped junction 422. When the plastic core material 424 is injected into the injection molding tool 400, the plastic core material 424 enters the open ends of the strap 410 and travels towards the X-shaped junction 422. In the embodiment in which one of the straps 414 is formed from two strap portions joined to the other strap 410, as the strap 414 begins to fill, the plastic core material 424 will follow the path of least resistance and penetrate through the edges of the casing of strap 410 and then through the open ends of the casing of strap 414. That is, the strap cavity of strap 414 is empty and thereby provides the least resistive path for the plastic core material 424 to flow. Accordingly, the casing of the strap 414 is filled with plastic core material 424 that enters into the strap 414 through the X-shaped junction 422. It should be understood to one of ordinary skill in the art that the above described configuration is not limited to injection points located at the open ends of one of the straps when forming the X-shaped junction 422. In some configurations, the X-shaped junction 422 may be formed with both straps having at least one injection points at their ends.

As illustrated, the T-shaped junction 420 and the X-shaped junction 422 may be used in combination to form a variety of headgear shapes and structures having multiple straps. Multiple strap junctions/joints can be formed in a single injection moulding step. Such strap configurations may be utilized in four-point headgear structures that are commonly used in conjunction with nasal and full-face masks.

Figure 9A:
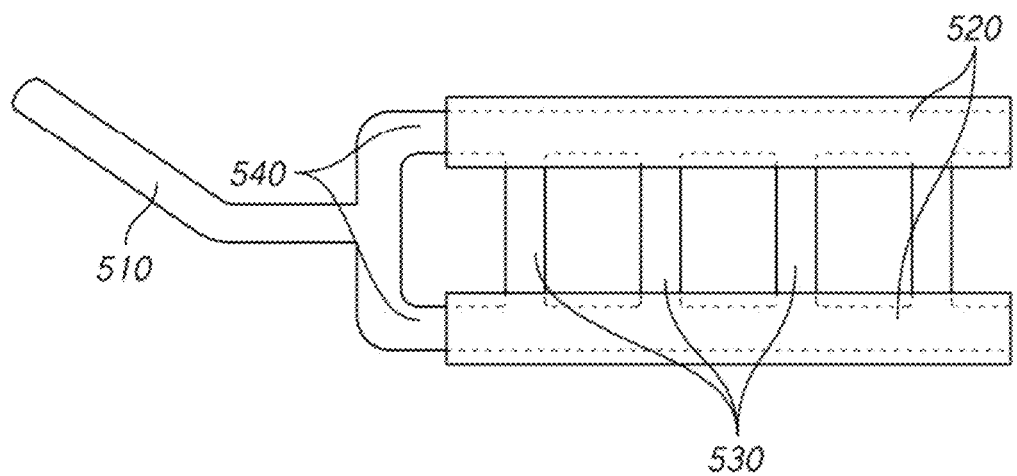
FIG. 9A illustrates a top-down view of an alternative intra-moulded strap arrangement having straps joined together by integrally formed linking members positioned between the straps.

FIG. 9A illustrates an alternative intra-moulded strap arrangement having straps 520 joined together by integrally formed linking members 530 positioned between the straps 520. The linking members 530 are formed by the plastic core material 510 bursting through the wall of the casings of the straps 520 and into another region of the mould cavity. That is, the injection moulding tool (not shown) may have cavities corresponding to the linking members 530 that fluidly connect the strap cavities for the straps 520. Accordingly, when molten plastic core material 510 is injected into the injection moulding tool, the plastic core material 510 enters into the casings of the straps 520 at the injection points 540. When the straps 520 begin to fill, the plastic core material 510 will follow the path of least resistance and penetrate through the walls of the casings (i.e., at the unsupported portions of the casings that are adjacent the cavities corresponding to the linking members 530) such that the plastic core material enters and fills the cavities corresponding to the linking members 530. In some configurations, the plastic core material 510 can be elastomeric such that the linking members 530 can stretch. Further, in such an embodiment, the casings may restrict the stretch of the plastic core material 510.

Figure 9B:
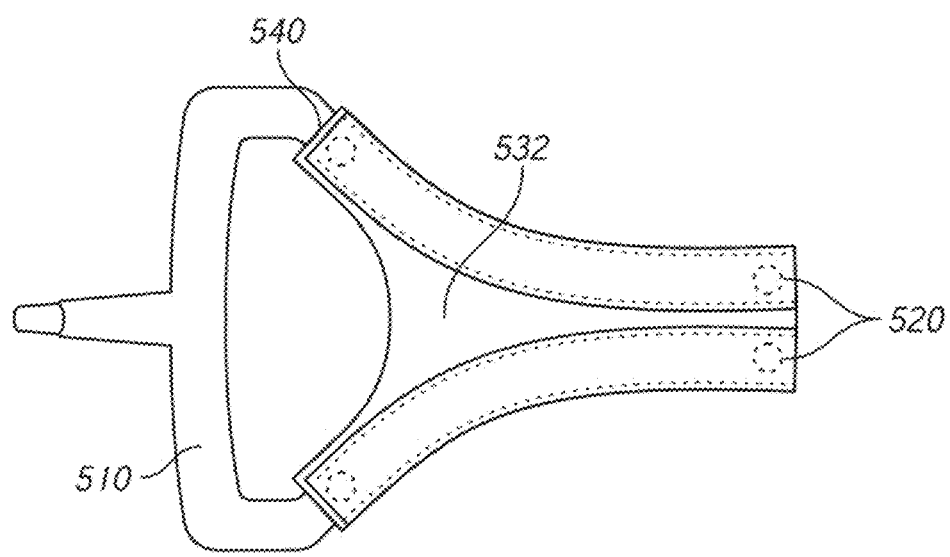
FIG. 9B illustrates a top-down view of an alternative intra-moulded strap arrangement having straps joined together by integrally formed web portion positioned between the straps.

FIG. 9B illustrates an alternative intra-moulded strap arrangement having straps 520 joined together by integrally formed web portion 532 positioned between the straps 520. Similar to the linking members 530 in FIG. 9A, the injection moulding tool (not shown) may have a cavity corresponding to the web portion 532 that fluidly connect the strap cavities for the straps 520. The cavity corresponding to the web portion 532 may have a depth that is shallower than the depth of the strap cavities for the straps 520. Accordingly, when molten plastic core material 510 is injected into the injection moulding tool, the plastic core material 510 enters into the casings of the straps 520 at the injection points 540. When the straps 520 begin to fill, the plastic core material will follow the path of least resistance and penetrate through the walls of the casings (i.e., at the unsupported portions of the casings that are adjacent the cavities corresponding to the web portion 532) such that the plastic core material enters and fills the cavity corresponding to the web portion 532. In some configurations, the plastic core material 510 can be elastomeric such that the web portion 532 can stretch. Further, in such an embodiment, the casings may restrict the stretch of the plastic core material 510.

Figure 10A:
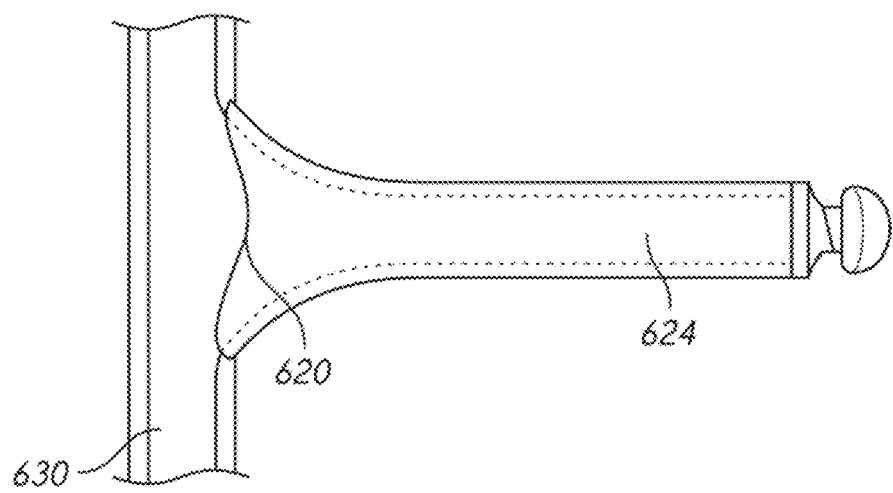
FIG. 10A illustrates a top-down view of an alternative intra-moulded strap arrangement having a filleted junction that connects a filleted strap to an adjoining strap.
Figure 10B:
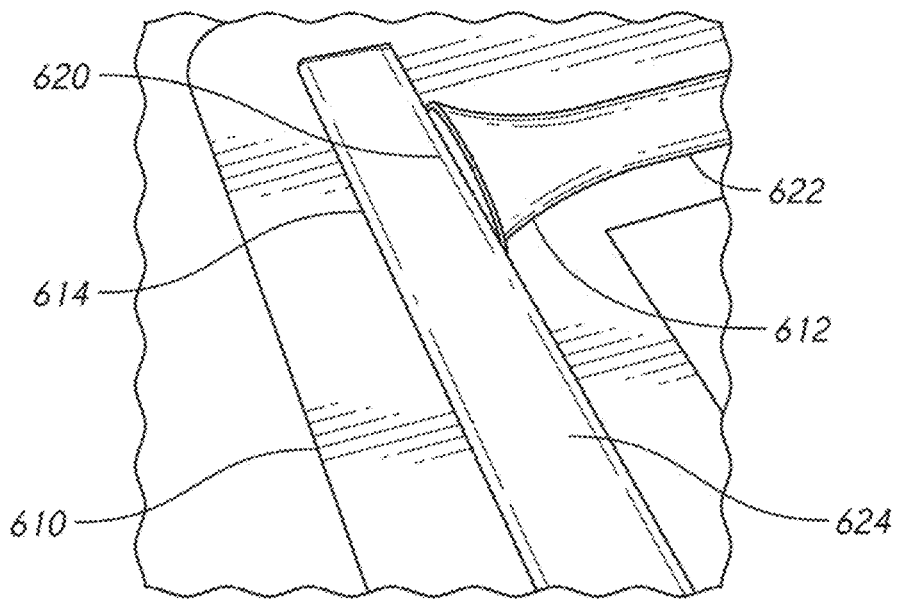
FIG. 10B illustrates a top perspective of the injection moulding tool for forming the filleted junction.

FIG. 10A illustrates an alternative intra-moulded strap arrangement having a filleted junction 620 that connects a filleted strap 622 to an adjoining strap 624 or headgear portion. The textile casing of the filleted strap 622 has a width that expands, flares and curves radially outwardly towards a filleted junction 620 with the adjoining strap 624 or headgear portion, to provide a smooth transition between straps 622, 624. In other words, a width or diameter of the textile casing of the filleted strap 622 increases along the length of the filleted strap 622 towards the end in abutting contact with the adjoining strap 624. Accordingly, the filleted junction 620 provides a larger connection area with the textile casing of the adjoining strap 624, which may provide increased strength and aesthetic appeal relative to a non-filleted junction. FIG. 10B shows the injection moulding tool 610 for forming the filleted junction 620. As shown, the injection moulding tool 610 has a filleted strap cavity 612 having a shape that corresponds to the shape of the textile casing of the filleted strap 622. In the illustrated embodiment, the textile casing of the filleted strap 622 is preformed from two layers of microfiber that have been sewn together and flipped inside-out to form a tube that curves outward at one open end. The adjoining strap 624 has a casing similar to the embodiments previously described. Further, the adjoining strap 624 is positioned within a correspondingly shaped strap cavity 614 in abutting contact with the open end of the filleted strap 622. Accordingly, plastic core material 630 is injected into an open end of the filleted strap 622 and/or the adjoining strap 624. The plastic core material 630 penetrates through the wall of the casing of the adjoining strap 624 at the filleted junction 620 such that plastic core material 630 is integrally formed within the filleted strap 622 and the adjoining strap 624. As illustrated, the textile casing of the filleted strap 622 can abut another intra-moulded strap portion (i.e., the casing of strap 624, as shown in FIG. 10B) or abut uncovered plastic core material 630, as shown in FIG. 10A. In some configurations, the casing of the filleted strap 622 may be made as a single piece of woven tube that is woven to shape to include the filleted end.

Figure 11A:
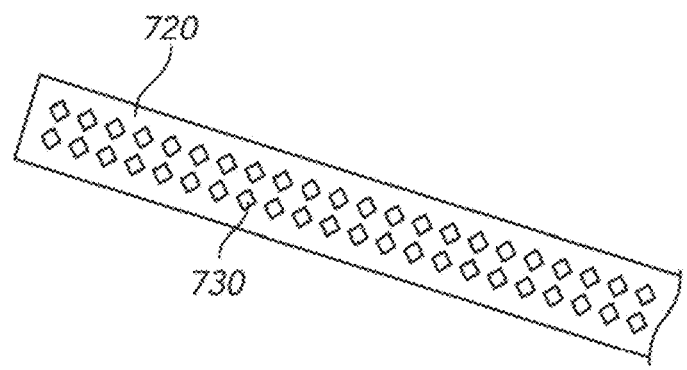
FIG. 11A illustrates a top-down view of an intra-moulded strap arrangement having a moulded square texture that is imprinted into a strap.
Figure 11B:
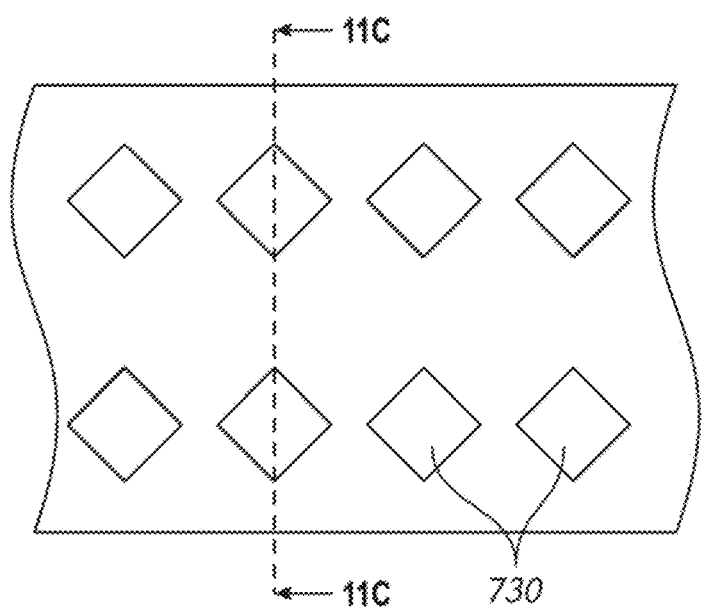
FIG. 11B illustrates a close-up top-down view of the moulded square texture imprinted into the strap.
Figure 11C:
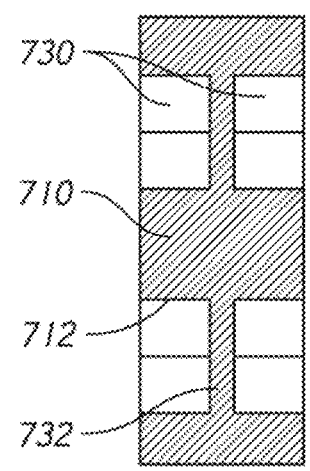
FIG. 11C illustrates a cross-sectional view of the moulded square texture imprinted into the strap along a line 11C-11C in FIG. 11B.
Figure 11D:
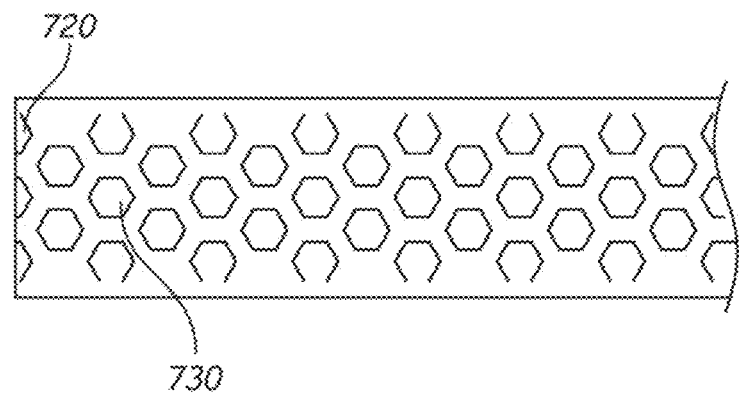
FIG. 11D illustrates a top-down view of an intra-moulded strap arrangement having a moulded hexagon texture that is imprinted into a strap.
Figure 11E:
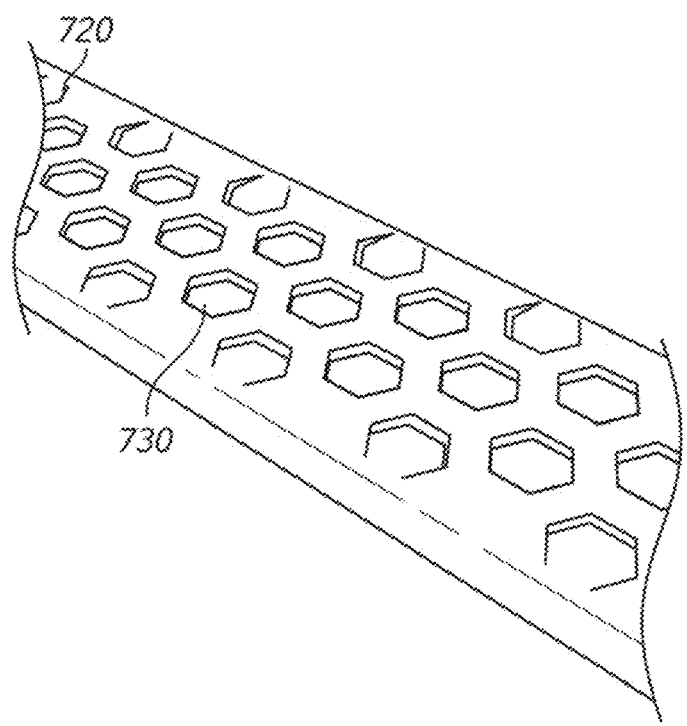
FIG. 11E illustrates a side perspective view of the moulded hexagon texture imprinted into the strap.

FIGS. 11A to 11E illustrate intra-moulded strap arrangements having a moulded texture that is imprinted into the straps. FIGS. 11A-C illustrate a strap 720 having a plurality of square diamond shaped indentations 730 arranged in rows along the length of the strap 710. As illustrated in FIG. 11C, which is a cross-section along line 11C-11C of FIG. 11B, the indentations 730 are formed on both sides of the strap 720 and are aligned to form thin regions 732 within the strap 720. The thin regions 732 may provide the plastic core 710 with a degree of give or stretch. Such flexibility may be beneficial in allowing a closed loop headgear to be pulled over a patient's head or to improve patient perception of the semi-rigid headgear. Further, the textured finish of the strap 720 may improve the aesthetic appearance of the headgear and also the tactile appeal of the strap 720. That is, the strap 720 may appear less rigid and more comfortable. In some embodiments, not shown, the indentations 730 may form shut-off areas where there is no plastic core material 710 between the layers of casing 712. The shut-off areas may improve breathability through the strap 720 which improves user comfort. FIGS. 11D and 11E illustrate a plurality of hexagonal shaped indentations 730 that are spaced along the length of the strap 720 in a honeycomb-like arrangement. It should be understood that the indentations 730 are not limited to diamond or hexagonal shapes and may include a variety of shapes, sizes, position on strap, geometries, combinations of shapes, etc. In FIGS. 11D and 11E, the plastic core and honeycomb pattern does not extend all the way to the edge of the casing of the strap 720. This provides a soft edge to improve user comfort.

The indentations 730 are formed during the burst-through intra-moulding process in a manner similar to the forming of the soft edges of the straps. That is, the strap cavity for the strap 720 may include a series of protrusions on the first and second tool halves. The protrusions project into the strap cavity and have a shape corresponding to the indentations 730. When the plastic core material is injected into the strap 720, the protrusions mold the shape of the indentation into the plastic core material.

FIGS. 12A to 13D illustrate an intra-moulded strap arrangement for a bifurcated headgear 1100 having an attachment member that increases the bonding strength at the junction between bonded straps. Similar to the bifurcated headgear 100 illustrated in FIGS. 1A to 7, the bifurcated headgear 1100 of FIG. 12A to 13D comprises a top strap 1140 and a bottom strap 1150. Similarly, an open end portion of the top strap 1140 is bonded to a non-end portion of the bottom strap 1150. In contrast to the bottom strap 150 in FIGS. 1A to 7, the bottom strap 1150 includes an attachment member 1156 protruding outward from a wall of the casing of the bottom strap 1150. As will be described in greater detail below, the top strap 1140 is overmoulded onto the attachment member 1156 to form a permanent connection between the top and bottom straps 1140, 1150.

Figure 13A:
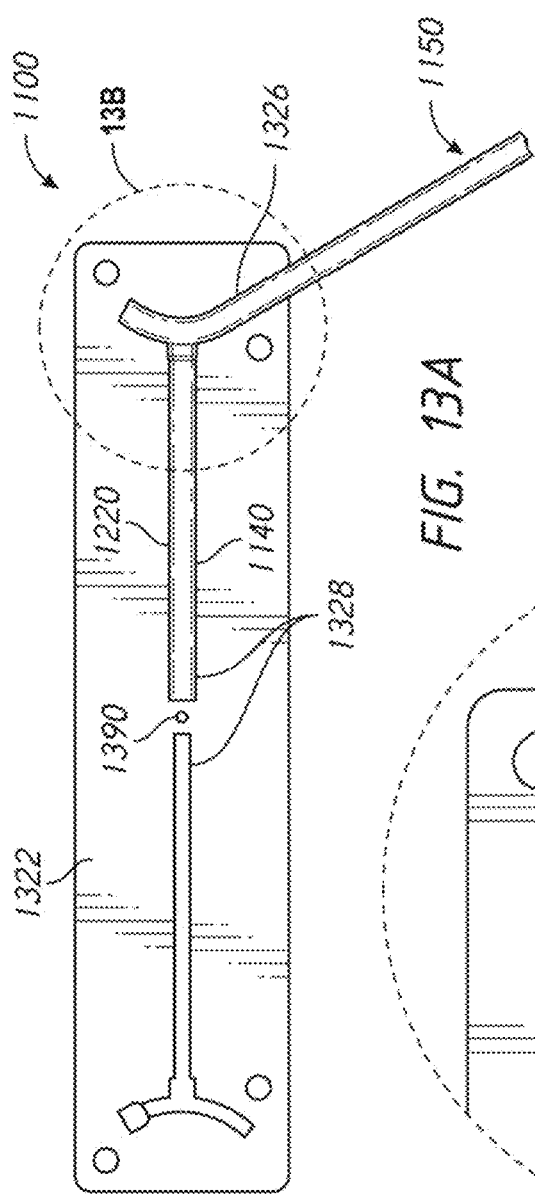
FIG. 13A a top-down view of a second moulding tool for forming a top strap over the attachment member.
Figure 13B:
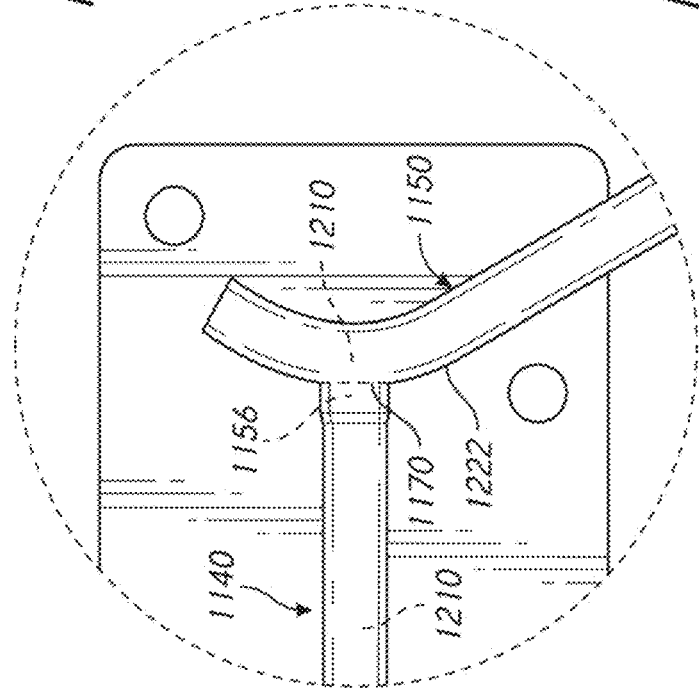
FIG. 13B illustrates a close-up top-down view of the second moulding tool showing the top strap attached to the bottom strap.
Figure 13C:
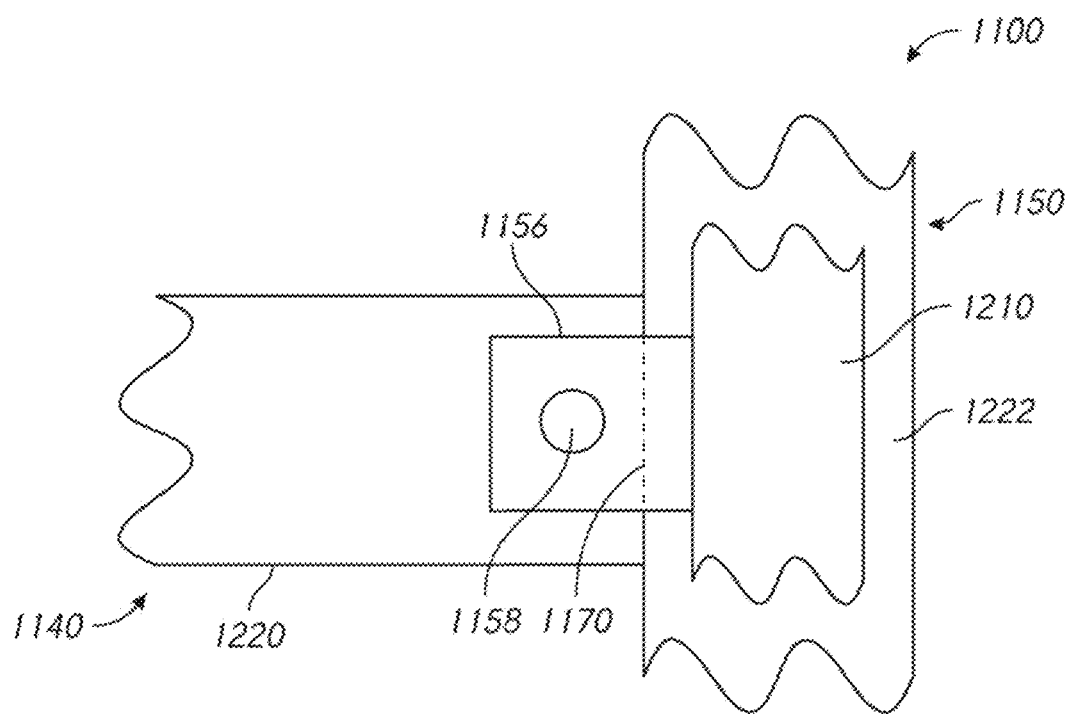
FIG. 13C illustrates a close-up cross-sectional view of the top strap positioned over the attachment member prior to the injection of plastic core material into the top strap.
Figure 13D:
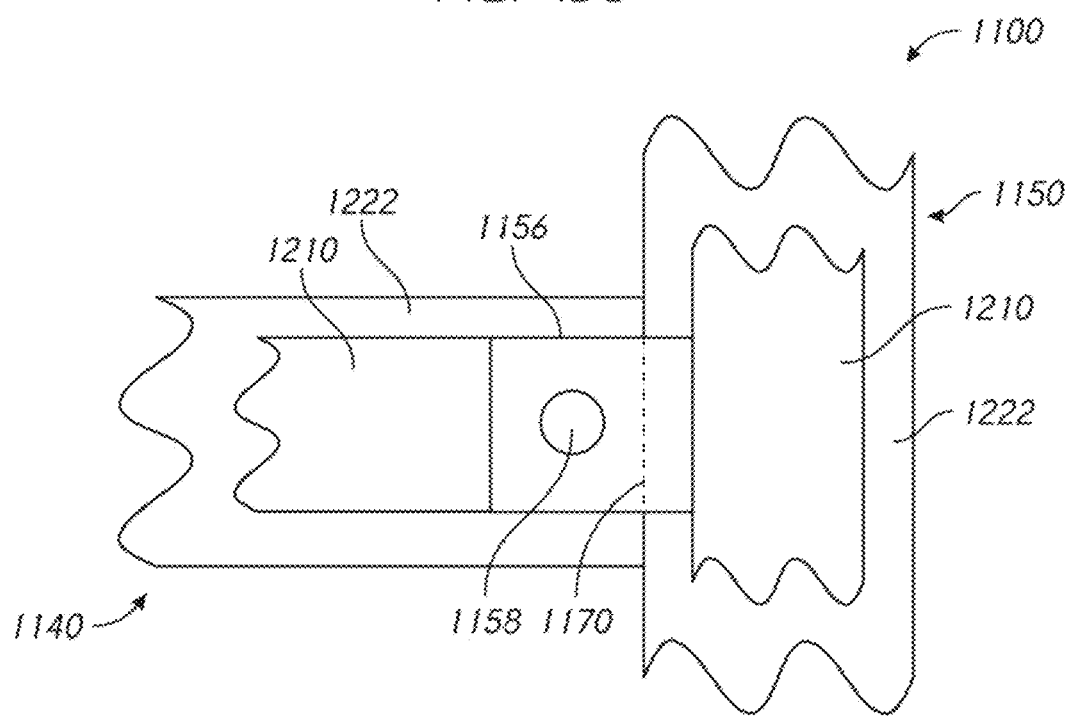
FIG. 13D illustrates a close-up cross-sectional view of the top strap attached to the attachment member after the injection of plastic core material into the top strap.

The bifurcated headgear 1100 is formed by a two-step intra-moulding process. That is, the bottom strap 1150 and the attachment member 1156 are intra-moulded using the burst-through intra-moulding process and then the top strap 1140 is intra-moulded onto the attachment member 1156 and the bottom strap 1150. FIGS. 12A and 12B illustrate the first step of the burst-through intra-moulding process for forming the bifurcated headgear 1100. As shown, the bottom strap 1150 and the attachment member 1156 are formed by positioning a casing 1220 of the bottom strap 1150 into a bottom strap cavity 1324 of a first moulding tool 1320. The attachment member 1156 is formed by plastic core material 1210 that has penetrated or burst-through the wall of the casing 1220 of the bottom strap 1150, similar to the penetration and burst-through techniques described above. For the sake of brevity, redundant discussion will be excluded. FIGS. 13A and 13D illustrate the second step of the intra-moulding process for forming the bifurcated headgear 1100. As shown, the fully formed bottom strap 1150 is positioned within a bottom strap cavity 1326 of a second moulding tool 1322. A casing 1220 for the top strap 1140 is positioned within a top strap cavity 1328 of the second moulding tool 1322. An open end of the top strap 1140 is positioned over the attachment member 1156 of the bottom strap 1150. That is, the casing 1220 for the top strap 1140 is placed into the second moulding tool 1322 such that the casing 1220 for the top strap 1140 is overlying and/or surrounding the attachment member 1156. The open end of the casing 1220 for the top strap 1140 abuts a soft edge 1222 of the bottom strap 1150. The casing 1220 for top strap 1140 is filled with plastic core material 1210 that enters the second moulding tool 1322 via an injection point 1390 in the second moulding tool 1322. During the injection, plastic core material 1210 within the casing 1220 for top strap 1140 overmoulds onto and/or around the attachment member 1156 to form a permanent connection between the top and bottom straps 1140, 1150. Further, a chemical and/or mechanical connection is formed between the attachment member 1156 and the plastic core material at the junction 1170 between the top and bottom straps 1140, 1150. The attachment member 1156 may include a mechanical interlocking structure which provides a partial interlock aperture 1157 (FIGS. 13A-B) or an interlock aperture 1158 (FIGS. 13C-D) through which the plastic core material 1210 within the casing 1220 for top strap 1140 passes through. The mechanical interlock may increase the amount of surface area of the bottom strap 1150 at the junction 1170 onto which the top strap 1140 may be chemically or mechanically bonded onto. Further, the plastic core material 1210 passing through the interlock aperture 1157, 1158 may provide an interlocking mechanical connection between the plastic core material 1210 of the top and bottom straps 1140, 1150. In some configurations, the top strap 1140 may be formed and attached to the bottom strap 1150 using the intra-moulding process. That is, the bottom strap 1150 and the attachment member 1156 may be formed using alternative strap forming techniques and, thereafter, the top strap 1140 may be overmoulded onto the attachment member 1156 using the intra-moulding process.

FIGS. 14A-D illustrate an alternative strap arrangement for a bifurcated headgear 1400 having a strap casing with sealed ends. The bifurcated headgear 1400 has top and bottom straps 1402, 1404 that are similarly arranged as the bifurcated headgear 100 with top and bottom straps 140, 150 of FIGS. 1A-7. Further, the top and bottom straps 1402, 1404 are joined at a junction 1470 using the burst-through intra-moulding process, similar to top and bottom straps 140, 150 at the junction 170.

Figure 14B:
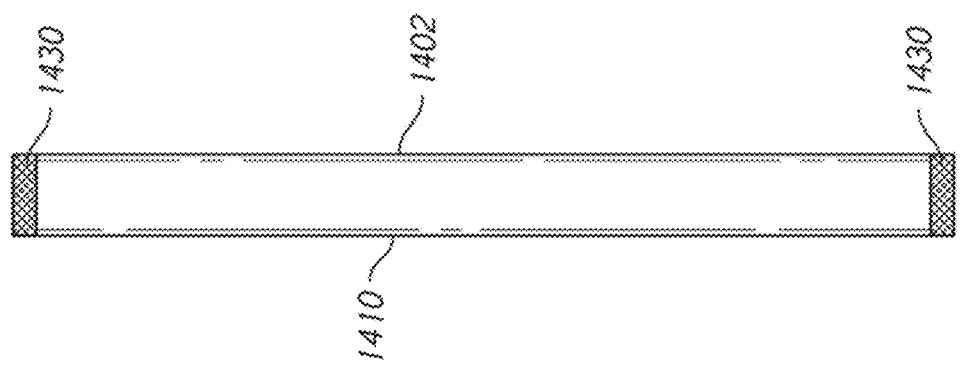
FIG. 14B illustrates a close-up side view of the top strap having the sealed end.
Figure 14A:
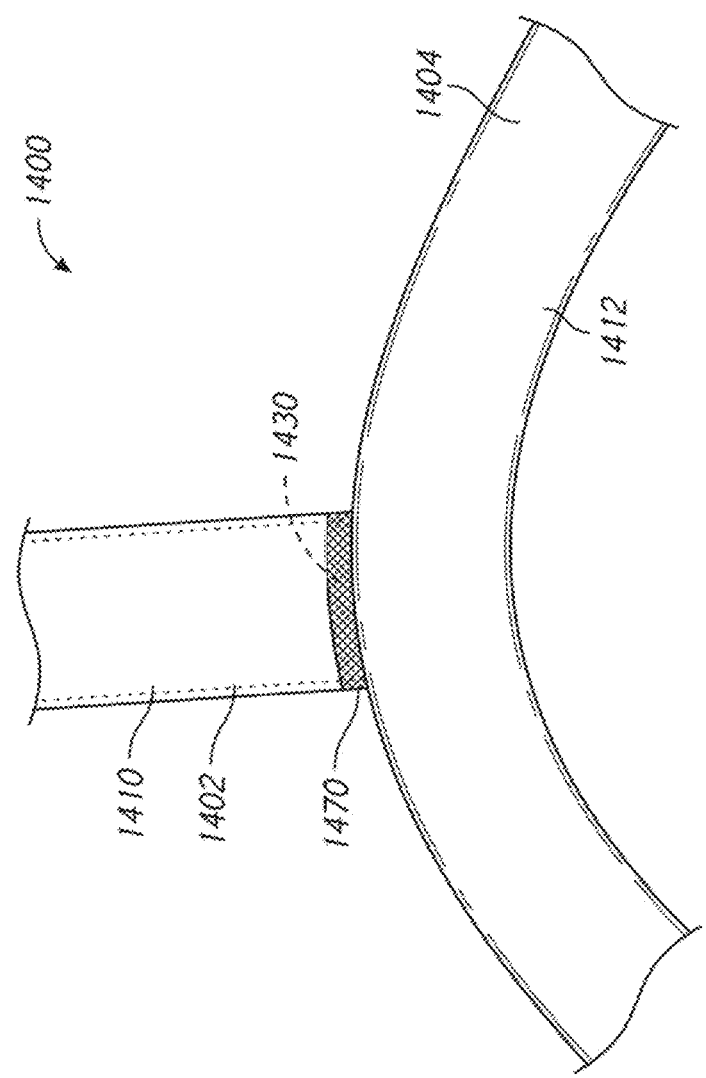
FIG. 14A illustrates a close-up side view of a top strap having sealed end at a junction with a bottom strap.
Figure 14D:
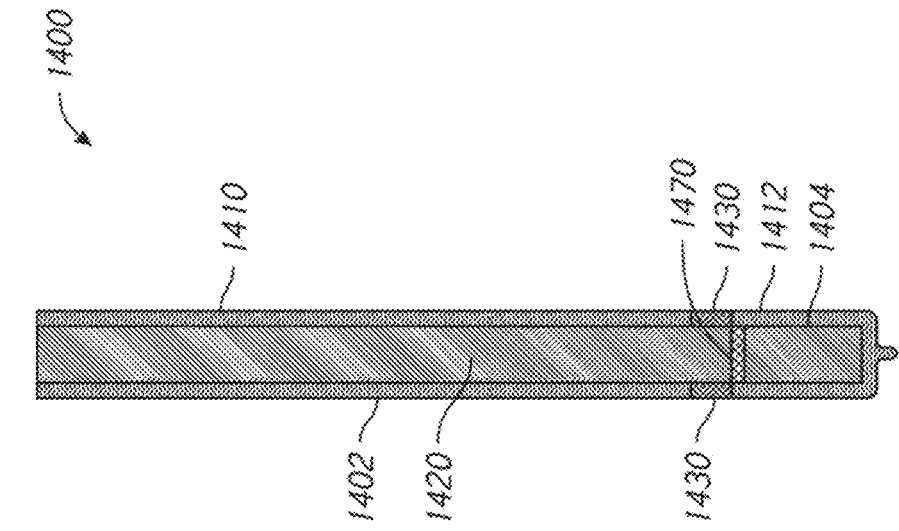
FIG. 14D illustrates a cross-sectional view of the junction between top and bottom straps.
Figure 14C:
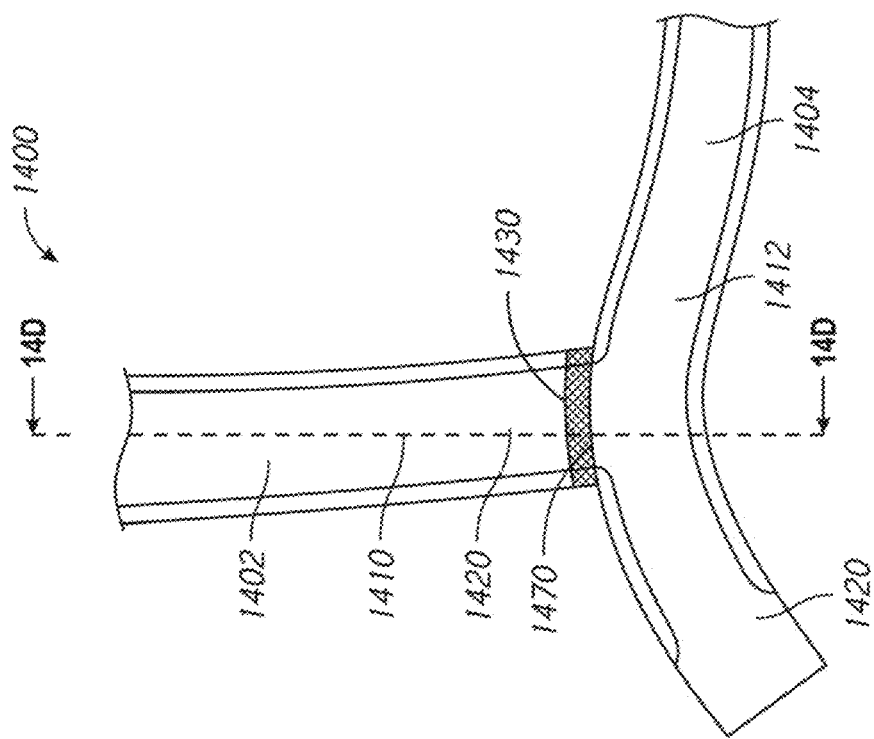
FIG. 14C illustrates a close-up side view of the top strap having sealed end attached to the bottom strap at a junction.

FIG. 14A shows a casing 1410 for a top strap 1402 having sealed open end portions 1430. The sealed open end portions 1430 are formed by cutting the ends of the casing 1410 with a hot knife. Where the casing is formed from a synthetic textile, cutting the casing 1410 with a hot knife melts the edges of the casing 1410 which seals or joins together the loose ends of the individual threads/yarn that would otherwise be exposed and/or frayed after the casing 1410 is cut to length. As a result, when a sealed open end portion 1430 is joined with the bottom strap 1404, the junction 1430 is devoid of loose or frayed individual threads/yarn which improves the aesthetics of the junction 1470 and the bifurcated headgear 1400. Further, the sealed open end portions 1430 may reduce excess flash that is formed outside of the casings 1410 around the junction 1470 after the plastic core material 1420 penetrates through the wall of a casing during the burst-through intra-moulding process. That is, the sealed open end portion 1430 provides a substantially sealed edge or surface (i.e., relative to a frayed open end portion of the casing 1410) that contacts the casing 1410 of the bottom strap 1402 which prevents or inhibits plastic core material 1420 from leaking through the casing 1410 of the top strap 1402 at the sealed open end portion 1430. FIG. 14C shows a junction 1470 formed between a sealed open end portion 1430 of a top strap 1402 and an edge of a casing 1412 of the bottom strap 1404. FIG. 14D shows a cross-section of the top and bottom straps 1402, 1404 along a line 14D-14D in FIG. 14C. The top and bottom straps 1400, 1402 are bonded to each other using the burst-through intra-moulding technique discussed above. In an alternative configuration, the open ends of the top strap 1402 may be overmoulded to seal the end of the top strap 1402 prior to injection moulding.

In another embodiment, a sealed open end portion may be formed by placing the casing into a heat sealer and an outer portion of the casing is sealed/melted, but not cut by the heat sealer. The casing is then cut in a middle portion of the sealed region (i.e., after the sealed region is cooled), creating an open end. The internal wall of the casing is not sealed or fused together, however the individual yarns are fused on the outside of the casing (i.e., external wall), thus securing the loose threads of the individual yarns which provides a clean aesthetic and prevents or inhibits plastic core material from leaking through the casing at the sealed open end portion.

FIGS. 15A-D illustrate a bifurcated headgear 1500 having a filament core 1550 having a core end portion 1512 that is anchored into the plastic core material 1510 within the bottom strap 1502. The filament core 1550 may be used in conjunction with the transformational lock arrangement as disclosed in U.S. patent application Ser. No. 14/856,193, which is incorporated by reference herein. The filament core 1550 and the transformational lock arrangement provide a length adjustment arrangement for adjusting the length and tension of the bottom straps of a headgear to loosen or tighten a mask interface against the user's face. For example, in some configurations, a locking mechanism may engage the filament core to adjust the effective length of the bottom strap.

The bifurcated headgear 1500 has top and bottom straps 1502, 1504 that are similarly arranged as the bifurcated headgear 100 with top and bottom straps 140, 150 of FIGS. 1A-7. Further, the top and bottom straps 1502, 1504 are joined at a junction 1570 using the burst-through intra-moulding process, similar to top and bottom straps 140, 150 at the junction 170.

Figure 15A:
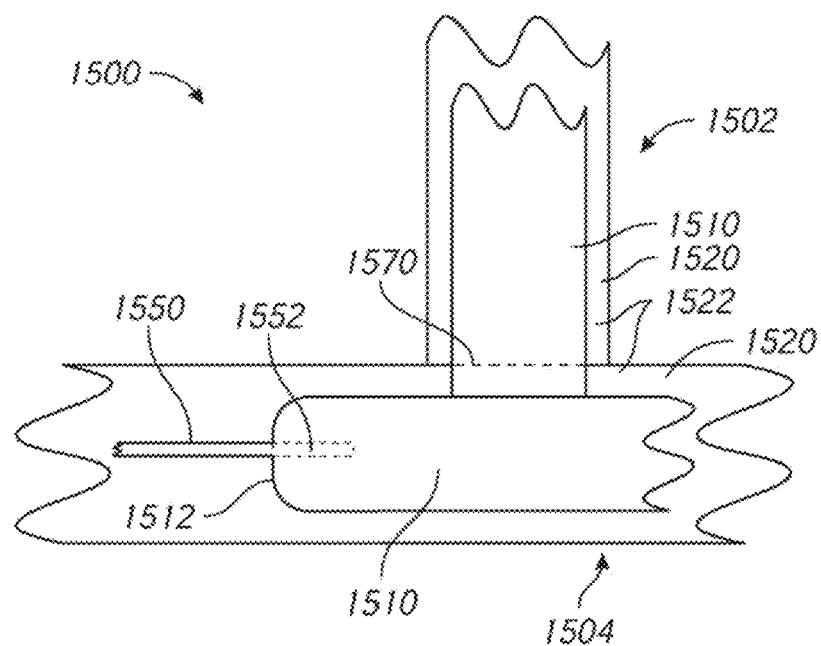
FIG. 15A illustrates a close-up cross-section side view of a top strap attached to a bottom strap having a filament core bonded to a bottom strap that engages a transformational lock arrangement.

As shown in FIG. 15A, a top strap 1502 is bonded to a bottom strap 1504 at a junction 1570. The top and bottom straps 1502, 1504 are bonded via formed plastic core material 1510 that is integrally formed within the casings 1520 of the top and bottom straps 1502, 1504 using the burst-through intra-moulding technique discussed above. Similarly, the top and bottom straps 1502, 1504 have soft edges 1522. As shown, a filament anchor portion 1552 of the filament core 1550 is positioned within a core end portion 1512 of the plastic core material 1510. The filament core 1550 is fixed within and anchored into the core end portion 1512 at a position forward of the junction 1570, (i.e., forward of the user's ear). In some configurations, the filament core 1550 is bonded to the plastic core material 1510 during the burst-through intra-moulding process. The filament core 1550 is surrounded by, but not attached to the casing 1520 of the bottom strap 1504. That is, between the core end 1512 and an open end 1524 of the casing 1520, the filament core 1550 is not attached to the casing 1520. Accordingly, the casing 1520 may move independently over the filament core 155, which is effectively inextensible. Further, similar to previous embodiments formed using the burst-through intra-moulding technique, the plastic core material 1510 is bonded to the casings 1520 of the top and bottom straps 1502, 1504.

Figure 15B:
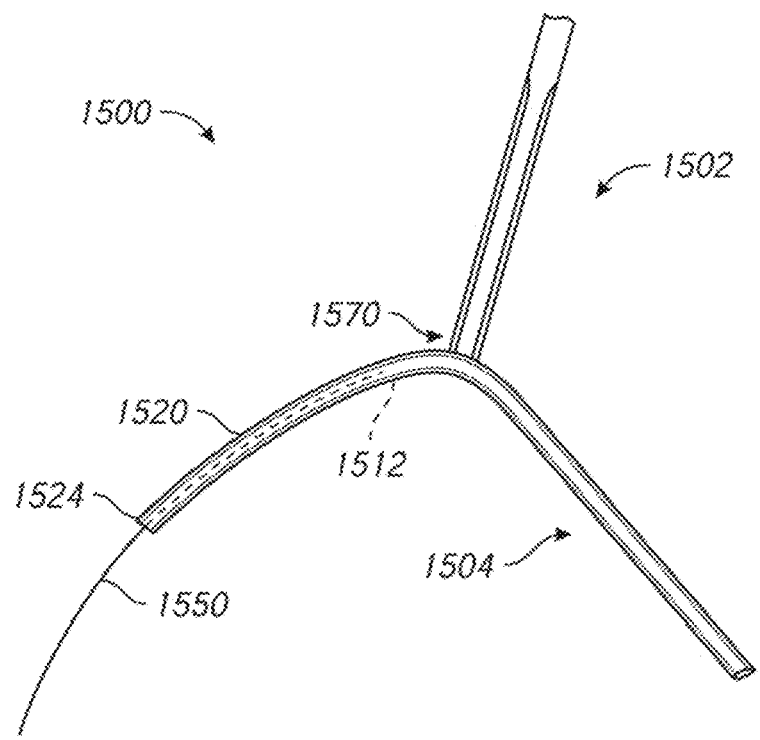
FIG. 15B illustrates a top-down view of a bifurcated headgear portion having the bottom strap with the filament core bonded.
Figure 15C:
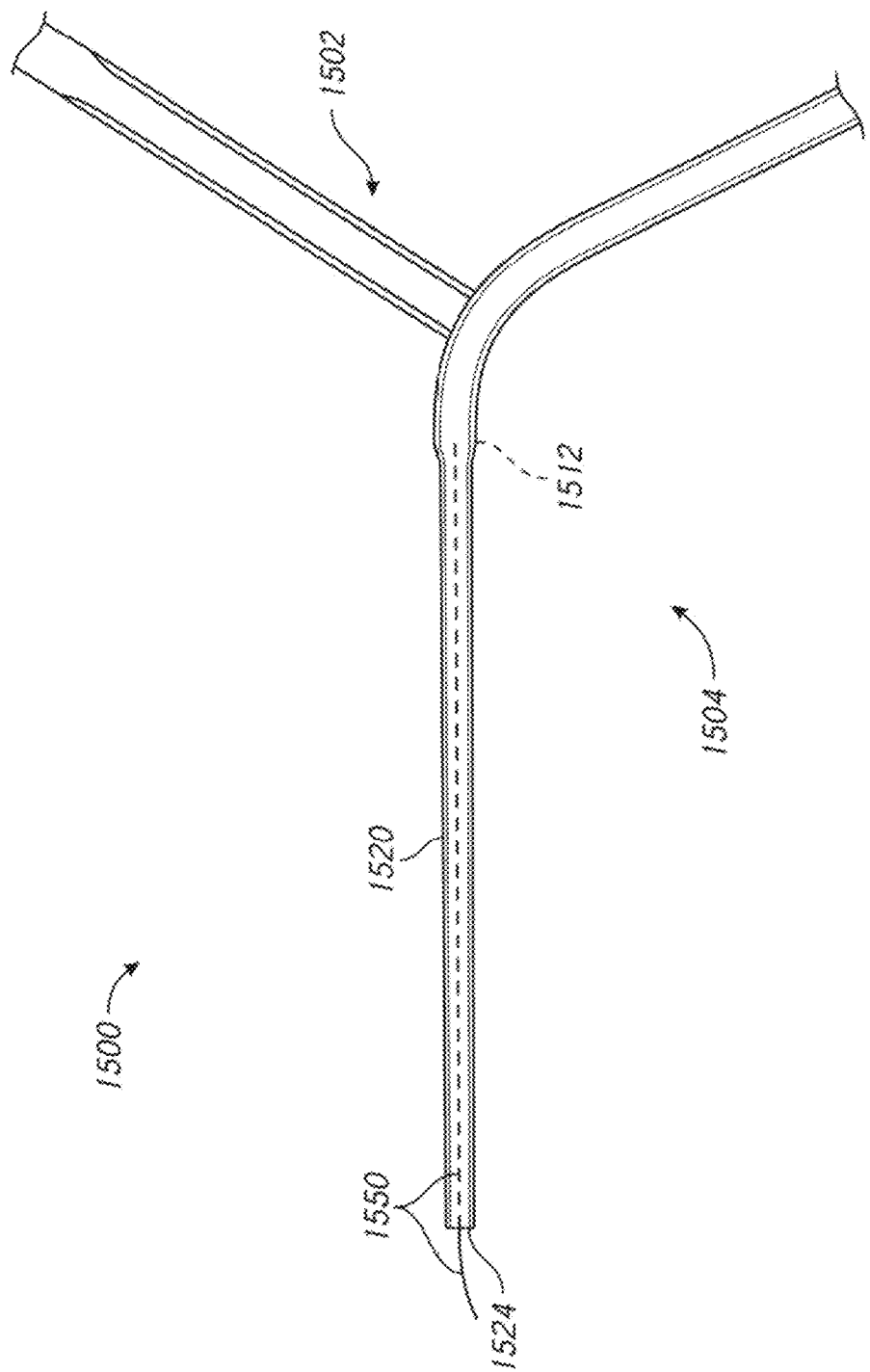
FIG. 15C illustrates a top-down view showing a stretched length of a casing for the bottom strap.

As shown in FIG. 15B, the bottom strap 1504 further differs from the bottom strap 150 in FIGS. 1A-7 in that the casing 1520 of bottom strap 1504 is longer in order to cover, surround and conceal a portion of the filament core 1550. Concealing the filament core 1550 may improve the aesthetic appearance of the headgear. The filament core 1550 extends forward from the core end portion 1512 of the bottom strap 1504 and has a length that is greater than a stretched or extended length of the casing 1520 of the bottom strap 1504, as shown in FIGS. 15B and 15C. FIG. 15B shows an unstretched length of the casing 1520 of the bottom strap 1504. FIG. 15C shows the casing 1520 of the bottom strap 1504 stretched to its maximum length while a portion of the filament core 1550 still extends further beyond the maximum length of the casing 1520. Accordingly, the casing 1520 of the bottom strap 1504 is configured to conceal the filament core 1550 throughout a range of positions between the filament core 1550 and a locking mechanism (not shown). The stretched and unstretched lengths of the casing 1520 may vary according to size of the headgear and the range of adjustability desired.

Figure 15D:
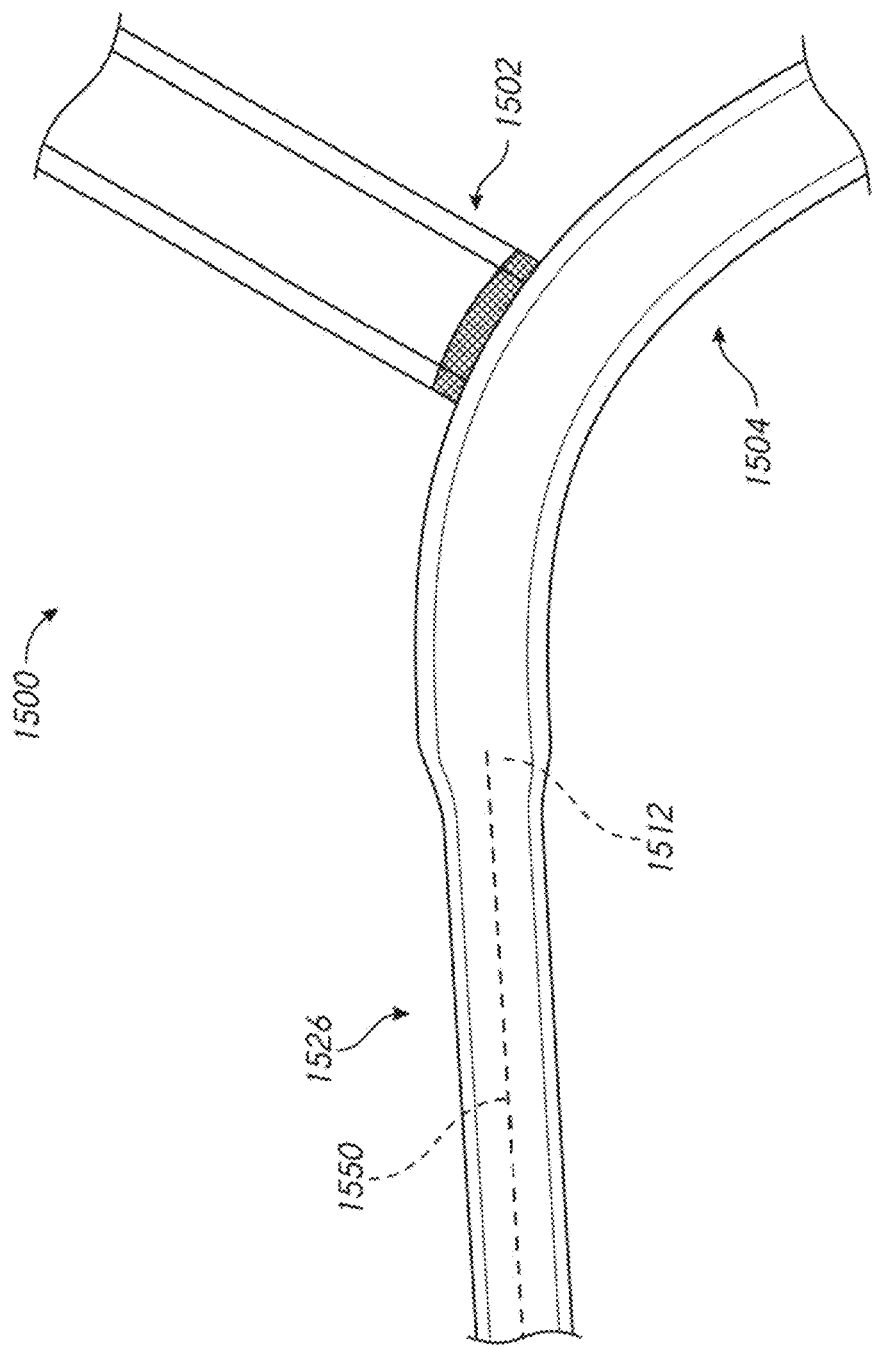
FIG. 15D illustrates a top-down view showing a narrowing of the casing for the bottom strap when stretched.

FIG. 15D shows a close-up view of the casing 1520 of the bottom strap 1504 in a stretched state. In a preferred embodiment, the casing 1520 of the second strap 1504 is braided and comprises inelastic yarns having linear elastic elements incorporated therein. The casing 1520 is able to extend and retract independently from the filament core 1550. As illustrated in FIG. 15D, when extended the casing 1520 of the bottom strap 1504 necks down or narrows when stretched, as shown by the necking region 1526 from the core end portion 1512, the individual yarns of the casing 1520 align, thus limiting the extended length of the braid. The filament core 1550 is longer than the extended length of the braid. The linear elastic elements of the casing 1520 retract the braid when no force is applied to the braid.

Figures 16A, 16B:
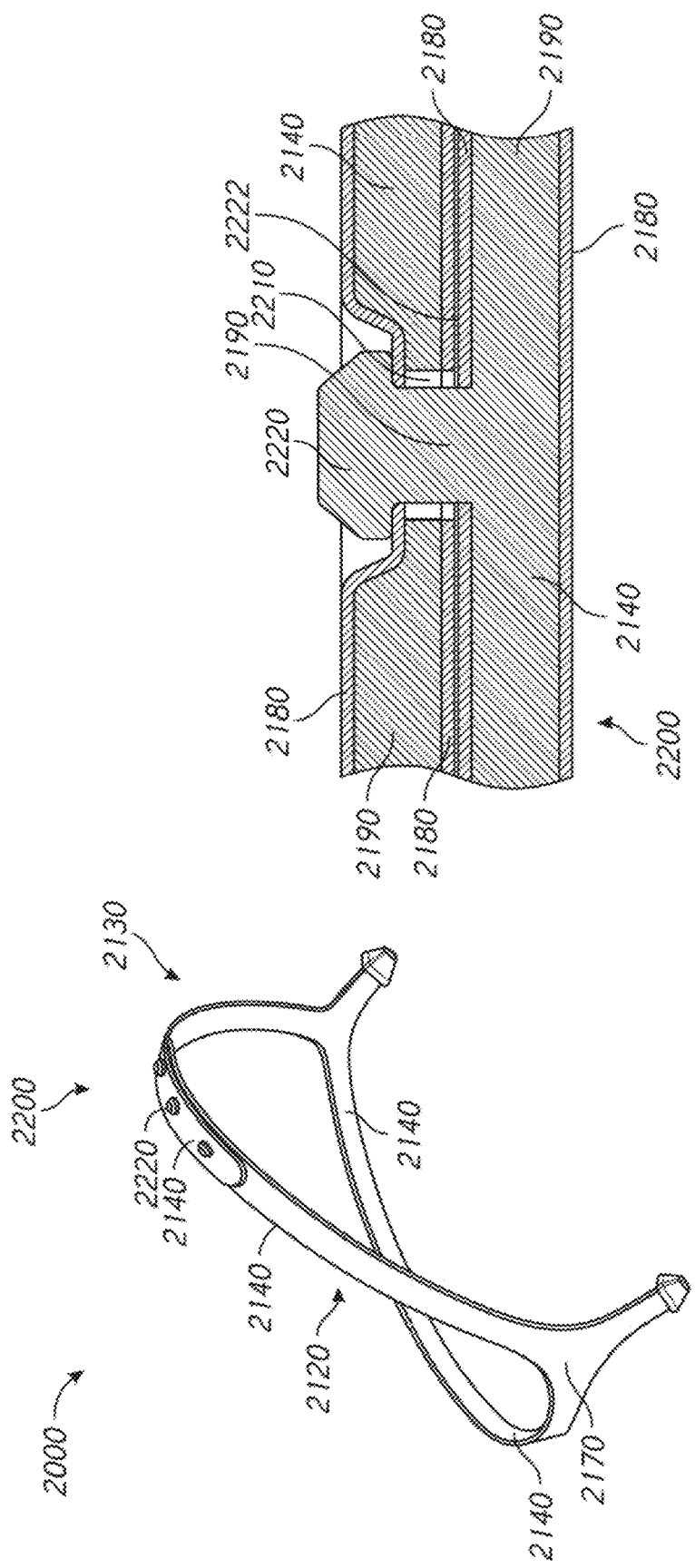
FIG. 16A illustrates a side perspective view of an alternative bifurcated headgear arrangement having a button and hole size adjustment system that is formed by the burst-through intra-moulding arrangement of the present disclosure.
FIG. 16B illustrates a cross-sectional view to top and bottom straps having the button and hole size adjustment system.

FIG. 16A illustrates a bifurcated headgear 2000 having top straps 2140 of right and left sides 2120, 2130 that are connected by a button and hole size adjustment system 2200. The button and hole size adjustment system 2200 may be similar to the 'snap fit' button and hole adjustment system, commonly used in baseball caps, but is moulded integrally as a part of the bifurcated headgear 2000. The size adjustment system 2200 comprises a plurality of holes 2210 extending through the top strap 2140 of the left side 2130 (not visible in FIG. 16A) and a plurality of buttons 2220 protruding from an upper surface 2222 of the top strap 2140 of the right side 2120. The positioning of the plurality of holes 2210 and the plurality of buttons 2220 relative to the right and left sides 2120, 2130 may be reversed such that the plurality of buttons 2220 extend from the top strap 2140 of the left side 2130 and the plurality of holes 2210 extending through the top strap 2140 of the right side 2120.

FIG. 16B is a close-up cross-sectional view of the button and hole size adjustment system 2200. That is, FIG. 16B shows a button 2220 extending through the hole 2210. With respect to features not specifically discussed, the bifurcated headgear 2000 can be the same as or similar to other headgear disclosed herein. That is, the bifurcated headgear 2000 has top and bottom straps 2140, 2150 that are similarly arranged as the bifurcated headgear 100 with top and bottom straps 140, 150 of FIGS. 1A-7. Further, the top and bottom straps 2140, 2150 are joined at a junction 2170 using the burst-through intra-moulding process, similar to top and bottom straps 140, 150 at the junction 170. That is, the top and bottom straps 2140, 2150 are formed from casings 2180 filled with a unitary plastic core material 2190.

FIGS. 16C to 16D illustrate an open/shut injection moulding tool 2300 configured to form a button 2220 of the hole size adjustment system 2200. For simplicity, FIG. 16C depicts a portion of first and second tool halves 2310, 2320 of the injection moulding tool 2300 for forming a single button 2220. The configuration of the mould tool 2300 and the process for forming a plurality of buttons 2220 is substantially similar to the process for forming a single button 2220. Further, the first and second tool halves 2310, 2320 are similar to the first and second tool halves 310, 320 in FIGS. 1A-7 and include strap cavities for burst-through intra-moulding plastic core material within top and bottom straps. In other words, the plurality of buttons 2220 of the hole size adjustment system 2200 may be formed during the burst-through intra-moulding process (i.e., in a single injection moulding process) for injecting plastic core material 2190 into the top and bottom straps 2140, 2150.

FIG. 16C illustrates a fully formed button 2220 protruding from an upper surface 2222 of the top strap 2140. The first and second tool halves 2310, 2320 have strap cavities 2312, 2322, respectively, within which the casing 2180 of the top strap 2140 is received and injected with plastic core material 2190. The first tool half 2310 also includes a button cavity 2314 fluidly connected to the strap cavities 2312, 2322 having a shape that corresponds to the button 2220, which is cylindrical in the illustrated embodiment. The button 2220 and corresponding button cavity 2314 are not limited to a cylindrical shape. It should also be understood to one of ordinary skill in the art that the technique for forming the plurality of buttons 2220 may be used to form alternative features (e.g., raised grips, logos, connector portions, etc.) on any surface of a strap.

FIG. 16D illustrates a cross-section along a line 16D-16D in FIG. 16C of the first and second tool halves 2310, 2320 during the process of forming the button 2220. As shown in Step 1, the casing 2180 is positioned within the strap cavities 2312, 2322. A portion of the casing 2180 is unsupported by the first tool half 2310 where the button cavity 2314 is connected with the strap cavity 2312. As shown in Steps 2 and 3, as the strap cavities 2312, 2322 fill with plastic core material 2190, the casing 2180 is pushed by the plastic core material 2190 into the button cavity 2314. As shown in Step 4, when the casing 2180 reaches the limit for containing the plastic core material 2190, the plastic core material 2190 will burst through the casing 2180 since there is remaining cavity to fill (i.e., the button cavity 2314). That is, when the casing 2180 is filled with plastic core material 2190 within a region where the casing 2180 is unsupported (e.g., by the button cavity 2314 in the illustrated embodiment), the plastic core material 2190 will penetrate and burst through the casing 2180 and fill the button cavity 2314. Similar to the burst-through intra-moulding process described above, the threads of the casing 2180 may be displaced or elastically deformed when under pressure of the injected plastic core material 2190. Displacement or elastic deformation of the threads may form gaps between the threads through which the injected plastic core material 2190 may flow into the button cavity 2314. In some configurations, the threads of the casing 2180 may tear such that a hole is formed through the casing 2180 through which the injected plastic core material 2190 may flow into the button cavity 2314.

In other embodiments, the plastic core material 2190 penetrates and bursts through the casing 2180 prior to the casing 2180 and strap cavities 2312, 2322 being filled with plastic core material 2190. This may occur, for example where the unsupported location of the casing 2180 is closer to an injection point, the plastic core material 2190 is of a low density or viscosity, the casing 2180 has a low thread density, and/or the unsupported portion is large with respect to the supported area.

Figure 17:
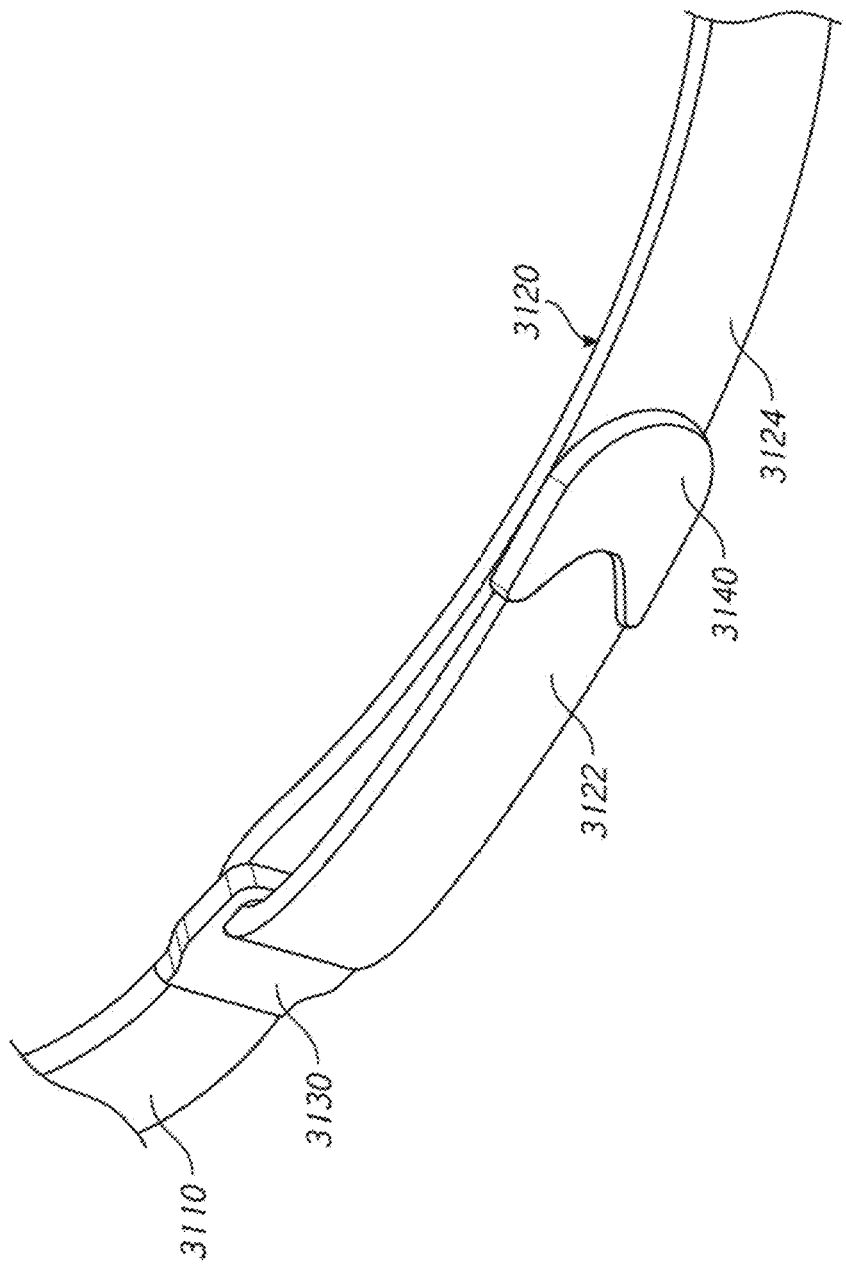
FIG. 17 illustrates an adjustable strap arrangement with adjustment and usability features formed by a burst-through intra-moulding process.

FIG. 17 illustrates an adjustable strap arrangement with adjustment and usability features formed by a burst-through intra-moulding process. The arrangement includes a first strap 3110 and a second strap 3120. The first strap 3110 includes a burst-through end loop 3130, which is configured to receive the second strap 3120. The second strap 3120 is received within the end loop 3130 and doubled back, a fastening arrangement is provided to removably fasten the free end of the second strap 3120. The second strap 3120 includes a burst-through end or grip tab 3140. In at least one embodiment, the second strap 3120 includes an inner surface 3122 and an outer surface 3124, each being of a different visual or tactile configuration. When the second strap 3120 is doubled back and fastened, the inner surface 3122 of the portion of the strap fed past the end loop 3130 of the second strap 3120 exposed. This provides a visual and/or tactile indication of adjusted length.

Figure 18:
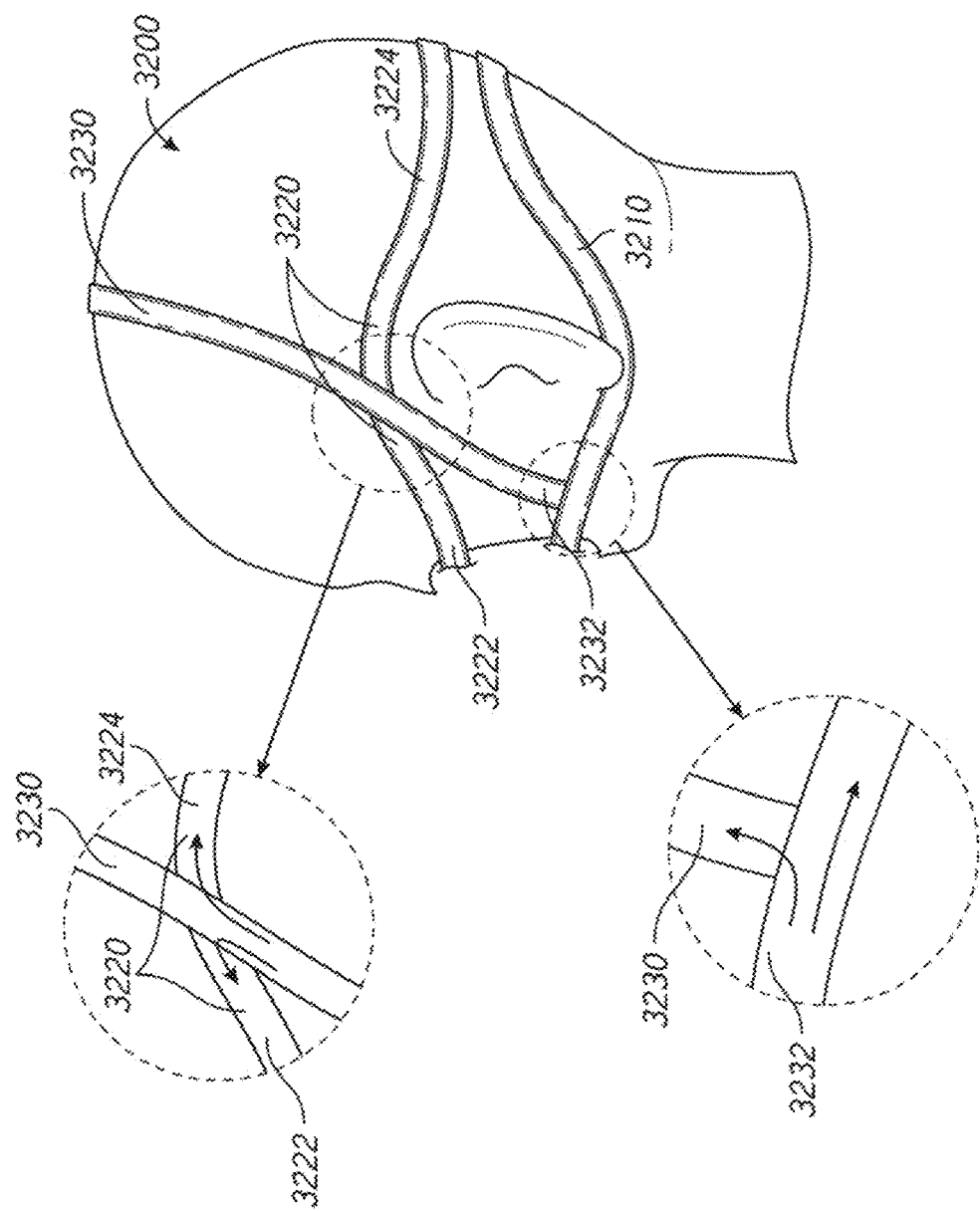
FIG. 18 illustrates an intra-moulded headgear having multiple straps and multiple burst-though junctions.

FIG. 18 shows a non-limiting exemplary embodiment of a headgear 3200 formed in accordance with the presently described intra-mould and/or burst-through processes. The headgear 3200 comprises a lower strap 3210, a middle strap 3220, and a vertical or top strap (hereafter referred to as "vertical strap") 3230. The lower strap 3210 extends from a patient interface (not shown), below the user's ear, around the rear of the user's head, below the user's other ear, to the patient interface. The middle strap 3220 extends from the patient interface, above the patient's ear, around the rear of the headgear 3200, above the user's other ear, to the patient interface. The vertical strap 3230 extends from the lower strap 3210, at a point forward of the user's ear up, over the top of the user's head to a point of the lower strap 3210 forward of the user's other ear.

In the embodiment shown in FIG. 18, the lower strap 3210 is a continuous strap, having a continuous casing. In other words, the casing of the lower strap 3210, prior to the intra-mould and/or burst-through process, is uninterrupted. After the intra-mould burst-through process, burst-through junctions are formed from the lower strap 3210. It should be noted that a continuous casing or strap may include preformed openings that allow for the injected material to be exposed.

As shown in FIG. 18, the vertical strap 3230 is a continuous strap, as the vertical strap 3230 is formed from a casing that is continuous or uninterrupted. After the intra-moulding burst-through process, end portions 3232 of the vertical strap 3230 casing are joined and intra-moulded to the lower strap 3210 by burst-through junctions.

The middle strap 3220 is a segmented strap. In other words, the middle strap 3220 is formed of multiple, or segmented casings. The segmented casings are joined to other straps during the intra-mould burst-through process. In the embodiment shown in FIG. 18, the middle strap 3220 is comprised of front portion casings 3222, each joined to the vertical or top strap 3230 at burst-through junctions, vertically spaced from the lower strap 3210 and above the user's ear. The middle strap 3220 further includes a rear portion casing 3224, ends of which are joined to the vertical or top strap 3230 during the intra-mould burst-though process, also above the user's ear.

The specification will now focus on the non-limiting exemplary embodiments shown in FIGS. 19-42. For the sake of simplicity, the description will focus on additional features introduced in the respective figures. As such, features or configurations previously described may not be included each and every time. Further, the features in the following non-limiting exemplary embodiments may be combined with any of the previously described non-limiting exemplary embodiments to the extent that they may be combined.

Figure 19:
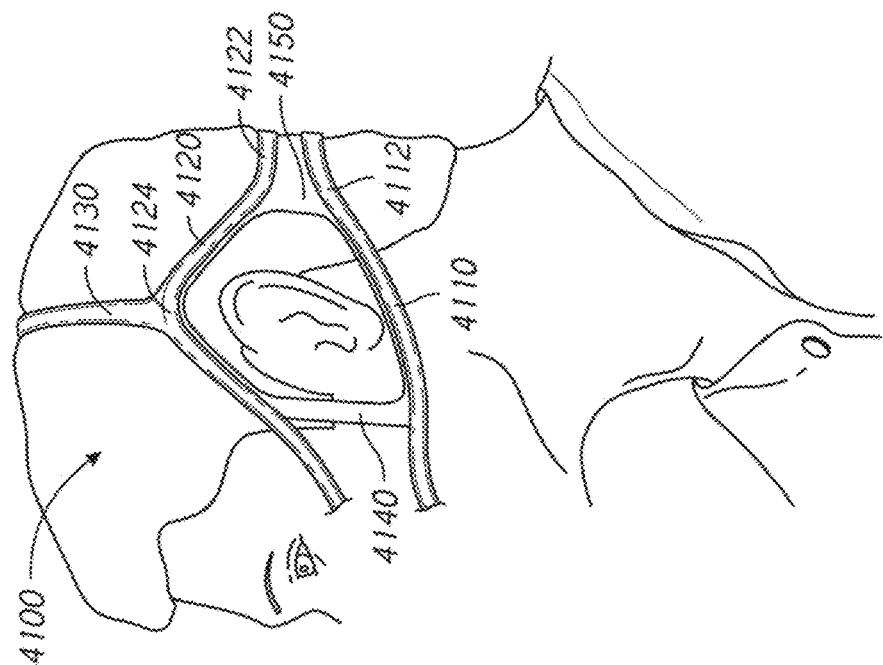
FIG. 19 illustrates an exemplary headgear incorporating intra-mould and burst-through processes, as well as additional comfort layers.

FIG. 19 illustrates a headgear 4100 formed using the intra-mould and/or burst-through process. The headgear 4100 includes a continuous lower strap 4110 and a continuous middle strap 4120. A vertical strap 4130 is formed by a burst-through joint above the user's ear, from an apex 4124 of the middle strap 4120. Forward of the ear, there is a joining strap 4140 between the lower and middle straps 4110, 4120, formed by burst-through junction. Rear portions 4112, 4122 of the lower and middle straps 4110, 4120 converge. A burst-through web portion 4150 joins the rear portions 4112, 4122 of the lower and middle straps 4110, 4120. In some configurations, the vertical strap 4130 and the burst-through web portion 4150 may be unitary and integrally formed.

Figure 20:
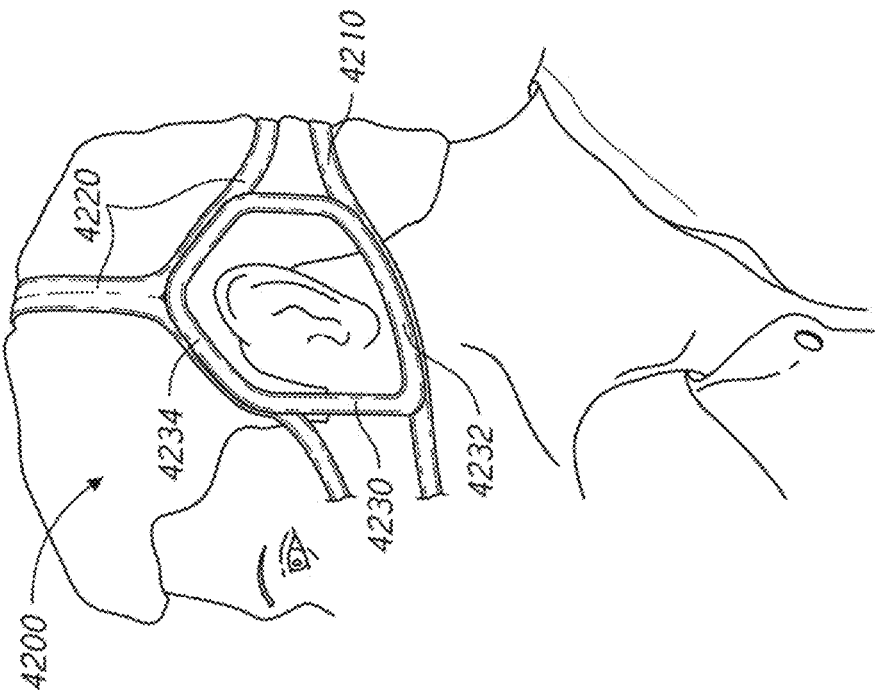
FIG. 20 illustrates another exemplary headgear incorporating intra-mould and burst-through processes, as well as additional comfort layers.
Figure 21:
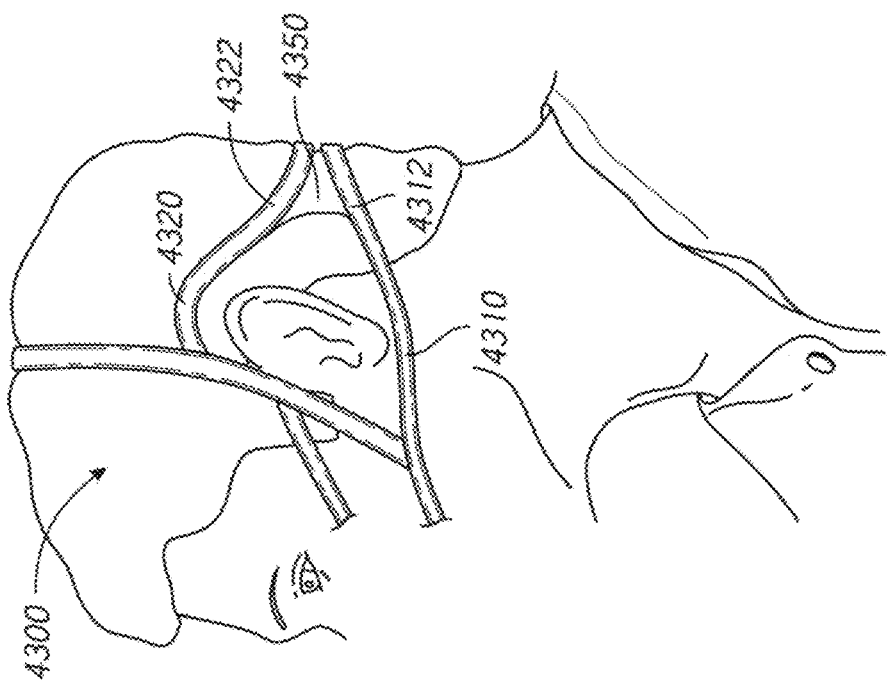
FIG. 21 illustrates an exemplary headgear incorporating intra-mould and burst-through processes, and having a web portion joining rear portions of the lower and middle straps.

FIG. 20 shows another headgear 4200 formed using the intra-mould and/or burst-through process. The headgear 4200 includes a continuous lower strap 4210 and a combined, continuous middle and vertical strap 4220. An ear loop 4230 is provided, and surrounds the user's ear. The lower strap 4210 is attached to the ear loop 4230 along a lower portion 4232 of the ear loop 4230. The continuous middle and vertical strap 4220 is attached along an upper portion 4234 of the ear loop 4230. FIG. 21 shows a headgear 4300 similar to the headgear 3200 shown in FIG. 18, however with a web portion 4350 joining rear portions 4312, 4322 of the lower and middle straps 4310, 4320.

Figure 22:
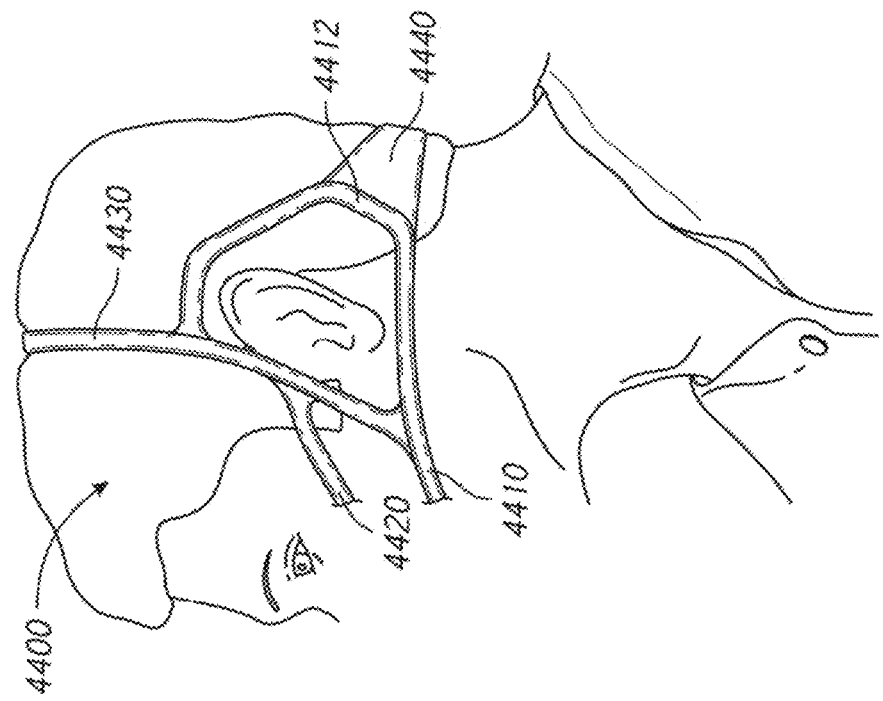
FIG. 22 illustrates another exemplary headgear incorporating intra-mould and burst-through processes, and having continuous lower strap.

FIG. 22 shows a headgear 4400 that includes a continuous lower strap 4410 that extends below the user's ear and extends vertically upward, behind the user's ear and forward above the user's ear to form a portion of an ear loop. A continuous vertical strap 4430 extends from the lower strap 4410 at a portion forward of the ear, the vertical strap 4430 forms a remainder of an ear loop. A middle strap 4420 is joined to the vertical strap 4430 by a burst-through junction. Lower rear portions 4412 of the lower strap 4410 are joined by a rear panel 4440.

Figure 23:
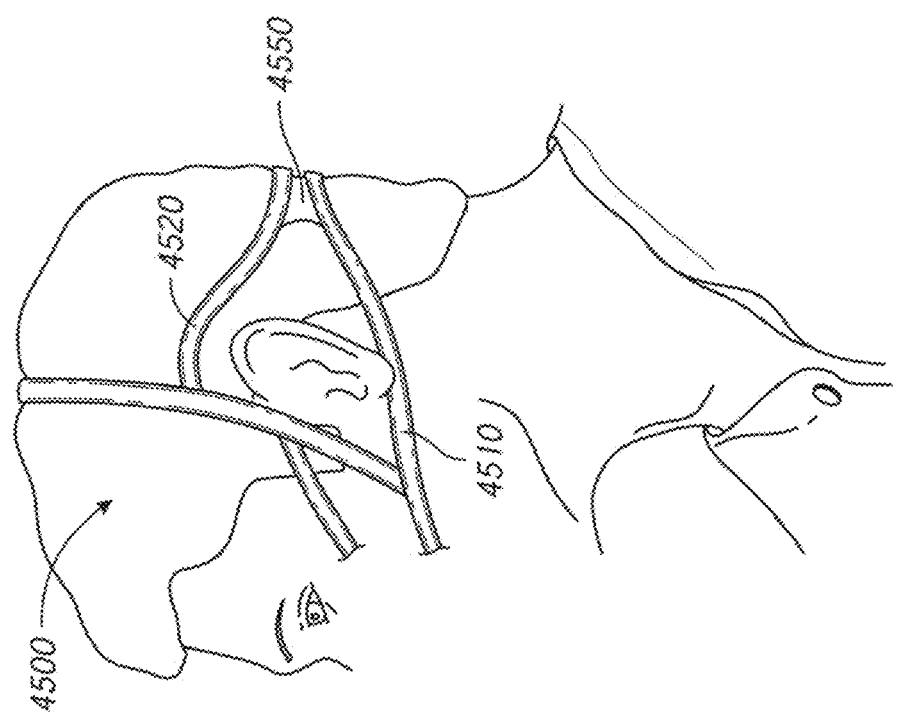
FIG. 23 illustrates an exemplary headgear incorporating intra-mould and burst-through processes, and having a web portion joining rear portions of the lower and middle straps.

FIG. 23 shows a headgear 4500 similar to the headgear 4300 shown in FIG. 21, however with a smaller web portion 4550 joining the lower and middle straps 4510, 4520.

Figure 24:
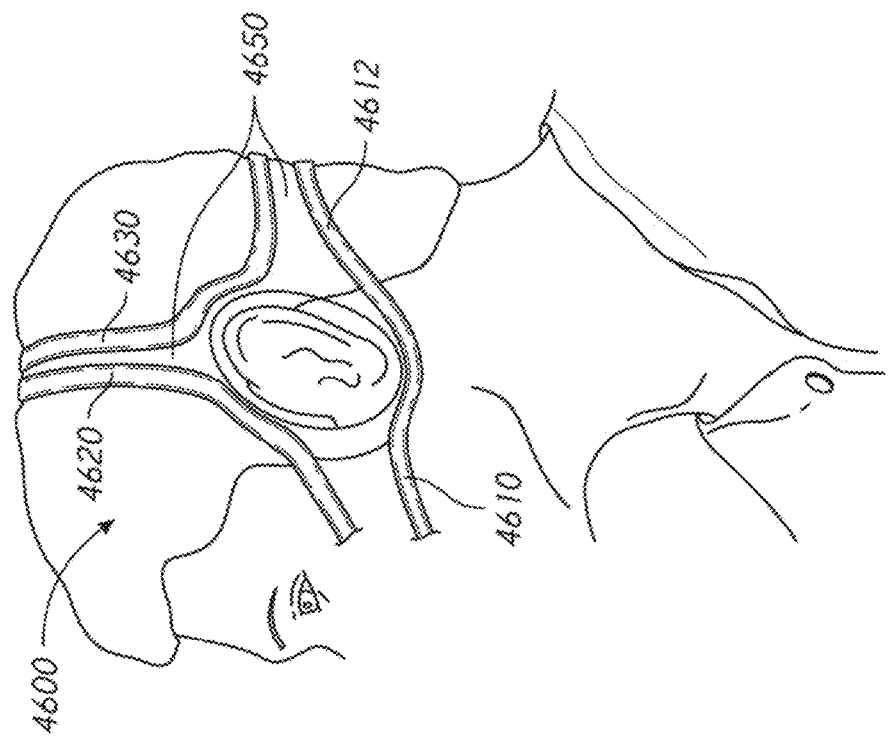
FIG. 24 illustrates an exemplary headgear incorporating intra-mould and burst-through processes, and having a continuous lower strap and a combination continuous middle and vertical strap.

FIG. 24 shows a headgear 4600 that includes a continuous lower strap 4610 and a combination continuous middle and vertical strap 4620. The headgear 4600 further includes a combination continuous upper rear strap and second vertical strap 4630. A web portion 4650 extends between the first and second vertical straps 4620, 4630 as well as between a rear portion 4612 of the continuous lower strap 4610 and the upper rear strap 4630. The web portion 4650 also forms an ear loop that surrounds the ear. That is, the web portion 4650 has a hole within which the ear may be positioned.

Figure 26:
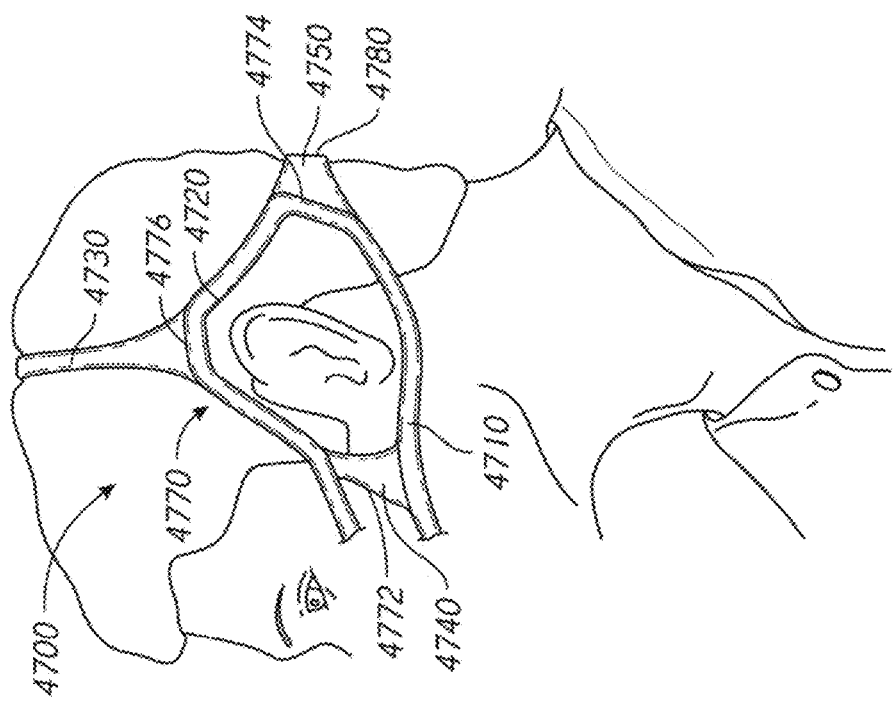
FIG. 26 illustrates another exemplary headgear incorporating intra-mould and burst-through processes, and having lower and middle straps that are formed from a continuous casing in the form of a closed loop structure.
Figure 25:
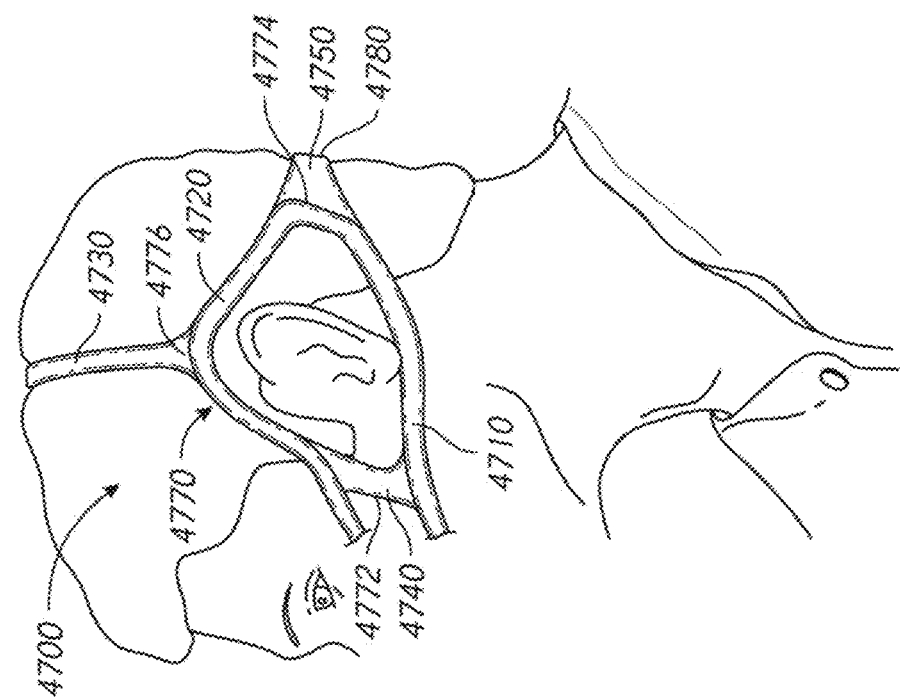
FIG. 25 illustrates an exemplary headgear incorporating intra-mould and burst-through processes, and having lower and middle straps that are formed from a continuous casing in the form of a closed loop structure.

FIGS. 25 and 26 show two examples of a headgear 4700 having lower and middle straps 4710, 4720 that are formed from a continuous casing in the form of a closed loop structure. The lower and middle straps 4710, 4720 form a portion of an ear loop 4770. A web portion 4740 extends between the lower strap 4710 and the middle strap 4720 to form a front portion 4772 of the ear loop 4770. The vertical strap 4730 is formed by a web portion extending between the upper portions 4766, 4776 of the right and left side ear loops 4760, 4770. A rear portion 4780 of the headgear 4700 is formed by rear web portion 4750 extending between lower, rear portions 4764, 4774 of the right and left side ear loops 4760, 4770.

Figure 28:
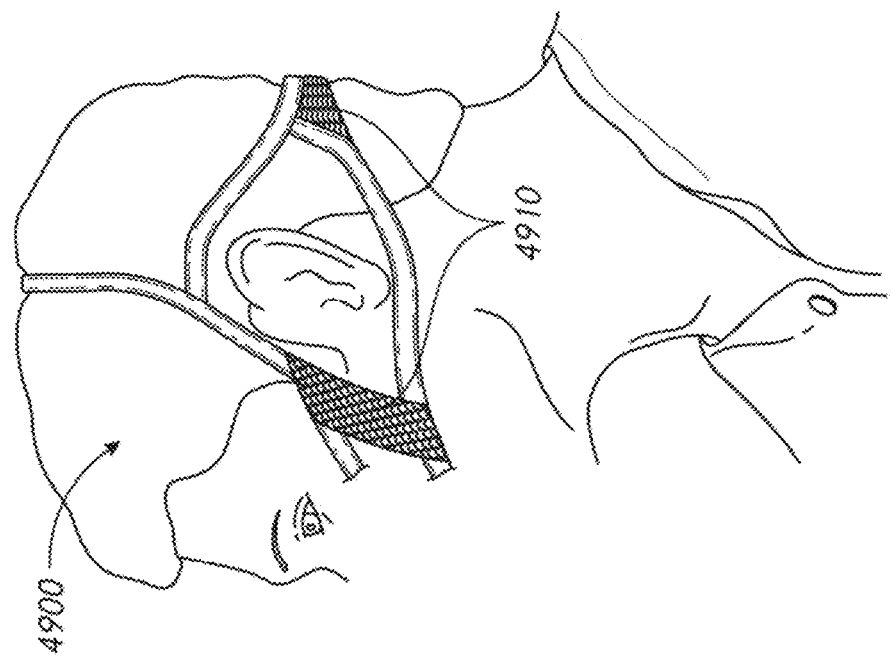
FIG. 28 illustrates another exemplary headgear incorporating intra-mould and burst-through processes, and having quilted fabric or material attached to portions of the headgear in direct contact with the user's skin or hair.
Figure 27:
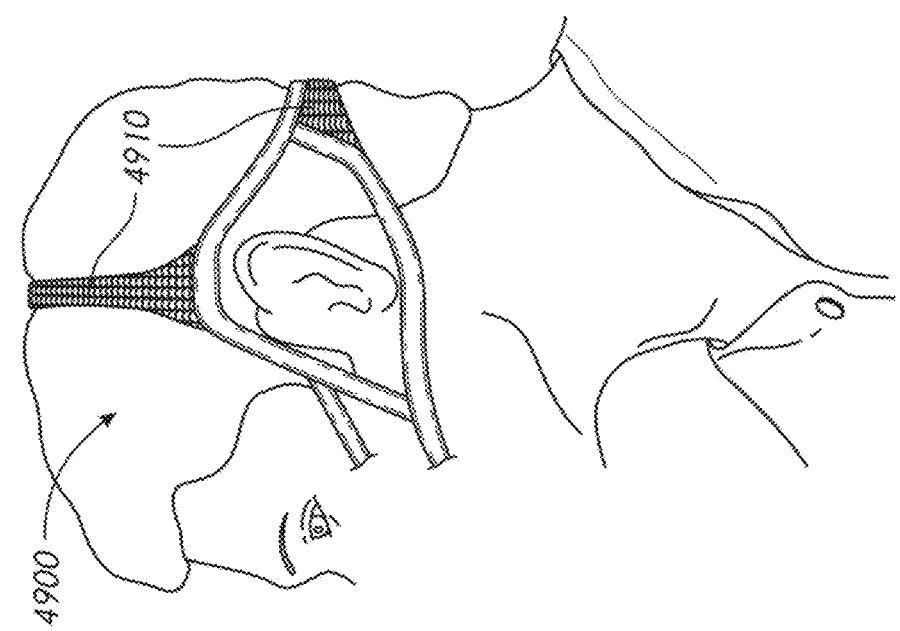
FIG. 27 illustrates an exemplary headgear incorporating intra-mould and burst-through processes, and having quilted fabric or material attached to portions of the headgear in direct contact with the user's skin or hair.

FIGS. 27 and 28 show two examples of a headgear 4900 having quilted fabric or material 4910 provided attached to portions of the headgear 4900 in direct contact with the user's skin or hair, for example on the user's face or at the back of the user's neck. Similar to a down comforter, the quilted material 4910 is soft in texture and provides cushioned padding which improves the comfort of the headgear 4900 such that the user will want to wear the headgear 4900 to bed. The quilted material 4910 may be stitched or welded to the intra-moulded straps or web portions of the headgear 4900. The disclosed configurations are not limited to quilted materials and may include fabrics and textiles having a variety of material properties, such as but not limited to, soft, padded, breathable, moisture-wicking, and grippy/tacky textures.

Figure 29:
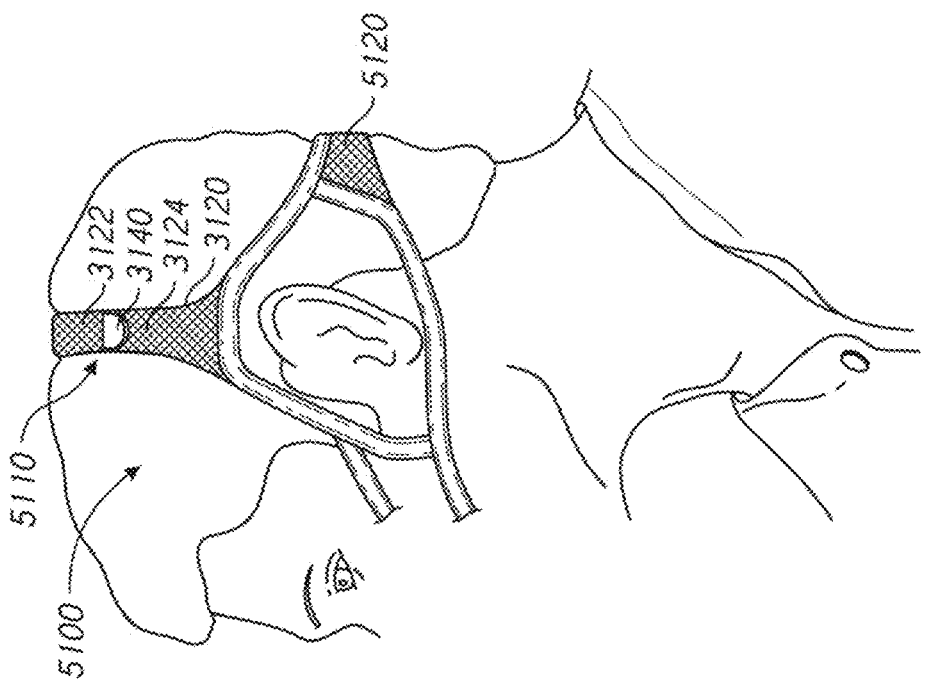
FIG. 29 illustrates an exemplary headgear incorporating intra-mould and burst-through processes, and having a vertical strap and a neck strap formed from a foam-lycra laminate material.

FIG. 29 shows a headgear 5100 that includes a vertical strap 5110 and a neck strap 5120 formed from a foam-lycra laminate material such as Breath-o-prene. Breath-o-prene allows air to pass through the strap and wicks perspiration away from the skin for enhanced comfort and compliance. Further, the Breath-o-prene provides padding to the strap to reduce pressure points against the user's head. The vertical strap 5110 comprises a first strap 3110 and a second strap 3120. The first strap 3110 includes a burst-through end loop 3130, which is configured to receive the second strap 3120. The second strap 3120 is received within the end loop 3130 and doubled back, a fastening arrangement is provided to removably fasten the free end of the second strap 3120. The second strap 3120 includes a burst-through end or grip tab 3140. In at least one embodiment, the second strap 3120 includes an inner surface 3122 and an outer surface 3124, each being of a different visual or tactile configuration. When the second strap 3120 is doubled back and fastened, the inner surface 3122 of the portion of the strap fed past the end loop 3130 of the second strap 3120 is exposed. This provides a visual and/or tactile indication of adjusted length.

Figure 30:
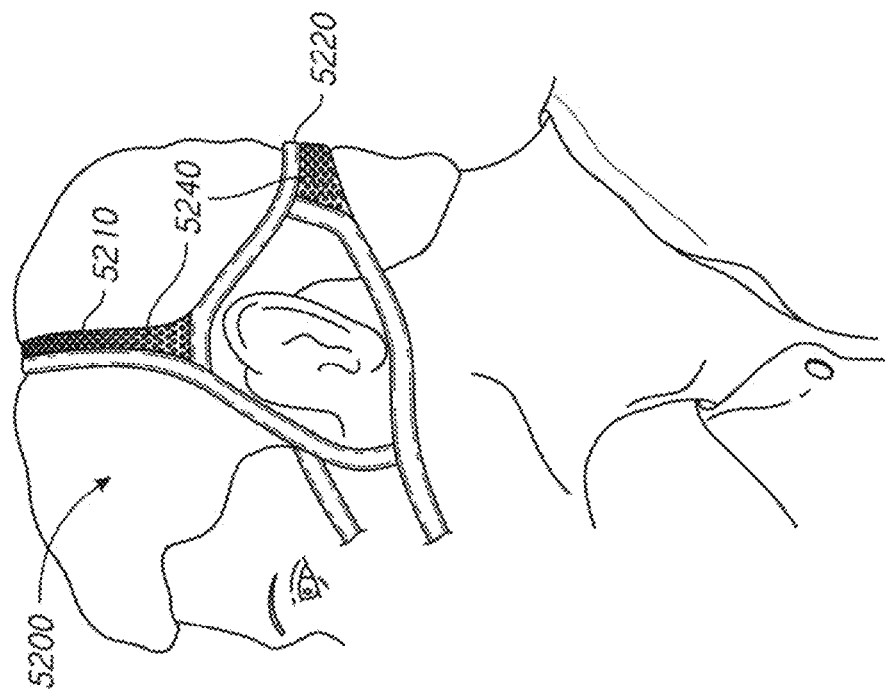
FIG. 30 illustrates an exemplary headgear incorporating intra-mould and burst-through processes, and having a breathable, moisture-wicking material on the vertical strap and the neck strap.

FIG. 30 shows a headgear 5200 having a breathable, moisture-wicking material 5240 on the vertical strap 5210 and the neck strap 5220. The breathable, moisture-wicking material 5240 may be an athletic and performance knit fabric that improves the breathability of the headgear 5200 at portions in contact with the user's skin or hair. The breathable, moisture-wicking material 5240 may also provide the headgear 5200 with an aggressive and athletic appearance.

Figure 31:
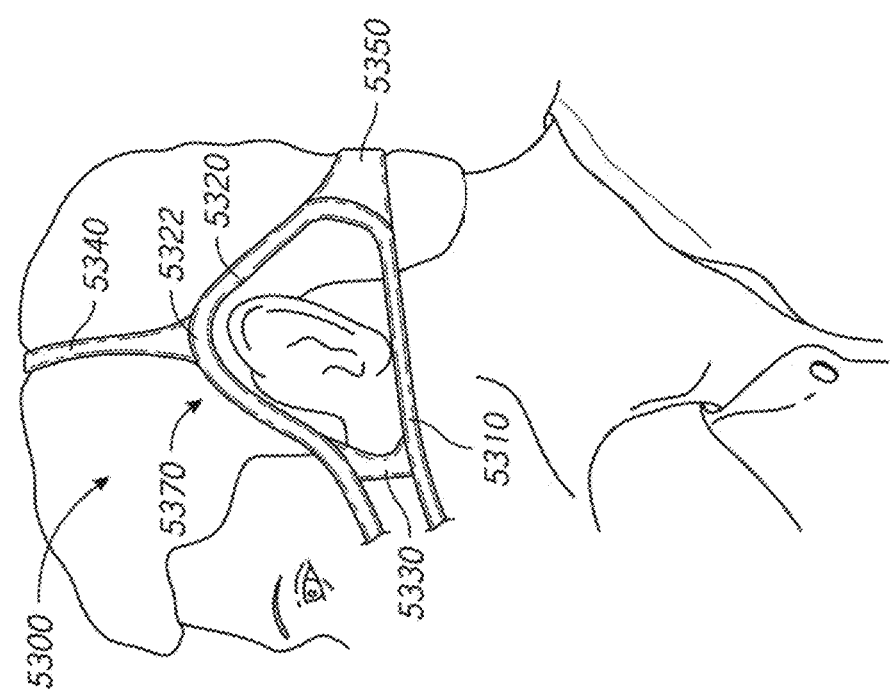
FIG. 31 illustrates an exemplary headgear incorporating intra-mould and burst-through processes, and lower and middle straps that are formed from a continuous casing in the form of a closed loop structure.

FIG. 31 shows a headgear 5300 having lower and middle straps 5310, 5320 that are formed from a continuous casing in the form of a closed loop structure. The continuous lower and middle straps 5310, 5320 form a substantial portion of the ear loop 5370. The continuous lower and middle straps 5310, 5320 are joined by a burst-through junction 5330 forward of the ear which forms a remaining portion of the ear loop 5370 forward of the ear. A vertical strap 5340 is formed at an apex 5322 of the middle strap 5320 and is formed from an exposed plastic via burst-through injection process. Similarly, a neck strap 5350 may also be formed from exposed plastic. Alternatively, the vertical strap 5340 and the neck strap 5350 may be comprised of an intra-moulded strap having a textile outer casing. The vertical strap 5340 and the neck strap 5350 may also be filleted at their junctions with the lower and middle straps 5310, 5320 to improve the connection strength with the lower and middle straps 5310, 5320.

Figure 32:
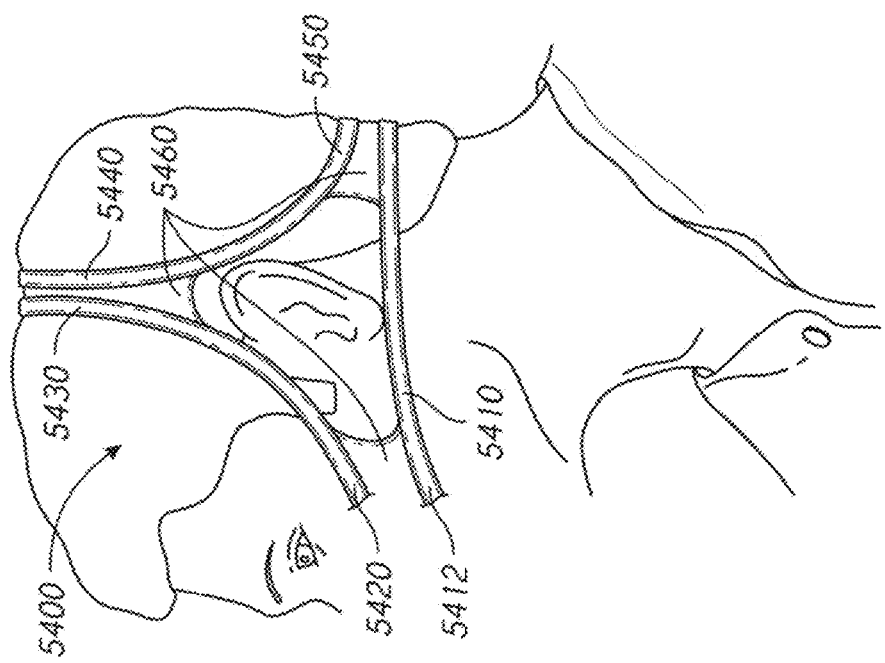
FIG. 32 illustrates an exemplary headgear incorporating intra-mould and burst-through processes, and having a bottom lower strap, a middle strap and a front vertical strap that are formed from a continuous casing in the form of a closed loop structure.

FIG. 32 shows a headgear 5400 having a bottom lower strap 5410, a middle strap 5420 and a front vertical strap 5430 that are formed from a continuous casing in the form of a closed loop structure. A rear vertical strap 5440 and a top lower strap 5450 are also a continuous strap and may form a closed loop structure. A web portion 5460 extends between the front and rear vertical straps 5430, 5440 as well as between the top and bottom lower straps 5450, 5410. A web portion 5460 also extends between a front portion 5412 of the bottom lower strap 5410 and the middle strap 5420. The web portion 5460 also forms an ear loop that surrounds the ear. That is, the web portion 5460 has a hole within which the ear may be positioned.

Figure 34:
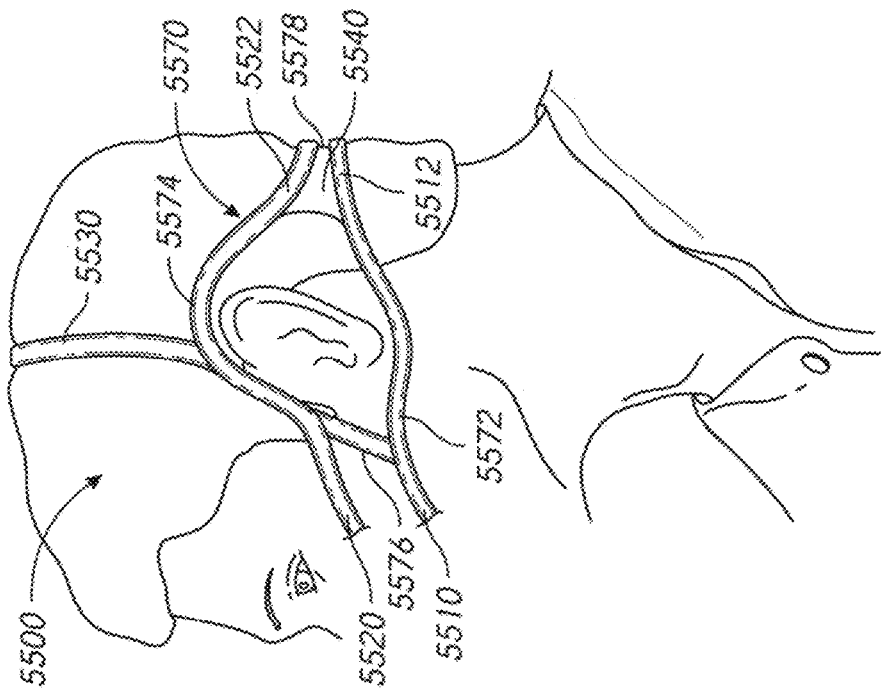
FIG. 34 illustrates an exemplary headgear incorporating intra-mould and burst-through processes, and having lower and middle straps that are formed from a continuous casing in the form of a closed loop structure.
Figure 33:
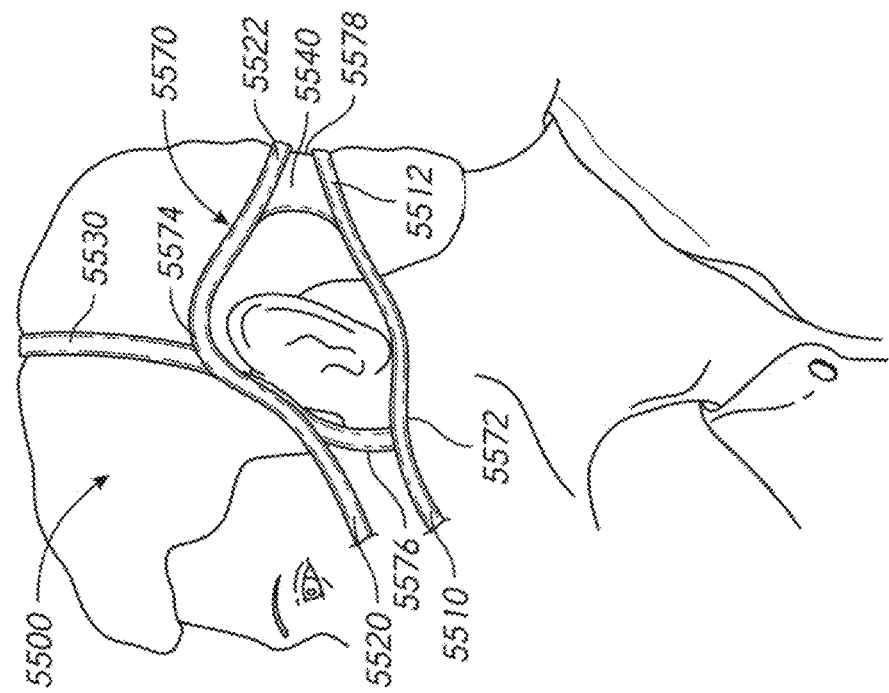
FIG. 33 illustrates an exemplary headgear incorporating intra-mould and burst-through processes, and having lower and middle straps that are formed from a continuous casing in the form of a closed loop structure.

FIGS. 33 and 34 show two examples of a headgear 5500 having lower and middle straps 5510, 5520 that are formed from a continuous casing in the form of a closed loop structure. An upper portion 5574 of an ear loop 5570 is defined by middle strap 5520. A lower portion 5572 of the ear loop 5570 is defined by lower strap 5510. A web portion 5540 extends between rear portions 5512, 5522 of the continuous lower and middle straps 5510, 5520 and defines a rear portion 5578 of the ear loop 5570. The continuous vertical strap 5530 extends from the lower strap 5510 at a portion forward of the ear and forms a forward portion 5576 of the ear loop 5570. The middle strap 5520 overlies the vertical strap 5530. A middle strap 5520 is joined to the vertical strap 5530 by a burst-through junction or arc welding. FIG. 34 illustrates a vertical strap 5530 having an outer casing that is formed from a different material than the material used to form the middle and lower straps 5520, 5510.

Figure 35:
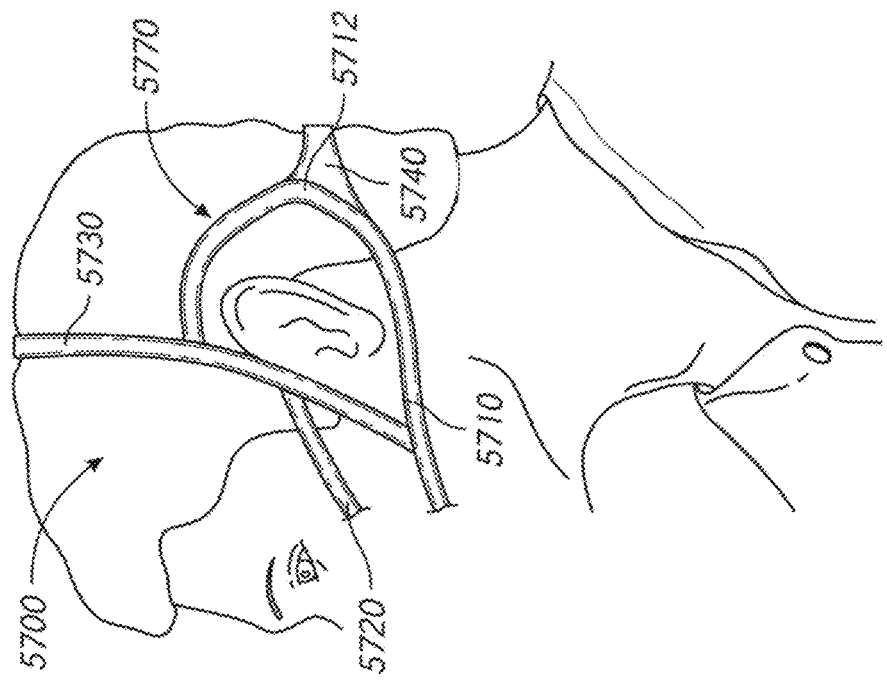
FIG. 35 illustrates an exemplary headgear incorporating intra-mould and burst-through processes, and having lower and middle straps having a continuous casing.

FIG. 35 shows a headgear 5700 having lower and middle straps 5710, 5720 having a continuous casing. The lower strap 5710 extends below the user's ear and extends vertically upward, behind the user's ear and forward above the user's ear to form a portion of an ear loop 5770. A continuous vertical strap 5730 extends from the lower strap 5710 at a portion forward of the ear, the vertical strap 5730 forms a remainder of an ear loop 5770. A middle strap 5720 is joined to the vertical strap 5730 by a burst-through junction. Lower rear portions 5712 of the lower strap 5710 are joined by a rear panel 5740.

Figure 36:
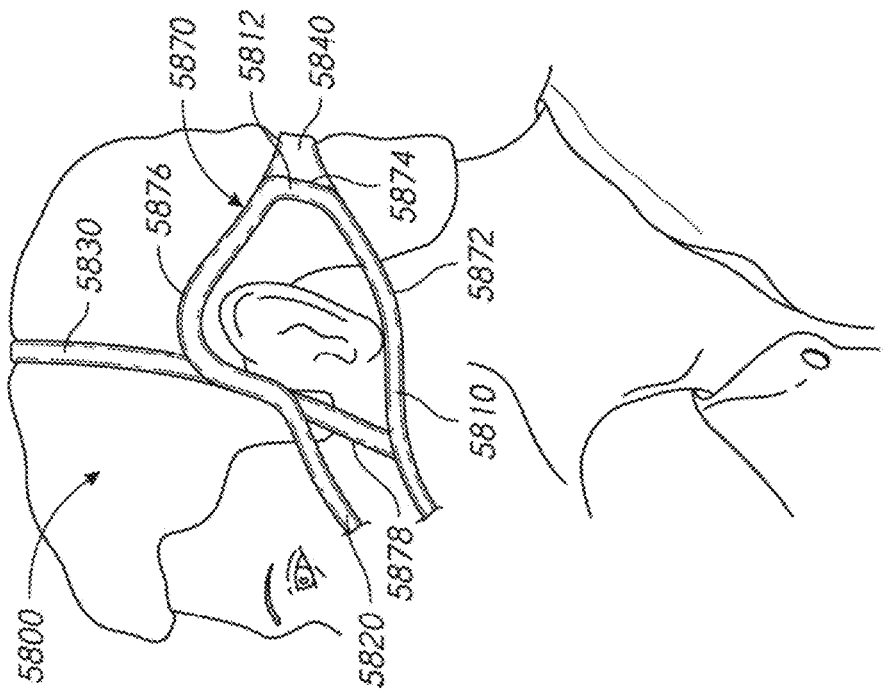
FIG. 36 illustrates an exemplary headgear incorporating intra-mould and burst-through processes, and having lower and middle straps that are formed from a continuous casing in the form of a closed loop structure.

FIG. 36 shows a headgear 5800 having lower and middle straps 5810, 5820 that are formed from a continuous casing in the form of a closed loop structure. The continuous lower and middle strap 5810, 5820 extend below the user's ear and extends vertically upward and around the user's ear to form bottom, rear and top 5872, 5874, 5876 portions of an ear loop 5870, and continues forward from a position forward of the user's ear to form a portion of the middle strap 5820. A continuous vertical strap 5830 extends from the lower strap 5810 at a portion forward of the ear, the vertical strap 5830 forms a forward portion 5878 of an ear loop 5870. The middle strap 5820 at a portion substantially parallel with the vertical strap 5830 overlies the vertical strap 5830 and is joined to the vertical strap 5830 by a burst-through junction. Lower rear portions 5812 of the lower strap 5810 are joined by a rear panel or a web portion 5840.

Figure 38:
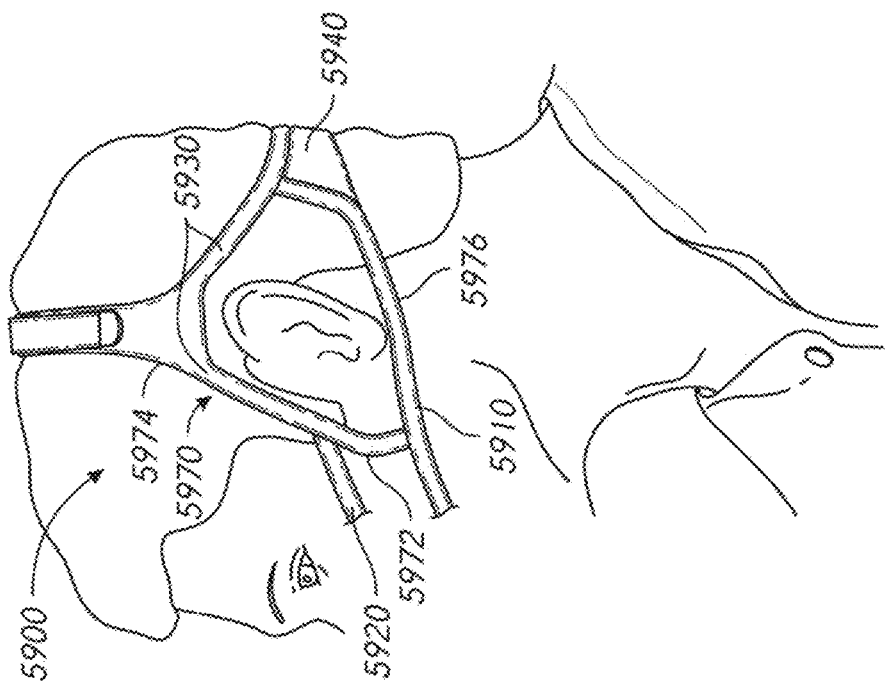
FIG. 38 illustrates another exemplary headgear incorporating intra-mould and burst-through processes, and having lower and middle straps that are formed from a continuous casing.
Figure 37:
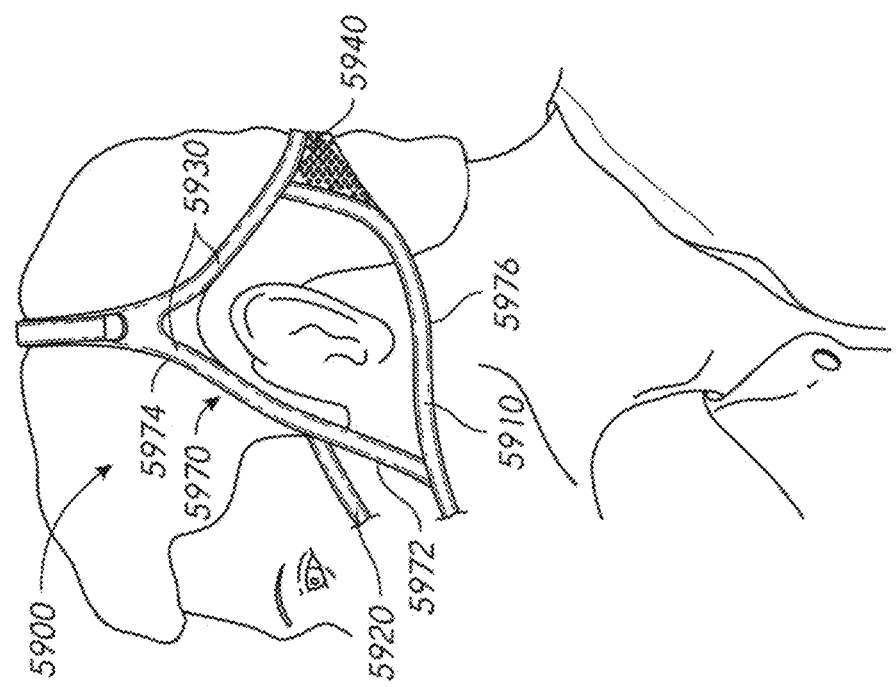
FIG. 37 illustrates an exemplary headgear incorporating intra-mould and burst-through processes, and having lower and middle straps that are formed from a continuous casing.

FIGS. 37 and 38 show two examples of a headgear 5900 having lower and middle straps 5910, 5920 that are formed from a continuous casing. A vertical strap 5930 extends from the lower strap 5910 at a portion forward of the ear and forms forward and top portions 5972, 5974 of an ear loop 5970. The vertical strap 5930 extends rearward and is connected to the lower strap 5910 at a position behind the user's ear. In some configurations, the vertical strap 5930 extends around the rear of the user's head. The lower strap 5910 forms a bottom portion 5976 of the ear loop 5970. The middle strap 5920 is connected to the vertical strap 5930 at a position forward of the user's ear. A neck strap 5940 is attached to both the vertical and lower straps 5930, 5910 and extends along the length of a portion of the vertical strap 5930 behind the user's head. In FIG. 37, the neck strap 5940 is formed from a breathable, moisture-wicking material may be an athletic and performance knit fabric. The vertical strap 5930 may be covered with textile material or exposed plastic core material.

Figure 39:
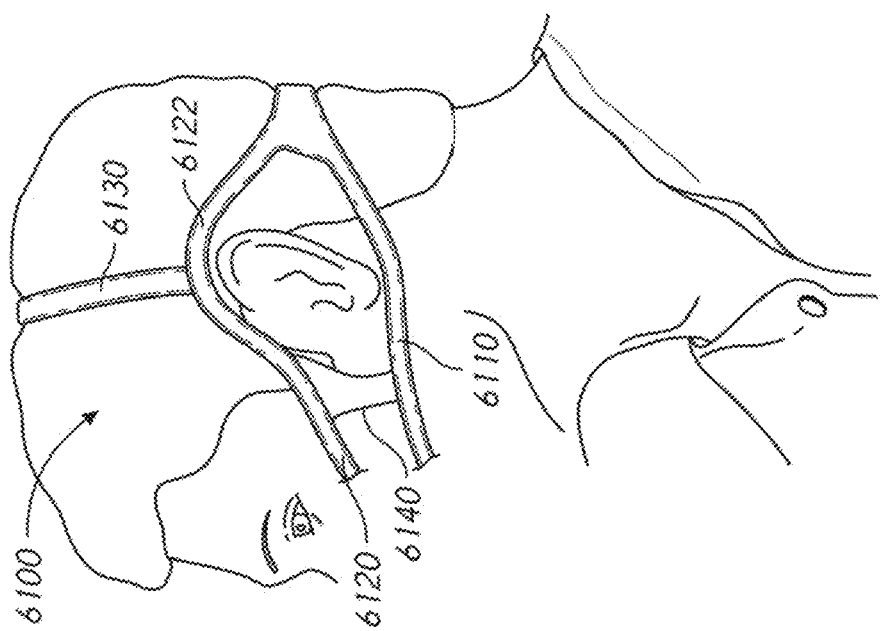
FIG. 39 illustrates an exemplary headgear incorporating intra-mould and burst-through processes, and having lower and middle straps that are formed from a continuous casing.

FIG. 39 shows an embodiment of a headgear 6100 having lower and middle straps 6110, 6120 that are formed from a continuous casing. The lower and middle straps 6110, 6210 converge at a location rear of the user's ear. A burst-through junction 6140 connects lower and middle straps 6110, 6120 at a location forward of the user's ear. A vertical strap 6130 is formed by a burst-through joint above the user's ear, from an apex 6122 of the middle strap 6120. The vertical strap 6130 may be covered with textile material or exposed plastic core material.

Figure 40:
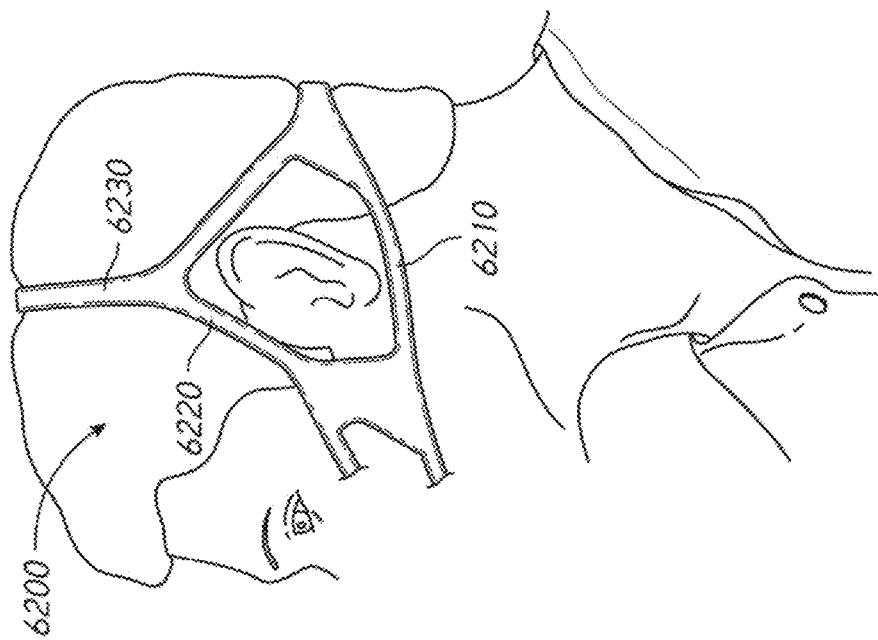
FIG. 40 illustrates an exemplary headgear incorporating intra-mould and burst-through processes, and having lower, middle and vertical straps that are formed from a continuous casing.

FIG. 40 shows an embodiment of a headgear 6200 having lower, middle and vertical straps 6210, 6220, 6230 that are formed from a continuous casing. In some non-limiting configurations, the continuous strap may be formed by fully knitting a continuous casing or joining together layers of a textile material.

Figure 41:
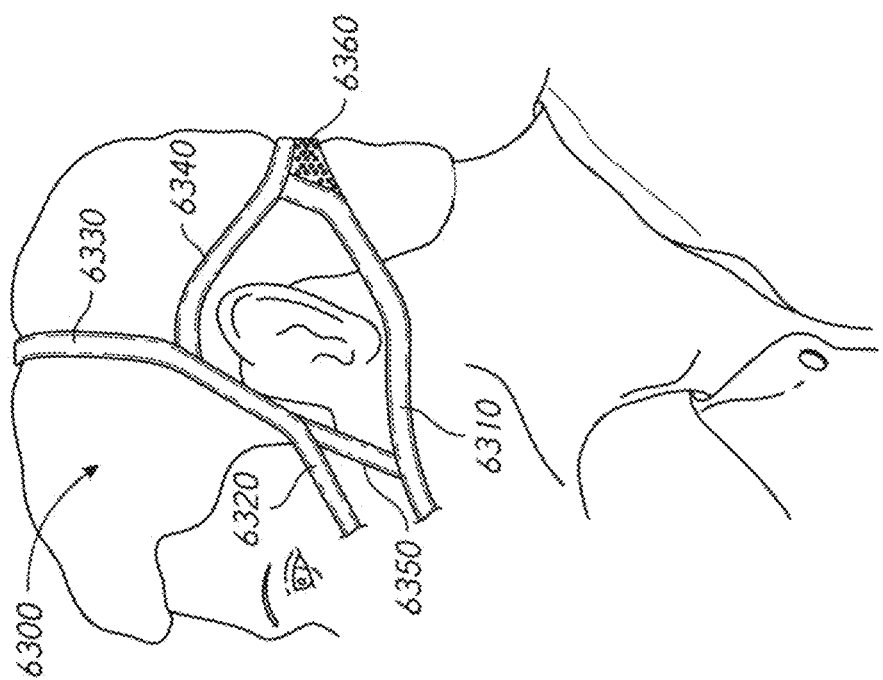
FIG. 41 illustrates an exemplary headgear incorporating intra-mould and burst-through processes, and having lower strap, and middle and vertical straps that are formed from a continuous casing.

FIG. 41 shows an embodiment of a headgear 6300 having lower strap 6310, and middle and vertical straps 6320, 6330 that are formed from a continuous casing. The continuous strap is connected to a rear strap 6340 at a junction with an end of a lower strap 6310 rearward of the user's ear, at a junction with the vertical strap 6330 at a position above the user's ear. A web portion 6350 joins the lower and middle straps 6310, 6320 at a position forward of the user's ear. Alternatively, the continuous strap may join the lower and middle straps 6310, 6320 at a position forward of the user's ear. A neck strap 6360 is attached to both the rear and lower straps 6340, 6310 and extends along the length of a portion of the rear strap 6340 behind the user's head. The neck strap 6360 is formed from a breathable, moisture-wicking material may be an athletic and performance knit fabric.

Figure 42:
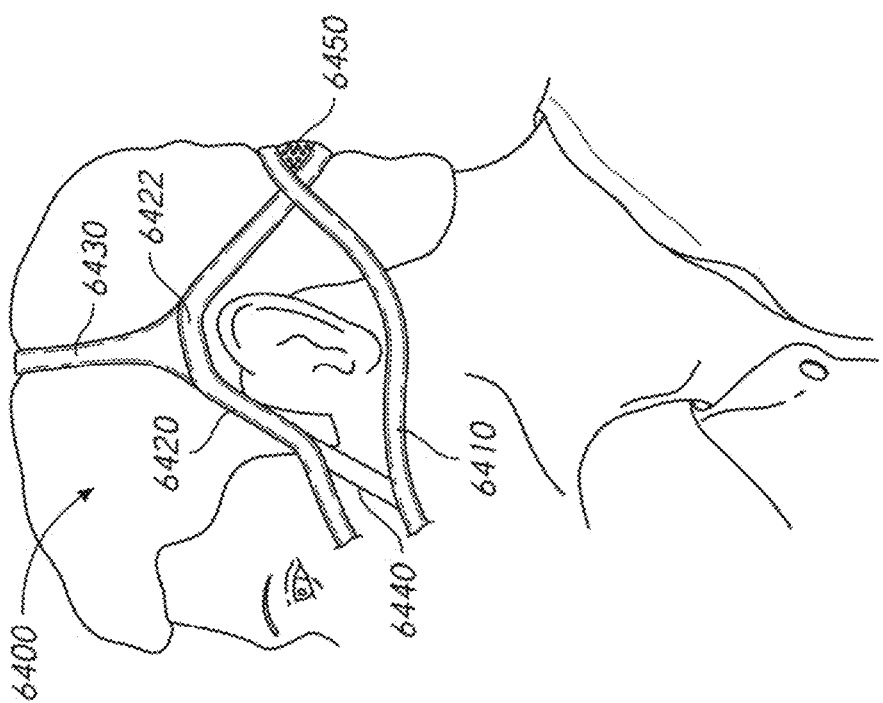
FIG. 42 illustrates an exemplary headgear incorporating intra-mould and burst-through processes, and having lower and middle strap that are formed from a continuous casing.

FIG. 42 shows an embodiment of a headgear 6400 having lower and middle strap 6410, 6420 that are formed from a continuous casing. In some configurations, the continuous strap forms a closed loop structure. The lower and middle straps 6410, 6420 cross at a position rearward of the user's ear. A breathable, moisture-wicking material may be positioned within an opening 6450 between the lower and middle straps 6410, 6420. The lower and middle straps 6410, 6420 are connected by an intra-moulded web portion or a strap 6440 at a position forward of the user's ear. A vertical strap 6430 is formed by a burst-through joint above the user's ear, from an apex 6422 of the middle strap 6420. In some configurations, the vertical strap 6430 is overlaid by the middle strap 6420 and extends toward the lower strap 6410 to connect the lower and middle straps 6410, 6420.

Figure 43B:
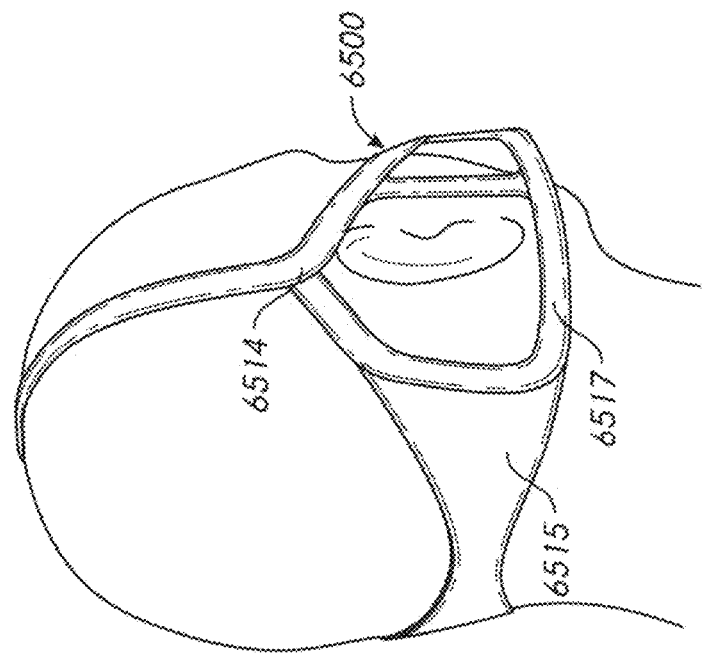
FIG. 43B is a rear perspective view of the exemplary headgear in FIG. 43A.
Figure 43A:
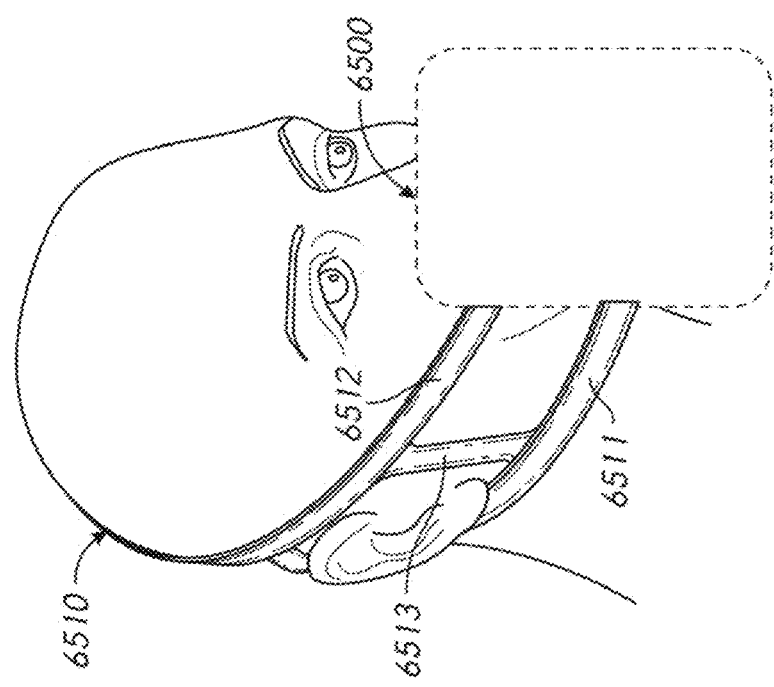
FIG. 43A is a front perspective view of an exemplary headgear that can be used with a patient interface.

FIGS. 43A-B show perspective views of an embodiment of a headgear 6510 that can be used with a patient interface 6500. The headgear 6510 includes a middle strap 6512, a lower strap 6511 and a vertical member 6513. The lower strap 6511 extends from the patient interface 6500 below the user's ear and extends vertically upward, behind the user's ear and forward above the user's ear to form a portion of an ear loop 6517. The middle strap 6512 extends from the connector over the user's ear forming an upper portion of the ear loop 6517, meeting the lower strap 6511 at a junction. The middle strap 6512 continues from the junction over the user's head. A vertical member 6513 extends from a junction with the lower strap 6511 at a portion forward of the ear, to a junction with the middle strap 6512 at a portion forward of the ear, forming the remainder of the ear loop 6517. The middle strap 6512 can include an adjustment mechanism to adjust the fitment of the headgear 6510 over the head of the user. The lower strap 6511 can include an adjustment mechanism. The rear portion 6515 can include an adjustment mechanism. The adjustment mechanisms may allow the lengths of the straps to be adjusted such that the headgear 6510 fits a range of head sizes.

The lower and middle straps 6511, 6512 are manufactured using an intra-moulding process including a casing that can be knitted from a material having a soft texture such that the middle strap 6512 and the lower strap 6511 are comfortable when in contact with the user's skin. Similarly, the casing can have a thickness and ply such that the headgear 6510 is comfortable when in contact with the user's skin. An interior of the casing includes a plastic material to provide rigidity to the headgear 6510. The middle strap 6512 and lower strap 6511 are integrally formed at the headgear junction 6514 using a burst-through intra-moulding technique. The vertical member 6513 is integrally formed with the middle and lower straps 6512, 6511 at each of its junctions through the same burst-through intra-moulding technique.

In the illustrated embodiment, the middle and lower straps 6512, 6511 are continuous straps, having continuous casings. In other words, the casings of the straps, prior to the intra-mould and/or burst-through process are uninterrupted. It should be noted that a continuous casing or strap can include pre-formed openings that allow for the injected material to be exposed.

The rear portion 6515 of the headgear 6510 passes around the rear of the user's head. It can be formed of a plastic web made in the burst-through process. Alternately, the rear portion 6515 can be formed from an elastic material such that the headgear 6510 can be configured to fit a wide variety of user head profiles. Appropriate materials may include Breath-o-prene, spacer fabric, or other stretchable and compliant fabrics. The fabric can be connected to the headgear 6510 using stitching, RF welding, ultrasonic welding, an adhesive bond or any other appropriate connection mechanism.

The description of the following embodiments, for the sake of simplicity will focus on additional features introduced in the respective figures. As such, features or configurations previously described may not be included each and every time.

Figure 44B:
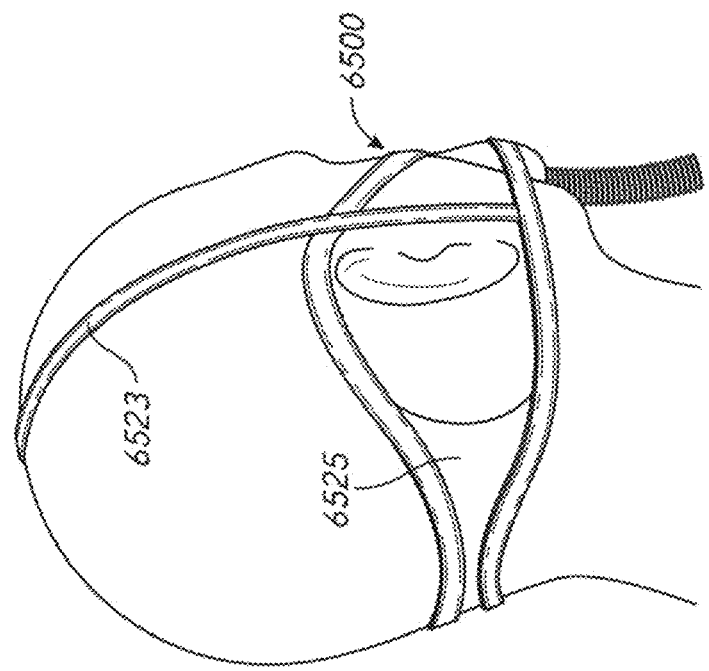
FIG. 44B is a rear perspective view of the exemplary headgear in FIG. 44A.
Figure 44A:
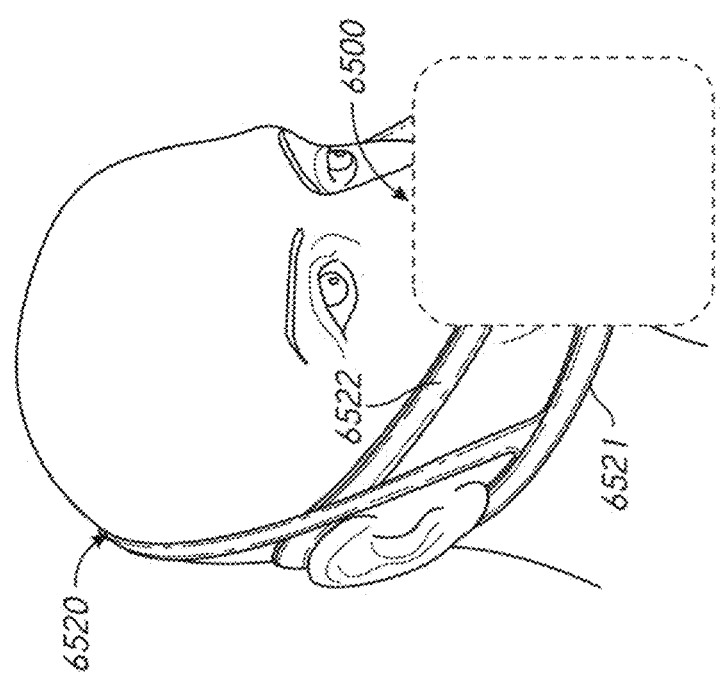
FIG. 44A is a front perspective view of an exemplary headgear that can be used with a patient interface.

FIGS. 44A-B show perspective views of an embodiment of a headgear 6520 that can be used with a patient interface 6500. The headgear 6520 includes a lower strap 6521, a middle strap 6522 and an upper, vertical or top strap 6523. The lower strap 6521 extends from a patient interface 6500, below the user's ear, around the rear of the user's head, below the user's other ear, to the patient interface 6500. The middle strap 6522 extends from the patient interface 6500, above the user's ear, around the rear of the user's head, above the user's other ear, to the patient interface 6500. The vertical strap 6523 extends from a junction on the lower strap 6521, at a point forward of the user's ear, to a junction with the middle strap 6522, and over the top of the user's head to another junction with the middle strap 6522, and to a point of the lower strap 6521 forward of the user's other ear. All the junctions of the illustrated configuration can be formed using burst-through intra-moulding.

The headgear 6520 includes a rear web portion 6525 at the rear of the user's head. The rear web portion 6525 can be formed by burst-through intra-moulding. The web portion 6525 can be integrally formed with the headgear 6520. Alternately, the web portion 6525 can be fabricated from a more flexible material (e.g., Breath-o-prene) and connected to the lower and middle straps 6521, 6522 through any appropriate means (stitching, RF welding, adhesive, etc.).

Figure 45B:
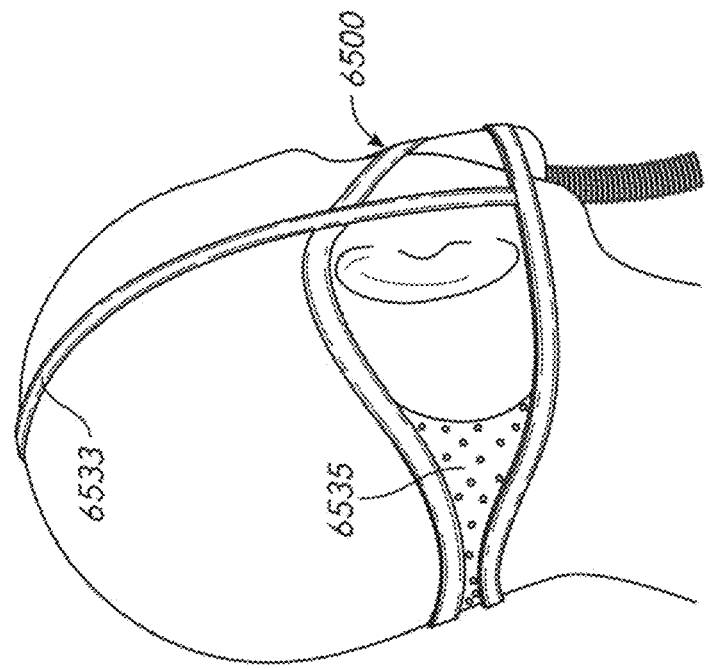
FIG. 45B is a rear perspective view of the exemplary headgear in FIG. 45A.
Figure 45A:
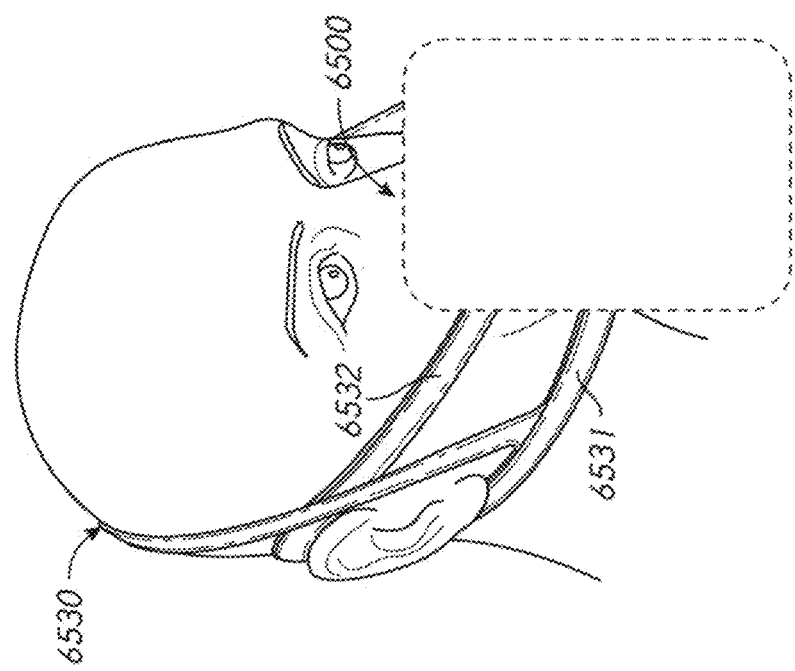
FIG. 45A is a front perspective view of an exemplary headgear that can be used with a patient interface.

FIGS. 45A-B show perspective views of an embodiment of a headgear 6530 that can be used with a patient interface 6500. The headgear 6530 includes a rear web portion 6535 that includes holes or voids. These holes act to increase the flexibility and breathability of the rear portion 6535. The web portion 6535 can be intra-moulded plastic formed by the burst-through process, or it can be an elastic fabric (e.g., Breath-o-prene, spacer fabric, etc.).

Figure 46B:
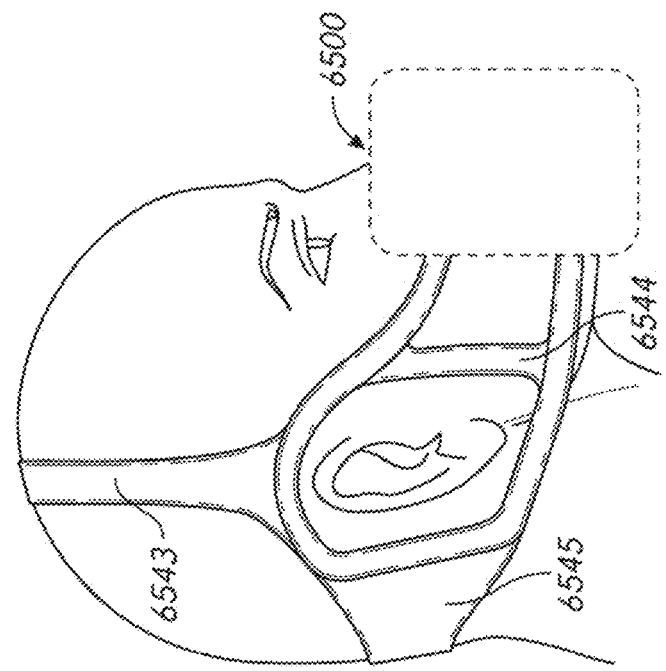
FIG. 46B is a side view of the exemplary headgear in FIG. 46A.
Figure 46A:
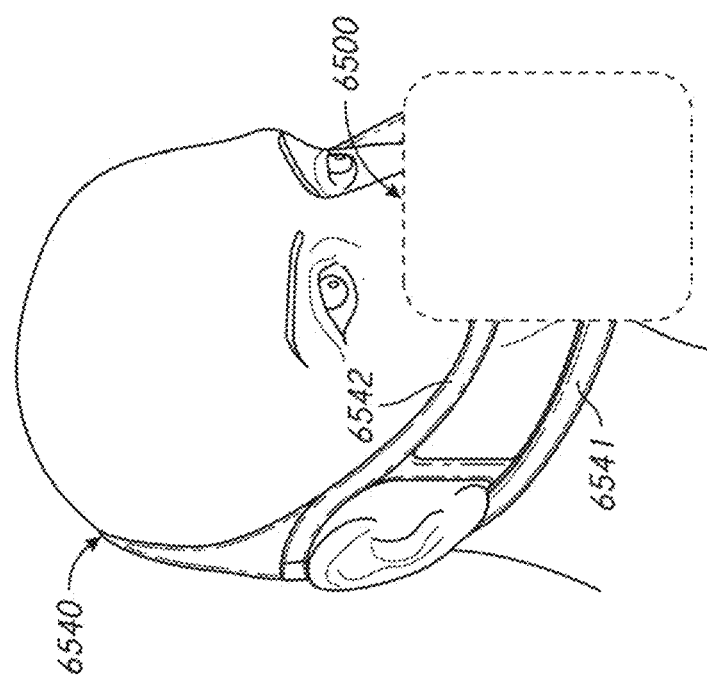
FIG. 46A is a front perspective view of an exemplary headgear that can be used with a patient interface.
Figure 46C:
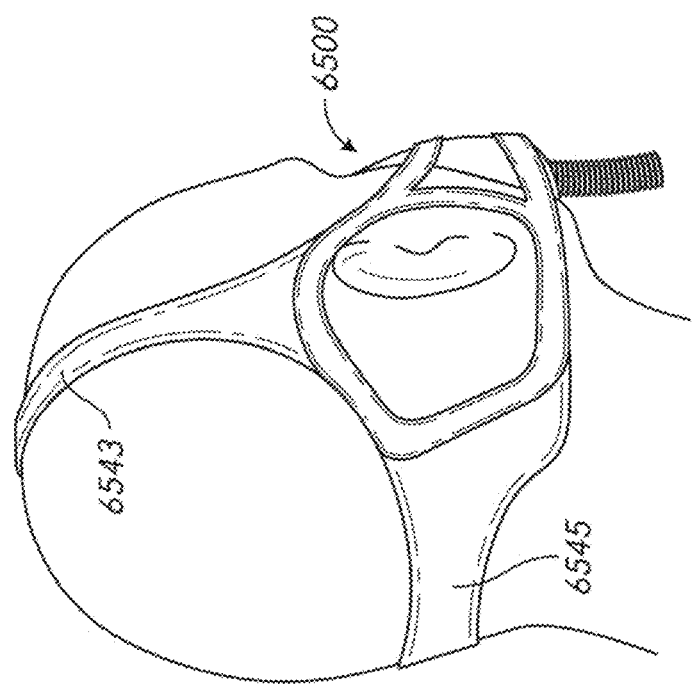
FIG. 46C is a rear perspective view of the exemplary headgear in FIG. 46A.

FIGS. 46A-C show perspective views of an embodiment of a headgear 6540 that can be used with a patient interface 6500. The headgear 6540 includes lower and middle straps 6541, 6542 that are formed from a continuous casing in the form of a closed loop structure. The lower and middle straps 6541, 6542 form a portion of an ear loop. A vertical member 6544 extends from a junction with the lower strap 6541 at a position forward of the ear, to a junction with the top strap 6543 at a position forward of the ear, forming the remainder of the ear loop. A top strap 6543 spans between the upper portions of the right and left side ear loops. A rear strap 6545 spans between the rear portions of the right and left side ear loops. In at least one embodiment, at least one of the top strap 6543 and the rear strap 6545 can be fabricated from a flexible material (e.g., Breath-o-prene) and connected to the lower and middle straps 6541, 6542 through any appropriate means (stitching, RF welding, adhesive, etc.). In at least one embodiment, either the top strap 6543 or the rear strap 6545 can be fabricated using the burst-through intra-moulding process. In at least one embodiment, both the top strap 6543 and the rear strap 6545 can be fabricated using the burst-through intra-moulding process. The rear strap 6545 can include an adjustment mechanism.

Figure 47B:
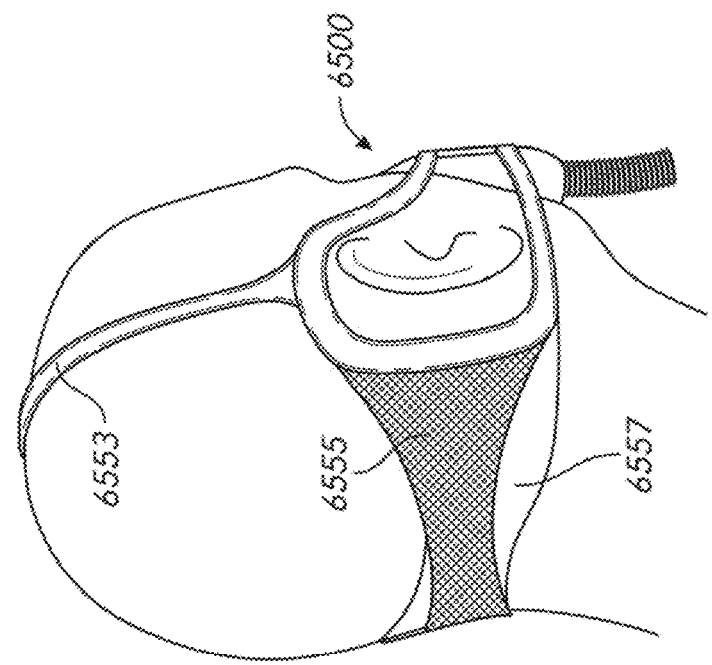
FIG. 47B is a rear perspective view of the exemplary headgear in FIG. 47A.
Figure 47A:
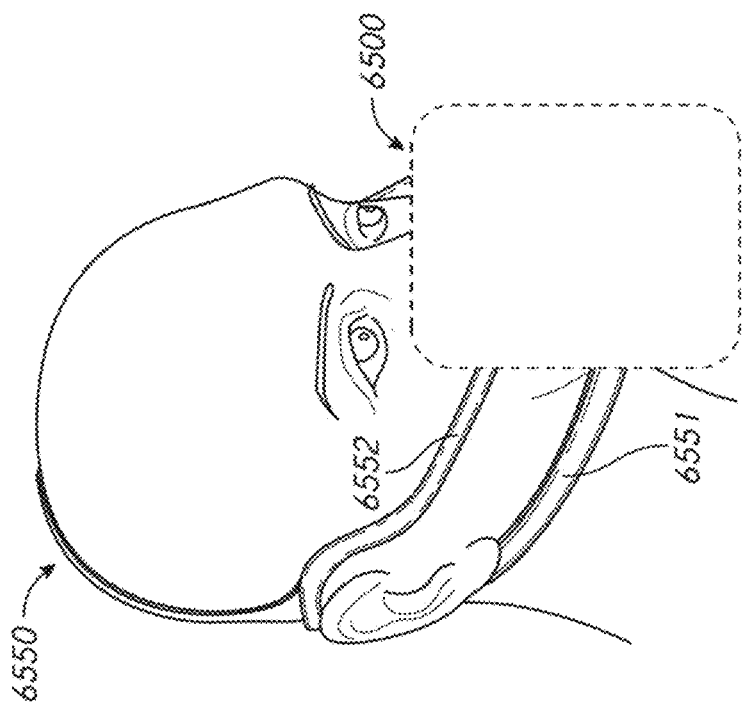
FIG. 47A is a front perspective view of an exemplary headgear that can be used with a patient interface.

FIGS. 47A-B show perspective views of an embodiment of a headgear 6550 that can be used with a patient interface 6500. The headgear 6550 includes a lower strap 6551 and a middle strap 6552 that are formed from a continuous casing in the form of a closed loop structure. The lower and middle straps 6551, 6552 form a portion of an ear loop. The top strap 6553 is formed by the burst-through intra-moulding process and extends from a junction on an upper portion of the right side ear loop to a junction on an upper portion of the left side ear loop. A rear strap first portion 6555 is formed from a quilted fabric or material that is soft in texture. A rear strap second portion 6557 of the headgear 6550 is formed by a rear web portion extending between the lower, rear portions of the right and left side ear loops. The rear strap second portion 6557 can be fabricated from a quilted fabric or material that is soft in texture, or can be fabricated from plastic material using the intra-moulding process.

FIGS. 48A-B show perspective views of an embodiment of a headgear 6560 that can be used with a patient interface 6500. The headgear 6560 includes a first lower strap 6564 that is formed from a continuous casing. The first lower strap 6564 extends laterally, below the right ear of the user, around the rear of the user's head, to meet the middle strap 6562 at a junction on the opposing side of the user's head. The junction, where the first lower strap 6564 and the middle strap 6562 meet, is located generally above the user's left ear. The headgear 6560 includes a second lower strap 6566 that is a segmented strap including two casing lengths. The second lower strap 6566 extends laterally, below the left ear of the user, around the rear of the user's head and intersects the first lower strap 6564 at a rear junction. The second lower strap 6566 continues from the rear junction to a junction at which it meets the middle strap 6562, which is located generally above the user's right ear. The core of the first lower strap 6564 and the second lower strap 6566 is integrally formed using burst-through intra-moulding.

The middle strap 6562 extends from the patient interface 6500 over the user's right ear, meeting the second lower strap 6566 at the junction. The middle strap 6562 continues from the junction over the user's head where it meets the first lower strap 6564 at the other junction. The middle strap 6562 continues to the patient interface 6500.

Figure 49B:
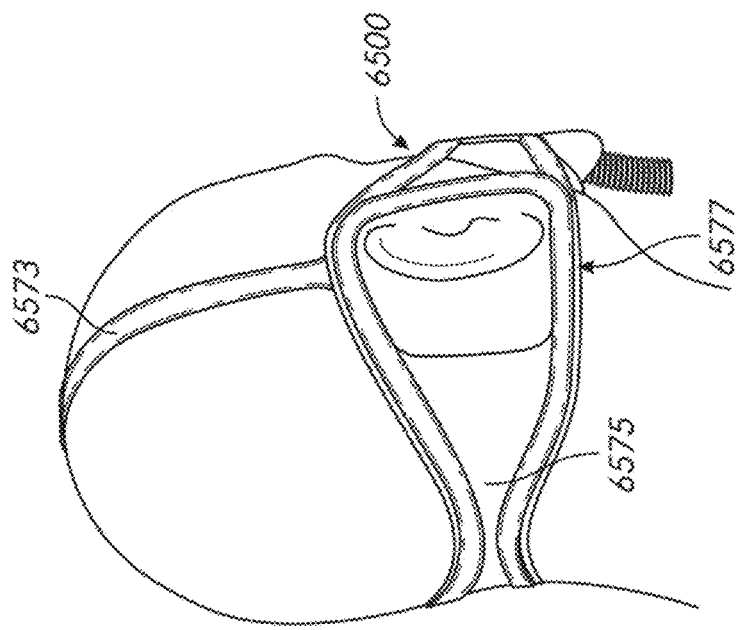
FIG. 49B is a rear perspective view of the exemplary headgear in FIG. 49A.
Figure 49A:
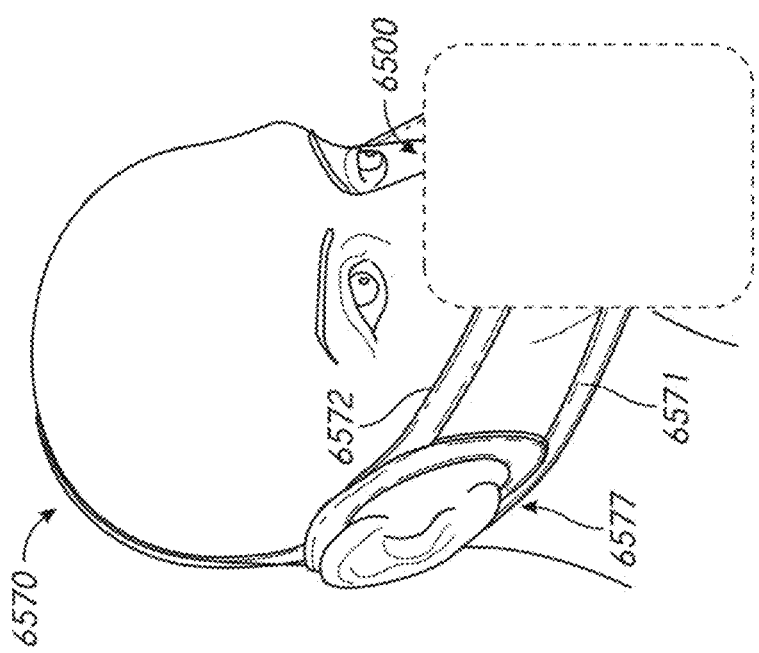
FIG. 49A is a front perspective view of an exemplary headgear that can be used with a patient interface.

FIGS. 49A-B show perspective views of an embodiment of a headgear 6570 that can be used with a patient interface 6500. The middle strap 6572 extends from the patient interface 6500, above the user's ear, around the rear of the user's head, above the user's other ear, to the opposing side of the patient interface 6500. The top strap 6573 can be formed from burst-through joints with the middle strap 6572. The lower strap 6571 extends from the patient interface 6500, below the user's ear, around the rear of the user's head, below the user's other ear, to the opposing side of the patient interface 6500.

The headgear 6570 includes an ear loop 6577. The ear loop 6577 extends from the rear of the user, above and around the front of the user's right ear. It extends below the user's right ear and continues around the rear of the user's head. It extends below and around the front of the user's left ear, continues above and behind the user's left ear, and meets itself at the rear of the user's head.

The ear loop 6577 includes a rear web portion 6575 at the rear of the user's head that spans between opposing lengths of the ear loop 6577. The rear web portion 6575 can be formed by burst-through intra-moulding. The web portion 6575 can be integrally formed with the headgear 6570. Alternately, the web portion 6575 can be fabricated from a more flexible material (e.g., Breath-o-prene) and connected to the lower and middle straps 6571, 6572 through any appropriate means (stitching, RF welding, adhesive, etc.). The ear loop 6577 is joined to the middle strap 6572 and lower strap 6571 of the headgear 6570 through the use of stitching, RF welding, ultrasonic welding, or an adhesive bond.

FIGS. 50A-B show perspective views of an embodiment of a headgear 6580 that can be used with a patient interface 6500. The headgear 6580 includes a lower strap 6581 that extends from the patient interface 6500, below the user's ear. A middle strap 6582 extends from the patient interface 6500 6500 above the user's ear. The middle strap 6582 and the lower strap 6581 converge and form a rear strap 6585 at the rear of the user's head. The middle and lower straps 6582, 6581 form an ear loop first portion 6587. A top strap 6583 is formed by burst-through joints above the user's ears. An ear loop second portion 6589 is formed by a burst-through web portion. In at least one embodiment, the ear loop second portion 6589 and the top strap 6583 can be integrally formed using the burst-through process and connected to the ear loop first portion 6587 using an appropriate method (stitching, etc.).

FIGS. 51A-B show a non-limiting exemplary embodiment of a headgear 6590 that can be used with a patient interface 6500. The headgear 6590 includes a lower strap 6591 and a middle strap 6592 that are formed from a continuous casing in the form of a closed loop structure. The lower and middle straps 6591, 6592 form a portion of an ear loop. A top strap 6593 is formed by the burst-through intra-moulding process. The top strap 6593 includes a first portion 6594 that extends towards a top of user's head from a filleted junction on an upper portion of the right side ear loop and a second portion 6595 that also extends towards a top of user's head from a filleted junction on an upper portion of the left side ear loop.

The first portion 6594 and second portion 6595 of the top strap 6593 cooperate such that the length of the top strap 6593 can be adjusted by a user of the patient interface 6500. The first portion 6594 and second portion 6595 of the top strap 6593 can cooperate through the inclusion of a push-fit adjustment mechanism. As shown in FIG. 51B, the push-fit adjustment mechanism can include a number or plurality of projections 6599 on the second portion 6595 of the top strap 6593, and a number or plurality of cooperating recesses 6598 on the first portion 6594 of the top strap 6593. The projections 6599 of the second portion 6595 can be pushed or pressed into the recesses 6598 on the first portion 6594 to fix the length of the top strap 6593 as desired. The projections 6599 can be formed from the burst-through intra-moulding process. Any other suitable adjustment mechanism is viable for connecting the first and second portions 6594, 6595 to set the length of the top strap 6593.

A rear strap 6597 is formed by the burst-through intra-moulding process and extends from a filleted junction on a rear portion of the right side ear loop to a filleted junction on a rear portion of the left side ear loop. In the illustrated configuration, the rear strap 6597 includes a casing surrounding the plastic core that spans the length of the strap. In at least one configuration, the rear strap 6597 may include a plastic structure spanning the rear of the headgear 6590. In at least one embodiment, the rear strap 6597 can include a length adjustment mechanism.

Figure 52B:
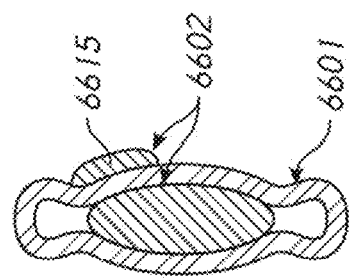
FIG. 52B is a cross-sectional view of the strap portions of the exemplary headgear in FIG. 52A.
Figure 52C:
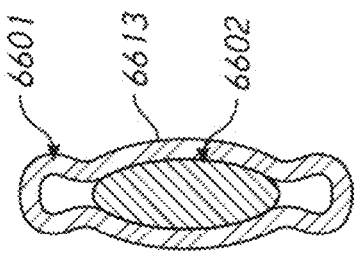
FIG. 52C is a cross-sectional view of the strap portions of the exemplary headgear in FIG. 52A.
Figure 52A:
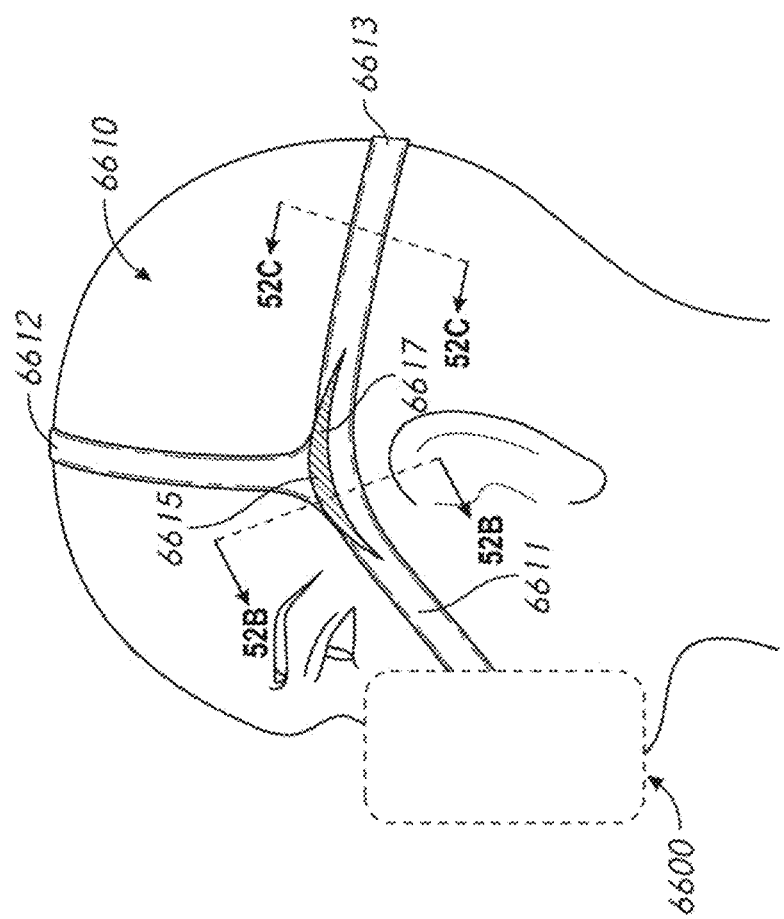
FIG. 52A is a side view of an exemplary headgear that can be used with a patient interface.

FIGS. 52A-C show a perspective view of an embodiment of a headgear 6610 that can be used with a patient interface 6600. The headgear 6610 includes a middle strap 6611 and a rear strap 6613 that are formed from a continuous casing 6601. A top strap 6612 is formed by the burst-through intra-moulding process. The top strap 6612 extends from a junction 6617 on an upper portion of the middle strap 6611 and/or rear strap 6613 and extends over the head of the user to a junction 6617 on an upper portion of the middle strap 6611 and/or rear strap 6613 on the opposing side of the user's head. In at least one embodiment, the top strap 6612 can be formed from filleted junctions.

The junction 6617 and adjacent portions of the middle strap 6611 and rear strap 6613 include a support structure 6615. FIG. 52B shows a cross-sectional view of the junction 6617 and adjacent portions along a line 52B-52B which illustrates the support structure 6615. In contrast, FIG. 52C shows a cross-sectional view of the rear strap 6613 along a line 52C-52C along a portion without the support structure 6615. The support structure 6615 can be arcuate, following a contour of the middle strap 6611, rear strap 6613 and junction 6617. The support structure 6615 can span from a first location forward of the user's ear to a second location rearward of a user's ear. In the illustrated configuration, the support structure 6615 is formed from a plastic or polymer material 6602. The support structure 6615 can be formed from the burst-through intra-moulding process. The support structure 6615 can be overmoulded onto the headgear 6610. The support structure 6615 can provide structure to assist the headgear 6610 with maintaining its shape and/or contribute to the structural integrity of the headgear 6610.

Figure 53B:
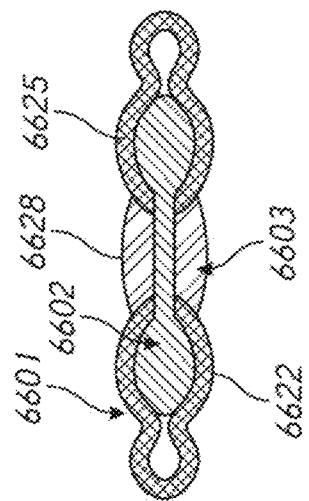
FIG. 53B is a cross-sectional view of the strap portions of the exemplary headgear in FIG. 53A.
Figure 53A:
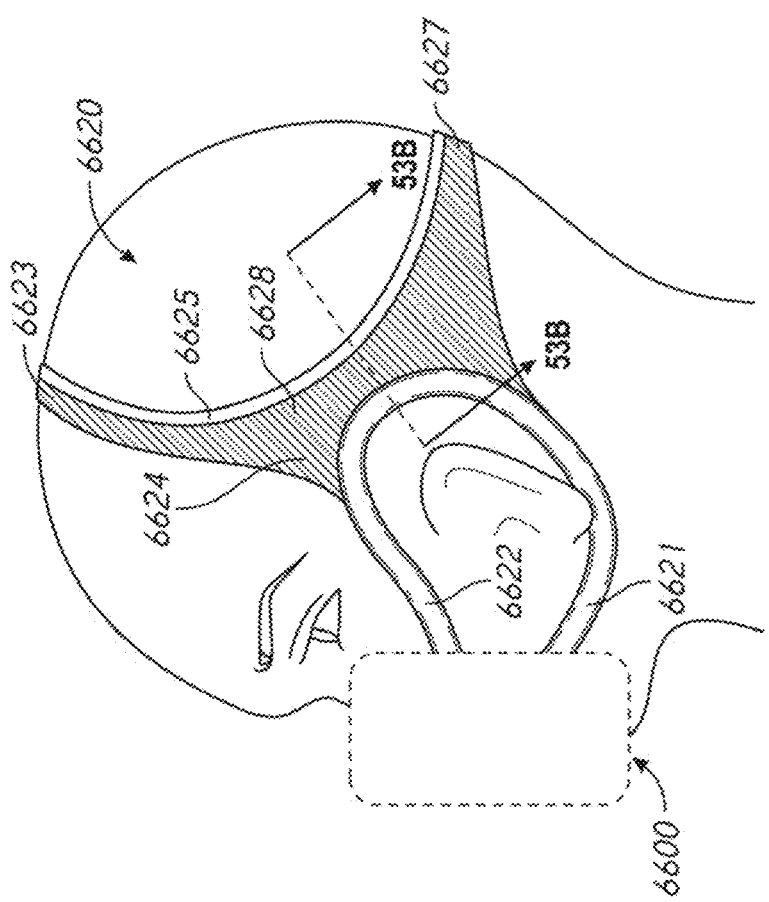
FIG. 53A is a side view of an exemplary headgear that can be used with a patient interface.

FIGS. 53A-B show a perspective view of an embodiment of a headgear 6620 that can be used with a patient interface 6600. The headgear 6620 includes a lower strap 6621 and a middle strap 6622 that are formed from a continuous casing in the form of a closed loop structure. The lower and middle straps 6621, 6622 form a portion of an ear loop. The headgear 6620 includes a first rear portion 6624 and a second rear portion 6625. The second rear portion 6625, the lower strap 6621 and the middle strap 6622 are integrally formed from the burst-through intra-moulding process. The lower strap 6621 and middle strap 6622 include a textile outer casing 6601 with an intra-moulded plastic core 6602. The second rear portion 6625 includes a textile outer casing 6601 with an intra-moulded plastic core 6602. A web portion 6628 formed from the burst-through intra-moulding process extends between the lower strap 6621 and middle strap 6622, and the second rear portion 6625.

The web portion 6628 forms a plastic core of the first rear portion 6624. As shown in FIG. 53B, the first rear portion 6624 includes an overmoulded material 6603 on at least one of the faces of the web. In the illustrated configuration, the first rear portion 6624 includes a soft-touch overmoulded material 6603 on both an exterior and interior surface of the first rear portion 6624. This overmoulded material 6603 can increase the level of comfort experienced by a user of the headgear 6620. The first rear portion 6624 and the second rear portion 6625 are configured to form a top strap 6623 that spans the top of a user's head, and a rear strap 6627 that spans the rear of a user's head.

FIGS. 54A-C show a headgear 6630 having lower and middle straps 6631, 6632 that are formed from a continuous casing. An upper portion of a partial ear loop is defined by the middle strap 6632. A lower portion of the partial ear loop is defined by the lower strap 6631. A web portion 6637 extends between rear portions of the continuous middle and lower straps 6632, 6631 and defines a rear portion of the partial ear loop. FIG. 54B is a close-up view of the web portion 6637. The web portion 6637 can be formed from the burst-through intra-moulding process. FIG. 54C shows a cross-sectional view of the web portion 6637 along a line 54C-54C in FIG. 54B. The web portion 6637 includes an overmoulded material 6603. In at least one embodiment, the overmoulded material 6603 can be a soft-touch material.

A top strap 6633 is formed by the burst-through intra-moulding process. The top strap 6633 extends from a junction on an upper portion of the middle strap 6632 and/or rear strap 6635 and extends over the head of the user to a junction on an upper portion of the middle strap 6632 and/or rear strap 6635 on the opposing side of the user's head. In at least one embodiment, the top strap 6633 can include filleted junctions. The top strap 6633 can include a soft-touch overmoulded material on at least its upper surface, lower surface or both.

FIGS. 55A-C show a headgear 6640 that includes a continuous lower strap 6641 and a combination continuous middle and vertical strap 6642. The headgear 6640 further includes a combination upper and rear strap 6643. A web portion 6645 extends between the first and second vertical straps. A web portion 6645 extends between the first and second rear straps. FIG. 55B shows a cross-section of the web portion 6645 along a line 55B-55B in FIG. 55A. FIG. 55C shows a close-up view of the web portion 6645. In at least one embodiment, the web portions 6645 can be formed from the burst-through intra-moulding process. In at least one embodiment, the straps can include a knitted tube casing 6601.

FIGS. 56A-B show a headgear 6650 having lower and middle straps 6651, 6652 that are formed from a continuous casing in the form of a closed loop structure. The continuous middle and lower straps 6652, 6651 form a substantial portion of an ear loop. A top strap 6653 extends from a junction 6655 on an upper portion of the right side of the partial ear loop to a junction on an upper portion of the left side of the partial ear loop. Similarly, a rear strap 6657 extends from a junction on a rear portion of the right side of the partial ear loop to a junction on a rear portion of the left side of the partial ear loop.

As shown in FIG. 56B, the top strap 6653 and the rear strap 6657 may be filleted or tapered at their junctions with the middle and lower straps 6652, 6651 to improve the connection strength with the middle and lower straps 6652, 6651. In at least one embodiment, the top strap 6653 can be formed from an exposed plastic. In at least one embodiment, the top strap 6653 can be comprised of an intra-moulded strap having a textile outer casing. In at least one embodiment, the rear strap 6657 can be formed from an exposed plastic. In at least one embodiment, the rear strap 6657 can be comprised of an intra-moulded strap having a textile outer casing.

Figure 57B:
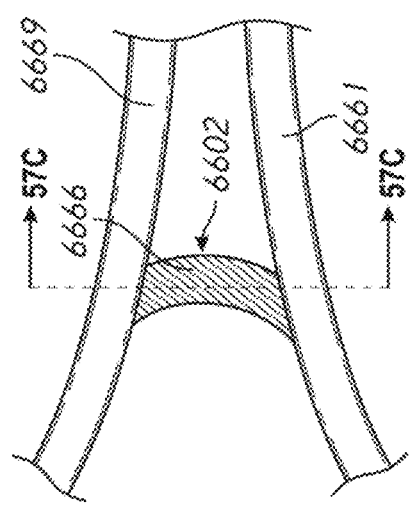
FIG. 57B is a close-up view of a second vertical member of the exemplary headgear in FIG. 57A.
Figure 57C:
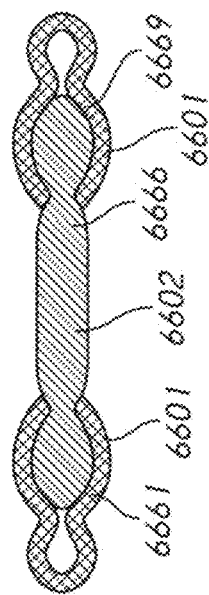
FIG. 57C is a cross-sectional view of the second vertical member along a line 57C-57C in FIG. 57B.
Figure 57A:
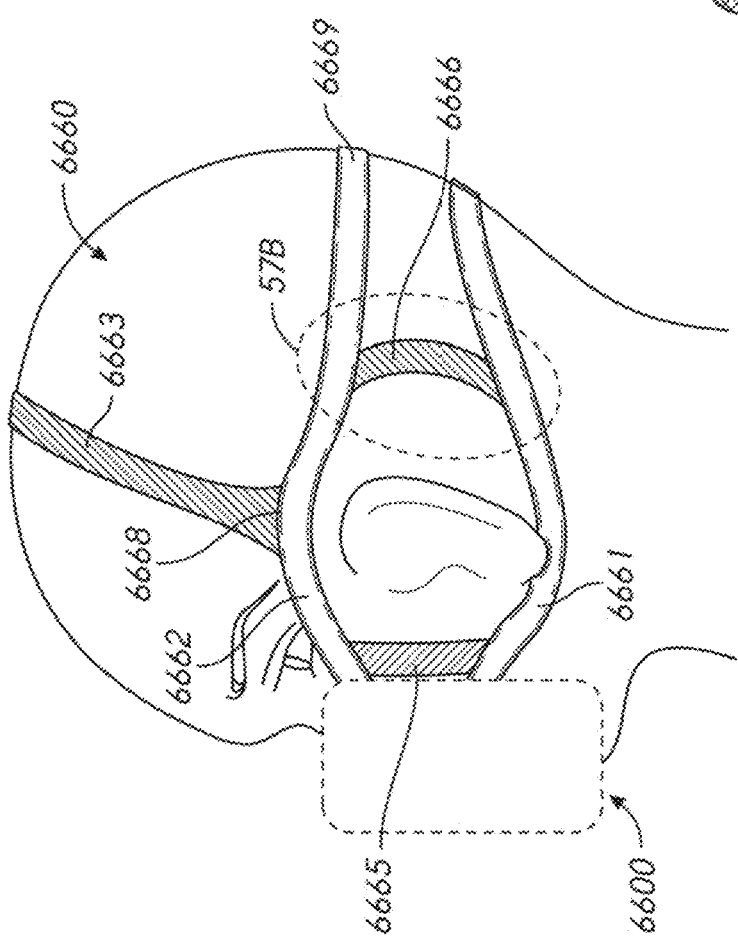
FIG. 57A is a side view of an exemplary headgear that can be used with a patient interface and having lower and middle straps that are formed from a continuous casing.

FIGS. 57A-C show a perspective view of an embodiment of a headgear 6660 that can be used with a patient interface 6600. The headgear 6660 has a middle strap 6662 that is formed from a continuous casing. The headgear 6660 has a lower strap 6661 that is formed from a continuous casing. The middle strap 6662 extends from a mask assembly over the user's ear and continues to span the rear of the user's head. An upper portion of an ear loop is defined by the middle strap 6662. The lower strap 6661 extends from the mask assembly below the user's ear and continues to span the rear of the user's head. A lower portion of the ear loop is defined by the lower strap 6661.

The headgear 6660 includes a first vertical member 6665 and a second vertical member 6666. The first vertical member 6665 spans the distance between the lower and middle straps 6661, 6662 forward of the user's ear, forming a forward portion of the ear loop. The first vertical member 6665 can be formed from the burst-through intra-moulding technique. The first vertical member 6665 can be exposed plastic. As shown in FIG. 57B, the second vertical member 6666 spans the distance between the lower and middle straps 6661, 6662 rearward of the user's ear, forming a rearward portion of the ear loop. The second vertical member 6666 can be formed from the burst-through intra-moulding technique. The second vertical member 6666 can be exposed plastic 6602. FIG. 57C is a cross-sectional view of the second vertical member 6666 along a line 57C-57C in FIG. 57B.

A top strap 6663 extends from a junction 6668 on an upper portion of the middle strap 6662 and/or rear strap 6669 and extends over the head of the user to a junction 6668 on an upper portion of the middle strap 6662 and/or rear strap 6669 on the opposing side of the user's head. The top strap 6663 can be formed by the burst-through intra-moulding process. The top strap 6663 can include exposed plastic.

Figure 58B:
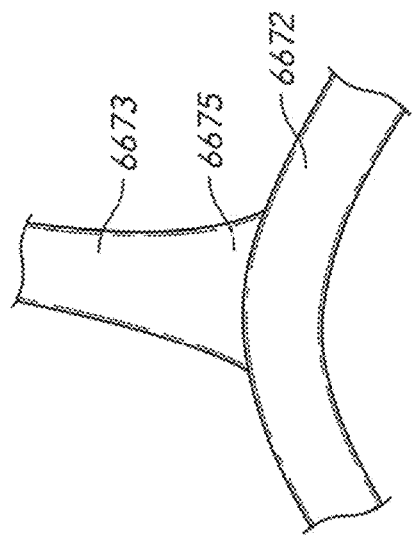
FIG. 58B is a close-up view of a junction of the exemplary headgear in FIG. 58A.
Figure 58A:
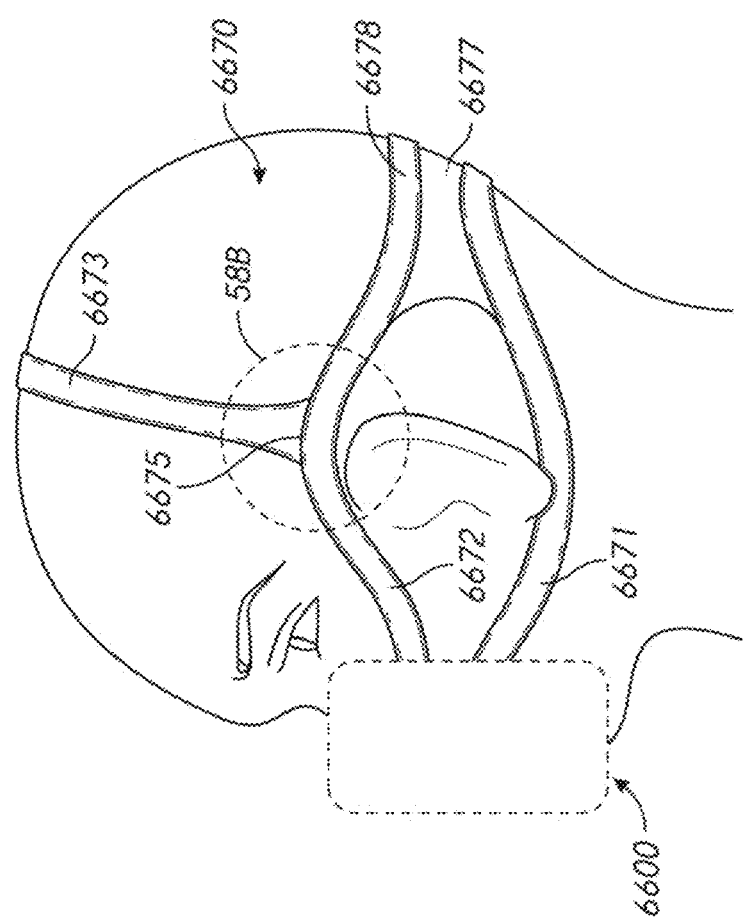
FIG. 58A is a side view of an exemplary headgear that can be used with a patient interface.

FIGS. 58A-B show a perspective view of an embodiment of a headgear 6670 that can be used with a patient interface 6600. The headgear 6670 has a middle strap 6672 that is formed from a continuous casing. The headgear 6670 has a lower strap 6671 that is formed from a continuous casing. The middle strap 6672 extends from a mask assembly over the user's ear and continues to span the rear of the user's head. An upper portion of a partial ear loop is defined by the middle strap 6672. The lower strap 6671 extends from the mask assembly below the user's ear and continues to span the rear of the user's head. A lower portion of the partial ear loop is defined by the lower strap 6671.

A web portion 6677 extends between rear portions of the continuous middle and lower straps 6672, 6671 and defines a rear portion of the partial ear loop. The web portion 6677 can be formed from the burst-through intra-moulding process.

A top strap 6673 is formed by the burst-through intra-moulding process. The top strap 6673 extends from a junction on an upper portion of the middle strap 6672 and/or rear strap 6678 and extends over the head of the user to a junction on an upper portion of the middle strap 6672 and/or rear strap 6678 on the opposing side of the user's head. In at least one embodiment, the top strap 6673 can include filleted junctions 6675. The top strap 6673 can be exposed plastic, can include a fabric case or can include at least one overmoulded material.

Figure 59B:
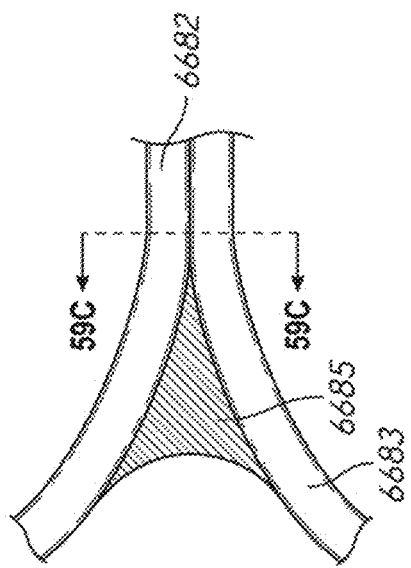
FIG. 59B is a close-up view of the continuous middle and vertical strap and a continuous upper and rear strap of the exemplary headgear in FIG. 59A.
Figure 59C:
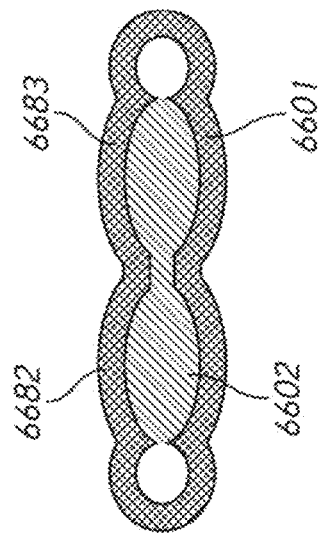
FIG. 59C is a cross-sectional view of the continuous middle and vertical strap and a continuous upper and rear strap along a line 59C-59C in FIGS. 59A and 59B.
Figure 59A:
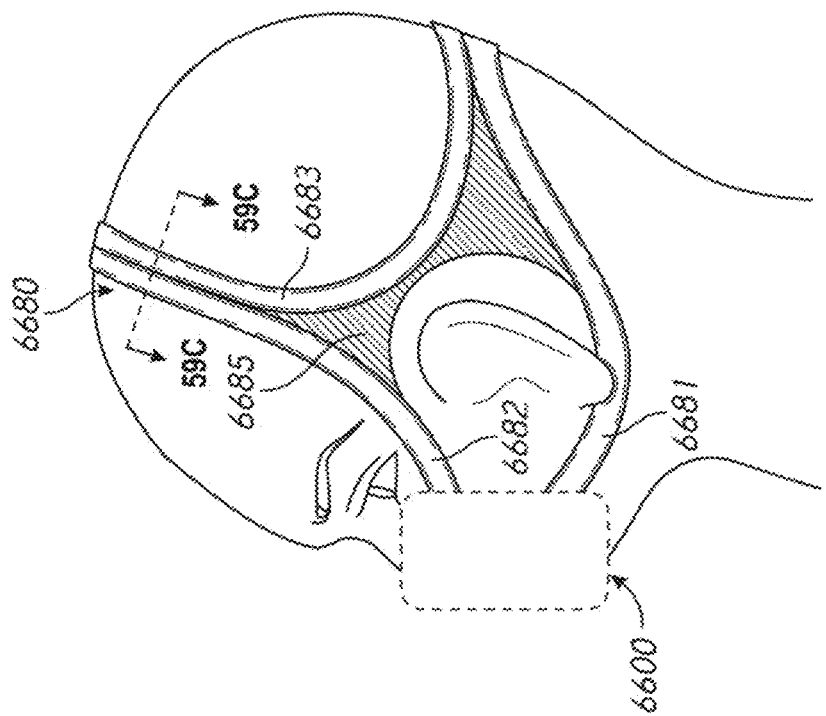
FIG. 59A is a side view of an exemplary headgear that can be used with a patient interface and having a continuous middle and vertical strap and a continuous upper and rear strap.

FIGS. 59A-C show a headgear 6680 that includes a continuous lower strap 6681 and a combination continuous middle and vertical strap 6682. The headgear 6680 further includes a combination upper and rear strap 6683. A web portion 6685 extends around a rear portion of a user's ear. The web portion 6685 can be formed from the burst-through intra-moulding process.

A length of the continuous middle and vertical strap 6682 and a length the continuous upper and rear strap 6683 are joined via an invisible join, as shown in FIG. 59B. Along this join, the plastic core of the continuous middle and vertical strap 6682 is integrally formed with the plastic core 6602 of the continuous upper and rear strap 6683. In at least one embodiment, the continuous middle and vertical strap 6682 and the continuous upper and rear strap 6683 can include a common textile casing 6601. In at least one embodiment, the continuous middle and vertical strap 6682 and the continuous upper and rear strap 6683 are formed from two separate textile casings that include at least one adjacent surface. Additionally, a length of the continuous upper and rear strap 6683 and a length of the lower strap 6681 are joined via an invisible join.

Figure 60B:
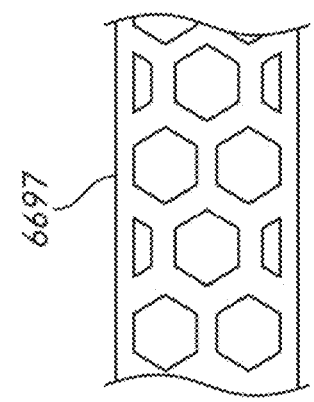
FIG. 60B is a close-up view of the rear strap of the exemplary headgear in FIG. 60A.
Figure 60A:
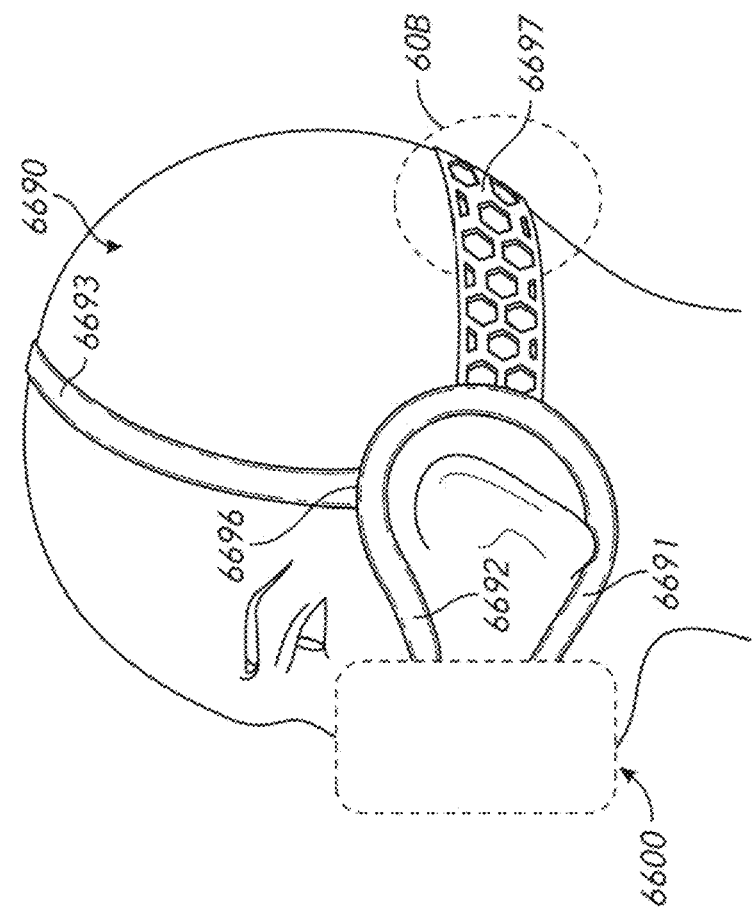
FIG. 60A is a side view of an exemplary headgear that can be used with a patient interface.

FIGS. 60A-B show a perspective view of an embodiment of a headgear 6690 that can be used with a patient interface 6600. The headgear 6690 includes a lower strap 6691 and a middle strap 6692 that are formed from a continuous casing in the form of a closed loop structure. The continuous middle and lower straps 6692, 6691 form a substantial portion of an ear loop. A top strap 6693 extends from a junction 6695 on an upper portion of the right side partial ear loop to a junction 6696 on an upper portion of the left side partial ear loop. The top strap 6693 can be formed from the burst-through intra-moulding process. In at least one embodiment, the top strap 6693 can be comprised of an intra-moulded strap having a textile outer casing.

The headgear 6690 includes a rear strap 6697. The rear strap 6697 extends from a junction on a rear portion of the right side partial ear loop to a junction on a rear portion of the left side partial ear loop. The rear strap 6697 can be formed by the intra-moulding process with a plastic core and a fabric or textile casing. The rear strap 6697 can have a moulded texture that is imprinted onto the strap 6697, or can include a profile that is determined during the moulding process. FIG. 60A illustrates a strap 6697 having a plurality of hexagonal shaped holes arranged in rows along the length of the strap 6697. FIG. 60B is a close-up view of the hexagonal shaped holes arranged in rows along the length of the rear strap 6697. The holes project through the thickness of the strap 6697. This profile may provide the plastic core with a degree of give or stretch. Such flexibility may be beneficial in allowing a headgear 6690 to be pulled over a patient's head or to improve the patient perception of the headgear 6690. Further, the textured finish of the strap 6697 may improve the aesthetic appearance of the headgear 6690 and also the tactile appeal of the strap 6697. That is the strap 6697 may appear less rigid and more comfortable. The holes may improve the breathability through the strap 6697 which can improve user comfort.

Alternatively, the rear strap 6697 can include a plurality of hexagonal shaped indentations arranged in rows along the length of the strap 6697. It should be understood that the holes are not limited to hexagonal shapes and may include a variety of shapes, sizes, positions on strap, geometries, combinations of shapes, etc. In at least one configuration, the plastic core of the honeycomb pattern does not extend all the way to the edge of the casing of the strap 6697. This provides a soft edge to improve user comfort. In at least one embodiment, the rear strap 6697 may be exposed plastic.

Figure 61B:
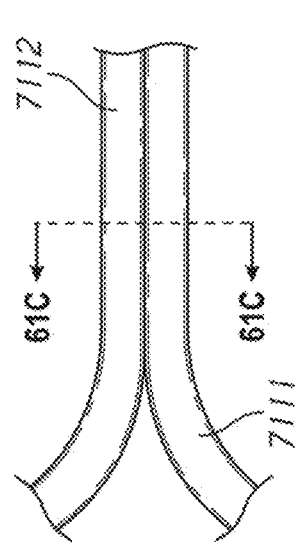
FIG. 61B is a close-up view of the rearward section of the middle and lower straps of the exemplary headgear in FIG. 61A.
Figure 61C:
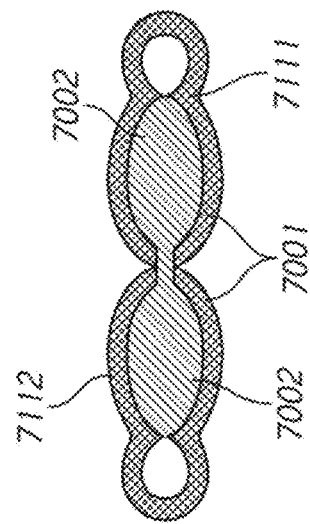
FIG. 61C is a cross-sectional view of the continuous middle and vertical strap and a continuous upper and rear strap along a line 61C-61C in FIG. 61B.
Figure 61A:
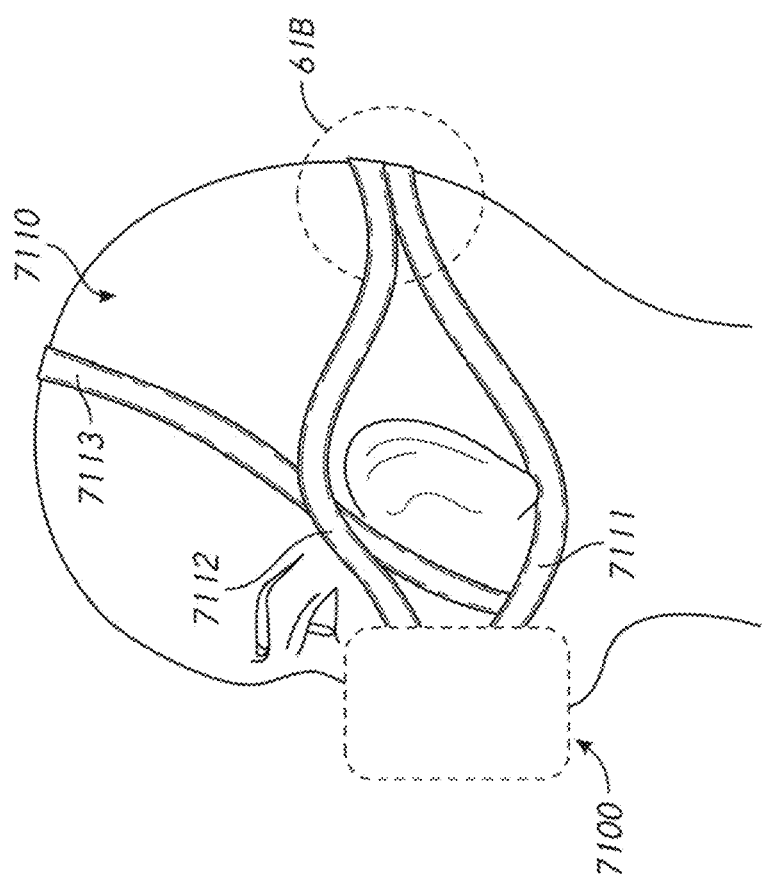
FIG. 61A is a side view of an exemplary headgear that can be used with a patient interface and having a continuous middle and vertical strap and a continuous upper and rear strap.

FIGS. 61A-C show a perspective view of an embodiment of a headgear 7110 that can be used with a patient interface. The headgear 7110 comprises a lower strap 7111, a middle strap 7112, and a vertical or top strap 7113. The lower strap 7111 is a continuous strap, having a continuous casing. The middle strap 7112 is a continuous strap, having a continuous casing. The vertical strap 7113 is a segmented strap. In other words, the vertical strap 7113 is formed of multiple, or segmented casings.

In at least one embodiment, the vertical strap 7113 can be a continuous strap, having a continuous casing. The vertical strap 7113 can pass underneath the middle strap 7112 as it extends over the head of the user. The vertical strap 7113 can pass over the middle strap 7112 as it extends over the head of the user. The vertical strap 7113 can be adhesively bonded to the middle strap 7112, can be connected via an appropriate connection mechanism, such as a hook and loop connection system, or can be independent of the middle strap 7112.

The middle strap 7112 and the lower strap 7111 include an invisible join spanning a rearward section of each strap, as shown in FIG. 61B. Along the invisible join, the middle strap 7112 and the lower strap 7111 can include a common plastic core 7002. FIG. 61C shows a cross-sectional view of FIG. 61B along a line 61C-61C. The middle strap 7112 and the lower strap 7111 can have independent textile or fabric casings 7001 that are configured such that the common plastic core 7002 of the straps is invisible.

Figure 62B:
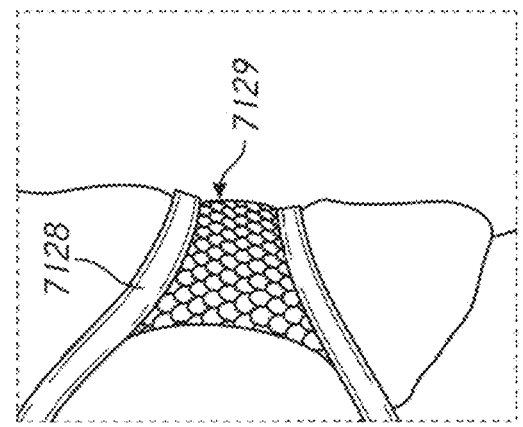
FIG. 62B is a close-up view of a variation of the exemplary headgear of FIG. 62A.
Figure 62A:
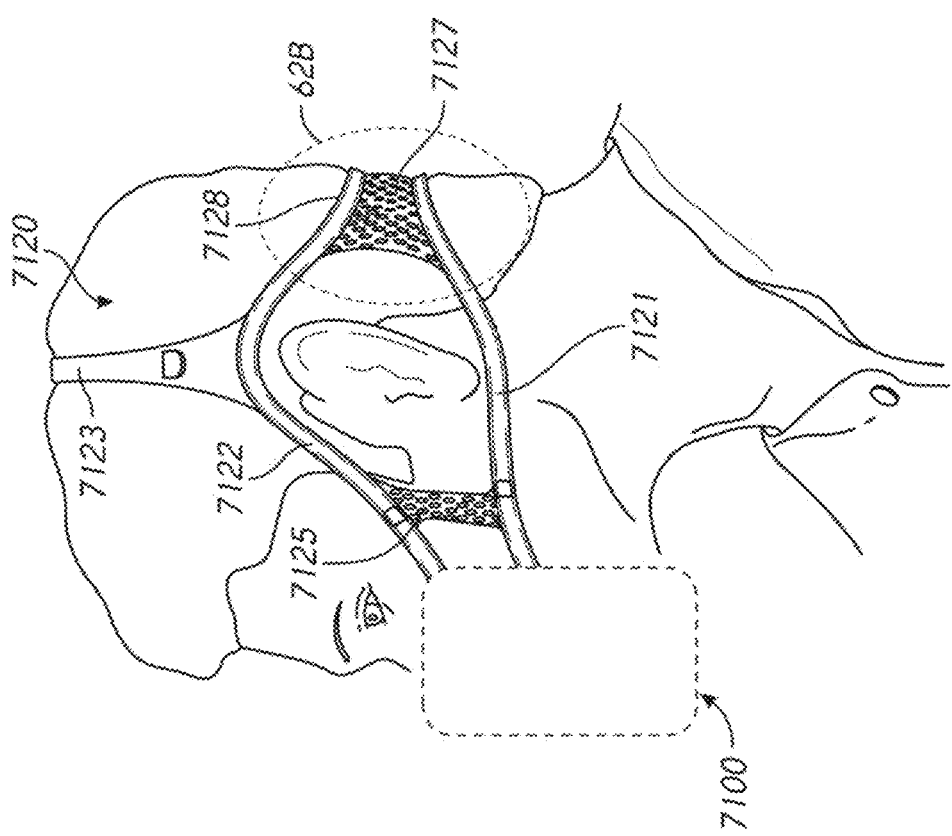
FIG. 62A is a side view of an exemplary headgear that can be used with a patient interface.

FIGS. 62A-B show a perspective view of an embodiment of a headgear 7120 that can be used with a patient interface 7100. The headgear 7120 has a middle strap 7122 that is formed from a continuous casing. The headgear 7120 has a lower strap 7121 that is formed from a continuous casing. The middle strap 7122 extends from a mask assembly over the user's ear and continues to span the rear of the user's head. An upper portion of an ear loop is defined by the middle strap 7122. The lower strap 7121 extends from the mask assembly below the user's ear and continues to span the rear of the user's head. A lower portion of the ear loop is defined by the lower strap 7121.

A top strap 7123 extends from a junction on an upper portion of the middle strap 7122 and/or rear strap 7128 and extends over the head of the user to a junction on an upper portion of the middle strap 7122 and/or rear strap 7128 on the opposing side of the user's head. The top strap 7123 is formed by the burst-through intra moulding process. The top strap 7123 can include filleted junctions. The top strap 7123 can be exposed plastic, can include a fabric case or can include at least one overmoulded material.

The headgear 7120 includes a vertical member 7125. The vertical member 7125 spans the distance between the lower and middle straps 7121, 7122, forward of the user's ear, forming a portion of the ear loop. The vertical member 7125 is formed from a soft-touch material, for instance a fabric or foam. In the illustrated configuration, the vertical member 7125 includes a plurality of holes. The plurality of holes can improve the elasticity and/or flexibility of the vertical member 7125, increasing the perceived comfort of the user.

A web portion 7127 extends between rear portions of the continuous middle and lower straps 7122, 7121 and defines a rear portion of the ear loop. The web portion 7127 can be made from a soft-touch material, for instance a fabric or foam. In the illustrated configuration, the web portion 7127 includes a plurality of holes. The plurality of holes can improve the elasticity and/or flexibility of the web portion 7127, increasing the perceived comfort of the user.

In at least one embodiment, the vertical member 7125 can be formed from a quilted fabric. In at least one embodiment, the vertical member 7125 can be formed from the burst-through intra-moulding process to include the plurality of holes. In at least one embodiment, the vertical member 7125 can include a plurality of indents instead of a plurality of holes. In at least one embodiment, the web portion 7127 can be formed from a quilted fabric 7129, as shown in FIG. 62B. In at least one embodiment, the web portion 7127 can be formed from the burst-through intra-moulding process to include the plurality of holes. In at least one embodiment, the web portion 7127 can include a plurality of indents instead of a plurality of holes.

Figure 63B:
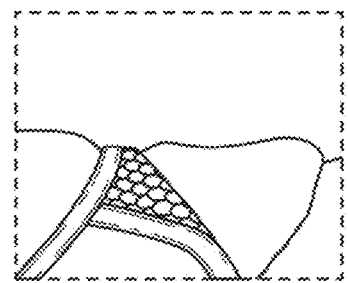
FIG. 63B is a close-up view of the quilted fabric of the exemplary headgear in FIG. 63A.
Figure 63C:
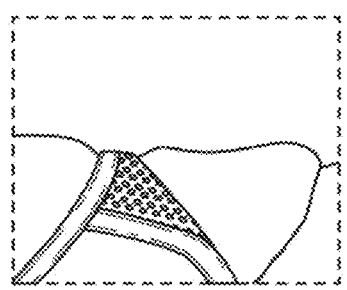
FIG. 63C is a close-up view of alternative web portion material of the exemplary headgear in FIG. 63A.
Figure 63A:
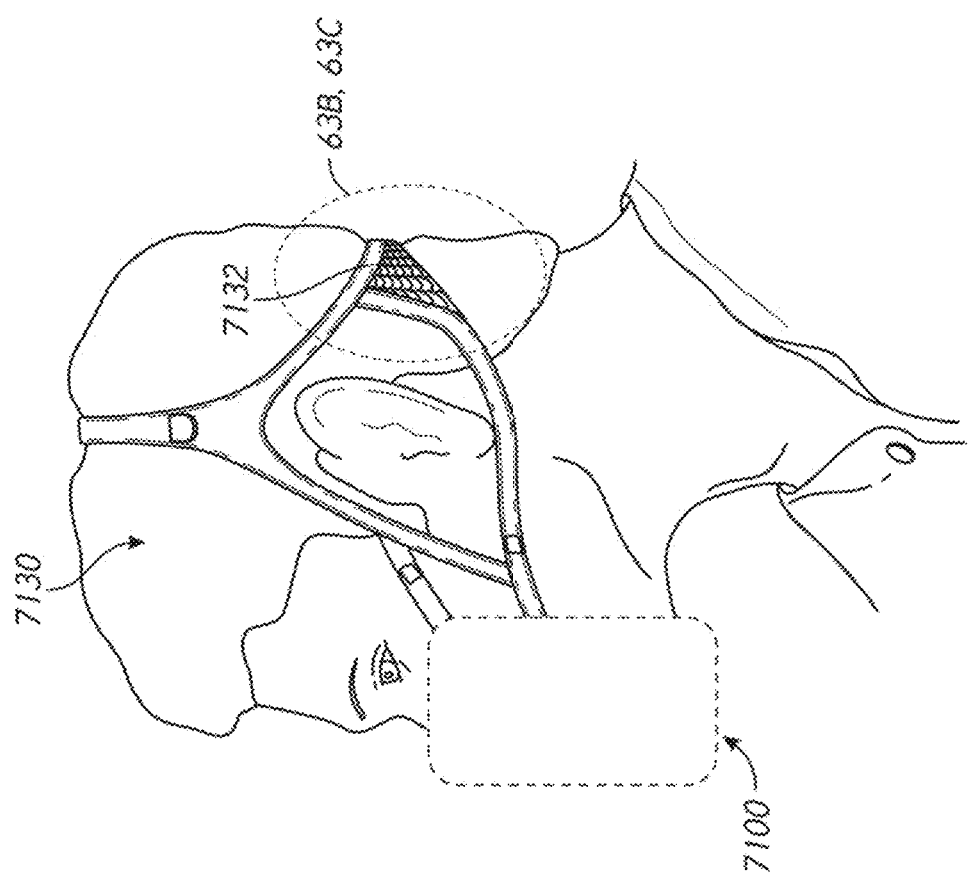
FIG. 63A is a side view of an exemplary headgear that can be used with a patient interface, and having a quilted fabric or material provided attached to portions of the headgear in direct contact with the user's skin or hair.

FIGS. 63A-B show an embodiment of a headgear 7130 having a quilted fabric or material 7132 provided attached to portions of the headgear 7130 in direct contact with the user's skin or hair, for example on the back of the user's neck. The quilted material 7132 is soft in texture and provides cushioned padding which improves the comfort of the headgear 7130 such that the user will want to wear the headgear 7130 to bed. The quilted material 7132 may be stitched or welded to the intra-moulded straps or web portions of the headgear 7130. The disclosed configurations are not limited to quilted materials (shown in FIG. 63B) and may include fabrics and textiles having a variety of material properties, such as but not limited to, soft, padded, breathable, moisture-wicking, and grippy/tacky textures (shown in FIG. 63C).

FIGS. 64A-B show an embodiment of a headgear 7140 have a fabric or textile material provided attached to portions of the headgear 7140 in direct contact with the user's skin or hair. The headgear 7140 includes a vertical member 7142 and a rear strap 7144 that are formed from the material to provide cushioned padding and improve the comfort of the headgear 7140. The material may be stitched or welded to the intra-moulded straps of the headgear 7140. The disclosed configurations are not limited to fabric or textile materials and may include quilted materials (shown in FIG. 64B). The materials may have a variety of material properties, such as but not limited to, soft, padded, breathable, moisture-wicking and grippy/tacky textures.

FIG. 65 shows an embodiment of a branded grip 3300 that can be used with an embodiment of the disclosed headgear. The branded grip 3300 can be formed of plastic from the burst-through intra-moulding process.

Intra-Mould Strap Connector

FIGS. 66A to 73 illustrate various views of a connector 3400 positioned over a joint between two straps in an intra-moulded headgear embodiment. The connector 3400 is used at a joint or junction 3500 between two or more adjoining straps in an intra-moulded headgear. More specifically, the connector 3400 is used to join two or more straps using burst-through intra-moulding. The connector 3400 can be used with any type of junction 3500 between two or more straps and the junction 3500 illustrated herein is merely one example. The connector 3400 provides a tidier and stronger connection between the straps and also improves the ease with which the straps can be aligned within a mould tool.

Figure 67:
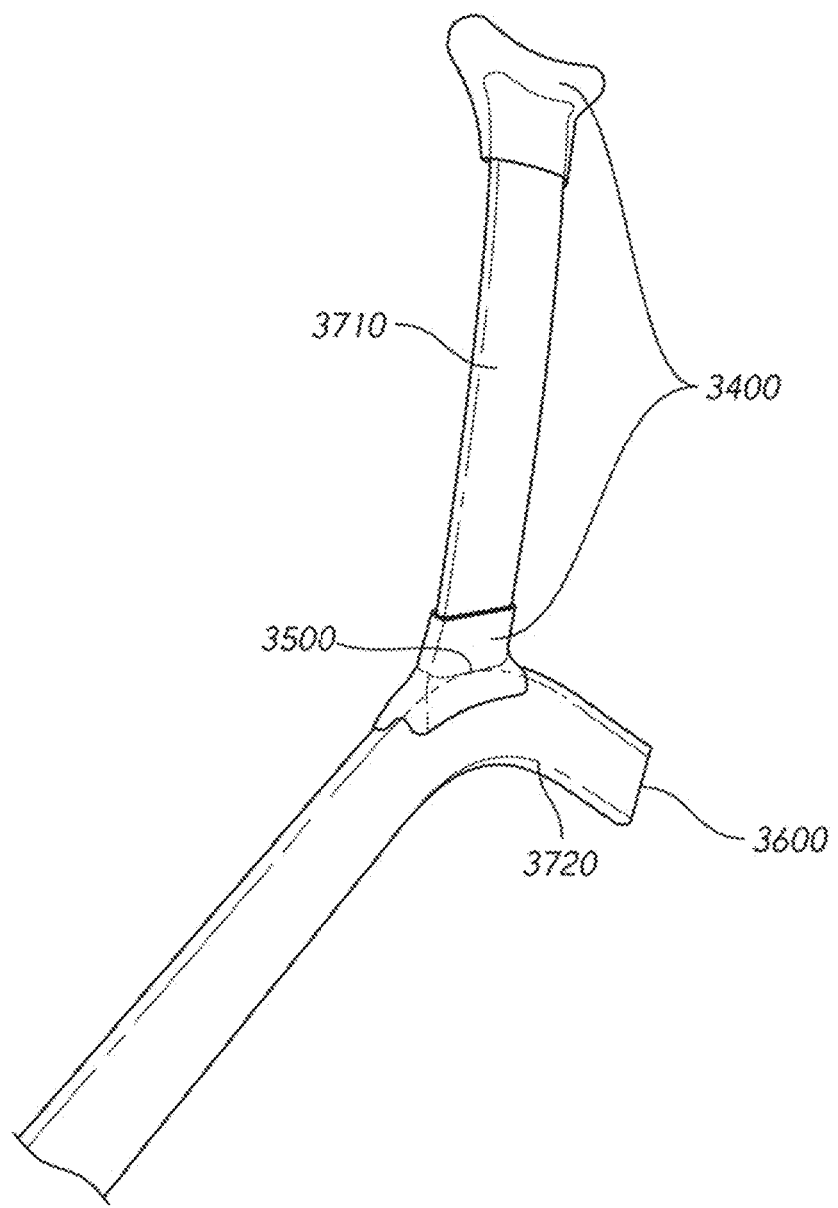

As illustrated in FIGS. 66A and 67, a first strap 3710 is joined with a second strap 3720 at a T-shaped junction between the end of the first strap 3710 and a central or intermediate portion of the second strap 3720 (i.e., a portion between the ends of second strap 3720). The connector 3400 is positioned over the first and second straps 3710, 3720 at the junction 3500. That is, the junction 3500 is positioned within the connector 3400 such that the connector 3400 surrounds the junction 3500. The first and second straps 3710, 3720 are joined via a burst-through intra-moulding process during which plastic core material 3800 is injected into the second strap 3720 at an injection point 3600 (shown at an end of the second strap 3720 in FIG. 66A). The plastic core material 3800 fills and travels through the second strap 3720. Upon reaching the junction 3500, the plastic core material 3800 bursts through the side wall of the textile casing of the second strap 3720 to fill all or a portion of the cavity of the textile casing of the first strap 3710, as shown by the red arrows at the junction in FIG. 66A. In some configurations, the connector 3400 has a cavity 3420 that is also filled with plastic core material 3800 that bursts through the side walls of the textile casings of the first and second straps 3710, 3720. The plastic core material 3800 may also bond with the connector 3400 such that the plastic core material 3800 and the connector 3400 are integrally formed. In some configurations, the plastic core material 3800 and the connector 3400 may be formed from the same or a similar material.

The connector 3400 contains any loose threads at the end of the straps within the connector 3400 such that the junction 3500 has a tidy aesthetic appearance. That is, loose ends of the first and/or second straps 3710, 3720 are contained within the connector 3400 which prevents further fraying of the straps 3710, 3720. Further, the connector 3400 may have an opaque colour which conceals the appearance of the loose ends such that the junction 3500 has a tidier aesthetic appearance. Even further, the connector 3400 defines the finished shape of the junction 3500 and contains any burst through plastic flash that escapes from the first and second straps 3710, 3720 ends such that the junction 3500 has a tidy aesthetic appearance.

The connector 3400 also provides an abutment edge 3417 for joining the first and second straps 3710, 3720 that is wider than the width of the end of the first textile strap 3710 (i.e., for a junction 3500 without a connector 3400) which provides a greater connection area between the first and second strap 3710, 3720. That is, the connector 3400 provides a wider filleted junction 3500 between the end of the first strap 3710 and the casing of the second strap 3720 which provides a greater connection area and thereby increases the strength of the junction 3500. As shown in FIG. 67, the end of the first strap 3710 is both filled and surrounded by plastic material rather than having the plastic material inside the tube of the strap casing. Accordingly, the strength of the junction 3500 is increased.

Figure 68B:
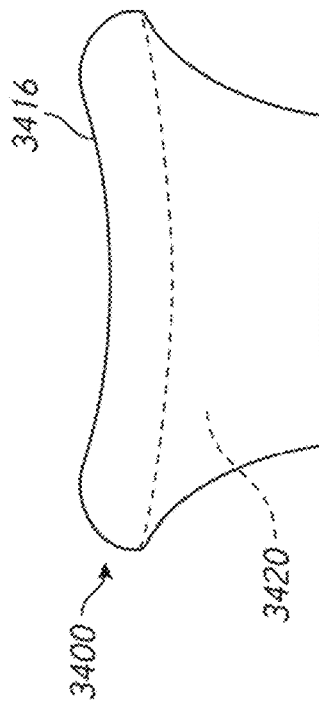
Figure 68D:
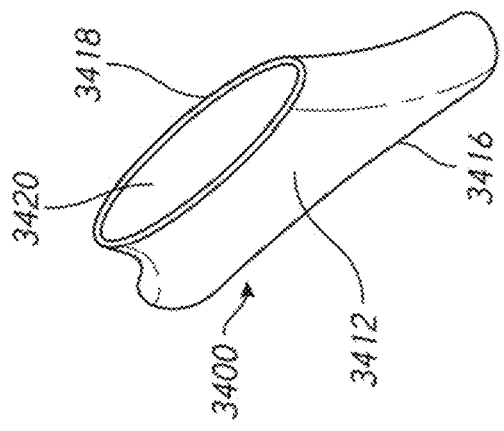

FIGS. 68A-D illustrate various views of the connector 3400. As shown, the connector 3400 comprises a tubular sheath having a cavity 3420 between a strap surrounding end 3418 and an abutment end 3416. The connector 3400 has a body 3410 comprised of a first half 3412 and second half 3414 that are joined along their opposing edges. In the illustrated configuration, the first and second halves 3412, 3414 are identical. In other configurations, the first and second halves 3412, 3414 are non-identical and/or asymmetrical. The open ends of the first and second halves 3412, 3414 form an abutment end 3416 and a strap surrounding end 3418 of the connector 3400. The strap surrounding end 3418 receives or surrounds the first strap 3710 and the abutment end 3416 receives or is abutted against the second strap 3720. As shown in FIG. 68B, the connector 3400 has a somewhat trapezoidal profile, such that one end is wider than the other. The wider end of the connector 3400 forms the abutment end 3416 and the narrower end forms the strap surrounding end 3418. In some configurations, the abutment end 3416 may have a width that is twice the width of the strap surrounding end 3418.

Figure 68A:
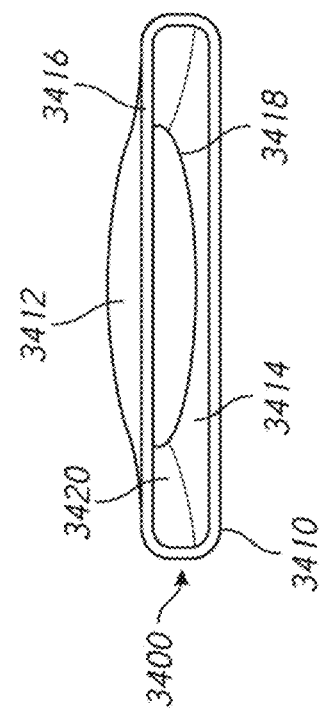
Figure 68C:
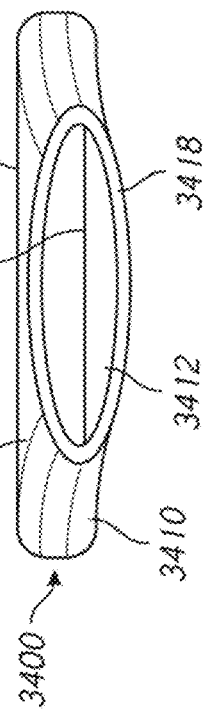

The strap surrounding end 3418 defines an elliptical aperture which is configured to fit snuggly onto and against the outer surface of the textile strap casing of the first strap 3710. The abutment end 3416 forms a substantially rectangular aperture having rounded ends, when viewed from below (as shown in FIG. 68A). The abutment end 3416 is curved to match a shape and curvature of the second strap 3720. The edges of the abutment end 3416 are configured to overhang over and surround the outer edge (the area between the abutment edge 3417 and the dashed line in FIG. 68B overhangs the second strap 3720) of the second strap 3720. The edges of the abutment end 3416 are also configured to be positioned over the outer surface of the textile strap casing of the second strap 3720. In some configurations, the overhanging edge 3419 may form a loose fit with the textile strap casing of the second strap 3720 such that the connector 3400 does not restrict flow of plastic core material 3800 through the second strap 3720.

When intra-moulding the first and second straps 3710, 3720, the connector 3400 allows the end of the first strap 3710 to be aligned with and abutted against the edge of the second strap 3720, rather than having a gap between the first and second straps 3710, 3720. That is, the snug fit with the first strap 3710 that is provided by the connector 3400 retains the first strap 3710 in alignment while in the mould tool prior to the injection of the plastic core material 3800. The connector 3400 is semi-rigid and retains its shape, unlike the straps 3710, 3720, which allows the connector 3400 to be positively located within the mould tool.

Figure 70:
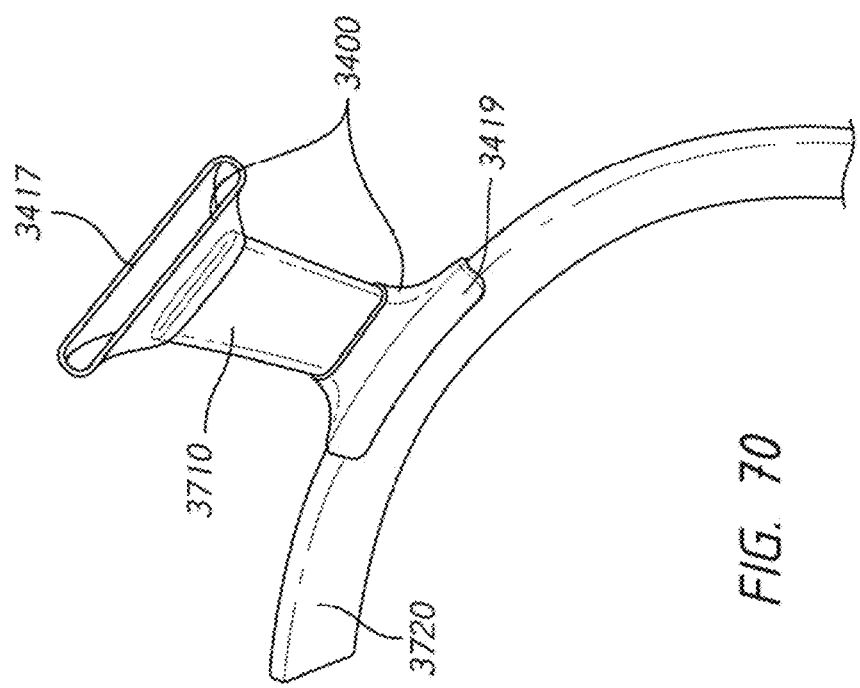
Figure 69:
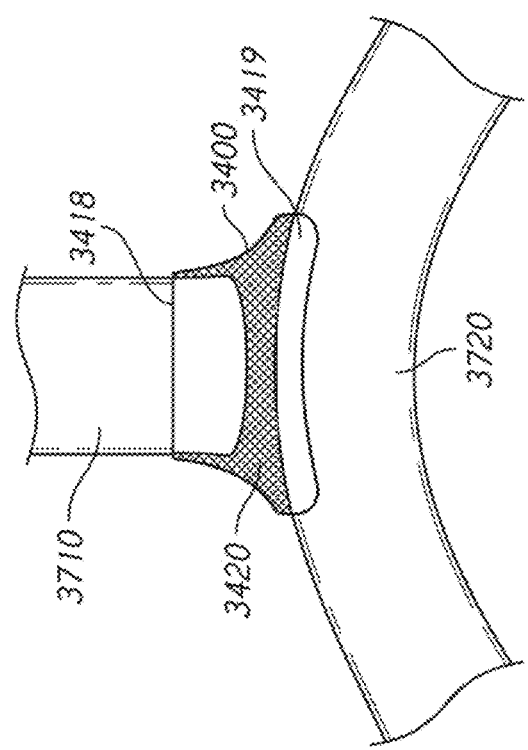

During assembly of the straps 3710, 3720 and the connector 3400, the connector 3400 is positioned over the tubular textile casing of the first strap 3710. That is, as shown in FIG. 69, the connector 3400 is slid over the first strap 3710 so that the end of the first strap 3710 is positioned inside of the connector 3400. Then, the abutment edge 3417 of the connector 3400 is abutted with an edge of the textile casing of the second strap 3720. As shown in FIG. 70, the end of the first strap 3710 is positioned adjacent to the edge of the second strap 3720 within a cavity 3420 of the connector 3400. The cavity 3420 is a hollow region defined by the first half 3412, the second half 3414, the strap surround end 3418 and the abutment end 3416. The connector 3400 is snuggly fit onto the first strap 3710 such that the connector 3400 remains fixed to the first strap 3710.

Figure 72:
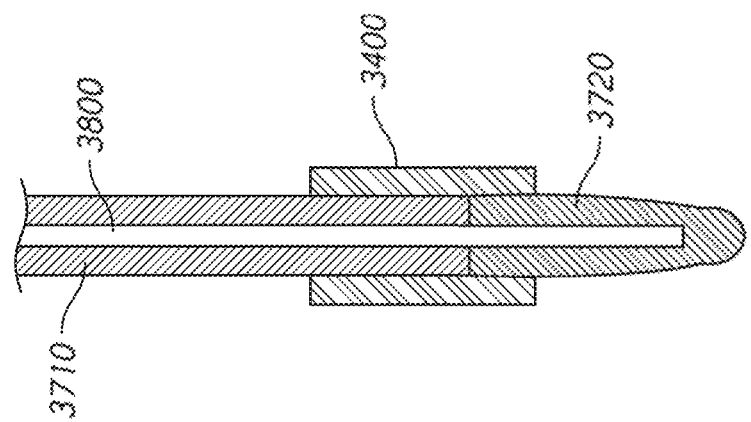
Figure 71:
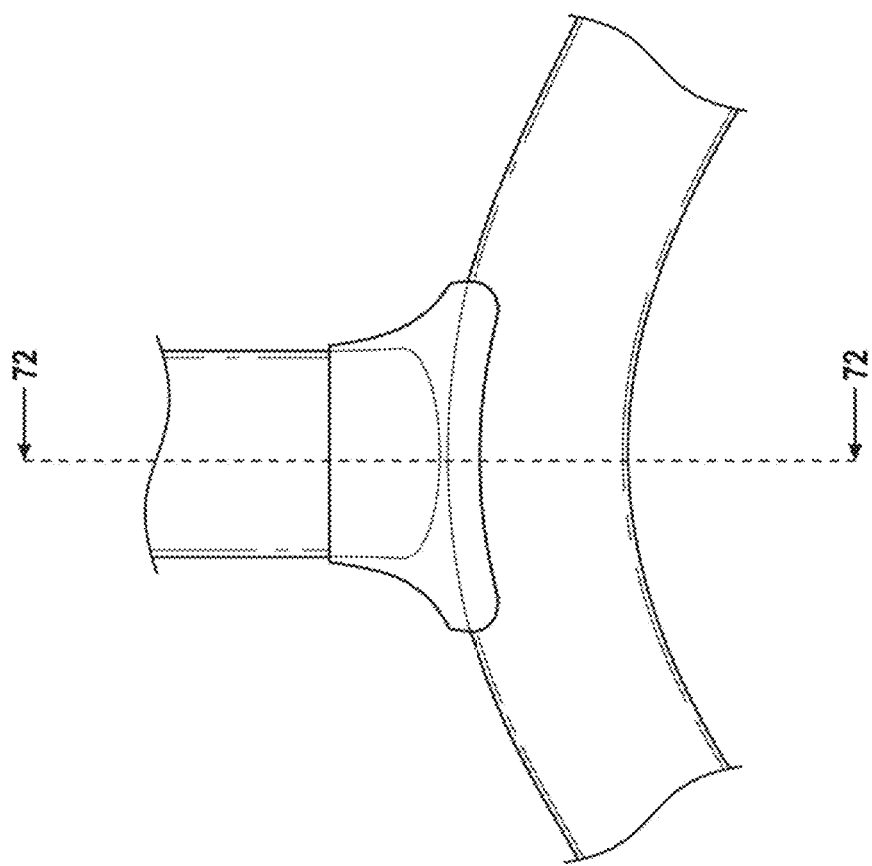

The assembled straps 3710, 3720 and connector 3400 are positioned and aligned within an injection moulding tool. Plastic core material 3800 is injected into the injection point 3600 at an end of the second textile strap 3720 and bursts through the side wall of the second strap 3720 to fill the first strap 3710 (see arrows in FIG. 66A). Accordingly, as shown in FIGS. 71 and 72, the cavity 3420 of the connector 3400 is also filled with the plastic core material 3800 that bursts through the side wall of the second strap 3720. The plastic core material 3800 within the straps 3710, 3720 and the cavity 3420 of the connector 3400 form a unitary structure. In some configurations, the plastic core material 3800 bonds with the connector 3400 such that the connector 3400, straps 3710, 3720 and plastic core material 3800 are formed as an integral structure.

It should be understood to one of ordinary skill in the art that the connector 3400 and strap arrangement is not limited to T-junctions and may connect straps 3710, 3720 having junctions 3500 at a variety of angles. Similarly, the connector 3400 may be shaped and configured to connect more than two straps together. For example, the connector 3400 may have multiple strap surround ends 3418 or abutment ends 3416.

Figure 73:
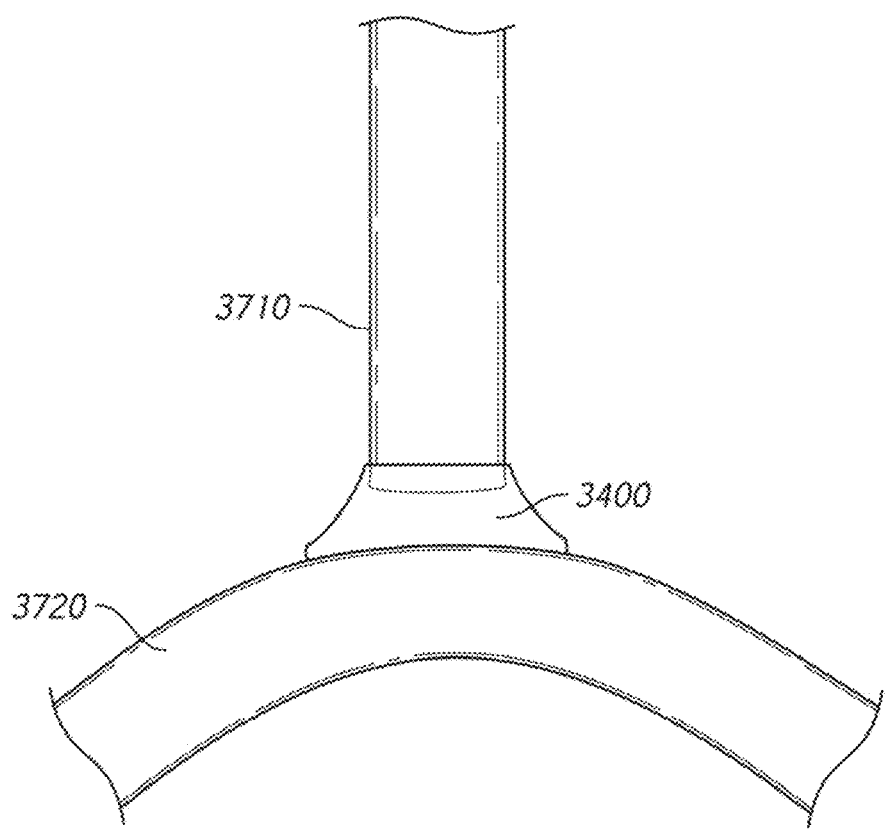

In an alternative configuration, the connector 3400 (substantially the same as the previously described embodiment) is formed integrally with the first strap 3710 by over-moulding an end of the tubular textile strap casing, as shown in FIG. 73. The abutment end 3416 of the connector 3400 extends from the end of the textile strap, such that it can be aligned and abutted with the second strap 3720. The cavity 3420 of the connector 3400 remains hollow such that the plastic core material 3800 can flow through the second strap 3720 and burst through into the first strap 3710. With such a configuration, the strength of the joint between the first and second straps 3710, 3720 is increased by providing a permanent bond between the strap surround end 3418 of the connector 3400 and the first strap 3710.

In some embodiments, at least one of the first and second straps 3710, 3720 can comprise a braided textile casing. The braided textile casing comprises a plurality of yarns that are provided in at least two different colours or shades. The braiding of the different coloured yarns forms a random or semi-random pattern of colour patches within the textile casing, which results in the textile casing having a mottled appearance. The mottled appearance may in some cases camouflage or hide some physical features formed by the plastic core, such as the transition between a soft edge (222 in FIG. 2B) and the core material, making the features (and headgear) appear softer.

In another alternative configuration, the connector 3400 may be configured such that the connector 3400 does not overhang over the edge of the second strap 3720. Rather, the connector 3400 is configured to abut directly with and against the edge of the second strap 3720, as shown in FIG. 73. Accordingly, the connector 3400 is substantially or completely bonded with the burst through plastic core material 3800. That is, in comparison to the connector arrangements previously described, the overhanging portions of the previous connector arrangements are not bonded with the plastic core material 3800.

Intra-Mould Connectors

FIGS. 74A-78B illustrate various views of intra-moulded straps, junctions and joints for forming the bifurcated headgear 100 illustrated in FIG. 1A. The bifurcated headgear 100 comprises a top strap 140, a bottom strap 150 and a mask connector 180. In some configurations, the bifurcated headgear 100 is assembled by joining the top strap 140 with the bottom strap 150. That is, prior to joining the top strap 140 with the bottom strap 150, each of the top and bottom straps 140, 150 are separately formed via intra-moulding. That is, in some configurations, the top and bottom straps 140, 150 are positioned within a moulding tool and joined via overmoulding. Once formed, the top and bottom straps 140, 150 are joined to form the bifurcated headgear 100. However, in some configurations, the top and bottom straps 140, 150 may move out of alignment with each other while being arranged within the moulding tool and/or during the overmoulding process. FIGS. 74A-78B illustrate various strap connectors that maintain the top and bottom straps 140, 150 in connection and alignment during the manufacturing and moulding process.

FIG. 74A illustrates the top strap 140 prior to assembly and 74B illustrates the bottom strap 150 prior to assembly. The top and bottom straps 140, 150 are formed separately by injecting a plastic core material 210 into a knitted or braided tubular casing 220 via intra-moulding. As shown in FIG. 74A, the top strap 140 comprises a substantially straight and continuous strap having a male connector portion 4002 formed at each end. The male connector portions 4002 are integrally formed and unitary with the plastic core material 210. The casing 220 is continuous throughout its length. An injection point of the top strap 140 may be located at one or both of its ends. That is, one or both male connectors may be the location of an injection point for injecting the plastic core material 210 into the casing 220.

The bottom strap 150 comprises a plastic core material 210 that is injected into first and second braided casing portions 220A, 220B. The casing portions 220A, 220B may form left- and right-side portions of the top and bottom straps 140, 150. The casing portions 220A, 220B have first and second free ends 4020, 4022. A central injection point 4010 is positioned between the first free ends 4020 such that the casing portions 220A, 220B are filled with plastic core material 210, from the first free ends 4020. The plastic core material 210 that fills the casing portions 220A, 220B is integrally formed and unitary throughout the length of the plastic core material 210. That is, the plastic core material 210 joins the casing portions 220A, 220B to connect the casing portions 220A, 220B and form the bottom strap 150.

In some configurations, the casing portions 220A, 220B are partially filled with the plastic core material 210. That is, the second ends 4022 of the casing portions 220A, 220B may be hollow such that the bottom strap 150 has hollow free ends 4030. The hollow free ends 4030 of the bottom strap 150 may accommodate and house portions of the mask connector 180 (see FIG. 1). That is, portions of the mask connector 180, such as the filament core 1550 (see FIGS. 15A-D) for example, may be housed within the casing portions 220A, 220B of the hollow free ends 4030. In some configurations, the casing portions 220A, 220B may be filled with the plastic core material 210 through the length of the bottom strap 150. That is, the plastic core material 210 may extend between the first and second free ends 4020, 4022 of the casing portions 220A, 220B. In some configurations, portions of the mask connector 180 may be formed on the second free end 4022 of the bottom strap 150.

The bottom strap 150 includes a female connector 4004 positioned between the first and second free ends 4020, 4022 of the casing portions 220A, 220B. The female connector 4004 is configured to interlock with the male connector 4002 such that the top strap 140 and the bottom strap 150 are connected. The female connector 4004 is formed from plastic core material 210 that has burst through the wall of the casing portions 220A, 220B. That is, the female connector 4004 is formed by a burst-through intra-moulding process. The female connector 4004 is integrally formed and unitary with the plastic core material 210 within the casing portions 220A, 220B. The female connector 4004 is positioned at the apex of a curvature of the bottom strap 150 which when in use is positioned substantially above the user's ear. In some configurations, the female connector 4004 may be formed on substantially straight portions of the bottom strap 150.

FIGS. 75A and 75B are views of the male connector 4002 of the top strap 140. As shown, the male connector 4002 extends and protrudes outwards beyond the end of the casing 220. The male connector 4002 is formed from plastic core material 210 that is positioned beyond the end 4024 of the casing 220. The male connector 4002 comprises a protrusion 4040 that is configured to interlock with a slot 4042 of the female connector 4004. The protrusion 4040 has a shape that corresponds to the shape of the slot 4042 such that the male connector 4002 mates and engages with the female connector 4004 like a puzzle piece.

The protrusion 4040 comprises a head 4050 and a stalk 4052. The stalk 4052 is an extension of plastic core material 210 that is positioned between the head 4050 and the end 4024 of the casing 220. The head 4050 is illustrated as having an inverted arrowhead shape which interlocks with the slot 4042 of the female connector 4004. The slot 4042 has a shape that corresponds to and interlocks with the inverted arrowhead shape of the head 4050. The head 4050 is not limited to an inverted arrowhead shape and any interlocking shape may be used.

FIG. 75B is a side view of the top strap 140. As shown, the head 4050 has a thickness $T_1$ and the stalk 4052 has a thickness $T_2$. The thickness $T_1$ of the head 4050 is greater than the thickness $T_2$ of the stalk 4052. The variance between thicknesses $T_1$ and $T_2$ allows for over-moulded plastic to flow around the head 4050 of the male connector 4002 when joining the top strap 140 to the bottom strap 150. In some configurations, the narrower thickness $T_2$ allows the head 4050 to be surrounded by the over-moulded plastic material.

FIGS. 76A to 76C are various views of the female connector 4004 of the top strap 150. The female connector 4004 has a triangular shape that extends and protrudes radially outwards beyond the surface of the casing portions 220A, 220B. The female connector 4004 is formed from plastic core material 210 that burst-through the casing portions 220A, 220B during the burst-through intra-moulding process. The female connector 4004 comprises a protrusion 4046 in the shape of a tab that is formed with the slot 4042. As shown in FIG. 76C, the protrusion 4046 has a central region 4044 and a peripheral region 4048 that extends outward from the central region 4044. The central region 4044 has a thickness $T_3$ that is greater than a thickness $T_4$ of the peripheral region 4048. The greater thickness $T_3$ of the central region increases the strength of the protrusion 4046 whilst allowing over-moulded plastic to flow around the protrusion 4046 when joining the top and bottom straps 140, 150. The thickness $T_3$ of the central region 4044 may be equal to the thickness $T_1$ of the head 4050 of the male connector 4002.

The slot 4042 is formed within and extends through both the central and peripheral regions 4044, 4048. The slot 4042 has a shape that matches and interlocks with the inverted arrowhead shape of the head 4050. The slot 4042 opens in a direction away from the casing portions 220A, 220B such that the head 4050 is inserted into and received by the slot 4042. The slot 4042 is centrally positioned on a radially outermost portion of the peripheral region 4048. The slot 4042 may be formed and shaped into the female connector 4004 when forming the female connector 4004 via the burst-through injection moulding process. In other configurations, plastic core material 210 may be removed from the female connector 4004 to form the slot 4042, for example, via a cutting process.

The slot 4042 is configured to receive at least the head 4050 of the male connector 4002 such that the top and bottom straps 140, 150 may be joined and over-moulded to form a permanent joint therebetween. That is, the top and bottom straps 140, 150 are loaded into an overmoulding tool and the head 4050 is inserted into the slot 4052 such that the male and female connectors 4002, 4004 are connected and the top and bottom straps 140, 150 are correctly aligned. Once the aligned, the overmoulding tool is closed and over-moulding plastic material is injected into the over-moulding tool to form a permanent over-moulded joint over the male and female connectors 4002, 4004. Connecting and aligning the straps 140, 150 prior to overmoulding the male and female connectors 4002, 4004 increases strap alignment accuracy and reduces the likelihood of the straps 140, 150 moving during over-moulding, and thus improves the efficiency of the manufacturing process.

FIG. 77A illustrates the male connector 4002 aligned with the female connector 4004 prior to insertion of the head 4050 into the slot 4042. FIG. 77B illustrates the head 4050 inserted into and received by the slot 4042 such that the male and female connectors 4002, 4004 are connected. FIG. 77C illustrates the comparative thicknesses of the male and female connectors 4002, 4004. The increased thicknesses $T_1$, $T_3$ of the head 4050 of the male connector 4002 and the central region 4044 of the female connector 4004, respectively, align and form an upper surface 4060 and a lower surface 4062. The upper and lower surfaces 4060, 4062 are configured to abut with opposing internal surfaces of a mould cavity in the overmoulding tool. This helps to align the top and bottom straps 140, 150 within the overmoulding tool. The upper and lower surfaces 4060, 4062 are illustrated as flat planar surfaces, which are not limiting. Accordingly, the opposing surfaces of the mould will have a corresponding shape to engage the upper and lower surfaces 4060, 4062.

In some configurations, the head 4050 and the slot 4052 may be sized and shaped such that an amount of clearance exists therebetween when the head 4050 and the slot 4052 are engaged. A tight connection fit without a clearance gap between the male and female connectors can result in there being no space for the over-moulding plastic material to flow between the connectors. This results in an overmoulded connection having a weak zone that is caused by gaps or voids within the over-moulded joint, which may reduce the durability of the headgear. FIGS. 78A and 78B illustrates a clearance gap 4064 between the head 4050 and the slot 4052 when the male and female connectors 4002, 4004 are in a connected state. The clearance gap 4064 in FIG. 78B is greater than the clearance gap 4064 in FIG. 78A. In FIG. 78A, the clearance gap 4064 is small such that the connection between the male and female connectors 4002, 4004 has a tight fit that is similar to a puzzle piece. In FIG. 78B, the clearance gap 4064 is greater which allows for a looser fit and general alignment of the top and bottom straps 140, 150 within the over-moulding tool. The greater clearance gap 4064 allows the over-moulding plastic to flow between the connectors 140, 150 to provide a robust joint. In FIG. 78B, the clearance gap 4064 is preferably about 1.0 mm. In some configurations, the clearance gap 4064 is between 0.1-1.0 mm.

FIG. 79A illustrates an alignment recess 4070 formed on the head 4050 of the male connector 4002 that is configured to receive an alignment locating pin 4072 positioned on an opposing internal surfaces of the mould cavity 4076 in an overmoulding tool portion 4074. FIG. 79B illustrates an overmoulding tool portion 4074 having a mould cavity 4076 with a locating pin 4072 protruding from a surface of the mould cavity 4076. The locating pin 4072 is configured to be inserted into and received by the recess 4070 such that the head 4050 of the male connector 4002 is aligned and maintained in position within the mould cavity 4076 during positioning of the top and bottom straps 140, 150 and during the overmoulding process. The locating pin 4072 may restrict movement of the head 4050 within the mould cavity 4076. The locating pin 4072 may also inhibit or prevent the male connector 4002 from becoming unlatched from the female connector 4004 prior to or during the overmoulding process. In some configurations, the locating pin 4072 may retain the head 4050 in a position so that the clearance gap 4064 between the male and female connectors 4002, 4004 is maintained.

In some embodiments the recess 4070 and the locating pin 4072 may have a corresponding shape, size and geometry. The recess 4070 is illustrated as, but not limited to, a triangular recess formed at an internal corner of the head 4050. The locating pin 4072 is illustrated as, but not limited to, a cylindrical post shape. The triangular recess 4070 is configured to receive the locating pin 4072 in one of the vertices of the triangular recess as indicated by the dashed circle in FIG. 79A. The locating pin 4072 has cylindrical sides that are configured to abut with a side surface of the head 4050 to align the head 4050 of the male connector 4002 within the mould cavity 4076.

FIGS. 80A to 80C illustrated the top and bottom straps 140, 150 after the overmoulding process. As shown, an overmoulded joint 4006 is molded over the male and female connectors 4002, 4004 such that the top and bottom straps 140, 150 are permanently bonded. In some configurations, the overmoulded joint 4006 may be formed from the same plastic core material 210 that is used to form the inner core of the top and bottom straps 140, 150 and also the male and female connectors 4002, 4004. In other configurations, the overmoulded joint 4006 may be formed from a different material such as an elastomer.

As shown in FIGS. 80A and 80B, the overmoulded joint 4006 has a top edge 4056 that extends over the edge of the top strap 140 and onto the surface of the top strap 140. That is, the overmoulded joint 4006 overlaps and is bonded to the casing 220 of the top strap 140. Similarly, the overmoulded joint 4006 has a bottom edge 4058 that extends over the edge of the bottom strap 150 and onto the surface of the bottom strap 150. That is, the overmoulded joint 4006 overlaps and is bonded to the casing 220 of the bottom strap 150. Bonding the overmoulded joint 4006 to the top and bottom straps 140, 150 increases the connection area between the overmoulded joint 4006 and the top and bottom straps 140, 150 which increases the strength of the overmoulded joint 4006. Further, extending the overmoulded joint 4006 beyond the ends of the casing 220 such that the ends of the casing 220 are enclosed within the overmoulded joint 4006 improves the durability and appearance of the finished headgear. That is, loose thread ends of the casing are enclosed and bonded within the overmoulded joint 4006.

As shown in FIG. 80C, the overmoulded joint 4006 has a thickness T that is substantially equal to the thickness of the top and bottom straps 140, 150 and also equal to the thickness of the male and female connectors 4002, 4004. That is, the thickness T of the overmoulded joint 4006 is equal to the thickness $T_1$ of the head 4050 and the thickness $T_3$ of the central region 4044. Accordingly, the equal thicknesses of the overmoulded joint 4006 and the top and bottom straps 140, 150 provide a continuous thickness throughout the lengths of the straps 140, 150 and the connection and transition between the straps 140, 150 which improve the aesthetics and comfort of the headgear.

Joining Tab with Alignment Posts

FIGS. 81A to 81C illustrate a bottom strap 150 that is formed by intra-moulding together two empty textile casings 220 of the bottom strap halves 150A, 150B. The joining of strap halves 150A, 150B is illustrated in the context of a bottom strap 150 but is not limited to the forming of a bottom strap and may be used to form any headgear strap. The bottom strap 150 is formed by intra-moulding together multiple textile casings 220 using a single injection moulded shot to form a unitary strap 150. The textile casings 220 are connected by a unitary plastic core material 210 that is formed within both casings 220. A joining tab 4008 is positioned between free ends 4026 of the casings 220 and is formed from plastic core material 210. The joining tab 4008 extends between the two strap halves 150A, 150B and provides a central injection point 4010 for injecting the strap halves with plastic core material 210. The joining tab 4008 is configured to be over-moulded to provide a tidy and durable joint between the strap halves 150A, 150B. Prior to over-moulding, any excess material or sprues formed at the injection point are trimmed.

The end portions of the joining tab 4008 include a pair of alignment posts 4078 that protrude and extend in opposing directions (e.g., a thickness direction) from upper and lower surfaces 4018, 4028 of the joining tab 4008. The alignment posts 4078 are illustrated as, but not limited to, rectangular-shaped protrusions that extend across the width of the upper and lower surfaces 4018, 4028 of the joining tab 4008. The alignment posts 4078 are configured to abut against an internal surface of the mould cavity of the over-moulding tool such that the ends 4026 of the strap halves 150A, 150B are aligned (e.g., in a thickness direction of the straps) within the over-moulding tool.

FIG. 81C shows the alignment posts 4078 extending from the upper and lower surfaces 4018, 4028 of the joining tab 4008. The joining tab 4008 is illustrated as having a thickness $T_6$. The regions of the joining tab 4008 that include the alignment posts 4078 have a thickness $T_5$. The thickness $T_5$ of the regions including the alignment posts 4078 is greater than the thickness $T_6$ of the regions without the alignment posts 4078. The alignment posts 4078 may also maintain a clearance gap between the upper and lower surfaces 4018, 4028 of the joining tab 4008 and the internal surface of the mould cavity which allows the over-moulding plastic to flow over the joining tab 4008 to provide a robust joint.

FIGS. 81D and 81E illustrate the strap halves 150A, 150B after the joining tab 4008 is overmoulded. As shown, an overmould 4080 is formed over the joining tab 4008. The overmould 4080 may be formed from the same material the bottom strap 150 (e.g., plastic core material 210) or from a different material. In some embodiments the overmould 4080 may comprise an elastomeric material to provide a flexible and comfortable contact between the overmould 4080 and a patient's head. The overmould comprises an outer surface 4082 configured to face away from a patient's head, in use, and an inner surface 4084 configured to contact the patient's head, in use.

FIG. 81D is top view of the overmould 4080 which illustrates the top surface 4082 of the overmould 4080 facing away from the patient's head. FIG. 81E is bottom view of the overmould 4080 which illustrates the bottom surface 4084 of the overmould 4080 facing the patient's head. Witness marks 4088 indicating the position of the alignment posts 4078 may be formed in or on the surfaces 4082, 4084 of the overmould 4080. The witness marks 4088 are visible through the surfaces 4082, 4084 because the thickness of the overmould 4080 is equal to the thickness $T_5$ of the alignment posts 4078. In other configurations, the thickness of the overmould 4080 may be greater than the thickness $T_5$ of the alignment posts 4078 such that the alignment posts 4078 are not visible through the surfaces 4082, 4084 of the overmould 4080. That is, the outer surface 4082 of the overmould 4080 may be smooth and continuous such that witness marks 4088 indicating the position of the alignment posts 4078 are not visible.

A product label or logo 4086 may also be formed in or on the outer surface 4082 of the overmould 4080. The logo 4086 is molded into the surface 4082 during the overmoulding process. In some configurations, the alignment posts 4078 may be configured to form a portion of the logo 4086. For example, in the illustrated configuration, one alignment post 4078 may have a shape comprising of the letter "F" while the other alignment post has a shape comprising of the letter "P". The thickness of the alignment post 4078 and/or the overmould 4080 may be varied such that the alignment posts 4078 are visible on the surface 4082. In other configurations, the logo 4086 may be formed by a finishing process (e.g., engraving, molding, stamping, etc.).

In some embodiments, the joining tab 4008 may be trimmed between the alignment posts 4078 prior to being over-moulded. This allows the overall length of the bottom strap 150 to be adjusted by increasing or decreasing the spacing between the alignment posts 4078 and thus the length of the over-mould. That is, in some configurations, the distance between the alignment posts 4078 (e.g., in a lengthwise direction of the bottom strap 150) may be shortened or lengthened to shorten or lengthen the overall length of the bottom strap 150. This approach can be used to provide different headgear sizes using the same bottom strap components.

Injection Housing

FIGS. 82A to 83E illustrate a strap end joint housing 4090 within which the ends 4026 of empty bottom strap halves 150A, 150B are inserted and intra-moulded to form a unitary bottom strap 150. The joining of strap halves 150A, 150B is illustrated in the context of a bottom strap 150 but is not limited to the forming of a bottom strap and may be used to form any headgear strap. The bottom strap 150 is formed by intra-moulding multiple textile casings 220 together using a single injection moulded shot to form a unitary strap. As such, the textile casings 220 are connected by a unitary plastic core material 210 that is formed within and extends through both casings 220.

The housing 4090 has an internal chamber 4092 configured to receive the open ends 4026 of the two textile casings 220. The housing 4090 may have a shape, size and geometry that corresponds to the shape, size and geometry of a region within the internal cavity of the intra-moulding tool such that the housing 4090 has a secure fit within the intra-moulding tool. As such, the housing 4090 may be aligned relative to the cavity of the intra-moulding tool which allows the ends 4026 of the textile casings 220 to be aligned by the housing 4090 when in the intra-mould tool. The housing 4090 is not limited to a rectangular shape or geometry.

The housing 4090 has an injection aperture 4094 on at least one side of the housing 4090 which provides a gate through which the intra-moulding plastic material 210 can be injected and flow therein. In some configurations, the injection apertures 4094 may be positioned on a plurality of sides of the housing 4090. FIG. 83E illustrates injection apertures 4094 located on opposing sides of the housing 4090. Plastic core material 210 can be injected into both apertures 4094 at the same time, or alternatively one aperture 4094 can be blocked off while plastic material 210 is injected into the other aperture 4094.

As shown in FIG. 83D, the injection aperture 4094 is fluidly connected to the internal chamber 4092 which receives the open ends 4026 of the textile casings 220. The ends 4026 of the textile casings 220 open towards the injection aperture 4094 such that the internal cavities of the textile casings 220 are in fluid communication with the injection aperture 4094. During the intra-moulding process plastic is injected into the textile casings 220 by intra-moulding plastic core material 210 that is injected into the aperture 4094 of the housing 4090. The intra-moulding plastic core material 210 flows into the internal chamber 4092 from the aperture 4094 and from the internal chamber 4092 into the textile casings 220. The housing 4090 provides a central injection point for intra-moulding the textile casings 220. In some configurations, the housing 4090 may provide an alternative to the overmoulding of an overmoulding joint over the ends of the textile casing 220. As such, the loose thread ends of the textile casings 220 are enclosed and contained within the housing 4090 which improves aesthetics and durability of the headgear.

The internal chamber 4092 has an inner cavity region 4092A located at a centre region of the housing 4090. The inner cavity region 4092A has one end that opens toward and into the injection aperture 4094 and has a second end that opens toward and into an outer cavity region 4092B. That is, the inner cavity region 4092A is positioned between the injection aperture 4094 and the outer cavity regions 4092B. The injection aperture 4094 directs injected plastic material 210 into the inner cavity region 4092A of the internal chamber 4092. End portions of the casings 220 abut an inner wall of the outer cavity regions 4092B which provides a fluid path from the injection aperture 4094 into the cavities of the casings 220 such that injected plastic material 210 flows from the injection aperture 4094 and into the textile casings 220.

The inner cavity region 4092A has a height $D_1$ that is less than a height $D_2$ of the outer cavity region 4092B. The difference in heights $D_1$, $D_2$ of the inner and outer cavity region 4092A, 4092B form a stepped profile within the internal chamber 4092 which allows the ends 4026 of the textile casings 220 to be spaced apart when positioned within the housing 4090. The height $D_1$ of the inner cavity region 4092A can be substantially equal to the thickness of the core material 210 through the textile casings 220.

In some configurations, the length L of the inner cavity region 4092A (as shown in FIG. 83D) may vary such that different lengths of the bottom strap 150 may be formed from the same textile casings 220. That is, bottom straps of varying lengths may be formed from textile casings 220 having a fixed length by varying the lengths of the housing 4090. The length L of the inner cavity region 4092A spaces the ends 4026 of the textile casings 220 closer or further apart which increases or decreases the finished length of the strap 150. For example, in some configurations, the bottom strap 150 for a medium size headgear and a medium-large size headgear may be formed using textile casings 220 of the same length and housings 4090 having different lengths L of the inner cavity regions 4092A. That is, the difference in lengths of the bottom straps 150 of the medium and medium-large sizes is provided by the difference in lengths L of the inner cavity regions 4092A.

Strap Cross-Section

FIGS. 84A and 84B illustrates a cross-sectional view of the top and bottom straps 140, 150 following the intra-moulding process in which the textile casings 220 are filled with plastic core material 210. The top and bottom straps 140, 150 both have an inner surface 4066 and an outer surface 4068, wherein the inner surface 4066 is configured to contact the patient's head and the outer surface 4068 is configured to face away from the patient's head. In this embodiment the plastic core material 210 of the straps 140, 150 has a substantially D-shaped cross-section, such that the outer surface 4068 has a convex curvature and the inner surface 4066 has a substantially flat, planar or straight profile. In some configurations, the inner surface 4066 may have a concave curvature.

The flat profile of the inner surface 4066 is configured to have an increased contact area with the patient's head to spread any load in the headgear more evenly (than a convex profile) across the patient's head. This improves stability of the headgear and comfort for the patient. The convex curvature of the outer surface 4068 provides a degree of rigidity to the straps and a soft or aesthetically appealing appearance to the headgear.

Strap Soft Edges

FIG. 84A illustrates top and bottom straps 140, 150 with a plastic core material 210 that include flange portions 4036 that fill the outer edge portions of the textile casing 220. The flange portions 4036 provide a hard and rigid edge treatment to the top and bottom straps 140, 150. FIG. 84B illustrates top and bottom straps 140, 150 having soft edge portions 4038 formed by the absence of plastic core material 210 within the soft edge portions 4038. The soft edge portions 4038 are a portion of the casing 220 that is not filled with plastic core material 210 such that the textile casing 220 remains supple and pliable. As a result, the soft edge portion 222 provides the top and bottom straps 140, 150 with a soft or cushioned edge that is comfortable against the user's skin and that is also aesthetically pleasing.

In some configurations, the soft edge portions 4038 is formed by crimping the edges of the tubular casing 220 prior to injecting of the plastic core material 210 such that the plastic core material 210 is inhibited or restricted from flowing into the portions of the casing 220 that are crimped. The edges are crimped by portions of the moulding tool that are adjacent the mould cavity. The depth of crimping of the edges of the top and bottom straps 140, 150 by the moulding tool may vary along the length of the top and bottom straps 140, 150 such that the width (the horizontal direction in FIGS. 84A and 84B) of the plastic core material 210 may vary along the length of the top and bottom straps 140, 150. As such, the width of plastic core material 210 may be wider at different regions of the top and bottom straps 140, 150 to reinforce and provide additional strength to those regions. Similarly, in some configurations, the width of the plastic core material 210 may be narrower at certain regions along the length of the top and bottom straps 140, 150 to provide flexibility to those narrower regions. It should be understood to one of ordinary skill in the art that the shape and geometry of the plastic core material may vary to provide strength and stiffness to the top and bottom straps 140, 150 in the desired directions.

FIG. 85 illustrates a top strap 140 joined to a bottom strap 150 that has soft edge portions 4038 provided along its length. The bottom strap 150 has a contoured curved shape to form an ear arch 4016 that is positioned above the user's ear, when in use. As shown, the soft edge portion 4038 at the ear arch 4016 has a width $W_1$ that is greater than a width $W_2$ the soft edge portion 4038 at remaining portions of the bottom strap 150. The soft edge portion 4038 in the ear arch 4016 has an increased width relative to other portions of the bottom strap 150 to provide increased softness/cushioning and comfort in the event that the ear arch should come into contact with the patient's ears, during use. The user's ear arch is a sensitive area and contact may cause discomfort.

In some configurations, the headgear can comprise a four point connection configuration, having upper and/or lower side straps (or other configurations). In such configurations, any strap that is proximal to the patient's ears, in use, can include an increased soft edge width.

Combined Top and Rear Strap with Overmoulded Connection

FIG. 86 illustrates a headgear arrangement 5000 comprised of rear and top strap portions 140, 150 that are integrally formed as a single halo or rear headgear loop strap 5002. The headgear loop strap 5002 is connected to a front strap 5004 via an overmoulded joint 5006. The front straps 5004 are formed separately from the headgear loop strap 5002 and then connected to the rear headgear loop 5010 by an overmoulded connection. The front straps 5004 may comprise either an intra-moulded strap portion, a braided filament housing for a locking mechanism, or a combination of both. In one embodiment the front straps 5004 of the headgear arrangement 5000 may be configured to include a size adjustment mechanism that comprises locking mechanisms and a filament This is advantageous as it allows the braided straps that house the filament to be manufactured and tested as individual components. This reduces the complexity of manufacturing these components and may prevent the wastage of headgears or a larger portion of the headgears when the tolerances or operation of the locking mechanism are compromised and/or defective. That is, since the front straps 5004 are formed separately from the headgear loop strap 5002, a faulty or defective locking mechanism does not require scrapping the entire headgear.

The ends of the headgear loop strap 5002 are joined together by an overmoulded joint 5008 to form a rear headgear loop 5010 (indicated by a dashed line) that cups or receives the rear of a patient's head. The overmoulded joint 5008 is located at the top of the patient's head during use. Positioning the overmoulded joint 5008 at the top of the patient's head is advantageous position because the top of the user's head does not contact a bed or pillow which may apply a force to the joint 5008 and cause it to dig into the patient's head. That is, positioning the overmoulded joint 5008 at the top of the patient's head may be more comfortable for the patient.

As shown in FIG. 87A, the headgear loop strap 5002 is formed from a single intra-moulded member that combines the top and rear straps 140, 150. The headgear loop strap 5002 is formed from a single length of textile casing material 220 that is filled with plastic core material 210. The headgear loop strap 5002 includes alignment tabs 5020 formed at and extend from the free ends of the top strap portions 140. The headgear loop strap 5002 also includes burst-through tabs 5030 positioned between the top and bottom strap portions 140, 150.

The alignment tabs 5020 are substantially similar to the joining tabs 4008 in FIGS. 81A to 81E. The alignment tabs 5020 are formed from plastic core material 210 and are configured to align the ends of the headgear loop strap 5002 within an over-moulding tool that forms an over-moulded joint between the top strap portions 140. The joining of the ends of the top straps forms 140 forms the closed loop of the rear headgear loop 5010.

The alignment tabs 5020 include alignment posts 5022 that are configured to align the ends of the top strap portions 140 within the overmoulding tool. As shown in FIGS. 88A and 88B, the alignment posts 5022 also have a raised abutment surface 5024 that is configured to abut against, engage and/or contact the internal walls of the over-mould tool cavity and to align the alignment tabs 5020 (e.g., in a thickness, width and/or lengthwise direction of the headgear loop strap 5002) within the tool. Similar to the joining tab 4008, when the alignment tabs 5020 are aligned within the overmoulding tool, the alignment tabs 5020 are overmoulded to join the ends of the headgear loop strap 5002.

The headgear loop strap 5002 includes two burst-through tabs 5030 that are configured to be overmoulded with ends of the front strap 5004. The burst-through tabs 5030 are substantially similar to the male connectors 4002 of the previous embodiment. As shown in FIGS. 89A and 89B, the burst-through tabs 5030 include a head portion 5032 that engages and interlocks with features of the overmould connection 5006 such that the headgear loop strap 5002 and the front strap 5004 are connected. The head portion 5032 is comprised of protrusions that form a raised abutment surface 5034. The abutment surface 5034 is configured to abut against, engage and/or contact the internal walls of the over-mould tool cavity and to align the burst-through tabs 5030 (e.g., in a thickness, width and/or lengthwise direction of the headgear loop strap 5002) within the tool. The abutment surface 5034 is flush with the outer surfaces 5008 of the overmoulded joint 5006 to provide a smooth transition between the headgear loop strap 5002 and the front strap 5004.

The headgear loop strap 5002 and the front strap 5004 are joined by overmoulding the overmoulded joint 5006 over the burst-through tabs 5030 and end portions of the front strap 5004. In some configurations, the overmoulded joint 4006 may be formed from the same plastic core material 210 that is used to form the inner core of the headgear loop strap 5002. In other configurations, the overmoulded joint 5006 may be formed from a different material such as an elastomer.

As shown in FIGS. 89A and 89B, the head portions 5032 of the burst-through tabs 5030 are surrounded by and retained within the overmoulded joint 5006. Clamping apertures 5036 are formed within the overmoulded joint 5006, which are configured to clamp the front strap 5004 in place.

The clamping apertures 5036 are formed into the overmoulded joint 5006 by protrusions protruding from the internal walls of the over-mould tool cavity.

In some configurations, the headgear loop strap 5002 and the front strap 5004 may be joined by a connector that is clamped over the burst-through tabs 5030 and end portions of the front strap 5004. As such, the connector may engage the head portion 5032 of the burst-through tabs 5030 while clamping the end portions of the front strap 5004 such that headgear loop strap 5002 and the front strap 5004 are joined.

Alignment Posts, Pin Holes and Indents

FIG. 90A to 92D illustrate intra-moulded top and bottom straps 140, 150 comprising alignment posts 5102 that protrude through the textile casing 220 and alignment recesses or pin holes 5104 that are recessed into the textile casing 220. The alignment posts 5102 are configured to abut with internal surfaces of an over-moulding tool cavity, similar to the male connector head 4002 and alignment tab 5020. The alignment posts 5102 align and position the ends of the straps within the over-moulding tool. The alignment posts 5102 protrude from at least one of top and bottom surfaces 5112, 5114 of the top and bottom straps 140, 150. The alignment posts 5102 protrude through the textile casing 220. The alignment posts 5102 are formed into the textile casing 220 during the intra-moulding of the top and bottom straps 140, 150. FIGS. 90B and 90D illustrate an alignment post 5102 formed on a burst-through tab 5120. The alignment post 5102 of the burst-through tab 5120 is formed from plastic core material 210 and is substantially similar to the alignment post 5022 of the alignment tab 5020.

The user-facing or bottom surface 5114 comprises pin holes 5104 that are recessed partially into the thickness of the straps 140, 150. The pin holes 5104 are configured to receive a pin that, for example, protrudes from a surface of the internal cavity of the over-moulding tool. The pin and pin holes 5140 are substantially similar to the recess 4070 and the locating pin 4072 in FIGS. 79A to 79C. The pins engage the pin holes 5104 to retain the straps 140, 150 in a predetermined position and alignment within the over-moulding tool and inhibit the intra-moulded straps 140, 150 from moving inside the over-moulding tool, when the over-moulding plastic is injected. The pin holes 5104 are formed on the bottom surface 5114 so as not to be visible when donned by the user. In some configurations, the pin holes 5104 may be formed in one or both of the top and bottom surfaces 5112, 5114 of the top and bottom straps 140, 150. In some configurations, the pin holes 5104 may have a depth that is less than the thickness of the top and bottom straps 140, 150. In some configurations, the pin holes 5104 may have a depth that is equal to the thickness of the top and bottom straps 140, 150.

The burst-through tab 5120 and the ends of the top and bottom straps 140, 150 both include indents on the inner and outer surfaces 5112, 5114. The indents 5106 are recessed into the plastic core material 210 of the burst-through tab 5120 and into the textile casing 220 at the ends of the top and bottom straps 140, 150. As shown in FIGS. 92A to 92D, the indents 5106 are configured to provide an increased thickness in the indent-engaging regions of the over-moulded joint 5130 and an increased surface area to form the mechanical connection between the over-moulded joint 5130 and the straps 140, 150. The increased surface area provided by the indent 5106 improves the strength of the over-moulded joint 5130.

FIGS. 92A to 92D illustrate the top and bottom straps 140, 150 after the overmoulded joint 5130 is overmoulded over the burst-through tab 5120 and the ends of the top and bottom straps 140, 150. The overmoulded joint 5130 provides a permanent over-moulded connection over the top and bottom straps 140, 150. The overmoulded joint 5130 is formed similarly to the overmoulded joints previously described. The alignment posts 5102 may cause witness marks to be formed in the overmoulded joint 5130 as a result of having the same thickness as the overmoulded joint 5130. In some configurations, a logo 5150 may be formed into the overmoulded joint 5130. FIGS. 92C and 92D illustrate the increased thickness of the over-mould joint material provided by the indents 5106. The overmoulded joint 5130 also overlaps the edge of the bottom strap 150 to improve the strength of the joint between the top and bottom straps 140, 150.

In some configurations, an overmoulded connector 5140 can be provided on the free ends of either of the straps 140, 150. The overmoulded connector 5140 is formed similarly to the overmoulded joint 5130 and may engage alignment posts 5102 and indents 5106 of the straps 140, 150. The connector 5140 can comprise a loop or clip configured to connect to another headgear or mask component.

The following disclosure relates to a headgear assembly 8000 for a patient interface 8002 configured to deliver a respiratory therapy to a patient or user. FIGS. 93A-93C show a non-limiting exemplary embodiment of the patient interface 8002 that includes a non-limiting embodiment of the headgear assembly 8000 and a mask assembly 8004. The mask assembly 8004 can be of any suitable arrangement to deliver a flow of breathing gas to the airways of the patient or user. The mask assembly 8004 can include a body and a sealing cushion or cushions. In some configurations, the body is more rigid than the sealing cushion(s). In some configurations, the body and the cushion(s) are integrally or unitarily formed. The sealing cushion is configured to form a seal with one or both of the nose and mouth of the patient or user. The mask assembly 8004 can be a full-face over-the-nose mask, a full-face under-nose mask, a nasal mask, nasal pillows or nasal cannula, for example and without limitation. Thus, the mask assembly 8004 is represented by a dashed line block in the figures.

The headgear assembly 8000 includes a headpiece 8006 and at least one connector 8008. In the illustrated arrangement, the at least one connector 8008 comprises a first connector 8008 and a second connector 8008 (not shown). The headgear assembly 8000 is substantially symmetric about the sagittal plane of the user. Thus, the second connector 8008 can be a mirror image of the illustrated first connector 8008 and the description of the first connector 8008 can be equally applied to the second connector 8008. Similarly, the left side (from the patient or user perspective) of the headpiece 8006 can be a mirror image of the right side. The first connector 8008 and the second connector 8008 each connect to the mask assembly 8004 at a front portion 8008a, and to the headpiece 8006 at a rear portion 8008b. In some configurations, the first connector 8008 and the second connector 8008 can be coupled to one another or can be of an integral or unitary construction.

The headpiece 8006 can include one or more of a top or vertical strap 8010, a forward or forehead strap 8012, a rear or back strap 8014 and an ear loop 8016. The forward strap 8012 passes substantially over the front of the user's head. That is, the forward strap 8012 can be located forward of the top of the head, such as on the forehead. The top strap 8010 passes substantially over the top of the user's head. The top strap 8010 and the forward strap 8012 converge at a junction 8020. The junction 8020 can be coupled to or form a portion of the ear loop 8016. The rear strap 8014 passes substantially around the rear of the user's head. That is, the rear strap 8014 can be located rearward of the top of the head. In some configurations, the end of the rear strap 8014 forms a portion of the ear loop 8016. The ear loop 8016 partially or completely encircles the ear of the user. In the illustrated arrangement, the ear loop 8016 completely encircles the ear of the user and forms a closed loop. The ear loops 8016 include at least one connector connecting surface 8022 so that the headpiece 8006 can connect to the first connector 8008 and/or the second connector 8008.

The first connector 8008 and/or the second connector 8008 includes at least one strap or other structure that extends between the mask assembly 8004 and the headpiece 8006. In the illustrated arrangement, one or both of the first connector 8008 and/or the second connector 8008 includes a first strap 8024 and a second strap 8026. The strap 8026 is referred to herein as the lower strap 8026. The strap 8024 is referred to herein as the middle strap 8024 because it is positioned vertically between the lower strap 8026 and the forward strap 8012 and/or top strap 8010. The middle strap 8024 extends from the front portion 8008a and the mask assembly 8004, above and behind the user's ear, when in use. The lower strap 8026 extends from the front portion 8008b and the mask assembly 8004, below and behind the user's ear, when in use. The middle strap 8024 meets the lower strap 8026 at the rear portion 8008b. In the illustrated configuration, the middle strap 8024 and lower strap 8026 are integrally formed.

In at least one embodiment, the first connector 8008 and/or the second connector 8008 can comprise an intermediate strap in the place of or in addition to the straps 8024, 8026. The intermediate strap can extend from the front portion 8008a and the mask assembly 8004 above and behind the user's ear. In at least one embodiment, the intermediate strap can extend from the front portion 8008a and the mask assembly 8004 below and behind the user's ear. In at least one embodiment, the intermediate strap can extend from the front portion 8008a and the mask assembly 8004, and diverge such that it extends both above and behind, and below and behind the user's ear.

FIG. 93B shows a perspective view of the headgear assembly 8000 with the first connecter 8008 disconnected from the headpiece 8006. In use, the first connector 8008 can be disconnected from the headpiece 8006 and extended outwards around the ear to release the mask assembly 8004 from the face of the user. The second connector 8008 (not shown) can be disconnected in a similar manner to completely disconnect the mask assembly 8004. In some embodiments, the front portion 8008a of the first connector 8008 and/or the second connector 8008 can remain connected to the mask assembly 8004 after its removal.

When the mask assembly 8004 and the connectors 8008 are disconnected from the headpiece 8006, the user can wear the headpiece 8006 independently, prior to the need to connect the mask assembly 8004. That is, the headpiece 8006 preferably is configured to be supported in a stable manner on the user's head without relying on the mask assembly 8004 and/or the connectors 8008 to remain in place, at least while the user's head is relatively upright. To reconnect the mask assembly 8004, one of the first connector 8008 and/or the second connector 8008 is connected to the headpiece 8006 at the relevant ear loop 8016. The mask assembly 8004 is positioned in the desired location. Then, the other of the first connector 8008 and/or the second connector 8008 is connected to the headpiece 8006 at the other ear loop 8016.

FIG. 93C shows a perspective view of the headgear assembly 8000 with the first connector 8008 connected to the headpiece 8006. A headpiece connecting surface 8030 on the first and/or second connector 8008 is used to facilitate the connection of the first and/or second connector 8008 with the headpiece 8006. As described, the connector connecting surface 8022 on the headpiece 8006 is used to facilitate the connection of the headpiece 8006 with the first and/or second connector 8008. The connector connecting surface 8022 and the headpiece connecting surface 8030 allow the first connector 8008 and/or the second connector 8008 to be removably connected to the headpiece 8006. The headpiece connecting surface 8030 and the connector connecting surface 8022 comprise cooperating or complementary shapes. In some configurations, portions of each of the headpiece connecting surface 8030 and the connector connecting surface 8022 have identical shapes or shapes configured to overlap one another when both the headpiece 8006 and the connector 8008 are properly positioned. Referring to FIG. 93C as an example, the connector connecting surface 8022 of the headpiece 8006 is curved along a portion of the ear loop 8016. The headpiece connecting surface 8030 is a cooperating curve on the first connector 8008. The connector connecting surface 8022 and the headpiece connecting surface 8030 cooperate to connect the first connector 8008 and the headpiece 8006.

In some embodiments, the first connector 8008 and the second connector 8008 connect to the headpiece 8006 through the use of a connection system. In at least one embodiment, this is a hook and loop connection system comprising a hook and loop fastener. One constituent of the connection system is located on the headpiece connecting surface 8030, whilst the other is located on the connector connecting surface 8022. The hook and loop connection system is configured to retain the headpiece connecting surface 8030 in place around the user's ear when the patient interface 8002 is in use. The connection system enables easy disconnection of the mask assembly 8004, the first connector 8008 and/or the second connector 8008 when desired by the user. Additionally, it enables the mask assembly 8004, the first connector 8008 and/or the second connector 8008 to be easily re-connected to the headpiece 8006 when desired.

Other configurations of the headgear assembly 8000 include a magnetic connection system between the headpiece 8006 and the connectors 8008. Some configurations include one or more magnets near or on the connector connecting surface 8022. In these configurations, the headpiece connecting surface 8030 can include one or more ferrous metal structures. Thus, the connector connecting surface 8022 and the headpiece connecting surface 8030, as illustrated, can represent components of the magnetic connection system. The connector 8008 and the headpiece 8006 are therefore connected by the magnetic attraction force between the magnets of the connector connecting surface 8022 and the ferrous structures of the headpiece connecting surface 8030. Alternately, the headpiece connecting surface 8030 can provide one or more magnets and the connector connecting surface 8022 can provide one or more ferrous metal structures.

In alternate configurations, the first connector 8008 and/or the second connector 8008 can include one or more magnets near or on the headpiece connecting surface 8030, and the headpiece 8006 can include one or more magnets near or on the connector connecting surface 8022. The one or more magnets on the connector connecting surface 8022 can be oriented such that their polarity is approximately opposite to that of the magnets on the headpiece connecting surface

8030. This configuration ensures that an incorrect attachment is indicated by magnetic repulsion.

The magnetic connection system is largely self-aligning. This assists the user in connecting the headpiece 8006 and the first connector 8008 and/or the second connector 8008 in the same location each time it is attempted. As such, the magnetic connection system enables easy donning and doffing of the mask assembly 8004 and connectors 8008.

In at least one embodiment, the connector connecting surface 8022 and the headpiece connecting surface 8030 overlap when connected. In at least one embodiment, the connector connecting surface 8022 and the headpiece connecting surface 8030 abut, such that the surfaces are complementary. For example, the headpiece connecting surface 9030 and the connector connecting surface 9022 can overlap along a connection area, which can be C-shaped and extend from above to below an ear of the user.

In at least one embodiment, the middle strap 8024 and the lower strap 8026 of the first connector 8008 and/or the second connector 8008 are adjustably connected to the mask assembly 8004. The middle strap 8024 and the lower strap 8026 can pass through corresponding holes on the mask assembly 8004 and fold back onto themselves or each other to adjustably secure in place. In at least one embodiment, the middle strap 8024 and the lower strap 8026 are fixedly connected to the mask assembly 8004. In at least one embodiment, the middle strap 8024 is fixedly connected to the mask assembly 8004, and the lower strap 8026 is adjustably connected to the mask assembly 8004. In at least one embodiment, the lower strap 8026 is fixedly connected to the mask assembly 8004, and the middle strap 8024 is adjustably connected to the mask assembly 8004.

Disconnecting the mask assembly 8004 from the headpiece 8006 using the first connector 8008 and/or the second connector 8008 enables the mask assembly 8004 to be removed without adjusting the sizing of the headgear assembly 8000. The mask assembly 8004 can be secured back in place via the first connector 8008 and/or the second connector 8008 without the need to adjust the sizing. This simplifies the donning and doffing process.

In some configurations of the headgear assembly 8000, the top strap 8010, the forward strap 8012, the rear strap 8014, or any combination of these includes an adjustment mechanism 8040. The adjustment mechanism can be of any suitable arrangement, such as a buckle, for example. Opposing side portions of the straps 8010, 8012, 8014 can pass through the buckle and double over onto themselves. The free ends of the straps 8010, 8012, 8014 can be secured to the remainder of the straps 8010, 8012, 8014 by a suitable fastener, such as a hook and loop fastener, for example.

In at least one embodiment, the top strap 8010 and forward strap 8012 form independent portions of the ear loop 8016. The portions of the ear loop 8016 defined by the top strap 8010 and the forward strap 8012 can couple to one another below and/or above the ear of the user.

In at least one embodiment, the headpiece 8006 includes a top strap 8010, spanning the top of a user's head, and a rear strap 8014, spanning the rear of a user's head.

In at least one embodiment, the first connector 8008 can be fixedly connected to the headpiece 8006. In this configuration, the second connector 8008 can be disconnected from the headpiece 8006 to remove the mask assembly 8004. In at least one embodiment, the second connector 8008 can be fixedly connected to the headpiece 8006. In this configuration, the first connector 8008 can be disconnected from the headpiece 8006 to remove the mask assembly 8004.

FIGS. 94A-94C show perspective views of a patient interface 9002 that includes a headgear assembly 9000 and a mask assembly 9004. The headgear assembly 9000 includes a headpiece 9006, a first connector 9008 and a second connector 9008 (not shown). As in the embodiment of FIGS. 93A-93C, the headgear assembly 9000 can be symmetrical about the sagittal plane of the user. Details of the headgear assembly 9000 not explicitly disclosed can be the same as or similar to corresponding elements of the headgear assembly 8000, or can be of another suitable arrangement. In this embodiment, the headgear assembly 9000 includes a partial ear loop 9016 (FIG. 94C). The first connector 9008 and the second connector 9008 each connect to the mask assembly 9004 at a front portion 9008a, and to the headpiece 9006 at a rear portion 9008b.

The headpiece 9006 includes a top or vertical strap 9010, a forward or forehead strap 9012 and a rear or back strap 9014. The forward strap 9012 passes substantially over the front of the user's head. The top strap 9010 passes substantially over the top of the user's head. The rear strap 9014 passes substantially around the rear of the user's head. The headpiece 9006 includes a connector connecting surface 9022 so that the headpiece 9006 can connect to the first connector 9008 and/or the second connector 9008.

The first connector 9008 and/or the second connector 9008 includes a middle strap 9024 and a lower strap 9026. The middle strap 9024 extends from the front portion 9008a and the mask assembly 9004, above and behind the user's ear. The lower strap 9026 extends from the front portion 9008a and the mask assembly 9004, below and behind the user's ear. The middle strap 9024 meets the lower strap 9026 at the rear portion 9008b. In the illustrated configuration, the middle strap 9024 and lower strap 9026 are integrally formed.

In at least one embodiment, the first connector 9008 and/or the second connector 9008 can comprise an intermediate strap. The intermediate strap can extend from the front portion 9008a and the mask assembly 9004 above and behind a user's ear. In at least one embodiment, the intermediate strap can extend from the front portion 9008a and the mask assembly 9004 below and behind a user's ear. In at least one embodiment, the intermediate strap can extend from the front portion 9008a and the mask assembly 9004, and diverge such that it extends both above and behind, and below and behind the user's ear.

FIG. 94B shows a perspective view of the headgear assembly 9000 with the first connecter 9008 disconnected from the headpiece 9006. In use, one or both of the connectors 9008 can be disconnected from the headpiece 9006 and extended outwards around the ear to release the mask assembly 9004 from the face of the user.

The headpiece connecting surface 9030 on the first connector 9008 and/or the second connector 9008 is used to facilitate the connection of the first and/or second connector 9008 with the headpiece 9006. The connector connecting surface 9022 on the headpiece 9006 is used to facilitate the connection of the headpiece 9006 with the first connector 9008 and/or the second connector 9008. The connector connecting surface 9022 and the headpiece connecting surface 9030 allow the first connector 9008 and/or the second connector 9008 to be removably connected to the headpiece 9006. The headpiece connecting surface 9030 and the connector connecting surface 9022 comprise cooperating or complementary shapes. In the illustrated embodiment of FIGS. 94A-94C, both the headpiece connecting surface 9030 and connector connecting surface 9022 are substantially reduced in size. The headpiece connecting surface 9030 and the connector connecting surface 9022 are rearwardly and vertically displaced from (e.g., above) the user's ear and connect along a connection line, which can be straight or slightly curved, for example. In some configurations, an entirety of the connection between the headpiece connecting surface 9030 and the connector connecting surface 9022 is located above a lowermost extent of the ear of the user.

In at least one embodiment, the first connector 9008 can be fixedly connected to the headpiece 9006. In this configuration, the second connector 9008 can be disconnected from the headpiece 9006 to remove the mask assembly 9004. In at least one embodiment, the second connector 9008 can be fixedly connected to the headpiece 9006. In this configuration, the first connector 9008 can be disconnected from the headpiece 9006 to remove the mask assembly 9004.

In at least one embodiment, the first connector 8008, 9008 and/or the second connector 8008, 9008 is fabricated from a continuous soft fabric cover with a plastic core. In some configurations, the plastic core can be an intra-moulded plastic core, in which molten plastic is introduced into a space between or within fabric portions or layers and allowed to cool. In other embodiments, the first connector 8008, 9008 and/or the second connector 8008, 9008 can be fabricated using a hard polymeric material. In at least one embodiment, the first connector 8008, 9008 and/or the second connector 8008, 9008 can be fabricated using a soft polymeric material such as silicone. In at least one embodiment, the first connector 8008, 9008 and/or the second connector 8008, 9008 can be fabricated using at least one hard polymeric material and at least one soft polymeric material. Some embodiments can include the use of a fabric material. In at least one embodiment, the first connector 8008, 9008 and/or the second connector 8008, 9008 can include combinations of a hard polymeric material, a soft polymeric material, a ceramic material, a fabric material, a foam material and/or a metallic material. In at least one embodiment, the first connector 8008, 9008 and/or the second connector 8008, 9008 can be fabricated from a foam and fabric composite material.

Closed-Loop Headgear

FIGS. 95 and 96 show front and rear perspective views of a patient interface 9100 that includes a headgear 9102, a mask assembly 9104 and a connector 9106. The headgear 9102 is a closed-loop headgear design having no breaks in the headgear 9102 and mask assembly 9104 loop. As shown in the Figures, the upper side strap 9108 and lower side strap 9110 are formed from a single continuous strap. Accordingly, the upper and lower side straps 9108, 9110 create a closed-loop or continuous connection created between the headgear 9102 and the mask assembly 9104 that is unbroken throughout the process of donning and doffing the patient interface 9100.

The closed-loop headgear 9102 design may be formed by an intra-moulding (i.e., burst-through) process in which the straps of the headgear 9102 are formed from textile casings that are filled with a plastic core material. The textile casings provide the straps with a soft and comfortable contact surface while the plastic core material provides rigidity and structure to the straps such that the headgear 9102 holds its shape.

Connector Overview

As shown in FIG. 95, the upper and lower side straps 9108, 9110 are connected to the mask assembly 9104 via a connector 9106 on each lateral side of the mask assembly 9104. In some configurations, the straps 9108, 9110 may form a portion of the connector 9106. The connector 9106 is configured to act as a mechanism for securing the mask assembly 9104 to the user's face while maintaining the closed-loop between the mask assembly 9104 and the headgear 9102.

As shown in FIGS. 97 and 98, the connector 9106 is configured to be disengaged (i.e., open or unlatched) from the mask assembly 9104 without breaking the closed-loop between the mask assembly 9104 and headgear 9102 such that the effective length of the closed-loop is increased. FIG. 97 shows a first perspective view of the connector 9106 initially disengaged from the mask assembly 9104. FIG. 98 shows a second perspective view of the connector 9106 of FIG. 97 further disengaged from the mask assembly 9104 and expanded to illustrate the effective increase in headgear loop length that is achieved by the disengaging of the connector 9106. Preferably, disengaging and expanding of the connector 9106 increases the length of the headgear loop by a minimum of 40 mm. Such an increase of the headgear loop allows the patient to be easily able to don and doff the headgear 9102. In some configurations, the minimum increase in length may be less than 40 mm if the headgear 9102 has a certain degree of elasticity.

Accordingly, the headgear 9102, the mask assembly 9104 and the connector arrangement 9106 provides a closed-loop headgear design that includes a symmetric connection mechanism to a mask assembly 9104. In other words, throughout the process of donning and doffing the patient interface 9100, the closed-loop between the mask assembly 9104 and the headgear 9102 remains unbroken, which improves the ease with which the mask 9104, when centered on a user's face, could be secured in place by the user interacting with the headgear 9102 and the connector 9106, without displacing the mask 9104. The closed-loop headgear design requires an 'over the head' method to don the patient interface 9100, which reduces the chance a patient may become confused when donning the interface 9100, or do so incorrectly. That is, the closed-loop headgear design and connector arrangement provides a comfortable, effective and intuitive to put on and take off patient interface headgear 9102. Further, the closed-loop headgear design and connector arrangement ensures that the patient interface seal remains central on the face when donning and doffing the headgear 9102.

Plastic Living Hinge

FIG. 99A shows a plastic living hinge connector 9106 including a mask connector member 9112, a headgear connector member 9114, a first mask hinge 9116, a second mask hinge 9118, a first connector hinge 9120 and a second connector hinge 9122. The connector 9106 can be in a closed position, where the mask connector member 9112 and the headgear connector member 9114 are adjacent (i.e., overlaying, collapsed on, etc.) or latched onto the mask assembly 9104, or in an open position where they are in an extended position. In some configurations, the connector 9106 is fastened and fixed against the mask assembly 9104 in the closed position such that the connector 9106 does not move or rotate. A benefit of the plastic living hinge connector 9106 is that the fastening system is self-locating, and the system is difficult to miss-use.

The headgear connector member 9114 is substantially 'U' shaped with a headgear connection point 9124 located at each of the lateral ends of the headgear connector member 9114. The headgear connector member 9114 is moulded as a single part. The headgear connector member 9114 can be made from a soft fabric cover 9114a with an intra-moulded plastic core 9114b (see, for example, FIG. 101B). Alternatively, the headgear connector member 9114 can be made from a moulded plastic component with a fabric layer on one side. In some configurations, the fabric layer can be on the outside surface of the headgear connector member 9114. In other configurations, the fabric layer can be on the inside surface of the member 9114.

The mask connector members 9112 are also formed from plastic. In the illustrated embodiment, there are two independent mask connector members 9112, where the first is vertically displaced from the second. That is, the first mask connector member 9112 may be positioned above the second mask connector member 9112 relative to a vertical plane.

At one end, the mask connector members 9112 are connected to a mask frame 9126 of the mask assembly 9104. At the other end, the mask connector members 9112 are connected to the headgear connector member 9114. The mask connector members 9112 can be integrally formed with the headgear connector member 9114, or can be connected using another method, such as adhesive bonding, RF welding, ultrasonic welding, overmoulding, a snap-fit mechanism, a mechanical stitching, etc. The mask connector member 9112 can also be integrally formed with the frame 9126 of the mask assembly 9104. Alternatively, the mask connector member 9112 can be connected using another method, such as those previously mentioned.

In the closed position, the illustrated connector 9106 is positioned in contact with the frame 9126 of the mask assembly 9104, as indicated by an arrow. A recessed channel 9128 is provided on the frame 9126 and has a corresponding shape and profile as the mask connection member 9112 and the headgear connection member 9114. In the closed position, the mask connection member 9112 and the headgear connection member 9114 fit into the recessed channel 9128. This reduces the profile of the connector 9106 on the frame 9126, and the overall profile of the mask assembly 9104.

When the connector 9106 is in the closed position, the mask assembly 9104 is secured on the user's face. A friction fit between the connector 9106 and the recessed channel 9128 can be used to retain the connector 9106 against the frame 9126 and within the recess channel 9128 when in the closed position. Alternatively, a snap fit, hook and post clip, magnets, Velcro connection system, a latching mechanism or any other connection system can be used.

In the open position, the illustrated connector 9106 rotates in a direction opposite to the indicated arrow. While opening, the connector 9106 rotates about both the mask hinges 9118 and the connector hinges 9122. That is, the connector 9106 is rotated away from the frame 9126 and the recessed channel 9128. In the illustrated embodiment, the mask hinges 9118 and the connector hinges 9122 are living hinges (i.e., thin, flexible hinges made from the same material as the mask connector member). As shown in FIG. 99B, in some configurations, the living hinge could be made as a single piece structure.

FIG. 100 shows a top view of a type of living hinge 9130 that can be incorporated into the mask connector member 9112. The living hinge 9130 includes a section of reduced thickness about which the living hinge 9130 provides rotation. Reducing the thickness of the indicated region increases the local flexibility. This allows the region of reduced thickness to act as a hinge point, or a 'living hinge' 9130. In some configurations, the living hinges 9130 may have a constant thickness along its length while still having flexibility to provide rotation.

FIG. 101A shows an exploded view of a plastic living hinge mask connector member arrangement 9106. The regions of the mask connector member 9112 that enable the hinging action can have a profile as shown in FIG. 100, or another profile that enables the living hinge configuration. In the configuration, the mask connector member 9112 includes a projection 9132 that fits into a corresponding hole 9134 in the headgear connector member 9114 to mate the two components. As shown in FIG. 101B, the projection 9132 is integrally formed with the mask connector member 9112. In some configurations, the projection 9132 may not be integrally formed with the connector member 9112. In other configurations, the headgear connector member 9114 can include the projection 9132, and the mask connector member 9112 can include the hole 9134. A similar connection mechanism can be used between the mask connector member 9112 and the mask assembly 9104, or a different connection mechanism can be used.

FIG. 102A shows a living hinge connector 9106 having a single mask hinge 9116, a single connector hinge 9122, a recessed channel 9128 and a recessed surface 9136. The recessed surface 9136 is configured to receive the mask connector member 9112 when the connector 9106 is in the closed position, and the recessed channel 9128 is configured to receive the headgear connector member 9114.

A cross-section is also shown in FIG. 102B depicting the core 9114b of the headgear connector member 9114 and the mask connector member 9112. In this configuration, the headgear connector member 9114 and the mask connector member 9112 are formed from one continuous moulded plastic component 9114b. The mask hinge spans the vertical length of the mask connector member 9112, providing a larger surface area on which the mask hinge is adjacent the mask assembly 9104. Additionally, a larger length of the mask connector member 9112 comprises the connector hinge. Increasing the length of the hinges increases the durability of the connector 9106.

Hook and Post Retaining System

FIGS. 103A and 103B show a plastic living hinge connector arrangement 9106 having a hook and post retaining system 9140. The connector 9106 of FIGS. 103A and 103B is retained in the closed position by the hook and post retaining system 9140. An elevated post 9140a is integrally formed on the mask assembly 9104, and a corresponding hook 9140b is located on the mask connector member 9112. The hook 9140b encloses the post 9140a in the closed position and retains the connector 9106 in the closed position via a snap-fit or interference-fit connection, etc. In some embodiments, the elevated post 9140a is integrally formed on the mask connector member 9112, and the corresponding hook 9140b is located on the mask assembly 9104.

In other embodiments, the connector of FIGS. 103A-B can be retained in the closed position through the use of a magnetic retaining system. One or more magnets can be located on the connector 9106, with one or more ferrous metallic structures located on the mask assembly 9104. The magnetic attraction between the magnet and the ferrous structure act to retain the connector 9106 in a closed position.

Other configurations of the connector 9106 can use a press-fit, for instance including one or more mushroom shaped protrusions on the connector 9106 and corresponding recesses on the mask assembly 9104. The mask hinge 9116 and connector hinge 9122 of FIG. 103B are enclosed by dashed boxes as they can be replaced by any of the aforementioned living hinge designs. In other embodiments, the hook and post retainer 9140 could alternatively be replaced with any other appropriate method of retaining the connector in the closed position.

Fabric Living Hinge

FIGS. 104A and 104B show a fabric living hinge connector arrangement 9142 where the connector 9106 is primarily thick fabric, with plastic supports included to increase stiffness. The fabric living hinge connector 9142 includes a mask connector member 9112, a headgear connector member 9114, two mask hinges 9116 and a connector hinge 9122. The mask connector member 9112 is substantially 'U' shaped, as is the headgear connector member 9114. The mask connector member 9112 and the headgear connector member 9114 are made from the same continuous piece of fabric (i.e., the piece of fabric consists of two 'U' shapes, which are joined at the bottom of the 'U').

The 'U' shaped mask connector member 9112 and headgear connector member 9114 each include a plastic support to increase their stiffness, however the lack of this plastic support near the connector hinge 9122 means the natural flexibility of the fabric is enough to facilitate the hinging motion. The fabric living hinge connector 9142 can be manufactured from at least one of multiple embodiments, two of which are described.

In a first embodiment, the fabric living hinge connector 9142 includes a single sheet of fabric, incorporating the 'U' shapes of the mask connector member 9112 and the headgear connector member 9114. This connector 9106 further includes a 'U' shaped plastic stiffener to re-enforce the mask connector member 9112, and another 'U' shaped plastic stiffener to re-enforce the headgear connector member 9114. A space exists between the two plastic stiffeners at the connector hinge 9122 to facilitate a living hinge between the two connector members 9112, 9114. Additionally, the plastic stiffener of the mask connector member 9112 stops short of the mask hinge 9116 to facilitate a fabric living hinge between the mask assembly 9104 and the mask connector member 9112.

In a second embodiment, the fabric living hinge connector 9142 includes two sheets of fabric, each of which incorporates both the 'U' shape of the mask connector member 9112 and the headgear connector member 9114 as a single sheet. These two pieces of fabric are aligned, such that two 'U' shaped plastic supports are sandwiched between the two fabric layers. The plastic supports are then sealed within the two fabric pieces. The fabric pieces can be connected through the use of stitching, RF welding, an adhesive bond or any other relevant connection mechanism. Similar to the first embodiment, the plastic supports provide rigidity to the 'U' shapes of the headgear connector member 9114 and the mask connector member 9112 whilst allowing the fabric to act as a living hinge at the mask hinge 9116 and the connector hinge 9122.

It should be noted that the preferred embodiment of the fabric living hinge connector 9142 includes two headgear connection points 9124. In alternate embodiments, a retaining member may join the upper and lower arms of the headgear connector member 9114 so that a different number of headgear connection points are possible.

Silicon Hinge

FIGS. 105A to 107B illustrate a connector arrangement 9106 having a silicon portion. The mask connector member 9112 is formed from silicon (or other soft polymer such as TPE, TPU, TPV, etc.) and the headgear connector member 9114 is formed from a rigid polymer.

FIGS. 105A-B illustrate a silicon hinge having a first end of the mask connector member 9112 that is pivotally connected to the mask assembly 9104 via the mask hinge 9116. A second end of the mask connector member 9112 is pivotally connected to the headgear connector member 9114 via the connector hinge 9122. In the illustrated embodiment, the mask connector member 9112 rotates about a central pin connected to the mask assembly 9104, forming the mask hinge 9116. Furthermore, the mask connector member 9112 rotates about a central pin on the connector hinge 9122, to which the headgear connector member 9114 is bound. This allows a wide range of motion for the connector 9106.

The illustrated configuration also includes a recessed center 9144 on the mask connector member 9112. This is a region 9144 where the thickness of the member 9112 is reduced. This region 9144 reduces the stiffness of the mask connector member 9112 allowing it to flex to a greater extent than would be possible without the recessed center 9144.

The illustrated mask connector member 9112 is retained to the mask assembly 9104 in the closed position via a projection on the mask mating with a corresponding hole on the mask connector member 9112. In other embodiments, the mask connector member 9112 can include the projection and the mask assembly 9104 can include the corresponding hole. Further embodiments can include any appropriate retaining mechanism (magnetic, Velcro, etc.).

FIGS. 106A-B illustrate an alternative silicon hinge arrangement. Instead of using a pivot hinge as the mask hinge, the mask hinge point 9116 is fixed such that the silicon would flex to fold over itself during the opening process. Accordingly, the connector 9106 has a bias force in the direction required to close the connector 9106. This simplifies the process of fixing the mask assembly 9104 to the user's face.

FIGS. 107A-B illustrate a mask connector member 9112 with an alternative silicon hinge arrangement. The mask connector member 9112 of this configuration includes a first portion 9112a of a first thickness and a second portion 9112b of a second thickness. The first portion 9112a has a thickness greater than that of the second portion 9112b. The first portion 9112a includes provision for the mask hinge 9118 and the connector hinge 9122. The second portion 9112b includes provision for the connector hinge 9122. The mask hinge 9118 includes a post in the mask assembly 9104 that the mask connector member 9112 rotates about. The connector hinge 9122 rotates about the mask hinge 9118 similarly about an axis as indicated.

The first portion 9112a has a greater thickness than the second portion 9112b to minimize flexing within the first portion 9112a when the connector 9106 is in the open position. The frame 9126 of the mask assembly 9104 includes a hole 9148 to accommodate the increased thickness of this portion 9112a.

The second portion 9112b has a reduced thickness to increase the allowable flex within the second portion 9112b. Allowing flex within the second portion 9112b increases the resilience of the connector 9106 when greater than required forces are exerted on it during the opening process. The second portion 9112b of the mask connector member 9112 includes a retaining cavity 9150 which is configured to mate with a retaining projection 9152 on the mask assembly 9104 when the connector 9106 is in the closed position.

The headgear connector member 9114 is fabricated from a rigid polymer. The central portion of the headgear connector 9114 includes a cavity 9154 that is sized to accommodate the mask connector member 9114 when the connector 9106 is in the closed position. This cavity 9154 ensures the profile of the connector 9106 is minimized.

The location of the connector hinge 9122 with respect to the mask connector member 9112 and the headgear connector member 9114 differs from connector arrangements previously described. The connector hinge 9122 is offset from the end of both the mask connector member 9112 and the headgear connector member 9114, as indicated by the dashed line in FIG. 107B. The advantage of offsetting this hinge 9122 is that a mechanical hard stop is created at a maximum extension of the connector 9106. This hard stop is a result of the forward edge of the headgear connector member 9114 impacting or contacting the interior surface of the mask connector member 9112. The hard stop is beneficial as it prevents the user from being able to over-rotate the headgear connector member 9114 with respect to the mask connector member 9112 at the connector hinge 9122, inverting the connector 9106. Furthermore, the hard stop acts to hold the connector 9106 wide when open. This improves the usability of the headgear 9102 and mask assembly 9104 during donning and doffing as it's easier to pass the headgear 9102 over the user's ears.

In some configurations, the mask connector member 9112 can be sized so that an interference fit is formed between the mask connector member 9112 and the central cavity 9154 of the headgear connector member 9114 when the connector 9106 is in the closed position. This is achieved by sizing the mask connector member 9114 slightly larger than the cavity 9154 of the headgear connector member 9114. As the mask connector member 9112 is silicon (or another soft polymer), when the connector 9106 is closed, an interference fit will be formed when the headgear connector member 9114 is pressed over the mask connector member 9112, compressing the mask connector member 9112. The interference fit assists in vertically stabilizing the headgear connector member 9114 when the connector 9106 is in the closed position. In an alternate embodiment, the mask connector member 9112 can be fabricated from a rigid polymer.

Headgear Connection

FIGS. 108A-C illustrate a headgear connection arrangement that is used to connect the connector 9106 to the headgear 9102. The lateral ends of the connector 9106 each include a headgear connection 9124. This headgear connection 9124 is in the form of an annular rigid structure with a hole configured to receive a strap of headgear 9102. The strap(s) of the headgear 9102 is designed to fold back on itself through the headgear connection 9124 and be fixed in place through one of a number of methods disclosed below. The headgear connection 9124 can be integrally formed with the intra-moulded core 9114b of the connector 9106.

Headgear Securement Mechanisms

FIGS. 109A-B illustrate headgear retaining mechanisms 9160 that are used to secure the length of the straps 9108, 9110. As shown, after being looped back on itself, the headgear 9102 can be retained in place at a fixed length through the use of a hook and loop fastener arrangement 9160a, a push-fit arrangement 9160b or a magnetic retaining system 9160c. In some configurations, alternative fastening arrangements may be used.

FIGS. 110A-B illustrate a push-fit headgear retaining mechanism 9162 that is used to secure the length of the straps 9108, 9110. The push fit components (e.g., protrusion 9162a and aperture 9162b) have a longer lateral profile than a vertical profile.

Over-Centered Clip Connector

FIGS. 111A-B illustrate an alternative connector arrangement 9170 having an over-centered clip design. The illustrated configuration uses a combination of pivots, hinges and plastic components to achieve an over-centered lock. The connector 9106 includes a mask connector member 9112, a headgear connector member 9114, a mask hinge 9118 and a connector hinge 9122. The over-centered connector operates in a similar manner to the silicon hinge; however, the mask connector member 9112 is rigid. A rigid member allows a hard stop to be created at the mask hinge 9118 as illustrated in FIG. 17B. This hard stop acts to maximize the rotation the connector 9106 can undergo during operation. An advantage of this is the location of the hard stop can be tuned such that the connector 9106 holds the headgear 9102 wide when in the open position, allowing the headgear 9102 to clear the ear easier when donning and doffing. The headgear connector member 9114 includes two headgear connection points 9124.

Extendable Pivot Connector

FIGS. 112A, 112B and 112C show a connector configuration 9180 that includes an extendable pivot clip. The illustrated configuration includes a mask connector member 9112 and a headgear connector member 9114 that are co-axially aligned and configured in such a way that the headgear connector member 9114 can move relative to the mask connector member 9112 along their common axis. The mask connector member 9112 projects perpendicularly to the mask hinge 9118. In the closed position, a clip retains the connector 9106 to the mask assembly 9104. To open, the user applies a force laterally to the mask assembly on the clip to disengage it. The mask connector member 9112 and headgear connector member 9114 then rotate outwards about the mask hinge 9118 (FIG. 112B). Once pivoted open, the mask connector member 9112 can be pulled outward, away from the mask assembly 9104 in a telescopic motion, extending the length of the connector 9106 (FIG. 112C). In addition to increasing the length of the headgear loop, this configuration assists in bringing the headgear 9102 away from the ear of a user, simplifying the doffing process.

Sliding Strap Hard Stop Connector

FIGS. 113A and 113B show a connector configuration having a hard stop sliding strap connector configuration 9190. In this configuration, the lateral portions of the headgear 9102 contact the cheeks of the user are incorporated into the connector 9106. A connector strap interface 9192 on the mask assembly 9104 acts as a fixation point for the headgear straps 9108, 9110. In the illustrated configuration, two headgear straps 9108, 9110 are incorporated into the connector 9106. The connection mechanism for each headgear strap 9108, 9110 at the connector strap interface 9192 is not limited. That is, the connector configuration may include a variety of types of connection mechanisms. In the illustrated configuration, the straps 9108, 9110 loop back onto themselves through an opening on the mask assembly 9104. The straps 9108, 9110 can be fixedly attached to themselves once looped through the mask assembly 9104, for example through stitching, or can be attached to themselves via a hook and loop fastener connection system.

Each strap 9108, 9110 passes through a first reversal point 9193a located on the headgear 9102. Passing through the first reversal point 9193a, the strap 9108, 9110 extends to a second reversal point 9193b where it is again looped back onto itself and fixed in place. In the illustrated configuration, the strap 9108, 9110 is fixed to itself after the second reversal point 9193b via a hook and loop fastener connection system. The fixation system is not limited to a hook and loop fastener connection system and may include other connection systems. Adjusting the strap length via the second reversal point 9193b is one way the user can adjust the tightness of the headgear 9102 in this configuration.

The second reversal points 9193b are located on a clip 9194. This clip 9194 acts as a part of the retaining mechanism for the connector 9106. A retaining point 9196 is located on the mask assembly 9104 which interacts with the clip 9194 to retain the connector 9106. In the illustrated configuration, the retaining point 9196 projects from the mask assembly 9104 and the clip 9194 is placed over the front of the retaining point 9196. The tension in the headgear 9102 and connector assembly 9106 then acts to pull the clip 9194 against the retaining point, as shown in FIG. 113A. The retaining mechanism 9190 including the clip 9194 and retaining point 9196 is not particularly limited and may include other retaining mechanisms. The retaining mechanism can be a hook and post connection mechanism, or any other mechanism.

Strap End Hard Stop Connector

FIGS. 114A and 114B show a connector configuration having a sliding strap hard stop 9200. In this configuration, each headgear strap 9108, 9110 loops over itself through the connector strap interface 9192 and then is retained in place by a retaining mechanism on the headgear strap end (e.g., hook and loop fastener). The headgear strap end 9202 however has a larger profile than the hole which each strap is passed through in the connector strap interface 9192. As a result, when the headgear strap ends 9108, 9110 are released, they are able to extend the headgear loop by retracting back through the connector strap interface 9192, but are not easily able to pass through the mask assembly 9104. This enables the user to remove the headgear 9102 without breaking the headgear/mask assembly loop. The upper and lower straps 9108, 9110 could be interconnected to allow adjustment of both at once.

Break-Fit Magnets and Tether Connector

FIGS. 115A and 115B show a connector assembly 9210 incorporating two clips 9212a, 9212b, a magnetic connection 9214 and a tether 9216. In the closed position as shown in FIG. 115A, the two components of the magnetic connection 9214 are in contact with each other, and the first and second clips 9212a, 9212b are secured on the mask assembly 9104. The first and second clips 9212a, 9212b can attach to the mask assembly 9104 through the use of a hook and post clip, a magnetic assembly or any other relevant mechanism.

As shown in FIG. 115B, the location of the magnetic connection 9214 on the ear loop of the headgear 9102 allows the user to unclip the second clip 9212b and break the magnetic connection when the user wishes to remove the mask assembly 9104. A tether 9216 is included with one end fixed at each point of the magnetic connection 9214 such that when the magnetic connection 9214 is broken, the tether 9216 acts as a bridge preventing the lower length of headgear 9102 from falling down completely. With the magnetic connection 9214 broken, the length of the headgear loop 9102 below the user's ear is longer, enabling the user to remove the headgear 9102 without the need to re-adjust the headgear 9102 when they wish to use the mask assembly 9104 next. In some configurations, the tether 9216 between the magnetic connections 9214 may not be included.

Break-Fit Clip and Tether Connector

FIGS. 116A and 116B show a connector assembly 9220 incorporating a hook or clip 9222, a post 9224 and a tether 9226 as illustrated. In the closed position, the hook 9222 is connected to the post 9224 on the mask assembly 9104. In the open position, the user releases the hook or clip 9222, which lengthens the headgear loop. The tether 9226 acts as a bridge between the hook or clip 9222 and the retaining member or post 9224 on the mask assembly 9104. This maintains the closed-loop of the headgear 9102 whilst lengthening the headgear loop enough to ensure the headgear 9102 is comfortably able to be removed by the user.

Clip and Continuous Tether Connector

FIGS. 117A and 117B show a clip and continuous tether connector 9230 incorporating a hook or clip 9232, a post 9234 and a continuous tether 9236 that links both connectors 9230 on the mask assembly 9104. In this configuration, each of the two connectors 9230 is linked by a common tether 9236. The tether 9236 passes through a tether channel 9238 located on the mask assembly 9104. The tether 9236 is preferably fabricated from an elastic material. In the closed position, the clip 9232 is fixed to the post 9234 of the mask assembly 9104. When the user wishes to open the connectors 9230, the user unclips the clips 9232 and pulls. The tether 9236 maintains the closed-loop of the headgear 9102 while allowing the headgear loop length to increase due to its elasticity. This enables the user to remove the mask assembly 9104 effectively.

FIGS. 118A and 118B show an alternative clip and continuous tether connector 9230 incorporating a first tether 9236a and a second tether 9236b. The first tether 9236a is vertically displaced with respect to the second tether 9236b. The first tether 9236a passes through a first tether channel 9238a. The second tether 9236b passes through a second tether channel 9238b. The tethers 9236a, 9236b can move approximately parallel with each other. The clips 9232 operate similarly to the first embodiment. A result of including a first tether 9236a and a second tether 9236b is the increased tendency of the clips 9232 to automatically align during donning and doffing. This can be due to the increased elasticity which is a result of the two tethers 9236a, 9236b.

Clip and Rigid Tether Connector

FIGS. 119A and 119B show a connector assembly 9230 having a clip 9232 and a pair of rigid tethers 9236 to retain each lateral headgear strap. In this configuration, the connector 9230 includes a clip and a rigid tether system. As per previous connectors 9230, the clip 9232 is used to retain the headgear 9102 to the mask assembly 9104 and can be a hook and post. Additionally, however, integrated into the mask assembly are two rigid tethers 9236. The lateral headgear straps 9108, 9110 are each fed through a slider hole in the rigid tether 9236 during the initial headgear setup such that when secured, the lateral headgear straps 9108, 9110 can slide through sliders 9240 of the rigid tether 9236. When the connector 9230 is put into the open position, the headgear 9102 can slide through the rigid tether sliders to increase the size of the headgear loop. The sliders 9240 however restrict the maximum extension of the headgear loop by acting as a hard stop when the clip 9232 is reached.

Hook and Post Loop Connector

FIGS. 120A and 120B show a connector assembly 9250 having a hook and post loop connector. The illustrated connector 9250 includes a fixed connector point 9252, a clip 9254 and a material length 9256. The fixed connector point 9252 is located on the upper portion of the mask assembly 9104. At this point, the material length 9256 passes through a loop; folds back onto itself and is adjustably secured in place (for instance using a hook and loop fastener or a magnetic connection). The material length 9256 passes through a first eye loop 9258, at which point it is redirected to a second eye loop 9260. The end of the material or fabric length 9256 includes the clip 9254, which allows the end of the fabric length 9256 to be removably connected to the mask assembly 9104.

To open the connector 9250, the clip 9254 is disconnected from the mask assembly 9104. In the illustrated embodiment, the clip 9254 is a hook and post clip. The clip 9254 could alternatively be magnetic, press-fit or another clip configuration. Releasing the clip 9254 increases the length of the headgear loop, allowing the patient to don and doff the headgear 9102 as shown. The clip 9254 acts as a hard stop on the second eye loop 9260, which allows the maximum length the headgear loop can be increased by to be restricted. The effective length of the material length 9256 can be adjusted at both the fixed connector point 9252 and the clip 9254.

The material length 9256 can be fabricated from a flexible material, such as breath-o-prene, leather or a synthetic leather, fabric, any combination of these or any other appropriate material.

FIGS. 121A and 121B show an alternative hook and post loop connector 9250, which is similar to the connector 9250 of FIGS. 120A and 120B. In FIGS. 121A and 121B, the clip 9254 is modified relative to the clip 9254 of FIGS. 120A and 120B. In other respects, the connector 9250 of FIGS. 121A and 121B can be the same as or substantially similar to the connector 9250 of FIGS. 120A and 120B.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A method for forming at least a portion of a headgear within a moulding tool, comprising:
   placing a first tubular textile casing into a cavity of a first moulding tool;
   positioning a portion of the first tubular textile casing in contact with an adjacent cavity having a shape of a connector portion;
   introducing molten plastic material into the first moulding tool and into the first tubular textile casing;
   pushing the molten plastic material into the adjacent cavity through the first tubular textile casing; and
   allowing the molten plastic material to solidify within the first tubular textile casing to form a first strap portion having an inner core and a connector portion formed from unitary plastic material.

2. The method for forming at least a portion of a headgear of claim 1, further comprising:
- placing the first strap portion into a second moulding tool;
- positioning an end portion of a second tubular textile casing over the connector portion and in contact with the first tubular textile casing of the first strap portion;
- introducing molten plastic material into the second moulding tool and into the second tubular textile casing; and
- allowing the molten plastic material to solidify within the second tubular textile casing to form a second strap portion having an inner core formed from unitary plastic material that is connected to the connector portion of the first strap portion.

3. The method for forming at least a portion of a headgear of claim 1, wherein pushing the molten plastic material into the adjacent cavity through the first tubular textile casing further comprises displacing threads of the first tubular textile casing to form gaps in a wall of the first tubular textile casings through which the molten plastic material flows into the adjacent cavity.

4. The method for forming at least a portion of a headgear of claim 1, wherein pushing the molten plastic material into the adjacent cavity through the first tubular textile casing further comprises tearing threads of the first tubular textile casing to form a hole in a wall of the first tubular textile casings through which the molten plastic material flows into the adjacent cavity.

5. The method for forming at least a portion of a headgear of claim 1, wherein pushing the molten plastic material into the adjacent cavity through the first tubular textile casing further comprises stretching the first tubular textile casing to form gaps or spaces in a wall in a wall of the first tubular textile casings through which the molten plastic material flows into the adjacent cavity.

6. The method for forming at least a portion of a headgear of claim 1, wherein a center portion of the cavity includes protrusions that depress a surface of the first tubular textile casing such that indentations are integrally formed on the surface of the first strap portion.

7. The method for forming at least a portion of a headgear of claim 1, further comprising inserting a connector insert into the first tubular textile casing.

8. The method for forming a portion of a headgear of claim 7, further comprising pushing the molten plastic material through an opening of the connector insert and into the first tubular textile casing.

9. The method for forming at least a portion of a headgear of claim 8, wherein the opening of the connector insert comprises an internal connection geometry that is configured to connect with an opposing male connector geometry.

10. The method for forming at least a portion of a headgear of claim 7, wherein the connector insert has a shape of the connector portion.

11. The method for forming at least a portion of a headgear of claim 7, wherein the connector insert pushes an opening of the first tubular textile casing outwardly towards walls of the cavity.

12. The method for forming at least a portion of a headgear of claim 1, wherein a width of the connector portion is equal to the width of the inner core.

13. The method for forming at least a portion of a headgear of claim 1, wherein outer edges of the cavity narrow relative to a center portion of the cavity such that the outer edges of the first tubular textile casing are clamped to prevent the molten plastic material from flowing between the outer edges of the first tubular textile casing.

14. The method for forming at least a portion of a headgear of claim 1, wherein at least one outer edge of the cavity in a lengthwise direction is narrow relative to a center portion of the cavity such that the at least one outer edge of the first tubular textile casing is clamped to prevent the molten plastic material from flowing along the at least one outer edge of the first tubular textile casing.

15. The method for forming at least a portion of a headgear of claim 14, wherein the first tubular textile casing being clamped forms a soft portion on the at least one outer edge which prevents the molten plastic material from flowing therethrough.

16. The method for forming at least a portion of a headgear of claim 1, wherein outer edges of the cavity narrow relative to a center portion of the cavity.

17. The method for forming at least a portion of a headgear of claim 1, wherein the first tubular textile casing is knitted.

18. The method for forming at least a portion of a headgear of claim 1, wherein the first tubular textile casing is woven, braided, or crocheted.

19. The method for forming at least a portion of a headgear of claim 1, wherein the connector portion comprises tabs.

* * * * *

UNITED STATES PATENT AND TRADEMARK OFFICE
CERTIFICATE OF CORRECTION

| | |
|---|---|
| PATENT NO. | : 11,850,365 B2 |
| APPLICATION NO. | : 17/646983 |
| DATED | : December 26, 2023 |
| INVENTOR(S) | : Paul Mathew Freestone et al. |

It is certified that error appears in the above-identified patent and that said Letters Patent is hereby corrected as shown below:

In the Specification

Column 1, Line 8 (approx.), after "TO" insert -- ANY --.

Column 1, Line 13, delete "35U.S.C." and insert -- 35 U.S.C. --.

Column 1, Line 18, after "2016," delete "and".

Column 6, Line 5, delete "that" and insert -- than --.

Column 8, Line 4, delete "that" and insert -- than --.

Column 31, Line 65, delete "FIG." and insert -- FIGS. --.

Column 61, Line 50, delete "filament" and insert -- filament. --.

Column 63, Line 12, delete "FIG." and insert -- FIGS. --.

Column 80, Line 28, delete "that that" and insert -- that --.

In the Claims

Column 81, Line 44, Claim 8, delete "forming a portion" and insert -- forming at least a portion --.

Signed and Sealed this
Second Day of April, 2024

Katherine Kelly Vidal
*Director of the United States Patent and Trademark Office*